United States Patent
Wizel et al.

(10) Patent No.: US 11,649,467 B2
(45) Date of Patent: May 16, 2023

(54) CHIKUNGUNYA VIRUS ANTIGEN CONSTRUCTS

(71) Applicant: GLAXOSMITHKLINE BIOLOGICALS SA, Rixensart (BE)

(72) Inventors: Benjamin Wizel, Rockville, MD (US); Martine Harvey, Laval (CA); Lucile Warter, Rixensart (BE); Kate Luisi, Rockville, MD (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 521 days.

(21) Appl. No.: 16/631,557

(22) PCT Filed: Jul. 19, 2018

(86) PCT No.: PCT/IB2018/055389
§ 371 (c)(1),
(2) Date: Jan. 16, 2020

(87) PCT Pub. No.: WO2019/016756
PCT Pub. Date: Jan. 24, 2019

(65) Prior Publication Data
US 2020/0172930 A1 Jun. 4, 2020

Related U.S. Application Data

(60) Provisional application No. 62/589,729, filed on Nov. 22, 2017, provisional application No. 62/535,371, filed on Jul. 21, 2017.

(51) Int. Cl.
*C12N 15/86* (2006.01)
*A61K 39/12* (2006.01)

(52) U.S. Cl.
CPC ............ *C12N 15/86* (2013.01); *A61K 39/12* (2013.01); *C12N 2710/10343* (2013.01); *C12N 2770/36123* (2013.01); *C12N 2770/36134* (2013.01)

(58) Field of Classification Search
None
See application file for complete search history.

(56) References Cited

U.S. PATENT DOCUMENTS

| 8,216,834 B2 * | 7/2012 | Colloca | A61P 31/14 435/456 |
| 10,369,208 B2 * | 8/2019 | Nabel | A61K 39/12 |
| 11,254,710 B2 * | 2/2022 | Colloca | C07K 14/075 |

FOREIGN PATENT DOCUMENTS

| WO | 2010062396 A2 | 6/2010 |
| WO | 2016198621 A1 | 12/2016 |
| WO | 2018014008 A1 | 1/2018 |

OTHER PUBLICATIONS

Heise, M. (eds) Chikungunya Virus. Current Topics in Microbiology and Immunology, copyright 2019, vol. 435. Springer, Champ. (Year: 2019).*
European Patent Office as International Searching Authority, International Search Report and Written Opinion for corresponding International Application No. PCT/IB2018/055389, dated Oct. 4, 2018 (14 pages).
Wang et al., "A complex adenovirus vaccine against chikungunya virus provides complete protection against viraemia and arthritis" 2011 Vaccine 29: 2803-2809.

* cited by examiner

Primary Examiner — Stacy B Chen

(57) ABSTRACT

The invention provides adenoviral vectors comprising transgenes encoding Chikungunya virus antigens. The vectors can be used to produce vaccines for the prophylaxis, amelioration and treatment of diseases caused by Chikungunya virus infections.

8 Claims, 15 Drawing Sheets

Specification includes a Sequence Listing.

Figure 2A

```
ChAd3    (1)   MKRKTSDEFNPVYPYDTESGPPSVPFLTPPFVSPDGFQESPPGVLSLEPLVTSHGMLALKMGGLSLDDAGNLTSQDTAPLKKTKTNLSL
PanAd3   (1)   MKRAKTSDFNPVYPYDTEGPPSVPFLTPPFVSPDGFQESPPGVLSLEPLVTSHGMLALKMGNGLSLDDAGNLTSQDVTPPLKKTKTNLSLQ
ChAd17   (1)   MKRKTSDEFNPVYPYDTESGPPSVPFLTPPFVSPDGFQESPPGVLSLLEPLVTSHGMLALKMGGLSLDDAGNLTSQDTTPPLKKTKTNLSL
ChAd19   (1)   MKRAKTSDKSFNPVYPYDTEGPPSVPFLTPPFVSPDGFQESPPGVLSLLEPLVTSHGMLALKMGGLSLDDAGNLTSQDVTTPPLKKTKTNLSL
ChAd24   (1)   MKRKTSDEFNPVYPYDTEGPPSVPFLTPPFVSPDGFQESPPGVLSLLEPLVTSHGMLALKMGGLSLDDAGNLTSQDVTTPPLKKTKTNLSL
ChAd155  (1)   MKRKTSDEFNPVYPYDTESGPPSVPFLTPPFVSPDGFQESPPGVLSLEPLVTSHGMLALKMGGLSLDDAGNLTSQDTAPLKKTKTNLSL
ChAd11   (1)   MKRKTSDEFNPVYPYDTEGPPSVPFLTPPFVSPDGFQESPPGVLSLEPLVTSHGMLALKMGGLSLDDAGNLTSQDTAPLKKTKTNLSL
ChAd20   (1)   MKRKTSDEFNPVYPYDTESGPPSVPFLTPPFVSPDGFQESPPGVLSLEPLVTSHGMLALKMGGLSLDDAGNLTSQDTAPLKKTKTNLSL
ChAd31   (1)   MKRKTSDFNPVYPYDTEGPPSVPFLTPPFVSPDGFQESPPGVLSLRIEPLVTSHGMLALKMGNGLSLDDAGNLTSQDVTPPLKKTKTNLSL
PanAd1   (1)   MKRAKTSDEFNPVYPYDTEGPPSVPFLTPPFVSPDGFQESPPGVLSLRIEPLVTSHGMLALKMGNGLSLDDAGNLTSQDVTPPLKKTKTNLSLQ
PanAd2   (1)   MKRAKTSDEFNPVYPYDTEGPPSVPFLTPPFVSPDGFQESPPGVLSLRIEPLVTSHGMLALKMGNGLSLDDAGNLTSQDVTPPLKKTKTNLSLQ

ChAd3    (101) TSPLTVSSGLTAAAPLAVAGTSLTMQSAPLVQDAKLLATGPLITVSEGKLLLQTSAPLTAADSSTLTATPPNVSSGSLDMEDPYTH
PanAd3   (101) TSPLTVS-SGLTAAAPLAVAGTSLTMQSAPLVQDAKLGLATQGPLITVSEGKLTLQTSAPLTAADSSTLTGTTPPVSSGSLDMEDPYTH
ChAd17   (101) TSPLTVSSGLTAAAPLAVAGTSLTMQSAPLVQDAKLLATGPLITVSEGKLLLQTSAPLTAADSSTLTTPPVSSGSLDMEDPYTH
ChAd19   (101) TSPLTVSSGLTAAAPLAVAGTSLTMQSAPLVQDAKLLATGPLITVSEGKLLLQTSAPLTAADSSTLTTPPVSSGSLDMEDPYTH
ChAd24   (101) TSPLTVSSGLTAAAPLAVAGTSLTMQSAPLVQDAKLLATGPLITVSEGKLLLQTSAPLTAADSSTLTTPPVSSGSLDMEDPYTH
ChAd155  (101) TSPLTVSSGLTAAAVPLAVAGTSLTMQSAPLVQDAKLLATGPLITVSEGKLLLQTSAPLTAADSSTLTTPPNVSSGSLDMENPYTH
ChAd11   (101) TSPLTVSSGLTAAAPLAVAGTSLTMQSAPLVQDAKLLATGPLITVSEGKLLLQTSAPLTAADSSTLTATPPSNGSLDMAPYTH
ChAd20   (101) TSPLTVSSGLTAAAPLAVAGTSLTMQSAPLVQDAKLLATGPLITVSEGKLLLQTSAPLTAADSSTLTATPPSNGSLDMAPYTH
ChAd31   (101) TSPLTVSSGLTAAAPLAVAGTSLTMQSAPLVQDAKLLATGPLITVSEGKLLLQTSAPLTAADSSTLTATPPSNGSLDMAPYTH
PanAd1   (101) TSPLTVS-SGLTAAAPLAVAGTSLTMQSAPLVQDAKLGLATQGPLITVSEGKLTLQTSAPLTAADSSTLTATPPSGSLSDMAPYTH
PanAd2   (101) TSPLTVS-SGLTAAAPLAVAGTSLTMQSAPLVQDAKLGLATQGPLITVSEGKLTLQTSAPLTAADSSTLTATPPSGSLSDMAPYTH
```

Figure 2B

```
ChAd3    (201) DGKLxxRIGxPLRVVDSLHTLTVVTGxGLTxDNNALQTRVxGALGYDxSGNLxxLRAxGMRxDxxGxLIIxNVAYPFDAQNNLSRLGQGPLxxxxDHNLD
PanAd3   (200) DGKLxxRIGxPLQVVDSLHTLTVVTGxGLTxVANNALQTVxVAGALGYDxSGNLELRAxGGMRxNTGGQLIIxVAYPFDAQNNLSRLGQGPLxxxNHNLD
ChAd17   (201) DGKLxxRIGxPLRVVDSLHTLTVVTGxGLTxDNNALQTRVxGALGYDxSGNLxxLRAxGGMRxDxxGxLIIxVAYPFDAQNNLSRLGQGPLxxxDHNLD
ChAd19   (201) DGKLxxRIGxPLRVVDSLHTLTVVTGxGxAxDNNALQTRVxGALGYDxSGNLxxLRAxGGMRxDxxGxLIIxVAYPFDAQNNLSRLGQGPLxxxDHNLD
ChAd24   (201) DGKLxxRIGxPLRVVDSLHTLTVVTGxGxAxDNNALQTRVxGALGYDxSGNLxxLRAxGGMRxDxxGxLIIxVAYPFDAQNNLSRLGQGPLxxxDHNLD
ChAd155  (201) xGKLxxxxxFGAPLHVVDSLNALTVVTGQGLIIxxGTALQTRVxGALNYDxSGNLELRAxGGMRxDxxGxLIIxGQLIIxGQGPLxxxAHNLD
ChAd11   (201) xGKLxxxxxFGAPLHVVDSLNALTVVTGQGLIIxxGTALQTRVxGALNYDxSGNLELRAxGGMRxDxxGxLIIxGKLIIxGQGPLxxxAHNLD
ChAd20   (201) xGKLxxxxxFGAPLHVVDSLNALTVVTGQGLIIxxGTALQTRVxGALNYDxSGNLELRAxGGMRxDxxGxLIIxGQLIIxVAYPFDAQNNLSRLGQGPLxxxAHNLD
ChAd31   (201) xGKLxxxxxFGAPLHVVDSLNALTVVTGQGLIIxxGTALQTRVxGALNYDxSGNLELRAxGGMRxDxxGxLIIxGQLIIxVAYPFDAQNNLSRLGQGPLxxxAHNLD
PanAd1   (200) xGKLxxxxxGAPLHVVDxLNALTVVTGQGLIIxxGRALQTRVxGALSYDxEGNxQLQAxGGMRxDNxGxLIIxNGQLIIxNVAYPFDAQNNLSRLGQGPLIxxNSAHNLD
PanAd2   (200) xGKLxxxxxGAPLHVVDxLNALTVVTGQGLIIxxGRALQTRVxGALSYDxEGNxQLQAxGGMRxDNxGxLIIxGQLIIxNGQGPLIxxNSAHNLD ChAd3    (301) xNCNRGLTTTxxNNTxKLET--------------------KxSSGLxYDxxGAxxIIKLGTGLxFDxTGAxTVGNTGDDKLTLWT
PanAd3   (300) xNCNRGLTTTxxSNTTKLET--------------------KxDSGLxYNAxGAxIAKLGTGLxFDxNTGAxTVGNTGDDKLTLWT
ChAd17   (301) xNCNRGLTTTxxNNTxKLET--------------------KxSSGLxYDxxGAxxIIKLGTGLxFDxTGAxTVGNTGDDKLTLWT
ChAd19   (301) xNCNRGLTTTxxNNTxKLET--------------------KxxSGLxYDxxGAxxIIKLGTGxxFDSTGAxxVGNTGDDKLTLWT
ChAd24   (301) xNCNRGLTTTxxNNTxKLET--------------------KxxSGLxYDxxGAxxIIKLGTGxxFDSTGAxxVGNTGDDKLTLWT
ChAd155  (301) xNYNRGLxxFTSGNTxKLExNIIxxTAxKGxIxDDTxIALAxNAGxxxQxDxGSSxDTNPLxKTKLxGLxQTKIGLxLQxGSxxxTNPLQxTKIGLxLxYDSxxAxIITKLGTGLxYDSxxAxTTKLGTGxxYDSxxAxIITKLGTGxxIAKLGTGxxYDSxxAxIITKLGTGxxFDxNTGAxxIxKxDDKLTLWT
ChAd11   (301) xNYNRGLxxFTSGNTxKLExNIIxxTAxKGxIxDDTxIALAxNAGxxxQxDxGSSxDTNPLxKTKLxGLxQTKIGLxLQxGSxxxTNPLQxTKIGLxLxYDSxxAxIITKLGTGxxFDxNTGAxxIVGNxDDKLTLWT
ChAd20   (301) xNYNRGLxxFTSGNTxKLExNIIxxTAxKGxIxDDTxIALAxNAGxxxQxDxGSSxDTNPLxKTKLxGLxQTKIGLxLQxGSxxxTNPLQxTKIGLxLxYDSxxAxIITKLGTGxxFDxNTGAxxIVGNxDDKLTLWT
ChAd31   (301) xNYNRGLxxFTSGNTxKLExNIIxxTAxKGxIxDDTxIALAxNAGxxxQxDxGSSxDTNPLxKTKLxGLxQTKIGLxLQxGSxxxTNPLQxTKIGLxLxYDSxxAxIITKLGTGxxFDxNTGAxxIVGNxDDKLTLWT
PanAd1   (300) xNLNRGLxxFTSGNTxKLExNIIxxTAxKGxFxDGTxAIAxNAGxxxQxCGSSxxNPLQxTKIGLxLxYDSxxAxITKLGTGLxYDSxxAxITKLGTGxxYDSxxAxITKLGTGxxFDxNTGAxxIVGNxDDKLTLWT
PanAd2   (300) xNLNRGLxxFTSGNTxKLExNIIxxTAxKGxFxDGTxAIAxNAGxxxQxCGSSxxxTNPLQxTKIGLxLxYDSxxAxITKLGTGxxFDxNTGAxxIVGNxDDKLTLWT
```

Figure 2C

```
ChAd3   (365) TPDPSPNCRI..KDCKFTLVITKCGSQ.LASV.AL.VSGNL.S..GTVASVTIFLRFDQNGVL.ENSSLDP.YWN.RNGN.TN..APYTNAVGFMPNLAA
PanAd3  (364) TPDPSPNCRI..KDCKFTLVITKCGSQ.LASV.AL.VSGNL.S..GTV.SVTIFLRFDQNGVL.ENSSLDKEYWN.RNGN.TN..PYTNAVGFMPNL.A
ChAd17  (365) TPDPSPNCRI..DKDCKFTLVITKCGSQ.LASV.AL.VSGNL.S..GTV.SVTIFLRFDQNGVL.ENSSLDK.YWN.RNGN.TN..APYTNAVGFMPNLAA
ChAd19  (365) TPDPSPNCRI..DKDCKFTLVITKCGSQ.LASV.AL.VSGNL.S..GTV..VTIFLRFDQNGVL.ENSSLDK.YWN.RNGN.TN..PYTNAVGFMPNLAA
ChAd24  (365) TPDPSPNCRI..DKDCKFTLVITKCGSQ.LASV.AL.VSGNL.S..GTV..VTIFLRFDENGVL.RFDENGVL.ENSSLDE.YWN.RKGDLTEGT.YTNAVGFMPNLAA
ChAd155 (401) TPDPSPNCRI..SEKDAKFTLVITKCGSQ.LASV.VL.V.GSLAP..GTV.TS.QI.LRFDENGVL.ENSSLDE.YWN.RKGDLTEGT.YTNAVGFMPNL.A
ChAd11  (401) TPDPSPNCRI..SEKDAKFTLVITKCGSQ.LASV.VL.V.GSLAP..GTV.TS.QI.LRFDENGVL.ENSSLDE.YWN.RKGDLTEGT.YTNAVGFMPNL.A
ChAd20  (401) TPDPSPNCRI..SEKDAKFTLVITKCGSQ.LASV.VL.V.GSLAP..GTV.TS.QI.LRFDENGVL.ENSSLDE.YWN.RKGDLTEGT.YTNAVGFMPNL.A
ChAd31  (401) TPDPSPNCRI..SEKDAKFTLVITKCGSQ.LASV.VL.V.GSLAP..GTV.TS.QI.LRFDENGVL.ENSSLDE.YWN.RKGDST.GT.YTNAVGFMPNL.A
PanAd1  (400) TPDPSPNCRIN.EKDAKLTLVITKCGSQ.LASV.VL.V.GSLAP..GTV.TS.QI.LRFDENGVL.ENSSLDE.YWN.RKGDST.GT.YTNAVGFMPNL.A
PanAd2  (400) TPDPSPNCRIN.EKDAKLTLVITKCGSQ.LASV.VL.V.GSLAP..GTV.TS.QI.LRFDENGVL.ENSSLDE.YWN.RKGDST.GT.YTNAVGFMPNL.A

ChAd3   (465) YPKTQSQTAKNNIVS.VYL.GDK.KPM.LTITLNGTNE..SET.QVSHYSMSF.WAWESG.YAT.TFATNSFTFSYIAEQ
PanAd3  (464) YPKTQSQTAKNNIVS.VYL.GDK.KPM.LTITLNGTNE..SET.QVSHYSMSF.WAWESG.YAT.TFATNSFTFSYIAEQ
ChAd17  (465) YPKTQSQTAKNNIVSEVYLHGDK.KPM.LTITLNGTNE..SET.QVSHYSMSF.WSWDSGKYAT.TFATNSFTFSYIAEQ
ChAd19  (465) YPKTQSQTAKNNIVS.VYL.GDK.KPM.LTITLNGTNE..SET.QVSHYSMSF.WAWESG.YAT.TFATNSFTFSYIAEQ
ChAd24  (465) YPKTQSQTAKNNIVS.VYL.GDK.KPM.LTITLNGTNE..SET.QVSHYSMSF.WAWESG.YAT.TFATNSFTFSYIAEQ
ChAd155 (501) YPKTQSQTAK.NIVS.VYL.GDK.KPMILTITLNGTNE.G.....VS.YSM.W.G.NY..ETFQTNSFTFSYIA.E
ChAd11  (501) YPKTQSQTAK.NIVS.VYL.GDK.KPMILTITLNGTNE.G.....VS.YSM.W.G.NY..ETFQTNSFTFSYIA.E
ChAd20  (501) YPKTQSQTAK.NIVS.VYL.GDK.KPM.LTITLNGTNE.G.....VS.YSM.W.G.NY..ETFQTNSFTFSYIA.E
ChAd31  (501) YPKTQSQTAK.NIVS.VYL.GDK.KPM.LTITLNGTNE.G.....VS.YSM.W.G.NY..ETFQTNSFTFSYIA.E
PanAd1  (500) YPKTQSQTAK.NIVS.VYL.GDK.KPM.LTITLNGTNE.G.....VS.YSM.W.G.NY..ETFQTNSFTFSYIA.E
PanAd2  (500) YPKTQSQTAK.NIVS.VYL.GDK.KPM.LTITLNGTNE.G.....VS.YSM.W.G.NY..ETFQTNSFTFSYIA.E
```

CHIKUNGUNYA VIRUS ANTIGEN CONSTRUCTS

SEQUENCE LISTING

The instant application contains a Sequence Listing which has been filed electronically in ASCII format and is hereby incorporated by reference in its entirety. Said ASCII copy, created on Jul. 17, 2018, is named VU66387 WO SeqL-stg.txt and is 374,654 bytes in size.

FIELD OF THE INVENTION

This invention is in the field of treating and preventing viral infections. In particular, the present invention relates to chimpanzee adenoviral vectors encoding a Chikungunya virus antigen. It includes the use of Chikungunya virus antigens for treating and preventing Chikungunya virus infections.

BACKGROUND

Chikungunya virus (CHIKV) is a single-stranded, positive-sense RNA virus in the family Togaviridae, within the *Alphavirus* genus. The virus is transmitted by infected female mosquitoes of the genus *Aedes*. About 2.5 billion people live in CHIKV-transmitting *Aedes* mosquito vector areas, and outbreaks can involve millions of people. Local transmission of CHIKV has been reported in over 100 countries or territories, and its range is expanding. Infections can cause myalgia, arthritis/arthralgia, fever, rash, headache, nausea and vomiting which typically last weeks to months. Approximately 35-50% of infected patients develop chronic symptoms that include sever joint pain that can persist for years.

The CHIKV genome encodes four non-structural proteins (nsP1-4) and five structural proteins, including a capsid (C), envelope proteins E1-E3, and membrane-associated peptide 6K. Three genotypes (lineages) of CHIKV have been identified: West African, Asian and East/Central/South African (ECSA). The three genotypes share 95.2-99.8% amino acid sequence identity.

Several vaccine approaches are currently under evaluation for the prevention of CHIKV infection, including live-attenuated or inactivated whole virus, virus-like particles (VLPs), recombinant subunit vaccines, DNA vaccines and recombinant vector vaccines. Wang et al., *Vaccine*. 29(15): 2803-2809 (2011). However, to date no licensed vaccine is available.

Adenovirus has been widely used for gene transfer applications due to its ability to achieve highly efficient gene transfer in a variety of target tissues and large transgene capacity. Conventionally, adenovirus E1 genes are deleted and replaced with a transgene cassette consisting of a promoter of choice, cDNA sequence of the gene of interest and a poly A signal, resulting in a replication defective recombinant virus.

Recombinant adenoviruses are useful in both gene therapy and as vaccines. However, the use of human-derived adenoviral vectors is complicated by pre-existing immunity to human adenoviruses, which may neutralize the vaccine vector. Viral vectors based on non-human simian adenovirus represent an alternative to the use of human derived vectors for the development of genetic vaccines. Certain adenoviruses isolated from non-human simians are closely related to adenoviruses isolated from humans, as demonstrated by their efficient propagation in cells of human origin.

There is a need for a CHIKV vaccine with a simplified dosing schedule, increased safety and an enhanced manufacturing profile. Accordingly, there is an unmet need to develop non-human simian adenoviral vectors for use in a CHIKV vaccine.

SUMMARY OF THE INVENTION

The present inventors provide constructs useful as components of immunogenic compositions for the induction of an immune response in a subject against Chikungunya virus (CHIKV) infection, methods for their use in treatment and prevention of EBV infection and EBV-associated diseases, and processes for their manufacture.

There is provided an isolated polynucleotide, wherein the polynucleotide encodes a polypeptide selected from the group consisting of:
  (a) a polypeptide having the amino acid sequence according to SEQ ID NO: 1,
  (b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
  (c) a polypeptide having the amino acid sequence according to SEQ ID NO: 3;
wherein the isolated polynucleotide comprises a nucleic acid sequence encoding a Chikungunya virus antigen.

Also provided is a recombinant polynucleotide comprising a polynucleotide selected from the group consisting of:
  (a) a polynucleotide which encodes a polypeptide having the amino acid sequence according to SEQ ID NO: 1,
  (b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
  (c) a polynucleotide which encodes a polypeptide having the amino acid sequence according to SEQ ID NO: 3;
wherein the recombinant polynucleotide comprises a nucleic acid sequence encoding a Chikungunya virus antigen.

Also provided is a recombinant vector comprising a polynucleotide selected from the group consisting of:
  (a) a polynucleotide which encodes a polypeptide having the amino acid sequence according to SEQ ID NO: 1,
  (b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
  (c) a polynucleotide which encodes a polypeptide having the amino acid sequence according to SEQ ID NO: 3;
wherein the recombinant vector comprises a nucleic acid sequence encoding a Chikungunya virus antigen.

Also provided is a recombinant adenovirus comprising at least one polynucleotide or polypeptide selected from the group consisting of:
  (a) a polynucleotide which encodes a polypeptide having the amino acid sequence according to SEQ ID NO: 1,
  (b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(c) a polynucleotide which encodes a polypeptide having the amino acid sequence according to SEQ ID NO: 3,
(d) a polypeptide having the amino acid sequence according to SEQ ID NO: 1,
(e) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(f) a polypeptide having the amino acid sequence according to SEQ ID NO: 3;
wherein the recombinant adenovirus comprises a nucleic acid sequence encoding a Chikungunya virus antigen; and wherein the nucleic acid sequence is operatively linked to one or more sequences which direct expression of said Chikungunya virus antigen in a host cell.

Also provided is a recombinant adenovirus comprising a polynucleotide encoding at least one polypeptide selected from the group consisting of:
(a) a polypeptide having the amino acid sequence according to SEQ ID NO: 1 or a functional derivative thereof,
(b) a polypeptide having the amino acid sequence according to SEQ ID NO: 3 or a functional derivative thereof, and
(c) a polypeptide having the amino acid sequence according to SEQ ID NO: 5 or a functional derivative thereof, wherein the adenovirus further comprises at least one nucleic acid sequence encoding a Chikungunya virus antigen, wherein the nucleic acid sequence is operatively linked to one or more sequences which direct expression of said Chikungunya virus antigen in a host cell.

Also provided is a composition comprising the recombinant adenovirus as described above, and a pharmaceutically acceptable excipient.

Also provided is a composition comprising at least one of the following:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(c) a polynucleotide which encodes a polypeptide having the amino acid sequence according to SEQ ID NO: 3,
(d) a polypeptide having the amino acid sequence according to SEQ ID NO: 1,
(e) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(f) a polypeptide having the amino acid sequence according to SEQ ID NO: 3,
(g) a vector comprising a polynucleotide as described in (a), (b) or (c) above, and
(h) a recombinant adenovirus comprising a polynucleotide as described in (a), (b) or (c) above and a pharmaceutically acceptable excipient.
wherein the composition comprises a nucleic acid sequence encoding a Chikungunya virus antigen or a Chikungunya virus antigen polypeptide sequence; and, optionally, the nucleic acid sequence is operatively linked to one or more sequences which direct expression of said Chikungunya virus antigen in a host cell.

Also provided is a cell comprising at least one of the following:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(c) a polynucleotide which encodes a polypeptide having the amino acid sequence according to SEQ ID NO: 3,
(d) a polypeptide having the amino acid sequence according to SEQ ID NO: 1,
(e) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(f) a polypeptide having the amino acid sequence according to SEQ ID NO: 3,
(g) a vector comprising a polynucleotide as described in (a), (b) or (c) above, and
(h) a recombinant adenovirus comprising a polynucleotide as described in (a), (b) or (c) above;
wherein the cell comprises an adenovirus comprising a nucleic acid sequence encoding a Chikungunya virus antigen; and wherein the nucleic acid sequence is operatively linked to one or more sequences which direct expression of said Chikungunya virus antigen in a host cell.

Also provided is an isolated adenoviral polypeptide selected from the group consisting of:
(a) a polypeptide having the amino acid sequence according to SEQ ID NO: 1,
(b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polypeptide having the amino acid sequence according to SEQ ID NO: 3; and
further comprising a Chikungunya virus antigen polypeptide sequence.

Also provided is an isolated polynucleotide, vector, recombinant adenovirus, composition or cell comprising the sequence according to SEQ ID NO: 6 and further comprising a Chikungunya virus antigen.

The recombinant adenoviruses and compositions may be used as medicaments, in particular for the stimulation of an immune response against Chikungunya virus infection.

Typically, the aim of the methods of the invention is to induce a protective immune response, i.e. to immunize or vaccinate the subject against a related pathogen. The invention may therefore be applied for the prophylaxis, treatment or amelioration of diseases due to infection by Chikungunya virus.

The invention may be provided for the purpose of both pre-exposure prophylaxis and post-exposure prophylaxis to diseases caused by Chikungunya virus infections. In some embodiments, the subject has previously been vaccinated with a Chikungunya virus vaccine. The approaches of the present invention may, for example, be used for a subject at least one year after Chikungunya virus vaccination, at least two years after Chikungunya virus vaccination, at least at least five years after Chikungunya virus vaccination or at least ten years after Chikungunya virus vaccination.

The Chikungunya virus antigen is an antigenic sequence, i.e. a sequence from a Chikungunya virus protein which comprises at least one B or T cell epitope. Suitably the Chikungunya virus antigen comprises at least one T cell epitope. In an embodiment of the invention the adenovirus comprises a nucleic acid sequence encoding a Chikungunya virus structural polyprotein antigen. In a specific embodiment of the invention, the adenovirus comprises a nucleic acid derived from SEQ ID NO: 21 or SEQ ID NO: 22. In another specific embodiment of the invention, the adenovirus comprises a nucleic acid encoding a polypeptide derived from SEQ ID NO: 23. Suitably, the nucleic acid sequence encoding a Chikungunya virus antigen comprises or consists of a polynucleotide at least 80%, at least 90%, at least 95% or at least 99% identical to SEQ ID NOs: 21 or 22.

The elicited immune response may be an antigen specific B cell response, which produces neutralizing antibodies. The elicited immune response may be an antigen specific T cell response, which may be a systemic and/or a local response. The antigen specific T cell response may comprise a CD4+ T cell response, such as a response involving CD4+ T cells expressing a plurality of cytokines, e.g. IFNgamma, TNFalpha and/or IL2. Alternatively, or additionally, the antigen specific T cell response comprises a CD8+ T cell response, such as a response involving CD8+ T cells expressing a plurality of cytokines, e.g., IFNgamma, TNFalpha and/or IL2.

DESCRIPTION OF THE DRAWINGS

FIG. 2A-C: Alignment of fiber protein sequences from the indicated simian adenoviruses.
ChAd3 (SEQ ID NO:11)
PanAd3 (SEQ ID NO:12)
ChAd17 (SEQ ID NO:13)
ChAd19 (SEQ ID NO:14)
ChAd24 (SEQ ID NO:15)
ChAd155 (SEQ ID NO:1)
ChAd11 (SEQ ID NO:16)
ChAd20 (SEQ ID NO:17)
ChAd31 (SEQ ID NO:18)
PanAd1 (SEQ ID NO:19)
PanAd2 (SEQ ID NO:20)

DESCRIPTION OF THE SEQUENCES

Figure 1:
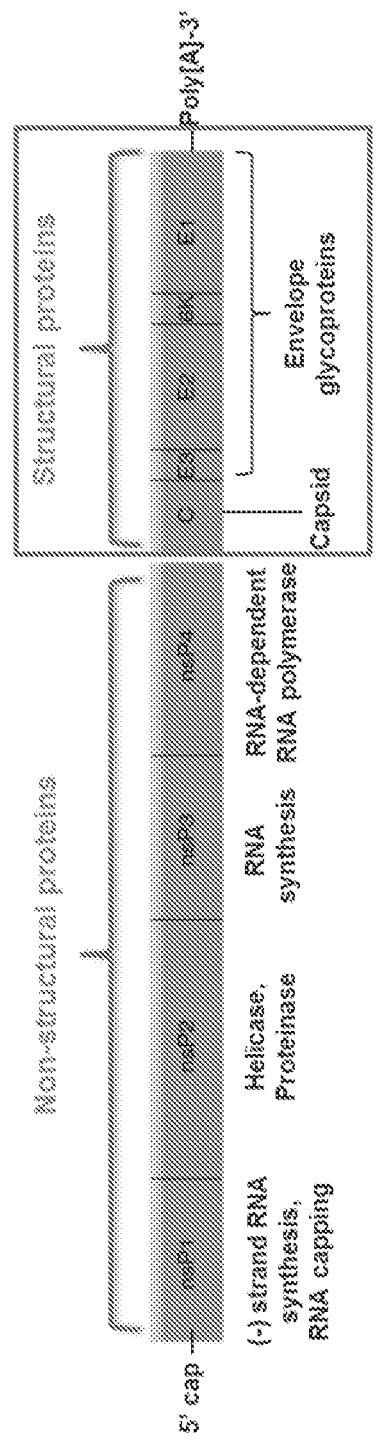
FIG. 1 Diagram of the Chikungunya virus genome encoding four non-structural proteins (nsP1-4) and five structural proteins: the capsid (C), and the envelope glycoproteins (E3, E2, 6k and E1).

SEQ ID NO: 1—Amino acid sequence of ChAd155 fiber
SEQ ID NO: 2—Nucleotide sequence encoding ChAd155 fiber
SEQ ID NO: 3—Amino acid sequence of ChAd155 penton
SEQ ID NO: 4—Nucleotide sequence encoding ChAd155 penton
SEQ ID NO: 5—Amino acid sequence of ChAd155 hexon
SEQ ID NO: 6—Nucleotide sequence encoding ChAd155 hexon
SEQ ID NO: 7—Nucleotide sequence encoding ChAd155 #1434
SEQ ID NO: 8—Nucleotide sequence encoding ChAd155 #1390

SEQ ID NO: 9—Nucleotide sequence encoding ChAd155 #1375

SEQ ID NO: 10—Nucleotide sequence encoding wild type ChAd155

SEQ ID NO: 11—Amino acid sequence for the fiber protein of ChAd3

SEQ ID NO: 12—Amino acid sequence for the fiber protein of PanAd3

SEQ ID NO: 13—Amino acid sequence for the fiber protein of ChAd17

SEQ ID NO: 14—Amino acid sequence for the fiber protein of ChAd19

SEQ ID NO: 15—Amino acid sequence for the fiber protein of ChAd24

SEQ ID NO: 16—Amino acid sequence for the fiber protein of ChAd11

SEQ ID NO: 17—Amino acid sequence for the fiber protein of ChAd20

SEQ ID NO: 18—Amino acid sequence for the fiber protein of ChAd31

SEQ ID NO: 19—Amino acid sequence for the fiber protein of PanAd1

SEQ ID NO: 20—Amino acid sequence for the fiber protein of PanAd2

SEQ ID NO: 21—Nucleotide sequence for CHIKV structural polypeptide, strain #37997 (wild type)

SEQ ID NO: 22—Nucleotide sequence for CHIKV structural polypeptide, strain #37997 (codon optimized)

SEQ ID NO: 23—Amino acid sequence for CHIKV structural polypeptide, strain #37997

SEQ ID NO: 24—Nucleotide sequence of plasmid pvjTetOhCMV CHIKV bghpolyA

SEQ ID NO: 25—Nucleotide sequence of expression vector the pChAd155 ΔE1, ΔE4_Ad5 orf6 hCMV-CHIKV

DETAILED DESCRIPTION OF THE INVENTION

Adenoviral Vectors

Adenovirus has been widely used for gene transfer applications due to its proven safety, ability to achieve highly efficient gene transfer in a variety of target tissues and large transgene capacity. Adenoviral vectors of use in the present invention may be derived from a range of mammalian hosts. Over 100 distinct serotypes of adenovirus have been isolated which infect various mammalian species. These adenoviral serotypes have been categorized into six subgenera (A-F; B is subdivided into B1 and B2) according to sequence homology and on their ability to agglutinate red blood cells.

In one embodiment, the adenoviral vector or recombinant adenovirus of the present invention is derived from a non-human simian adenovirus, also referred to simply as a simian adenovirus. Numerous adenoviruses have been isolated from nonhuman simians such as chimpanzees, bonobos, rhesus macaques and gorillas, and vectors derived from these adenoviruses induce strong immune responses to transgenes encoded by these vectors (Colloca et al. (2012) Sci. Transl. Med. 4:1-9; Roy et al. (2004) Virol. 324: 361-372; Roy et al. (2010) J. of Gene Med. 13:17-25). Some advantages of vectors based on nonhuman simian adenoviruses include the relative lack of cross-neutralizing antibodies to these adenoviruses in the target population, thus their use overcomes the pre-existing immunity to human adenoviruses. For example, cross-reaction of certain chimpanzee adenoviruses with pre-existing neutralizing antibody responses is only present in 2% of the target population compared with 35% in the case of certain candidate human adenovirus vectors.

Specifically, the adenoviral vector may be derived from a non-human adenovirus, such as a simian adenovirus and in particular a chimpanzee adenovirus such as ChAd3, ChAd63, ChAd83, ChAd155, Pan 5, Pan 6, Pan 7 (also referred to as C7) or Pan 9 and may include, in whole or in part, a nucleotide encoding the fiber, penton or hexon of a non-human adenovirus. Examples of such strains are described in WO03/000283, WO2010/086189 and GB1510357.5 and are also available from the American Type Culture Collection, 10801 University Boulevard, Manassas, Va. 20110-2209, and other sources. Alternatively, adenoviral vectors may be derived from nonhuman simian adenoviruses isolated from bonobos, such as PanAd1, PanAd2 or PanAd3. Examples of such vectors described herein can be found for example in WO2005/071093 and WO2010/086189. Adenoviral vectors may also be derived from adenoviruses isolated from gorillas as described in WO2013/52799, WO2013/52811 and WO2013/52832.

Adenoviral Vector Structure

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The hexon accounts for the majority of the structural components of the capsid, which consists of 240 trimeric hexon capsomeres and 12 penton bases. The hexon has three conserved double barrels, while the top has three towers, each tower containing a loop from each subunit that forms most of the capsid. The base of the hexon is highly conserved between adenoviral serotypes, while the surface loops are variable. The penton is another adenoviral capsid protein that forms a pentameric base to which the fiber attaches. The trimeric fiber protein protrudes from the penton base at each of the 12 vertices of the capsid and is a knobbed rod-like structure. The primary role of the fiber protein is the tethering of the viral capsid to the cell surface via the interaction of the knob region with a cellular receptor, and variations in the flexible shaft as well as knob regions of fiber are characteristic of the different serotypes.

The adenoviral genome has been well characterized. The linear, double-stranded DNA is associated with the highly basic protein VII and a small peptide pX (also termed mu). Another protein, V, is packaged with this DNA-protein complex and provides a structural link to the capsid via protein VI. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The 5' end of the adenoviral genome contains the 5' cis-elements necessary for packaging and replication; i.e., the 5' ITR sequences (which function as origins of replication) and the native 5' packaging enhancer domains (that contain sequences necessary for packaging linear adenoviral genomes and enhancer elements for the E1 promoter). The 3' end of the adenoviral genome includes the 3' cis-elements (including the ITRs) necessary for packaging and encapsidation. The virus also comprises a virus-encoded protease, which is necessary for processing some of the structural proteins required to produce infectious virions.

The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. During the late phase of infection, expression of the late genes L1-L5, which encode the structural components of the virus particles, is activated.

Adenovirus Capsid Proteins and Their Encoding Polynucleotides

As outlined above, the adenoviral capsid comprises three major proteins, hexon, penton and fiber. The hexon accounts for the majority of the structural components of the capsid, which consists of 240 trimeric hexon capsomeres and 12 penton bases. The hexon has three conserved double barrels, while the top has three towers, each tower containing a loop from each subunit that forms most of the capsid. The base of hexon is highly conserved between adenoviral serotypes, while the surface loops are variable.

The penton is another adenoviral capsid protein that forms a pentameric base to which fiber attaches. The trimeric fiber protein protrudes from the penton base at each of the 12 vertices of the capsid and is a knobbed rod-like structure. A remarkable difference in the surface of adenovirus capsids compared to that of most other icosahedral viruses is the presence of the long, thin fiber protein. The primary role of the fiber protein is the tethering of the viral capsid to the cell surface via its interaction with a cellular receptor.

The fiber proteins of many adenovirus serotypes share a common architecture: an N-terminal tail, a central shaft made of repeating sequences, and a C-terminal globular knob domain (or "head"). The central shaft domain consists of a variable number of beta-repeats. The beta-repeats connect to form an elongated structure of three intertwined spiraling strands that is highly rigid and stable. The shaft connects the N-terminal tail with the globular knob structure, which is responsible for interaction with the target cellular receptor. The globular nature of the adenovirus knob domain presents large surfaces for binding the receptor laterally and apically. The effect of this architecture is to project the receptor-binding site far from the virus capsid, thus freeing the virus from steric constraints presented by the relatively flat capsid surface.

Although fibers of many adenovirus serotypes have the same overall architecture, they have variable amino acid sequences that influence their function as well as structure. For example, a number of exposed regions on the surface of the fiber knob present an easily adaptable receptor binding site. The globular shape of the fiber knob allows receptors to bind at the sides of the knob or on top of the fiber knob. These binding sites typically lie on surface-exposed loops connecting beta-strands that are poorly conserved among human adenoviruses. The exposed side chains on these loops give the knob a variety of surface features while preserving the tertiary and quaternary structure. For example, the electrostatic potential and charge distributions at the knob surfaces can vary due to the wide range of isoelectric points in the fiber knob sequences, varying from a pI of approximately 9 for adenovirus "Ad" 8, Ad 19, and Ad 37 to approximately 5 for subgroup B adenoviruses. As a structurally complex virus ligand, the fiber protein allows the presentation of a variety of binding surfaces (knob) in a number of orientations and distances (shaft) from the viral capsid.

One of the most obvious variations between some serotypes is fiber length. Studies have shown that the length of the fiber shaft strongly influences the interaction of the knob and the virus with its target receptors. Further, fiber proteins between serotypes can also vary in their ability to bend. Although beta-repeats in the shaft form a highly stable and regular structure, electron microscopy (EM) studies have shown distinct hinges in the fiber. Analysis of the protein sequence from several adenovirus serotype fibers pinpoints a disruption in the repeating sequences of the shaft at the third beta-repeat from the N-terminal tail, which correlates strongly with one of the hinges in the shaft, as seen by EM. The hinges in the fiber allow the knob to adopt a variety of orientations relative to the virus capsid, which may circumvent steric hindrances to receptor engagement requiring the correct presentation of the receptor binding site on the knob. For example, the rigid fibers of subgroup D Ads thus require a flexible receptor or one prepositioned for virus attachment, as they are unable to bend themselves.

The identification of specific cell receptors for different Ad serotypes and the knowledge of how they contribute to tissue tropism have been achieved through the use of fiber pseudotyping technology. Although Ads of some subgroups use Coxsackievirus and adenovirus receptor ("CAR") as a primary receptor, it is becoming clear that many Ads use alternate primary receptors, leading to vastly different tropism in vitro and in vivo. The fibers of these serotypes show clear differences in their primary and tertiary structures, such as fiber shaft rigidity, the length of the fiber shaft, and the lack of a CAR binding site and/or the putative HSPG binding motif, together with the differences in net charge within the fiber knob. Pseudotyping Ad 5 particles with an alternate fiber shaft and knob therefore provides an opportunity to remove important cell binding domains and, in addition, may allow more efficient (and potentially more cell-selective) transgene delivery to defined cell types compared to that achieved with Ad 5. Neutralization of fiber-pseudotyped Ad particles may also be reduced if the fibers used are from Ads with lower seroprevalence in humans or experimental models, a situation that favours successful administration of the vector. Furthermore, full length fiber as well as isolated fiber knob regions, but not hexon or penton alone, are capable of inducing dendritic cell maturation and are associated with induction of a potent CD8+ T cell response. Taken together, adenoviral fiber plays an important role in at least receptor-binding and immunogenicity of adenoviral vectors.

"Low seroprevalence" may mean having a reduced pre-existing neutralizing antibody level as compared to human adenovirus 5 (Ad5). Similarly or alternatively, "low seroprevalence" may mean less than about 20% seroprevalence, less than about 15% seroprevalence, less than about 10% seroprevalence, less than about 5% seroprevalence, less than about 4% seroprevalence, less than about 3% seroprevalence, less than about 2% seroprevalence, less than about 1% seroprevalence or no detectable seroprevalence. Seroprevalence can be measured as the percentage of individuals having a clinically relevant neutralizing titer (defined as a 50% neutralisation titer>200) using methods as described in Aste-Amézaga et al., Hum. Gene Ther. (2004) 15(3):293-304.

Illustrating the differences between the fiber proteins of Group C simian adenoviruses is the alignment provided in FIG. 2. A striking feature is that the fiber sequences of these adenoviruses can be broadly grouped into having a long fiber, such as ChAd155, or a short fiber, such as ChAd3. This length differential is due to a 36 amino acid deletion at approximately position 321 in the short fiber relative to the long fiber. In addition, there are a number of amino acid substitutions that differ between the short versus long fiber subgroup yet are consistent within each subgroup. While the exact function of these differences have not yet been elucidated, given the function and immunogenicity of fiber, they are likely to be significant. It has been shown that one of the determinants of viral tropism is the length of the fiber shaft. It has been demonstrated that an Ad5 vector with a shorter shaft has a lower efficiency of binding to CAR receptor and a lower infectivity. It has been speculated that this impairment is the result of an increased rigidity of the shorter fiber leading to a less efficient attachment to the cell receptor. These studies may explain the improved properties of ChAd155 carrying a longer and more flexible fiber in comparison with the previously described ChAd3 and PanAd3 carrying a fiber with a shorter shaft.

In one aspect of the invention there is provided isolated polynucleotides encoding the fiber, penton and hexon capsid polypeptides of chimp adenovirus ChAd155, and a Chikungunya virus antigen. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

All three capsid proteins are expected to contribute to low seroprevalence and can, thus, be used independently from each other or in combination to suppress the affinity of an adenovirus to pre-existing neutralizing antibodies, e.g. to manufacture a recombinant adenovirus with a reduced seroprevalence. Such a recombinant adenovirus may be a chimeric adenovirus with capsid proteins from different serotypes with at least a fiber protein from ChAd155.

In one embodiment of the adenovirus according to the invention, the polynucleotide encodes at least two polypeptides selected from the group consisting of:
  (a) a polypeptide having the amino acid sequence according to SEQ ID NO: 1 or a functional derivative thereof,
  (b) a polypeptide having the amino acid sequence according to SEQ ID NO: 3 or a functional derivative thereof, and
  (c) a polypeptide having the amino acid sequence according to SEQ ID NO: 5 or a functional derivative thereof.

In one embodiment of the adenovirus according to the invention, the polynucleotide encodes:
  (a) a polypeptide having the amino acid sequence according to SEQ ID NO: 1 or a functional derivative thereof,
  (b) a polypeptide having the amino acid sequence according to SEQ ID NO: 3 or a functional derivative thereof, and
  (c) a polypeptide having the amino acid sequence according to SEQ ID NO: 5 or a functional derivative thereof.

In one embodiment, the adenovirus according to the invention comprises at least one polynucleotide selected from the group consisting of:
  (a) a polynucleotide having the sequence of SEQ ID NO: 2;
  (b) a polynucleotide having the sequence of SEQ ID NO: 4; and
  (c) a polynucleotide having the sequence of SEQ ID NO: 6.

Transgenes

Adenoviral vectors may be used to deliver desired RNA or protein sequences, for example heterologous sequences, for in vivo expression. A vector may include any genetic element including naked DNA, a phage, transposon, cosmid, episome, plasmid, or virus. Such vectors contain DNA of ChAd155 as disclosed herein and an expression cassette. By "expression cassette" (or "minigene") is meant the combination of a selected heterologous gene ("transgene") and the other regulatory elements necessary to drive translation, transcription and/or expression of the gene product in a host cell.

Typically, "heterologous" means derived from a genotypically distinct entity from that of the rest of the entity to which it is being compared. A heterologous nucleic acid sequence refers to any nucleic acid sequence that is not isolated from, derived from, or based upon a naturally occurring nucleic acid sequence of the adenoviral vector. "Naturally occurring" means a sequence found in nature and not synthetically prepared or modified. A sequence is "derived" from a source when it is isolated from a source but modified (e.g., by deletion, substitution (mutation), insertion, or other modification), suitably so as not to disrupt the normal function of the source gene.

Typically, an adenoviral vector is designed such that the expression cassette is located in a nucleic acid molecule which contains other adenoviral sequences in the region native to a selected adenoviral gene. The expression cassette may be inserted into an existing gene region to disrupt the function of that region, if desired. Alternatively, the expression cassette may be inserted into the site of a partially or fully deleted adenoviral gene. For example, the expression cassette may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the expression cassette). Suitably, E1 genes of adenovirus are deleted and replaced with an expression cassette consisting of a promoter of choice, a cDNA sequence of the gene of interest and a poly A signal, resulting in a replication defective recombinant virus.

As used herein, induction of an immune response refers to the ability of a protein, also known as an "antigen" or "immunogen," to induce a T cell and/or a humoral immune response to the protein. For example, an immunogenic composition may induce a memory T and/or B cell population relative to an untreated subject following CHIKV infection, particularly in those embodiments where the composition comprises a nucleic acid comprising a sequence which encodes a CHIKV antigen or comprises a CHIKV antigen. In some embodiments, the subject is a vertebrate, such as a mammal e.g. a human or a veterinary mammal.

In an embodiment, the transgene is a nucleic acid sequence, heterologous to the vector sequences flanking the transgene, which encodes a CHIKV protein capable of inducing an immune response in a subject. The nucleic acid coding sequence of the transgene is operatively linked to regulatory components in a manner which permits transgene transcription, translation, and/or expression in a host cell.

In an embodiment the transgene encodes an immunogen derived from at least one Chikungunya virus, for example from a CHIKV West African genotype, from a CHIKV East/Central/South African (ECSA) genotype, and/or from a CHIKV Asian genotype.

Representative CHIKV antigen sequences can be derived from known CHIKV variants, including those described in Genbank Accession Nos. KX702402.1, KY055011.1, KY435486.1 and DQ443544.2. In a specific embodiment, the immunogen is from the West African genotype strain 37997, corresponding to Genbank Accession No. ABX40011.

Suitably, the Chikungunya virus antigen is derived from Chikungunya virus strain #37997.

Suitably, the Chikungunya virus antigen comprises a sequence which is an immunogenic fragment of at least 20 amino acid residues.

Such immunogens may be derived from one or more CHIKV structural proteins. In an embodiment, the antigen consists of, or alternatively comprises, a CHIKV capsid protein (C) or a fragment thereof (suitably a fragment of at least 20, at least 30, at least 40, at least 50, at least 60, at least 70, at least 80, at least 90, at least 100, at least 150, at least 200 or at least 250 amino acids). As used herein, a "CHIKV capsid protein" is intended to mean a protein having a polypeptide sequence corresponding to amino acids 1 to 261 of SEQ ID NO: 23, or a protein having at least 90% sequence identity to amino acids 1 to 261 of SEQ ID NO: 23 such as at least 91.0%, at least 93.0%, at least 95.0%, at least 97.0%, at least 98.0%, at least 99.0%, at least 99.2%, at least 99.4%, at least 99.5%, at least 99.6%, at least 99.8% or at least 99.9% identity over its entire length to amino acids 1 to 261 of SEQ ID NO: 23.

In an embodiment, the antigen consists of, or alternatively comprises, a CHIKV E3 protein or a fragment thereof (suitably a fragment of at least 20, at least 30, at least 40 or at least 50 amino acids). As used herein, a "CHIKV E3 protein" is intended to mean a protein having a polypeptide sequence corresponding to amino acids 262 to 325 of SEQ ID NO:23, or a protein having at least 90% sequence identity to amino acids 262 to 325 of SEQ ID NO: 23, such as at least 91.0%, at least 93.0%, at least 95.0%, at least 97.0%, at least 98.0%, at least 99.0%, at least 99.2%, at least 99.4%, at least 99.5%, at least 99.6%, at least 99.8% or at least 99.9% identity over its entire length to amino acids 262 to 325 of SEQ ID NO: 23.

In an embodiment, the antigen consists of, or alternatively comprises, a CHIKV E2 protein or a fragment thereof (suitably a fragment of at least 20, at least 30, at least 40, at least 50, at least 60, at least 70, at least 80, at least 90, at least 100, at least 150, at least 200, at least 250, at least 300, at least 350 or at least 400 amino acids). As used herein, a "CHIKV E2 protein" is intended to mean a protein having a polypeptide sequence corresponding to amino acids 326 to 748 of SEQ ID NO: 23, or a protein having at least 90% sequence identity to amino acids 326 to 748 of SEQ ID NO: 23, such as at least 91.0%, at least 93.0%, at least 95.0%, at least 97.0%, at least 98.0%, at least 99.0%, at least 99.2%, at least 99.4%, at least 99.5%, at least 99.6%, at least 99.8% or at least 99.9% identity over its entire length to amino acids 326 to 748 of SEQ ID NO: 23.

In an embodiment, the antigen consists of, or alternatively comprises, a CHIKV 6k protein or a fragment thereof (suitably a fragment of at least 20, at least 30, at least 40 or at least 50 amino acids). As used herein, a "CHIKV 6k protein" is intended to mean a protein having a polypeptide sequence corresponding to amino acids 749 to 809 of SEQ ID NO: 23, or a protein having at least 90% sequence identity to amino acids 749 to 809 of SEQ ID NO: 23, such as at least 91.0%, at least 93.0%, at least 95.0%, at least 97.0%, at least 98.0%, at least 99.0%, at least 99.2%, at least 99.4%, at least 99.5%, at least 99.6%, at least 99.8% or at least 99.9% identity over its entire length to amino acids 749 to 809 of SEQ ID NO: 23.

In an embodiment, the antigen consists of, or alternatively comprises, a CHIKV E1 protein or a fragment thereof (suitably a fragment of at least 20, at least 30, at least 40, at least 50, at least 60, at least 70, at least 80, at least 90, at least 100, at least 150, at least 200, at least 250, at least 300, at least 350 or at least 400 amino acids). As used herein, a "CHIKV E1 protein" is intended to mean a protein having a polypeptide sequence corresponding to amino acids 810 to 1248 of SEQ ID NO: 23, or a protein having at least 90% sequence identity to amino acids 810 to 1248 of SEQ ID NO: 23, such as at least 91.0%, at least 93.0%, at least 95.0%, at least 97.0%, at least 98.0%, at least 99.0%, at least 99.2%, at least 99.4%, at least 99.5%, at least 99.6%, at least 99.8% or at least 99.9% identity over its entire length to amino acids 810 to 1248 of SEQ ID NO: 23.

In an embodiment, the immunogen(s) expressed by the vectors of the invention comprise, or alternatively consist of, a CHIKV structural polyprotein, or a fragment thereof (suitably a fragment of at least 20, at least 30, at least 40, at least 50, at least 60, at least 70, at least 80, at least 90, at least 100, at least 150, at least 200, at least 250, at least 300, at least 350 or at least 400, at least 450, at least 500, at least 600, at least 700, at least 800, at least 900, at least 1000, at least 1100 or at least 1200 amino acids). As used herein, a "CHIKV structural polyprotein" is intended to mean a protein having a polypeptide sequence corresponding to amino acids 1 to 1248 of SEQ ID NO: 23, or a protein having at least 90% sequence identity to amino acids 1 to 1248 of SEQ ID NO: 23, such as at least 91.0%, at least 93.0%, at least 95.0%, at least 97.0%, at least 98.0%, at least 99.0%, at least 99.2%, at least 99.4%, at least 99.5%, at least 99.6%, at least 99.8% or at least 99.9% identity over its entire length to amino acids 1 to 1248 of SEQ ID NO: 23.

Alternatively or in addition, a transgene sequence may include a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

In addition to the transgene, the expression cassette also may include conventional control elements which are operably linked to the transgene in a manner that permits its transcription, translation and/or expression in a cell transfected with the adenoviral vector. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

A "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, native, constitutive, inducible and/or tissue-specific, are known in the art and may be utilized.

Examples of constitutive promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41:521-530 (1985)), the CASI promoter (WO2012/115980), the SV40 promoter, the dihydrofolate reductase promoter, the β-actin promoter, the phosphoglycerol kinase (PGK) promoter, and the EF1a promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MD promoter and the dexamethasone (Dex)-inducible mouse mammary tumor virus (MMTV) promoter. Other inducible systems include the T7 polymerase promoter system; the ecdysone insect promoter, the tetracycline-repressible system and the tetracycline-inducible system. Other systems include the FK506 dimer, VP16 or p65 using castradiol, diphenol murislerone, the RU486-inducible system and the rapamycin-inducible system. The effectiveness of some inducible promoters increases overtime. In such cases one can enhance the effectiveness of such systems by inserting multiple repressors in tandem, e.g., TetR linked to a TetR by an IRES.

In another embodiment, the native promoter for the transgene may be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

The transgene may be operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters. Examples of promoters that are tissue-specific are known for liver; hepatitis B virus core; alpha-fetoprotein, bone osteocalcin; bone sialoprotein, lymphocytes, immunoglobulin heavy chain; T cell receptor chain), neuronal such as neuron-specific enolase (NSE) promoter, neurofilament light-chain gene, and the neuron-specific vgf gene, among others.

In some embodiments, the Woodchuck Hepatitis Virus Posttranscriptional Regulatory Element (WPRE) (Zuffrey et al. (1999) J. Virol.; 73(4):2886-9) may be operably linked to the transgene.

Suitably, the adenovirus according to the invention has a seroprevalence of less than 10% in human subjects and preferably no seroprevalence in human subjects.

Suitably, the adenovirus according to the invention is capable of infecting a mammalian cell.

The transgene may be used for treatment, e.g., as a vaccine, for induction of an immune response, and/or for prophylactic vaccine purposes. As used herein, induction of an immune response refers to the ability of a protein to induce a T cell and/or a humoral immune response to the protein.

Immune responses can be measured by methods known in the art, including assays of the induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self-replicating RNA molecule that encodes a CHIKV antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Adenoviral Vector Construction

Adenoviral vectors are generated by modifying wild type adenovirus to express heterologous genes and/or delete or inactivate undesirable adenoviral sequences. Adenoviral vectors may also have altered replication competency. For example the vector may be replication defective or have limited replication such that it has a reduced ability to replicate in non-complementing cells, compared to the wild type virus. This may be brought about by mutating the virus e.g., by deleting a gene involved in replication, for example deleting the adenoviral E1A, E1B, E3 or E4 gene.

The adenoviral vectors in accordance with the present invention may comprise a functional E1 deletion. Thus the adenoviral vectors according to the invention may be replication defective due to the absence of the ability to express adenoviral E1A and/or E1B. The recombinant adenoviruses may also bear functional deletions in other genes for example, deletions in E3 or E4 genes. The adenovirus delayed early gene E3 may be eliminated from the adenovirus sequence which forms part of the recombinant virus. The function of E3 is not necessary to the production of the recombinant adenovirus particle. Thus, it is unnecessary to replace the function of this gene product in order to package a recombinant adenovirus useful in the invention. In one particular embodiment the recombinant adenoviruses have functionally deleted E1 and E3 genes. The construction of such vectors is described in Roy et al., Human Gene Therapy 15:519-530, 2004.

Recombinant adenoviruses may also be constructed having a functional deletion of the E4 gene. In a particular embodiment, the recombinant adenoviruses have functionally deleted E1 and E4 genes as described in Colloca et al. (2012) Sci. Transl. Med. 4:1-9; Roy et al. (2004) Virol. 324: 361-372. In some embodiments, it may be desirable to retain the E4 ORF6 function. In one embodiment, the E4 ORF6 region may be replaced by a heterologous E4 ORF6, such as from human adenovirus 5 (Ad5). Thus, in one particular embodiment, the adenoviral vector may be functionally deleted in E1 and have the E4 ORF6 region from Ad5. Adenovirus vectors according to the invention may also contain a functional deletion in the delayed early gene E2a. Deletions may also be made in any of the late genes L1 through to L5 of the adenovirus genome. Similarly, deletions in the intermediate genes IX and IVa may be useful.

Other deletions may be made in the other structural or non-structural adenovirus genes. The above deletions may be used individually, e.g. an adenovirus sequence for use in the present invention may contain deletions of E1 only. Alternatively, deletions of entire genes or portions thereof effective to destroy their biological activity may be used in any combination. For example in one exemplary vector, the adenovirus sequences may have deletions of the E1 genes and the E4 gene, or of the E1, E2a and E3 genes, or of the E1 and E3 genes (such as functional deletions in E1a and E1b, and a deletion of at least part of E3), or of the E1, E2a and E4 genes, with or without deletion of E3 and so on. Such deletions may be partial or full deletions of these genes and may be used in combination with other mutations, such as temperature sensitive mutations to achieve a desired result.

These vectors are generated using techniques known to those of skill in the art. Such techniques include conventional cDNA cloning techniques such as those described in texts, the use of overlapping oligonucleotide sequences of the adenovirus genomes, polymerase chain reaction, and any suitable method which provides the desired nucleotide sequence. Particularly suitable methods include standard homologous recombination methods such as those provided in Colloca et al. (2012) Sci. Transl. Med. 4:1-9; Roy et al. (2004) Virol. 324: 361-372; Roy et al. (2010) J. of Gene Med. 13:17-25; and WO2010/085984 or recombineering methods as described in Warming et al. Nuc. Acids Res. (2005) 33:e36.

In one embodiment of the adenovirus according to the invention, the polynucleotide comprises at least one of the following:
(a) an adenoviral 5'-end, preferably an adenoviral 5' inverted terminal repeat;
(b) an adenoviral E1A region, or a fragment thereof selected from among the E1A_280R and E1A_243R regions;
(c) an adenoviral E1B or IX region, or a fragment thereof selected from among the group consisting of the E1B_19K, E1B_55K or IX regions;
(d) an adenoviral E2b region; or a fragment thereof selected from among the group consisting of the E2B_pTP, E2B_Polymerase and E2B_IVa2 regions;
(e) an adenoviral L1 region, or a fragment thereof, said fragment encoding an adenoviral protein selected from the group consisting of the L1_13.6k protein, L1_52k and L1_IIIa protein;
(f) an adenoviral L2 region, or a fragment thereof, said fragment encoding an adenoviral protein selected from the group consisting of the L2_penton protein, L2_pVII, L2_V, and L2_pX protein;
(g) an adenoviral L3 region, or a fragment thereof, said fragment encoding an adenoviral protein selected from the group consisting of the L3_pVI protein, L3_hexon protein and L3_protease;
(h) an adenoviral E2A region;
(i) an adenoviral L4 region, or a fragment thereof said fragment encoding an adenoviral protein selected from the group consisting of the L4_100k protein, the L4_33k protein and protein L4_VIII;
(j) an adenoviral E3 region, or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;
(k) an adenoviral L5 region, or a fragment thereof said fragment encoding the L5_fiber fiber protein;
(l) an adenoviral E4 region, or a fragment thereof selected from the group consisting of E4 ORF7, E4 ORF6, E4 ORF4, E4 ORF3, E4 ORF2, and E4 ORF1;
(m) an adenoviral 3'-end, preferably an adenoviral 3' inverted terminal repeat; and
(n) an adenoviral VAI or VAII RNA region, preferably an adenoviral VAI or VAII RNA region from an adenovirus other than ChAd155, more preferably from Ad5.

Suitably, the polynucleotide comprises at least one of the following:
(a) an adenoviral 5'-end, preferably an adenoviral 5' inverted terminal repeat;
(b) an adenoviral L1 region, or a fragment thereof, said fragment encoding an adenoviral protein selected from the group consisting of the L1_13.6k protein, L1_52k and L1_IIIa protein;
(c) an adenoviral L2 region, or a fragment thereof, said fragment encoding an adenoviral protein selected from the group consisting of the L2_penton protein, L2_pVII, L2_V, and L2_pX protein;
(d) an adenoviral L3 region, or a fragment thereof, said fragment encoding an adenoviral protein selected from the group consisting of the L3_pVI protein, L3_hexon hexon protein and L3_protease;
(e) an adenoviral L4 region, or a fragment thereof said fragment encoding an adenoviral protein selected from the group consisting of the L4_100k protein, the L4_33k protein and protein L4_VIII;
(f) an adenoviral L5 region, or a fragment thereof said fragment encoding the L5_fiber fiber protein; and
(g) an adenoviral 3'-end, preferably an adenoviral 3' inverted terminal repeat.

Alternatively, the polynucleotide comprises an adenoviral VAI or VAII RNA region. Suitably the VAI or VAII RNA region is from an adenovirus other than ChAd155. Alternatively, the VAI or VAII RNA region is from Ad5.

Adenoviral Vector Production

The adenoviral vectors can be produced in any suitable cell line in which the virus is capable of replication. In particular, complementing cell lines which provide the factors missing from the viral vector that result in its impaired replication characteristics (such as E1) can be used.

Without limitation, such a cell line may be HeLa (ATCC Accession No. CCL 2), A549 (ATCC Accession No. CCL 185), HEK 293, KB (CCL 17), Detroit (e.g., Detroit 510, CCL 72) and WI-38 (CCL 75) cells, among others. These cell lines are all available from the American Type Culture Collection, 10801 University Boulevard, Manassas, Va. 20110-2209, USA. Other suitable parent cell lines may be obtained from other sources, such as PGK-E1 retinoblasts, e.g., PER.C6™ cells, as represented by the cells deposited under ECACC no. 96022940 at the European Collection of Animal Cell Cultures (ECACC) at the Centre for Applied Microbiology and Research (CAMR, UK) or Her 96 cells (Crucell).

In many circumstances, a cell line expressing the one or more missing genes which are essential to the replication and infectivity of the virus, such as human E1, can be used to transcomplement a chimp adenoviral vector. This is particularly advantageous because, due to the diversity between the chimp adenovirus sequences of the invention and the human adenovirus sequences found in currently available packaging cells, the use of the current human E1-containing cells prevents the generation of replication-competent adenoviruses during the replication and production process.

Alternatively, if desired, one may utilize the sequences provided herein to generate a packaging cell or cell line that expresses, at a minimum, the E1 gene from ChAd155 under the transcriptional control of a promoter for expression in a selected parent cell line. Inducible or constitutive promoters may be employed for this purpose. Examples of such promoters are described in detail elsewhere in this document. A parent cell is selected for the generation of a novel cell line expressing any desired ChAd155 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209, USA.

Such E1-expressing cell lines are useful in the generation of recombinant adenovirus E1 deleted vectors. Additionally, or alternatively, cell lines that express one or more adenoviral gene products, e.g., E1A, E1B, E2A, E3 and/or E4, can be constructed using essentially the same procedures as used in the generation of recombinant viral vectors. Such cell lines can be utilised to transcomplement adenovirus vectors deleted in the essential genes that encode those products, or to provide helper functions necessary for packaging of a helper-dependent virus (e.g., adeno-associated virus). The preparation of a host cell involves techniques such as the assembly of selected DNA sequences.

In an embodiment, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including insect cells, yeast cells and mammalian cells.

Host cells may be selected from among any mammalian species, including, without limitation, cells such as A549, WEHI, 3T3, 10T1/2, HEK 293 cells or Per.C6 (the latter two of which express functional adenoviral E1), Saos, C2C12, L cells, HT1080, HepG2 and primary fibroblast, hepatocyte and myoblast cells derived from mammals including human, monkey, mouse, rat, rabbit, and hamster.

A particularly suitable complementation cell line is the Procell92 cell line. The Procell92 cell line is based on HEK 293 cells which express adenoviral E1 genes, transfected with the Tet repressor under control of the human phosphoglycerate kinase-1 (PGK) promoter, and the G418-resistance gene (Vitelli et al. PLOS One (2013) 8(e55435):1-9). Procell92.S is adapted for growth in suspension conditions and is also useful for producing adenoviral vectors expressing toxic proteins (www.okairos.com/e/inners.php?m=00084, last accessed 29 Jun. 2017).

Adenoviral Delivery Methods and Dosage

The adenoviral vectors may be as administered in immunogenic compositions. An immunogenic composition as described herein is a composition comprising one or more recombinant vectors capable of inducing an immune response, for example a humoral (e.g., antibody) and/or cell-mediated (e.g., a cytotoxic T cell) response, against a transgene product delivered by the vector following delivery to a mammal, suitably a human. A recombinant adenovirus may comprise (suitably in any of its gene deletions) a gene encoding a desired immunogen and may therefore be used in a vaccine. The recombinant adenoviruses can be used as prophylactic or therapeutic vaccines against any pathogen for which the antigen(s) crucial for induction of an immune response, is able to limit the spread of the pathogen and for which cDNA is available.

Such vaccine or other immunogenic compositions may be formulated in a suitable delivery vehicle. The levels of immunity of the selected gene can be monitored to determine the need, if any, for boosters. Following an assessment of antibody titers in the serum, optional booster immunizations may be desired.

Optionally, a vaccine or immunogenic composition of the invention may be formulated to contain other components, including, e.g., adjuvants, stabilizers, pH adjusters, preservatives and the like. Examples of suitable adjuvants are provided below under "Adjuvants." Such an adjuvant can be administered with a priming DNA vaccine encoding an antigen to enhance the antigen-specific immune response compared with the immune response generated upon priming with a DNA vaccine encoding the antigen only. Alternatively, such an adjuvant can be administered with a polypeptide antigen which is administered in an administration regimen involving the vectors of the invention.

The adenoviral vector may be prepared for administration by being suspended or dissolved in a pharmaceutically or physiologically acceptable carrier such as isotonic saline, isotonic salt, solution or other formulations that will be apparent to those skilled in the art. The appropriate carrier will be evident to those skilled in the art and will depend in large part upon the route of administration. The compositions described herein may be administered to a mammal in a sustained release formulation using a biodegradable biocompatible polymer, or by on-site delivery using micelles, gels and liposomes.

In some embodiments, the recombinant adenovirus of the invention is administered to a subject by intramuscular injection, intravenous injection, intraperitoneal injection, subcutaneous injection, epicutaneous administration, intradermal administration, transdermal administration, intravaginal administration nasal administration, rectal administration or oral administration.

If the therapeutic regimen involves co-administration of one or more adenoviral vectors and a further component, each formulated in different compositions, they are favorably administered co-locationally at or near the same site. For example, the components can be administered (e.g. via an administration route selected from intramuscular, transdermal, intradermal, sub-cutaneous) to the same side or extremity ("co-lateral" administration) or to opposite sides or extremities ("contra-lateral" administration).

Dosages of the viral vector will depend primarily on factors such as the condition being treated, the severity of the condition being treated and the age, weight and health of the patient, thus may vary among patients. For example, a therapeutically effective adult human dosage of the viral vector generally contains $1\times10^5$ to $1\times10^{15}$ viral particles, such as from $1\times10^8$ to $1\times10^{12}$ (e.g., $1\times10^8$, $5\times10^8$, $1\times10^9$, $5\times10^9$, $1\times10^{10}$, $2.5\times10^{10}$, $5\times10^{10}$, $1\times10^{11}$ $5\times10^{11}$ or $1\times10^{12}$ particles). Alternatively, a viral vector can be administered at a dose that is typically from $1\times10^5$ to $1\times10^{10}$ plaque forming units (PFU), such as $1\times10^5$ PFU, $5\times10^5$ PFU, $1\times10^6$ PFU, $5\times10^6$ PFU, $1\times10^7$ PFU, $5\times10^7$ PFU, $1\times10^8$ PFU, $5\times10^8$ PFU, $1\times10^9$ PFU, $5\times10^9$ PFU, or $1\times10^{10}$ PFU. Dosages will vary depending upon the size of the subject and the route of administration. For example, a suitable human dosage (for about an 80 kg subject) for intramuscular injection is in the range of about $1\times10^5$ to about $5\times10^{12}$ particles per ml, for a single site. Optionally, multiple sites of administration may be used. In another example, a suitable human or veterinary dosage may be in the range of about $1\times10^7$ to about $1\times10^{15}$ particles for an oral formulation.

The adenoviral vector can be quantified by Quantitative PCR Analysis (Q-PCR), for example with primers and probes designed based on the CMV promoter region, using as the standard curve serial dilutions of plasmid DNA containing the vector genome with the expression cassette, including the human CMV (hCMV) promoter. The copy number in the test sample is determined by the parallel line analysis method. Alternative methods for vector particle quantification include analytical HPLC or spectrophotometric methods based on $A_{260}$ nm.

An immunologically effective amount of a nucleic acid may suitably be between 1 ng and 100 mg. For example, a suitable amount can be from 1 μg to 100 mg. An appropriate amount of the particular nucleic acid (e.g., vector) can readily be determined by those of skill in the art.

Exemplary effective amounts of a nucleic acid component can be between 1 ng and 100 μg, such as between 1 ng and 1 μg (e.g., 100 ng-1 μg), or between 1 μg and 100 μg, such as 10 ng, 50 ng, 100 ng, 150 ng, 200 ng, 250 ng, 500 ng, 750 ng, or 1 μg. Effective amounts of a nucleic acid can also include from 1 μg to 500 μg, such as between 1 μg and 200 μg, such as between 10 and 100 μg, for example 1 μg, 2 μg, 5 μg, 10 μg, 20 μg, 50 μg, 75 μg, 100 μg, 150 μg, or 200 μg. Alternatively, an exemplary effective amount of a nucleic acid can be between 100 μg and 1 mg, such as from 100 μg to 500 μg, for example, 100 μg, 150 μg, 200 μg, 250 μg, 300 μg, 400 μg, 500 μg, 600 μg, 700 μg, 800 μg, 900 μg or 1 mg.

Generally a human dose will be in a volume of between 0.1 ml and 2 ml, such as 0.5 ml and 2 ml. Thus the composition described herein can be formulated in a volume of, for example 0.1, 0.25, 0.5, 1.0, 1.5 or 2.0 ml human dose per individual or combined immunogenic components.

One of skill in the art may adjust these doses, depending on the route of administration and the therapeutic or vaccine application for which the recombinant vector is employed. The levels of expression of the transgene, or for an adjuvant, the level of circulating antibody, can be monitored to determine the frequency of dosage administration.

If one or more priming and/or boosting steps are used, this step may include a single dose that is administered hourly, daily, weekly or monthly, or yearly. As an example, mammals may receive one or two doses containing between about 10 μg to about 50 μg of plasmid in carrier. The amount or site of delivery is desirably selected based upon the identity and condition of the mammal.

The therapeutic level of, or the level of immune response against, the protein encoded by the selected transgene can be monitored to determine the need, if any, for boosters. Following an assessment of CD8+ T cell response, or optionally, antibody titers, in the serum, optional booster immunizations may be desired. Optionally, the adenoviral vector may be delivered in a single administration or in various combination regimens, e.g., in combination with a regimen or course of treatment involving other active ingredients or in a prime-boost regimen.

Recombinant Adenoviruses or Compositions Comprising Polypeptide Sequences

Suitably the polynucleotides of the invention are recombinant. Recombinant means that the polynucleotide is the product of at least one of cloning, restriction or ligation steps, or other procedures that result in a polynucleotide that is distinct from a polynucleotide found in nature. A recombinant adenovirus is an adenovirus comprising a recombinant polynucleotide. A recombinant vector is a vector comprising a recombinant polynucleotide. A "recombinant virus" includes progeny of the original recombinant virus. A "recombinant vector" includes replicates of the original recombinant vector. A "recombinant polynucleotide" includes replicates of the original recombinant polynucleotide.

A "functional derivative" of a polypeptide suitably refers to a modified version of a polypeptide, e.g. wherein one or more amino acids of the polypeptide may be deleted, inserted, modified and/or substituted. A derivative of an unmodified adenoviral capsid protein is considered functional if, for example:

(a) an adenovirus comprising the derivative capsid protein within its capsid retains substantially the same or a lower seroprevalence compared to an adenovirus comprising the unmodified capsid protein and/or (b) an adenovirus comprising the derivative capsid protein within its capsid retains substantially the same or a higher host cell infectivity compared to an adenovirus comprising the unmodified capsid protein and/or (c) an adenovirus comprising the derivative capsid protein within its capsid retains substantially the same or a higher immunogenicity compared to an adenovirus comprising the unmodified capsid protein and/or (d) an adenovirus comprising the derivative capsid protein within its capsid retains substantially the same or a higher level of transgene productivity compared to an adenovirus comprising the unmodified capsid protein.

Suitably the recombinant adenovirus or composition of the invention comprises a polypeptide having the amino acid sequence according to SEQ ID NO: 1. Suitably the recombinant adenovirus or composition of the invention comprises a polypeptide which is a functional derivative of a polypeptide having the amino acid sequence according to SEQ ID NO: 1, wherein the functional derivative has an amino acid sequence which is at least 80% identical over its entire length to the amino acid sequence of SEQ ID NO: 1. Suitably the functional derivative of a polypeptide having the amino acid sequence according to SEQ ID NO: 1 has an amino acid sequence which is at least 80% identical, such as at least 85.0% identical, such as at least 90% identical, such as at least 91.0% identical, such as at least 93.0% identical, such as at least 95.0% identical, such as at least 97.0% identical, such as at least 98.0% identical, such as at least 99.0% identical, such as at least 99.2% identical, such as at least 99.4% identical, such as 99.5% identical, such as at least 99.6% identical, such as at least 99.8% identical, such as 99.9% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2 and more suitably no more than 1 addition(s), deletion(s) and/or substitutions(s) compared to SEQ ID NO: 1.

Suitably the recombinant adenovirus or composition according to the invention further comprises:
(a) a polypeptide having the amino acid sequence according to SEQ ID NO: 3; or
(b) a functional derivative of a polypeptide having the amino acid sequence according to SEQ ID NO: 3, wherein the functional derivative has an amino acid sequence which is at least 50.0% identical over its entire length to the amino acid sequence of SEQ ID NO: 3,
and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 50% identical over its entire length to the amino acid sequence of SEQ ID NO: 5.

Suitably the functional derivative of a polypeptide having the amino acid sequence according to SEQ ID NO: 3 has an amino acid sequence which is at least 60.0%, such as at least 70.0%, such as at least 80.0%, such as at least 85.0%, such as at least 90.0%, such as at least 91.0% identical, such as at least 93.0% identical, such as at least 95.0% identical, such as at least 97.0% identical, such as at least 98.0% identical, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 3. Alternatively the functional derivative has no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2 and more suitably no more than 1 addition(s), deletion(s) and/or substitutions(s) compared to SEQ ID NO: 3.

Suitably the functional derivative of a polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 91.0% identical, such as at least 93.0% identical, such as at least 95.0% identical, such as at least 97.0% identical, such as at least 98.0% identical, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2 and more suitably no more than 1 addition(s), deletion(s) and/or substitutions(s) compared to SEQ ID NO: 5.

Suitably the recombinant adenovirus or composition of the invention comprises a polypeptide having the amino acid sequence according to SEQ ID NO: 3.

Suitably the recombinant adenovirus or composition of the invention further comprises:
(a) a polypeptide having the amino acid sequence according to SEQ ID NO: 1; or
(b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1
and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 60% identical over its entire length to the amino acid sequence of SEQ ID NO: 5.

Suitably the functional derivative of a polypeptide having the amino acid sequence according to SEQ ID NO: 1 has an amino acid sequence which is at least 60.0% identical, such as at least 70.0% identical, such as at least 80.0% identical, such as at least 85.0% identical, such as at least 87.0% identical, such as at least 89.0% identical, such as at least 91.0% identical, such as at least 93.0% identical, such as at least 95.0% identical, such as at least 97.0% identical, such as at least 98.0% identical, such as at least 99.0% identical, such as at least 99.2%, such as at least 99.4%, such as 99.5% identical, such as at least 99.6%, such as at least 99.8% identical, such as 99.9% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2 and more suitably no more than 1 addition(s), deletion(s) and/or substitutions(s) compared to SEQ ID NO: 1.

Suitably the functional derivative of a polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 95.0%, such as at least 97.0%, such as at least 99.0%, such as at least 99.0%, such as at least 99.2%, such as at least 99.4%, such as 99.5% identical, such as at least 99.6%, such as at least 99.8% identical, such as 99.9% identical over its entire length to the amino acid sequence of SEQ ID NO:5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2 and more suitably no more than 1 addition(s), deletion(s) and/or substitutions(s) compared to SEQ ID NO: 5.

Suitably the recombinant adenovirus or composition of the invention comprises a polynucleotide which encodes a polypeptide having the amino acid sequence according to SEQ ID NO: 1. Suitably the polynucleotide has a sequence according to SEQ ID NO: 2.

Alternatively, the recombinant adenovirus or composition of the invention comprises a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1. Suitably the functional derivative of a polypeptide having the amino acid sequence according to SEQ ID NO: 1 has an amino acid sequence which is at least 80% identical, such as at least 85.0% identical, such as at least 90% identical, such as at least 91.0% identical, such as at least 93.0% identical, such as at least 95.0% identical, such as at least 97.0% identical, such as at least 98.0% identical, such as at least 99.0% identical, such as at least 99% identical, such as at least 99.4% identical, such as at least 99.6% identical or such as at least 99.8% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2 and more suitably no more than 1 addition(s), deletion(s) and/or substitutions(s) compared to SEQ ID NO: 1.

Suitably the recombinant adenovirus or composition of the invention further comprises a polynucleotide encoding:
(a) a polypeptide having the amino acid sequence according to SEQ ID NO: 3; or
(b) a functional derivative of a polypeptide having the amino acid sequence according to SEQ ID NO: 3, wherein the functional derivative has an amino acid sequence which is at least 50.0% identical over its entire length to the amino acid sequence of SEQ ID NO: 3,
and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 50% identical over its entire length to the amino acid sequence of SEQ ID NO: 5.

Suitably the functional derivative of the polypeptide having the amino acid sequence according to SEQ ID NO: 3 has an amino acid sequence which is at least 60.0%, such as at least 70.0%, such as at least 80.0%, such as at least 85.0%, such as at least 90.0%, such as at least 91.0% identical, such as at least 93.0% identical, such as at least 95.0% identical, such as at least 97.0% identical, such as at least 98.0% identical, such as at least 99.0%, such as at least 99%, such as at least 99.4%, such as at least 99.6%, such as at least 99.8% identical over its entire length to the amino acid sequence of SEQ ID NO: 3.

Alternatively the functional derivative has no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2 and more suitably no more than 1 addition(s), deletion(s) and/or substitutions(s) compared to SEQ ID NO: 3.

Suitably the functional derivative of the polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 95.0%, such as at least 97.0%, such as at least 98.0%, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2 and more suitably no more than 1 addition(s), deletion(s) and/or substitutions(s) compared to SEQ ID NO: 5.

Suitably the recombinant adenovirus or composition of the invention comprises a polynucleotide which encodes a polypeptide having the amino acid sequence according to SEQ ID NO: 3. Suitably the polynucleotide has a sequence according to SEQ ID NO: 4.

Suitably the recombinant adenovirus or composition of the invention further comprises a polynucleotide encoding:
(a) a polypeptide having the amino acid sequence according to SEQ ID NO: 1; or
(b) a functional derivative of a polypeptide having the amino acid sequence according to SEQ ID NO: 1, wherein the functional derivative has an amino acid sequence which is at least 50% identical over its entire length to the amino acid sequence of SEQ ID NO: 1
and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 50% identical over its entire length to the amino acid sequence of SEQ ID NO: 5.

Suitably the functional derivative of a polypeptide having the amino acid sequence according to SEQ ID NO: 1 has an amino acid sequence which is at least 60.0% identical, such as at least 70.0% identical, such as at least 80.0% identical, such as at least 85.0% identical, such as at least 87.0% identical, such as at least 89.0% identical, such as at least 91.0% identical, such as at least 93.0% identical, such as at least 95.0% identical, such as at least 97.0% identical, such as at least 98.0% identical, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2 and more suitably no more than 1 addition(s), deletion(s) and/or substitutions(s) compared to SEQ ID NO: 1.

Suitably the functional derivative of a polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 95.0%, such as at least 97.0%, such as at least 98.0%, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2 and more suitably no more than 1 addition(s), deletion(s) and/or substitutions(s) compared to SEQ ID NO: 5.

There is also provided a non-human simian adenovirus comprising the penton of SEQ ID NO: 3, the hexon of SEQ ID NO: 5 and/or the fiber of SEQ ID NO: 1 and also comprising a transgene encoding a Chikungunya virus antigen. Suitably, the non-human simian adenovirus comprises the penton (SEQ ID NO: 3), hexon (SEQ ID NO: 5) and fiber (SEQ ID NO: 1) protein from ChAd155 and also comprising a transgene encoding a Chikungunya virus antigen. Suitably, the encoded antigen comprises a sequence having at least 90% identity to SEQ ID NO: 23. Suitably, the non-human simian adenovirus is a replication deficient adenovirus. For example, the non-human simian adenovirus comprises a functional inactivation (such as deletion) of the E1 gene, a functional inactivation (such as deletion) of the E4 gene, a functional inactivation (such as deletion) of the E3 gene, and or an Ad5E4orf6 gene substitution.

There is also provided an adenovirus comprising a polynucleotide having a sequence at least 80%, at least 90%, at least 95% or at least 99% identical over its entire length identical to SEQ ID NO: 24.

There is also provided an adenovirus comprising a polynucleotide having a sequence at least 80%, at least 90%, at least 95% or at least 99% identical over its entire length identical to SEQ ID NO: 25.

ChAd155 Backbones

The present application describes isolated polynucleotide sequences of chimpanzee adenovirus ChAd155, including that of wild type, unmodified ChAd155 (SEQ ID NO: 10) and modified backbone constructs of ChAd155. These modified backbone constructs include ChAd155 #1434 (SEQ ID NO: 7), ChAd155 #1390 (SEQ ID NO: 8) and ChAd155 #1375 (SEQ ID NO: 9). ChAd155 backbones may be used in the construction of recombinant replication-competent or replication-incompetent adenoviruses for the delivery of transgenes.

The term "construct" refers to a nucleic acid that encodes polypeptide sequences described herein and may comprise DNA or non-naturally occurring nucleic acid monomers.

The term "replication-competent" adenovirus refers to an adenovirus which can replicate in a host cell in the absence of any recombinant helper proteins comprised in the cell. Suitably, a "replication-competent" adenovirus comprises the following intact or functional essential early genes: E1A, E1B, E2A, E2B, E3 and E4. Wild type adenoviruses isolated from a particular animal will be replication competent in that animal.

The sequences of the invention are useful as therapeutic and/or prophylactic agents and in construction of a variety of vector systems, recombinant adenovirus and host cells. Suitably the term "vector" refers to a nucleic acid that has been substantially altered (e.g., a gene or functional region that has been deleted and/or inactivated) relative to a wild type sequence and/or incorporates a heterologous sequence, i.e., nucleic acid obtained from a different source (also called an "insert"), and replicating and/or expressing the inserted polynucleotide sequence, when introduced into a cell (e.g., a host cell). For example, the insert may be all or part of the ChAd155 sequences described herein. In addition or alternatively, a ChAd155 vector may be a ChAd155 adenovirus comprising one or more deletions or inactivations of viral genes, such as E1 or other viral gene or functional region described herein. Such a ChAd155, which may or may not comprise a heterologous sequence, is often called a "backbone" and may be used as is or as a starting point for additional modifications to the vector.

The term "replication-incompetent" or "replication-defective" adenovirus refers to an adenovirus which is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc., or a complete removal of a gene encoding a gene product that is essential for viral replication, such as one or more of the adenoviral genes selected from E1A, E1B, E2A, E2B, E3 and E4 (such as E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF4, E4 ORF3, E4 ORF2 and/or E4 ORF1). Particularly suitably E1, and optionally E3 and/or E4, are deleted. If deleted, the aforementioned deleted gene region will suitably not be considered in the alignment when determining % identity with respect to another sequence.

Annotation of the ChAd155 wild type sequence (SEQ ID NO: 10) sequence is provided below.

```
LOCUS       ChAd155        37830 bp    DNA    linear
10-JUN-2015
    DEFINITION  Chimp adenovirus 155, complete genome.
    COMMENT     Annotation according to alignment of ChAd155 against
the human
                        Adenovirus 2 reference strain NC_001405
                        Two putative ORFs in the E3 region added manually
    FEATURES            Location/Qualifiers
        source          1..37830
                        /organism="Chimpanzee adenovirus 155"
                        /mol_type="genomic DNA"
                        /acronym="ChAd155"
        repeat_region   1..101
                        /standard_name="ITR"
                        /rpt_type=inverted
        gene            466..1622
                        /gene="E1A"
        TATA_signal     466..471
                        /gene="E1A"
        prim_transcript 497..1622
                        /gene="E1A"
        CDS             join(577..1117,1231..1532)
                        /gene="E1A"
                        /product="E1A_280R"
        CDS             join(577..979,1231..1532)
                        /gene="E1A"
                        /product="E1A_243R"
        polyA_signal    1600..1605
                        /gene="E1A"
        gene            1662..4131
                        /gene="E1B"
        TATA_signal     1662..1667
                        /gene="E1B"
        prim_transcript 1692..4131
                        /gene="E1B"
        CDS             1704..2267
                        /gene="E1B"
                        /product="E1B_19K"
        CDS             2009..3532
                        /gene="E1B"
                        /product="E1B_55K"
        gene            3571..4131
                        /gene="IX"
        TATA_signal     3571..3576
                        /gene="IX"
        prim_transcript 3601..4131
                        /gene="IX"
        CDS             3628..4092
                        /gene="IX"
                        /product="IX"
        polyA_signal    4097..4102
                        /note="E1B, IX"
        gene            complement(4117..27523)
                        /gene="E2B"
        prim_transcript complement(4117..27494)
                        /gene="E2B"
        gene            complement(4117..5896)
                        /gene="IVa2"
        prim_transcript complement(4117..5896)
                        /gene="IVa2"
        CDS             complement(join(4151..5487,5766..5778))
                        /gene="IVa2"
                        /product="E2B_IVa2"
        polyA_signal    complement(4150..4155)
                        /note="IVa2, E2B"
        CDS             complement(join(5257..8838,14209..14217))
                        /gene="E2B"
                        /product="E2B_polymerase"
        gene            6078..34605
                        /gene="L5"
        gene            6078..28612
                        /gene="L4"
        gene            6078..22658
                        /gene="L3"
        gene            6078..18164
                        /gene="L2"
        gene            6078..14216
                        /gene="L1"
        TATA_signal     6078..6083
                        /note="L"
```

| | | |
|---|---|---|
| prim_transcript | 6109..34605 | |
| | /gene="L5" | |
| prim_transcript | 6109..28612 | |
| | /gene="L4" | |
| prim_transcript | 6109..22658 | |
| | /gene="L3" | |
| prim_transcript | 6109..18164 | |
| | /gene="L2" | |
| prim_transcript | 6109..14216 | |
| | /gene="L1" | |
| CDS | join(8038..8457,9722..9742) | |
| | /gene="L1" | |
| | /product="L1_13.6K" | |
| CDS | complement(join(8637..10640,14209..14217)) | |
| | /gene="E2B" | |
| | /product="E2B_pTP" | |
| gene | 10671..10832 | |
| | /gene="VAI" | |
| misc_RNA | 10671..10832 | |
| | /gene="VAI" | |
| | /product="VAI" | |
| gene | 10902..11072 | |
| | /gene="VAII" | |
| misc_RNA | 10902..11072 | |
| | /gene="VAII" | |
| | /product="VAII" | |
| CDS | 11093..12352 | |
| | /gene="L1" | |
| | /product="L1_52K" | |
| CDS | 12376..14157 | |
| | /gene="L1" | |
| | /product="L1_pIIIa" | |
| polyA_signal | 14197..14202 | |
| | /gene="L1" | |
| CDS | 14254..16035 | |
| | /gene="L2" | |
| | /product="L2_penton" | |
| CDS | 16050..16646 | |
| | /gene="L2" | |
| | /product="L2_pVII" | |
| CDS | 16719..17834 | |
| | /gene="L2" | |
| | /product="L2_V" | |
| CDS | 17859..18104 | |
| | /gene="L2" | |
| | /product="L2_pX" | |
| polyA_signal | 18143..18148 | |
| | /gene="L2" | |
| CDS | 18196..18951 | |
| | /gene="L3" | |
| | /product="L3_pVI" | |
| CDS | 19063..21945 | |
| | /gene="L3" | |
| | /product="L3_hexon" | |
| CDS | 21975..22604 | |
| | /gene="L3" | |
| | /product="L3_protease" | |
| polyA_signal | 22630..22635 | |
| | /gene="L3" | |
| gene | complement(22632..27523) | |
| | /gene="E2A" | |
| prim_transcript | complement(22632..27494) | |
| | /gene="E2A" | |
| gene | complement(22632..26357) | |
| | /gene="E2A-L" | |
| prim_transcript | complement(22632..26328) | |
| | /gene="E2A-L" | |
| polyA_signal | complement(22649..22654) | |
| | /note="E2A, E2A-L" | |
| CDS | complement(22715..24367) | |
| | /gene="E2A" | |
| | /note="DBP; genus-common; DBP family" | |
| | /codon_start=1 | |
| | /product="E2A" | |
| CDS | 24405..26915 | |
| | /gene="L4" | |
| | /product="L4_100k" | |
| TATA_signal | complement(26352..26357) | |
| | /gene="E2A-L" | |

| | | |
|---|---|---|
| CDS | join(26602..26941,27147..27529) /gene="L4" /product="L4_33K" | |
| CDS | 26602..27207 /gene="L4" /product="L4_22K" | |
| TATA_signal | complement(27518..27523) /note="E2A, E2B; nominal" | |
| CDS | 27604..28287 /gene="L4" /product="L4_pVIII" | |
| gene | 27969..32686 /gene="E3B" | |
| gene | 27969..31611 /gene="E3A" | |
| TATA_signal | 27969..27974 /note="E3A, E3B" | |
| prim_transcript | 27998..32686 /gene="E3B" | |
| prim_transcript | 27998..31611 /gene="E3A" | |
| CDS | 28288..28605 /gene="E3A" /product="E3 ORF1" | |
| polyA_signal | 28594..28599 /gene="L4" | |
| CDS | 29103..29303 /gene="E3A" /product="E3 ORF2" | |
| CDS | 29300..29797 /gene="E3A" /product="E3 ORF3" | |
| CDS | 29826..30731 /gene="E3A" /product="E3 ORF4" | |
| CDS | 30728..31579 /gene="E3A" /product="E3 ORF5" | |
| CDS | 31283..31579 /gene="E3A" /product="E3 ORF6" | |
| polyA_signal | 31578..31584 /gene="E3A" | |
| CDS | 31591..31863 /gene="E3B" /product="E3 ORF7" | |
| CDS | 31866..32264 /gene="E3B" /product="E3 ORF8" | |
| CDS | 32257..32643 /gene="E3B" /product="E3 ORF9" | |
| polyA_signal | 32659..32664 /gene="E3B" | |
| gene | complement(<32678..32838) /gene="U" | |
| CDS | complement(<32678..32838) /gene="U" /note="exon encoding C terminus unidentified; genus-common" /product="protein U" | |
| CDS | 32849..34585 /gene="L5" /product="L5_fiber" | |
| polyA_signal | 34581..34586 /gene="L5" | |
| gene | complement(34611..37520) /gene="E4" | |
| prim_transcript | complement(34611..37490) /gene="E4" | |
| polyA_signal | complement(34625..34630) /gene="E4" | |
| CDS | complement(join(34794..35069,35781..35954)) /gene="E4" /product="E4 ORF7" | |
| CDS | complement(35070..35954) /gene="E4" /product="E4 ORF6" | |

| | |
|---|---|
| CDS | complement(35875..36219)<br>/gene="E4"<br>/product="E4 ORF4" |
| CDS | complement(36235..36582)<br>/gene="E4"<br>/product="E4 ORF3" |
| CDS | complement(36579..36971)<br>/gene="E4"<br>/product="E4 ORF2" |
| CDS | complement(37029..37415)<br>/gene="E4"<br>/product="E4 ORF1" |
| TATA_signal | complement(37515..37520)<br>/gene="E4" |
| repeat_region | 37740..37830<br>/standard_name="ITR"<br>/rpt_type=inverted |

Sequence Identity

Identity with respect to a sequence is defined herein as the percentage of amino acid residues in the candidate sequence that are identical with the reference amino acid sequence after aligning the sequences and introducing gaps, if necessary, to achieve the maximum percent sequence identity, and not considering any conservative substitutions as part of the sequence identity.

Sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 (a standard scoring matrix can be used in conjunction with the computer program. For example, the percent identity can then be calculated as the total number of identical matches multiplied by 100 and then divided by the sum of the length of the longer sequence within the matched span and the number of gaps introduced into the shorter sequences in order to align the two sequences.

Where the present disclosure refers to a sequence by reference to a UniProt or Genbank accession code, the sequence referred to is the current version as of the filing date of the present application.

The skilled person will recognise that individual substitutions, deletions or additions to a protein which alters, adds or deletes a single amino acid or a small percentage of amino acids is an "immunogenic derivative" where the alteration(s) results in the substitution of an amino acid with a functionally similar amino acid or the substitution/deletion/addition of residues which do not substantially impact the immunogenic function.

Conservative substitution tables providing functionally similar amino acids are well known in the art. In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Suitably such substitutions do not occur in the region of an epitope, and do not therefore have a significant impact on the immunogenic properties of the antigen.

Immunogenic derivatives may also include those wherein additional amino acids are inserted compared to the reference sequence. Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Immunogenic derivatives include those wherein amino acids have been deleted compared to the reference sequence. Suitably such deletions do not occur in the region of an epitope, and do not therefore have a significant impact on the immunogenic properties of the antigen. The skilled person will recognise that a particular immunogenic derivative may comprise substitutions, deletions and additions (or any combination thereof).

Adjuvants

An "adjuvant" as used herein refers to a composition that enhances the immune response to an immunogen. A composition according to the invention that comprises an adjuvant can be used as a vaccine, e.g. for human subjects. The adjuvant accelerates, prolongs and/or enhances the quality and/or strength of an immune response to an antigen/immunogen in comparison to the administration of the antigen alone, thus, reduces the quantity of antigen/immunogen necessary in any given vaccine, and/or the frequency of injection necessary in order to generate an adequate immune response to the antigen/immunogen of interest.

Examples of adjuvants that may be used in the context of the compositions of the invention include inorganic adjuvants (e.g. inorganic metal salts such as aluminum phosphate or aluminum hydroxide), gel-like precipitates of aluminum hydroxide (alum); $AlPO_4$; alhydrogel; bacterial products from the outer membrane of Gram-negative bacteria, in particular monophosphoryl lipid A (MPLA), lipopolysaccharides (LPS), muramyl dipeptides and derivatives thereof; Freund's incomplete adjuvant; liposomes, in particular neutral liposomes, liposomes containing the composition and optionally cytokines; AS01B, AS01E, AS02; non-ionic block copolymers; ISCOMATRIX adjuvant; unmethylated DNA comprising CpG dinucleotides (CpG motif), in particular CpG ODN with a phosphorothioate (PTO) backbone (CpG PTO ODN) or phosphodiester (PO) backbone (CpG PO ODN); synthetic lipopeptide derivatives, in particular Pam₃Cys; lipoarabinomannan; peptidoglycan; zymosan; heat shock proteins (HSP), in particular HSP 70; dsRNA and synthetic derivatives thereof, in particular Poly I:poly C; polycationic peptides, in particular poly-L-arginine; taxol; fibronectin; flagellin; imidazoquinoline; cytokines with adjuvant activity, in particular GM-CSF, interleukin-(IL-)2, IL-6, IL-7, IL-18, type I and II interferons, in particular interferon-gamma, TNF-alpha; 25-dihydroxyvitamin D3 (calcitriol); and synthetic oligopeptides, in particular MHCII-presented peptides. Non-ionic block polymers containing polyoxyethylene (POE) and polyoxypropylene (POP), such as POE-POP-POE block copolymers may be used as an adjuvant.

Additional examples of adjuvants include inorganic adjuvants (e.g. inorganic metal salts such as aluminum phosphate or aluminum hydroxide), organic adjuvants (e.g. saponins, such as QS21, or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immunostimulatory complexes (ISCOMS), liposomes, biodegradable microspheres, virosomes, bacterial adjuvants (e.g. monophosphoryl lipid A, such as 3-de-O-acylated monophosphoryl lipid A (3D-MPL), or muramyl peptides), synthetic adjuvants (e.g. monophosphoryl lipid A (MPL), in particular 3-de-O-acylated monophosphoryl lipid A (3D-MPL and muramyl peptide analogues, or synthetic lipid A, and synthetic polynucleotides adjuvants, e.g., polyarginine or polylysine.

Saponins are also suitable adjuvants, for example, the saponin Quil A, derived from the bark of the South American tree *Quillaja Saponaria Molina*, and fractions thereof. Purified fractions of Quil A are also known as immunostimulants, such as squalene, QS21, QS17 and QS7, a non-haemolytic fraction of Quil-A. Combinations of QS21 and polysorbate or cyclodextrin are also suitable.

Another example of an adjuvant is an immunostimulatory oligonucleotide containing unmethylated cytosine-guanosine dinucleotide motifs present in DNA ("CpG"). CpG is known as an adjuvant when administered by both systemic and mucosal routes. When formulated into vaccines, it may be administered in free solution together with free antigen or covalently conjugated to an antigen or formulated with a carrier such as aluminum hydroxide.

Activation of specific receptors can stimulate an immune response. Such receptors are known to the skilled artisan and comprise, for example, cytokine receptors, in particular type I cytokine receptors, type II cytokine receptors, TNF receptors; and a vitamin D receptor acting as transcription factor; and the Toll-like receptors 1 (TLR1), TLR-2, TLR 3, TLR4, TLR5, TLR-6, TLR7, and TLR9. Agonists to such receptors have adjuvant activity, i.e., are immunostimulatory. Other suitable adjuvants include alkyl glucosaminide phosphates (AGPs) or pharmaceutically acceptable salts of AGPs. Some AGPs are TLR4 agonists, and some are TLR4 antagonists. An adjuvant of the composition of the present invention may be one or more Toll-like receptor agonists. In a more preferred embodiment, the adjuvant is a Toll-like receptor 4 agonist. In a particular preferred embodiment, the adjuvant is a Toll-like receptor 9 agonist.

Adjuvants such as those described above may be formulated together with carriers, such as liposomes, oil in water emulsions, and/or metallic salts (including aluminum salts such as aluminum hydroxide). For example, 3D-MPL may be formulated with aluminum hydroxide or oil in water emulsions; QS21 may be formulated with cholesterol containing liposomes, oil in water emulsions or alum; CpG may be formulated with alum or with other cationic carriers.

Combinations of adjuvants may be utilized in the present invention, in particular a combination of a monophosphoryl lipid A and a saponin derivative, more particularly the combination of QS21 and 3D-MPL or a composition where the QS21 is quenched in cholesterol-containing liposomes (DQ). Alternatively, a combination of CpG plus a saponin such as QS21 is an adjuvant suitable for use in the present invention, as is a potent adjuvant formulation involving QS21, 3D-MPL and tocopherol in an oil in water emulsion. Saponin adjuvants may be formulated in a liposome and combined with an immunostimulatory oligonucleotide. Thus, suitable adjuvant systems include, for example, a combination of monophosphoryl lipid A, preferably 3D-MPL, together with an aluminum salt. A further exemplary adjuvant comprises QS21 and/or MPL and/or CpG. QS21 may be quenched in cholesterol-containing liposomes.

The fusion of the invariant chain to an antigen which is comprised by an expression system used for vaccination increases the immune response against said antigen, if it is administered with an adenovirus. Accordingly, in one embodiment of the invention, the immunogenic transgene may be co-expressed with invariant chain in a recombinant ChAd155 viral vector.

In another embodiment, the invention provides the use of the capsid of ChAd155 (optionally an intact or recombinant viral particle or an empty capsid is used) to induce an immunomodulatory response, or to enhance or adjuvant a cytotoxic T cell response to another active agent by delivering a ChAd155 capsid to a subject. The ChAd155 capsid can be delivered alone or in a combination regimen with an active agent to enhance the immune response thereto. Advantageously, the desired effect can be accomplished without infecting the host with an adenovirus.

DESCRIPTION OF THE SEQUENCES

SEQ ID NO: 1—Polypeptide sequence of ChAd155 fiber
SEQ ID NO: 2—Polynucleotide sequence encoding ChAd155 fiber
SEQ ID NO: 3—Polypeptide sequence of ChAd155 penton
SEQ ID NO: 4—Polynucleotide sequence encoding ChAd155 penton
SEQ ID NO: 5—Polypeptide sequence of ChAd155 hexon
SEQ ID NO: 6—Polynucleotide sequence encoding ChAd155 hexon
SEQ ID NO: 7—Polynucleotide sequence encoding ChAd155 #1434 backbone construct
SEQ ID NO: 8—Polynucleotide sequence encoding ChAd155 #1390 backbone construct
SEQ ID NO: 9—Polynucleotide sequence encoding ChAd155 #1375 backbone construct
SEQ ID NO: 10—Polynucleotide sequence encoding wild type ChAd155
SEQ ID NO: 11—ChAd3 fiber amino acid sequence
SEQ ID NO: 12—PanAd3 fiber amino acid sequence
SEQ ID NO: 13—ChAd17 fiber amino acid sequence
SEQ ID NO: 14—ChAd19 fiber amino acid sequence
SEQ ID NO: 15—ChAd24 fiber amino acid sequence
SEQ ID NO: 16—ChAd11 fiber amino acid sequence
SEQ ID NO: 17—ChAd20 fiber amino acid sequence
SEQ ID NO: 18—ChAd31 fiber amino acid sequence SEQ ID NO: 19—PanAd1 fiber amino acid sequence
SEQ ID NO: 20—PanAd2 fiber amino acid sequence
SEQ ID NO: 21—Nucleotide sequence for CHIKV structural polypeptide, strain #37997 (wild type, nts 7569-11315 of Genbank Accession No. EU224270)
SEQ ID NO: 22—Nucleotide sequence for CHIKV structural polypeptide, strain #37997 (codon optimized)
SEQ ID NO: 23—Amino acid sequence for CHIKV structural polypeptide, strain #37997
SEQ ID NO: 24—Nucleotide sequence of plasmid pvjTetOhCMV CHIKV bghpolyA
SEQ ID NO: 25—Nucleotide sequence of expression vector the pChAd155 ΔE1, ΔE4_Ad5 orf6 hCMV-CHIKV General Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount ±10%.

The invention will be further described by reference to the following, non-limiting, examples and figures.

EXAMPLES

Example 1: ChAd155-CHIKV Vector Construction

Wild type chimpanzee adenovirus type 155 (ChAd155) was isolated from a healthy young chimpanzee housed at the New Iberia Research Center facility (New Iberia Research Center, The University of Louisiana at Lafayette) using standard procedures as described in Colloca et al. (2012) Sci. Transl. Med. 4:1-9 and WO2010086189, the latter of which is hereby incorporated by reference for the purpose of describing adenoviral isolation and characterization techniques.

Figure 3:
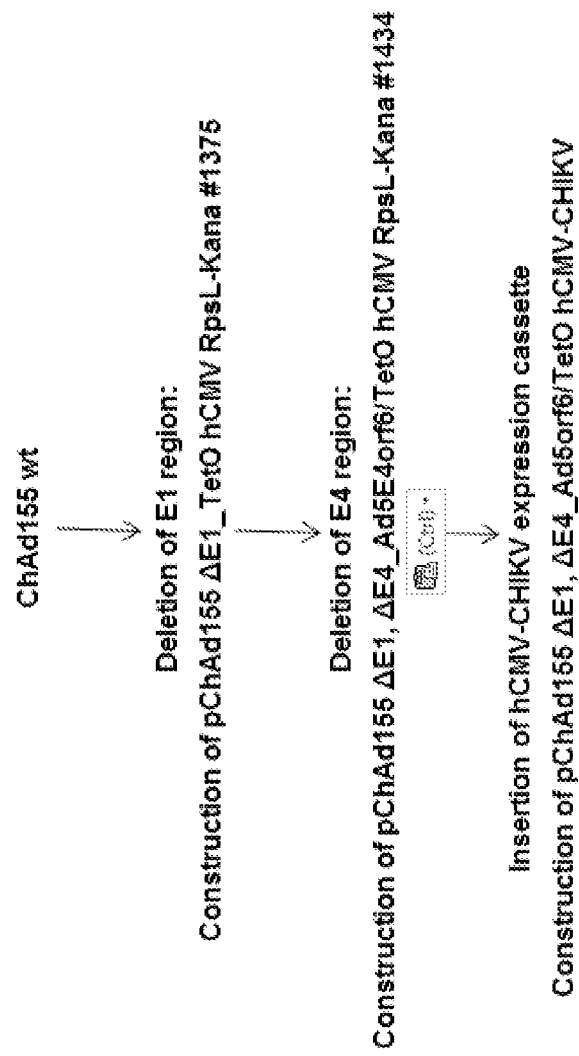
FIG. 3: Flow diagram for the production of ChAd155 plasmids and vectors. The final step involves insertion of an expression construct encoding the CHIKV structural proteins into the pChAd155 #1434 vector, to produce the vector pChAd155 ΔE1, ΔE4_Ad5 orf6 hCMV-CHIKV.

The ChAd155 viral genome was then cloned in a plasmid and subsequently modified as described in WO2016/198621 (which is hereby incorporated by reference for the purpose of describing adenoviral vector construction) and as shown in FIG. 3:
a) deletion of the E1 region (from bp 449 to bp 3529) of the viral genome;
b) deletion of the E4 region (from bp 34731 to bp 37449) of the viral genome;
c) insertion of the E4orf6 derived from human Ad5; and
d) insertion of hCMV-CHIKV expression cassette.

Figure 4:
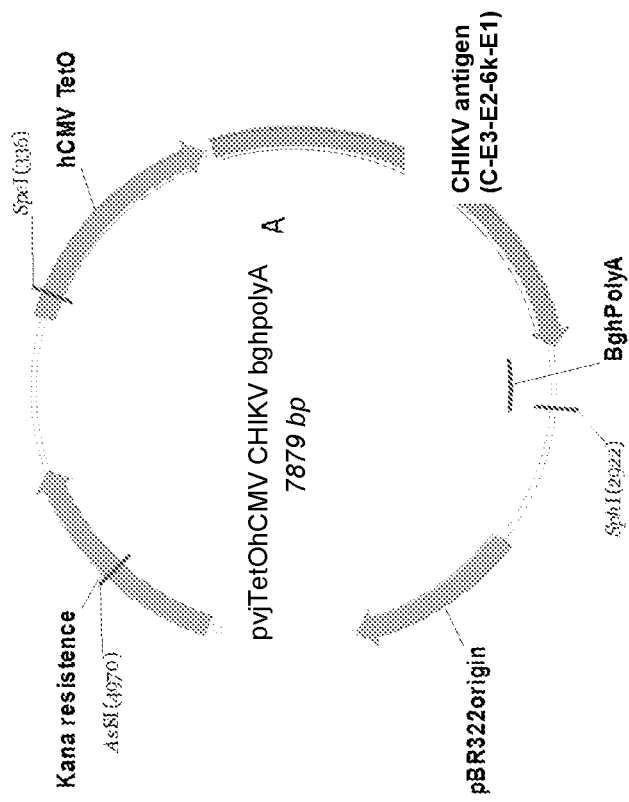
FIG. 4: Diagram of plasmid pvjTetOhCMV CHIKV bghpolyA.
Figure 5:
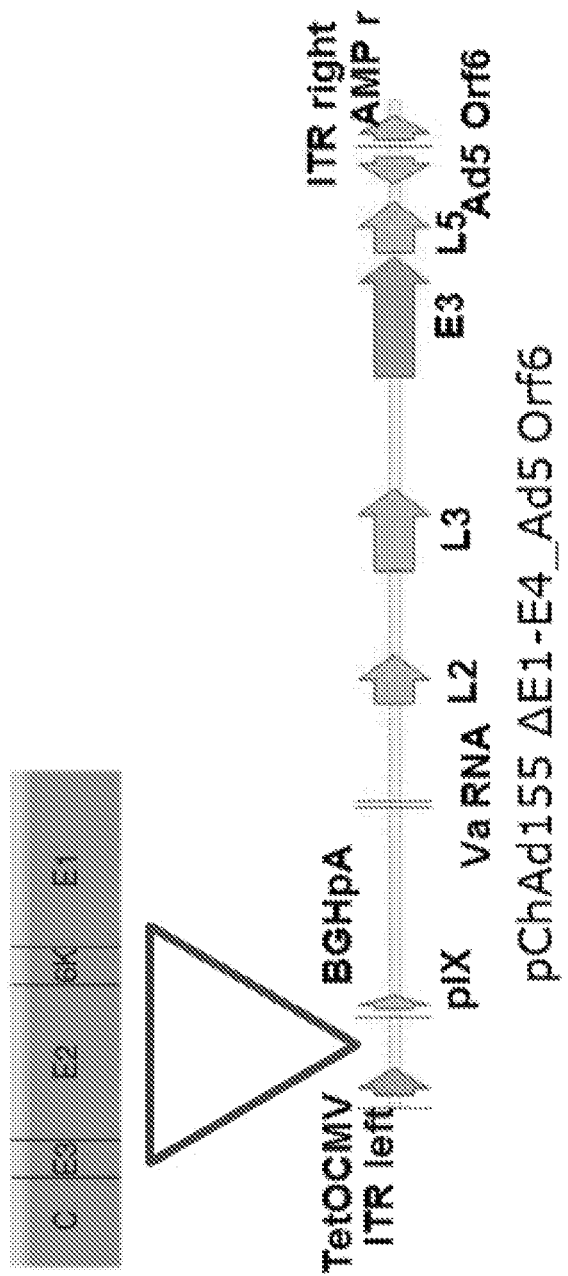
FIG. 5: Diagram of vector pChAd155 ΔE1, ΔE4_Ad5 orf6 hCMV-CHIKV.

The expression cassette encoding CHIKV antigens was inserted into the ChAd155 #1434 expression vector (SEQ ID NO: 7) using methods described in WO2016/198621. Briefly, the wild type DNA encoding the CHIKV strain #37997 structural polyprotein (C-E3-E2-6K-E1, SEQ ID NO: 21) was codon optimized by GENEWIZ (Plainfield, N.J.) to produce a coding sequence appropriate for expression in human cells. The codon optimized CHIKV coding sequence (SEQ ID NO: 22) was synthesized and cloned into plasmid pvjTetOhCMV-bghpolyA (FIG. 4). Plasmid pvjTetOhCMV-bghpolyA contains the tetOhCMV promoter and bovine growth hormone poly-adenylation signal (BGH pA). The nucleic acid sequence of the resulting plasmid (pvjTetOhCMV CHIKV bghpolyA) is shown in SEQ ID NO: 24. The CHIKV expression cassette was then transferred into the ChAd155 #1434 modified vector backbone (SEQ ID NO: 7) by homologous recombination in E. coli BJ5183 competent cells to produce the pChAd155 ΔE1, ΔE4_Ad5 orf6 hCMV-CHIKV vector. A diagram of the pChAd155 ΔE1, ΔE4_Ad5 orf6 hCMV-CHIKV vector is shown in FIG. 5, and the nucleic acid sequence of the vector is shown in SEQ ID NO: 25. ChAd155-CHIKV vector construction was confirmed by transgene sequencing and restriction analysis.

Position 15,997 of SEQ ID NO: 25 can be any nucleotide (A, T, C, G). In a preferred embodiment, position 15,997 of SEQ ID NO: 25 is A.

Using these methods, CHIKV adenoviral vectors can be prepared using alternative modified ChAd155 backbones, including ChAd155 #1390 (SEQ ID NO: 8) and ChAd #1375 (SEQ ID NO: 9).

Example 2: ChAd155-CHIKV Viral Particle Production

Recombinant chimp adenoviruses were generated by linearizing pChAd155 ΔE1-E4_Ad5 orf6 hCMV-CHIKV with the restriction endonuclease PmeI and transfecting the linear vectors into a HEK293-derived cell line (Procell92.S), as described in Vitelli et al., PLOS One (2013) 8(e55435):1-9. These cells are genetically modified to constitutively express the TetO repressor in order to repress transgene expression during virus generation. Two lots of the same CHAd155-CHIKV adenovirus construct were tested: CHIKV-1 and CHIKV-2. Viral amplification was performed at small scale (shake flask) and viruses were purified on double CsCl gradient from 1 liter scale suspension culture.

Purified viral particles were used to infect HeLa cells at Multiplicities of Infection (MOI) of 250, 500 and 1250 to determine the expression of the encoded transgene. Cell lysates and supernatants of infected cells were collected and analyzed by Western blot.

Figure 7:
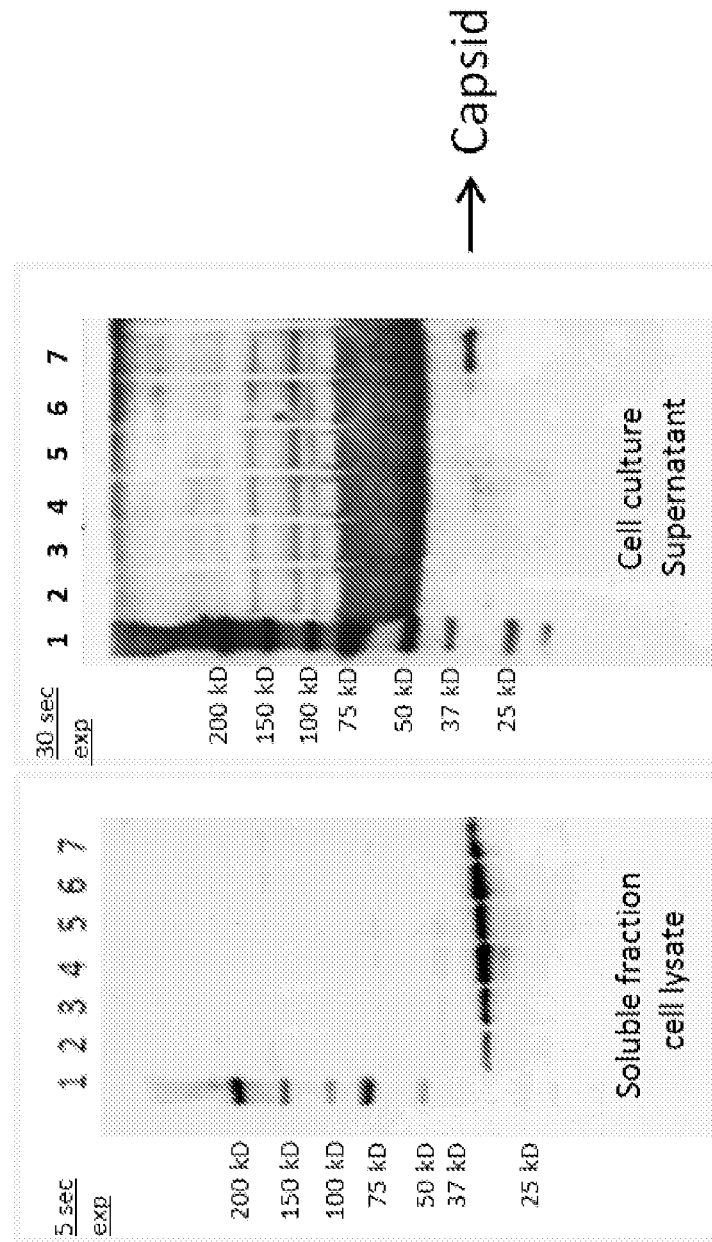
FIG. 7: Characterization of ChAd155-CHIKV expressed in HeLa cells. Two different lots of ChAd155-CHIKV were evaluated (CHIKV-1 and CHIKV-2). CHIKV capsid protein was detected in both the soluble cell lysate fraction (left panel) and the supernatant (right panel) of infected Hela cells. Lane1: Molecular weight markers (Ladder precision plus); Lane 2: ChAd155-CHIKV-1 (MOI 250); Lane 3: ChAd155-CHIKV-1 (MOI 500); Lane 4: ChAd155-CHIKV-1 (MOI 1250); Lane 5: ChAd155-CHIKV-2 (MOI 250); Lane 6: ChAd155-CHIKV-2 (MOI 500); and Lane 7: ChAd155-CHIKV-2 (MOI 1250).

For Western analysis, a polyclonal antibody against the CHIKV structural polyprotein was generated by immunizing mice with DNA encoding CHIKV C-E3-E2-6K-E1 using DNA Electro Gene Transfer (EGT) (Takis Biotech, Roma, Italy). The immunodominant response was against the capsid protein. Expected protein sizes were observed, as shown in FIG. 7. Specifically, CHIKV capsid protein was detected in both the soluble cell lysate fraction (left panel) and the supernatant (right panel) of infected HeLa cells. Lane 1: Molecular weight markers (Ladder precision plus); Lane 2: ChAd155-CHIKV-1 (MOI 250); Lane 3: ChAd155-CHIKV-1 (MOI 500); Lane 4: ChAd155-CHIKV-1 (MOI 1250); Lane 5: ChAd155-CHIKV-2 (MOI 250); Lane 6: ChAd155-CHIKV-2 (MOI 500); and Lane 7: ChAd155-CHIKV-2 (MOI 1250).

ChAd155-CHIKV viral particle titers were determined by QPCR targeting the tetOhCMV promoter and expressed as genome equivalents (gE)/mL, and by CCID50 (Cell Culture Infectious Dose, 50%) for infectivity and expressed as CCID50/mL. Data are summarized in Table 1:

TABLE 1

| ChAd155-CHIKV seed | QPCR (gE/ml) | CCID50/ml or ifu/ml | Ratio gE/CCID50 (<300) |
|---|---|---|---|
| ChAd155- CHIKV | $7.46 \times 10^{10}$ | $4.5 \times 10^8$ | 166 |

Example 3: CHIKV VLP Production

Molecular Cloning

Figure 6:
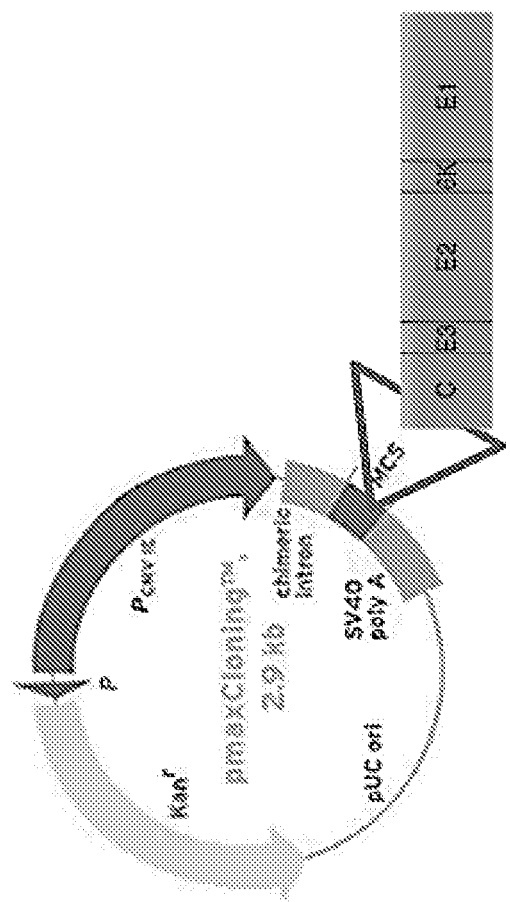
FIG. 6: Diagram of pMax-CHIKV VLP expression vector.

To generate CHIKV VLP expression plasmids, the codon-optimized nucleic acid encoding CHIKV C-E3-E2-6k-E1 (SEQ ID NO: 22) was inserted into the pMAX eukaryotic expression vector (Lonza, Basel Switzerland) using routine molecular biology techniques. See, e.g., Sambrook et al., Molecular Cloning: A Laboratory Manual, Cold Spring Harbor Laboratory Press, Cold Spring Harbor, N.Y., 2000; and Ausubel et al. Short Protocols in Molecular Biology, 4th ed., John Wiley & Sons, Inc., 15 1999. A diagram of the resulting pMAX-CHIKV plasmid is shown in FIG. 6.

Production

HEK293 cells (EXPI293-F cells; Thermo Fisher Scientific, Waltham, Mass.) were grown in EXPI293 expression medium (Thermo Fisher Scientific). The cells were transfected with the pMAX-CHIKV plasmid prepared above (FIG. 6), and EXPIFECTAMINE transfection reagent (Thermo Fischer Scientific). One day after transfection, EXPIFECTAMINE 293 Transfection Enhancer was added. Production proceeded for 4 days post-transfection at 37° C., and cell culture supernatants were collected for purification.

Purification

Cell culture supernatants were centrifuged and filtered on 0.22 µm filters. Samples were diluted 1:2 (v:v) in 50 mM Hepes buffer (pH 8.5) and EDTA-free protease inhibitor cocktail (COMPLETE; Roche, Basel, Switzerland). Anion Exchange Chromatography Hicap Chromotography was used as the first purification step, followed by concentration steps (ViVaspin 70-30,000; Sigma Aldrich, St. Louis, Mo.). A second purification step was carried out, using a sucrose discontinuous gradient (20-60%) followed by a polishing step (SUPERDEX 200 size exclusion chromatography; GE Healthcare Life Sciences; Little Chalfont, United Kingdom) in buffer (50 mM Tris, 100 mM NaCl, 1 mM EDTA pH7.5).

Fractions containing CHIKV VLP antigen were selected on the basis of purity by SDS-PAGE. Protein concentration was determined using Lowry RC/DC Protein Assay of BioRad. The purified bulk was sterile-filtered on 0.22 µm filters and stored at −80° C.

Characterization

Purified CHIKV VLPs were analyzed for expression of CHIKV structural proteins by Western blot. The results confirmed expected protein sizes for CHIKV structural proteins (data not shown).

Purified CHIKV VLP antigen was also examined by electron microscopy (EM) using standard techniques. Briefly, samples were prepared for EM negative staining analysis according to a standard two-step negative staining method using phosphotungstic acid as contrasting agent (Hayat M. A. & Miller S. E., 1990, Negative Staining, McGraw-Hill ed., 253 pp.) A glow discharge was applied to the grids to improve the adsorption of the particles on the grids. A nickel grid (400 mesh) with carbon-coated formvar film was floated on a drop of the sample for 10 min at room temperature to allow adsorption of the material. Excess solution was blotted. To remove most of the sample salts, the grid was briefly floated on a drop of distilled water. The grid was then transferred on a drop of stain prepared according to Harris (Harris, J. R., 1994, Proc. ICEM XIII, Les Editions de Physique, ed., p. 557): 2% (w/v) Na phosphotungstate in water supplemented with 1% trehalose (w/v). The grid was blotted dry after 30 s. The material was left to dry completely and examined under the LIBRA 120 transmission electron microscope (Carl Zeiss AG, Oberkochen, Germany) at 100 kV.

Figure 8:
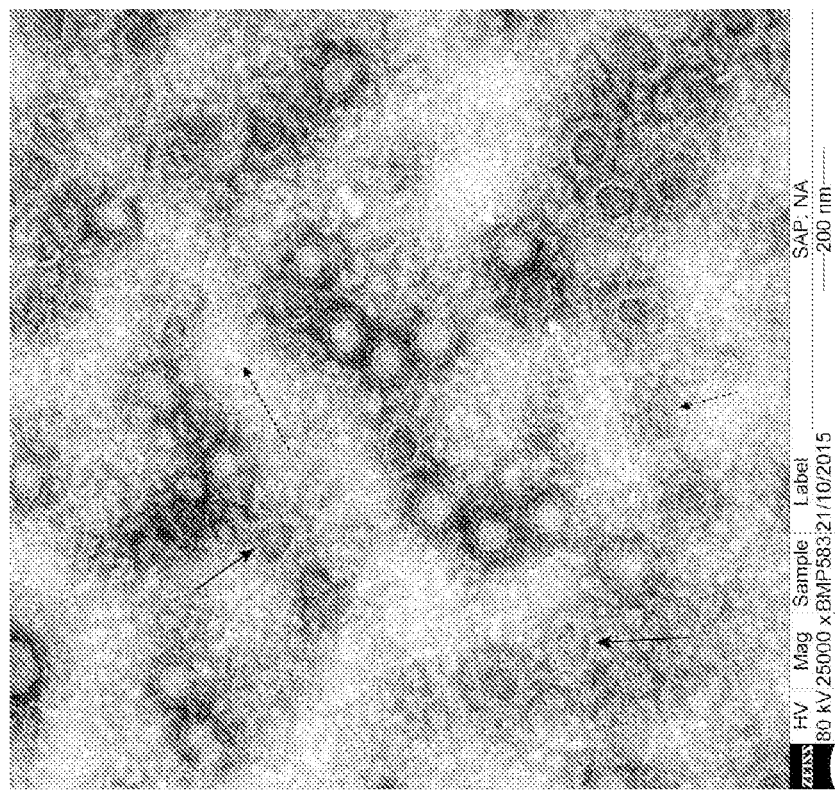
FIG. 8: Electron micrograph of CHIKV VLPs showing intact VLPs of the expected diameter.

An example of an electron micrograph of CHIKV VLPs is shown in FIG. 8. The results show intact VLPs of the expected diameter.

Example 4: Immunogenicity of ChAd155-CHIKV and VLP-CHIKV

Mouse Study Design

Immunogenicity of the ChAd155-CHIKV vector expressing the structural polyprotein C-E3-E2-6K-E1 was evaluated in C57BL/6 (B6) mice (10/group), immunized intramuscularly (IM) with a single dose of ChAd155-CHIKV at $10^7$, $10^8$ or $10^9$ viral particles. Sera were collected before immunization and at day 21 (d21).

A separate study was conducted to evaluate the immunogenicity of CHIKV viral like particles (VLPs) expressing the same CHIKV structural polyproteins. C57BL/6 (B6) mice (10/group) were immunized intramuscularly at days 0 and 28 (d0, d28) with 10, 1 or 0.1 µg VLP. In addition, to evaluate the effect of adjuvant on CHIKV VLP immunogenicity, immunizations were performed with either no adjuvant, or with an adjuvant selected from aluminum hydroxide (alum), AS01E or AS04. AS01E is an Adjuvant System containing MPL, QS-21 and liposome (25 g MPL and 25 µg QS-21). See, e.g., Fochesato et al., Human Vaccines & Immunotherapeutics, 2016, Vol. 12, No. 8, 2092-2095. AS04 is an Adjuvant System containing MPL (50 µg MPL) adsorbed on Al salt (500 µg Al3+). Id.

Neutralization Assay

Micro-neutralisation assays were performed essentially as previously described using Vero cells (ATCC® CCL81™) and CHIKV prepared using C6/36 cells (ATCC® CRL-1660™). See Gardner et al. (2010) J Virol 84:8021-8032; and Wang et al. (2011) Vaccine 29:2803-2809.

All cells and viruses were tested for mycoplasma and shown to be negative. Cell line identification was confirmed by Short Tandem Repeats profiling (Promega Geneprint 10). A single fetal calf serum batch (Gibco) was used throughout and confirmed to be endotoxin free by bioassay (Johnson et al. (2005) J Biol Chem 280:4037-4047).

Two viruses were used in the neutralization assay: (i) a La Reunion Island isolate (LR2006-OPY1) sequence representing the ECSA genotype (Indian Ocean Lineage) (Poo et al. (2014) PLoS NegI Trop Dis 8:e3354) and (ii) an isolate from a traveler who had returned to Australia from the Caribbean (Asia genotype). Single production batches (aliquoted) of each virus were used for all assays. The two viruses behaved differently in the neutralization assays with the Caribbean isolate generating full cytopathic effect (CPE) after 6 days, whereas the La Reunion isolate showed full CPE after 5 days. The virus doses were adjusted to the minimum dose that provided about 100% CPE after 6 or 5 days, respectively, and approximated to a dose of 200 $CCID_{50}$ per well.

The neutralization assay was performed as follows. Mouse sera were heat inactivated and tested in duplicate starting at a 1-in-40 dilution with 3-fold serial dilutions. Sera were mixed with an equal volume of virus preparation (about 200 CCID50/well) and incubated prior to being transferred onto previously seeded Vero cells. Five to six days later, plates were stained with crystal violet, optical density (OD) was measured at 590 nm and titration curves were plotted. The 50% and 90% virus neutralization titers were interpolated from 2 point linear curve fitting, with 100% and 0% determined by 8 wells each for each 96-well plate. Occasionally 3 points were used for interpolation.

Immunogenicity Results

Figure 9:
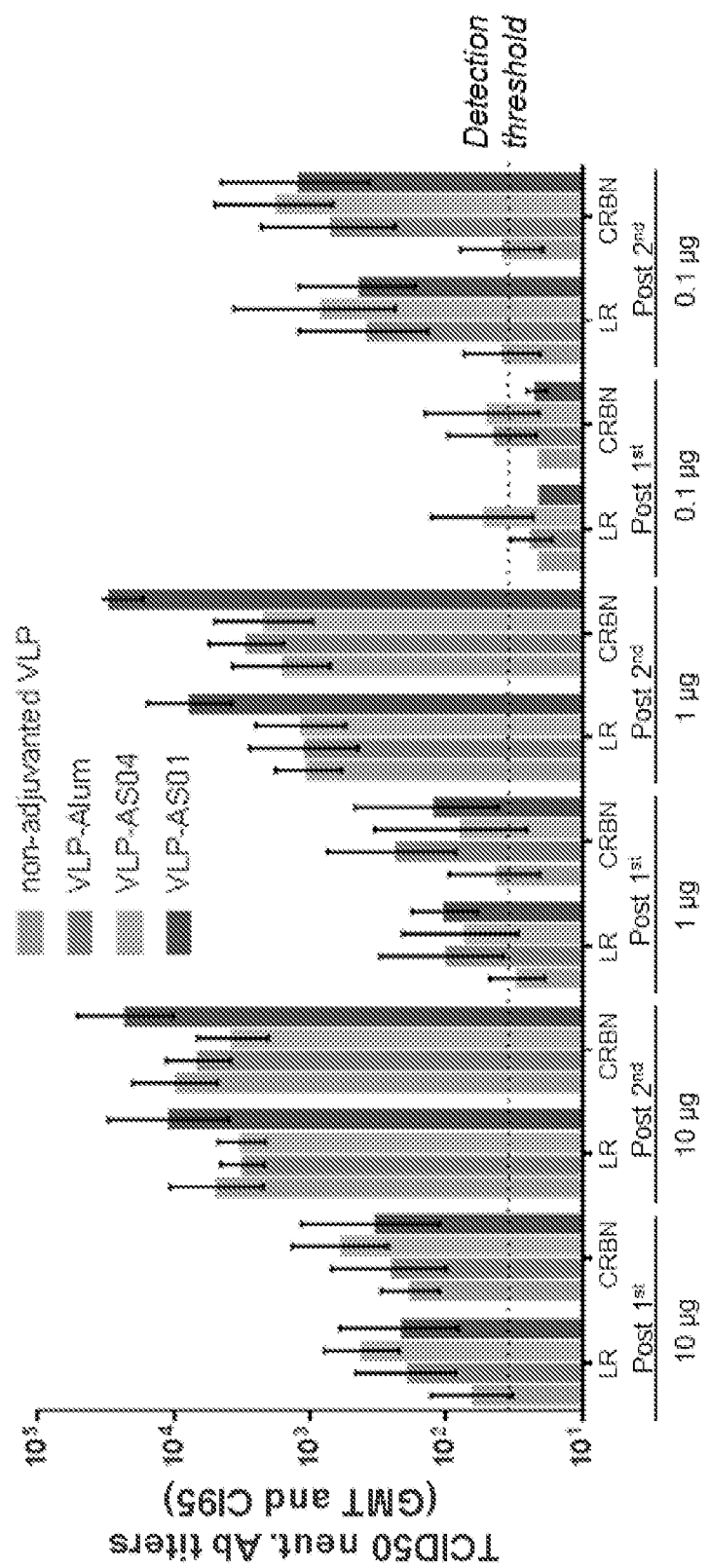
FIG. 9: Immunogenicity of CHIKV VLPs in mice. CHIKV VLPs induced high neutralizing antibody (nAb) titers in a dose-dependent fashion. nAbs elicited to VLPs based on the West-African CHIKV strain (#37997) exhibited activity against La Reunion and Caribbean strains. Adjuvants enhanced immunogenicity at the 1 and 0.1 µg doses.
Figure 10:
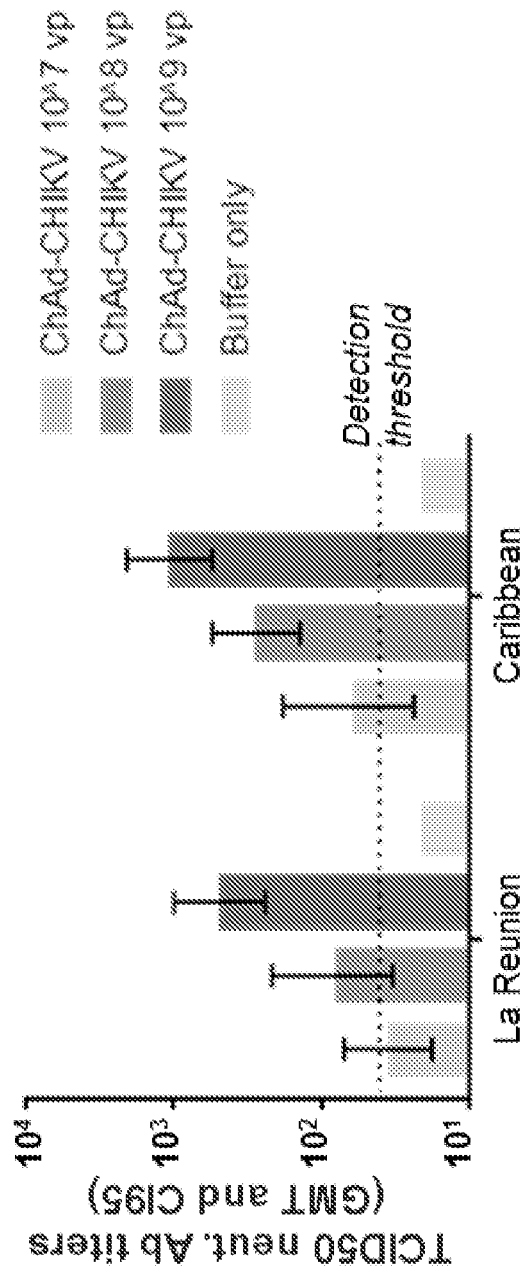
FIG. 10: Immunogenicity of CHAd155-CHIKV in mice. ChAd155-CHIKV induced high nAb titers after a single immunization with doses of $10^8$ or $10^9$ viral particles (vp).

Results of the immunogenicity assays are shown in FIG. 9 (CHIKV VLPs) and FIG. 10 (ChAd155-CHIKV). All vaccine groups induced CHIKV-neutralizing antibody (nAb) titers above the detection threshold, for both the La Reunion and Caribbean CHIKV strains used in the neutralization assay. Immunogenicity of the 0.1 μg dose of CHIKV VLPs was enhanced by co-administration of adjuvants (Alum, AS01 or AS04). ChAd155-CHIKV induced high nAb titers after a single immunization with doses of $10^8$ or $10^9$ viral particles (FIG. 10). The results indicate that neutralizing antibody responses elicited by the West African CHIKV strain have activity against the La Reunion strain (ECSA genotype) and the Caribbean strain (Asian genotype).

Example 5: Durability of Immune Response to ChAd155-CHIKV and VLP-CHIKV

Mouse Study Design

To evaluate the durability of the immune response to ChAd155-CHIKV and VLP-CHIKV immunizations, a study was designed as shown in Table 2. Specifically, C57BL/6 mice (4-6 weeks old; n=10/group) were immunized with either 1) ChAd155-CHIKV viral particles produced as described in Example 2 (single intramuscular immunization with $5\times10^8$ viral particles); or 2) CHIKV VLPs produced as described in Example 3 (one or two immunizations with 1 ug/dose). Groups 2, 5 and 6 were also administered Adjuvant System AS01E, containing MPL, QS-21 and liposome (25 g MPL and 25 μg QS-21). See, e.g., Fochesato et al., Human Vaccines & Immunotherapeutics, 2016, Vol. 12, No. 8, 2092-2095. Control animals received phosphate buffered saline vehicle only.

TABLE 2

| Group | n | Number of immunizations (immunization day) | dose | Vaccine Format | Adjuvant |
|---|---|---|---|---|---|
| 1 | 10 | 1 (d 28) | $5 \times 10^8$ | ChAd155 | n/a |
| 2 | 10 |  |  |  | AS01 |
| 3 | 10 | 1 (d 28) | 1 ug | VLP | n/a |
| 4 | 10 | 2 (d 0, d 28) | 1 ug |  |  |
| 5 | 10 | 1 (d 28) | 1 ug |  | AS01 |
| 6 | 10 | 2 (d 0, d 28) | 1 ug |  |  |
| 7 | 10 | N/A | N/A | Control | n/a |

Neutralization Assay

CHIKV-specific neutralizing antibody titers were determined using the La Reunion (LR) and Caribbean (CRBN) strains in the micro-neutralisation assays described in Example 4.

Immunogenicity Results

Figure 11:
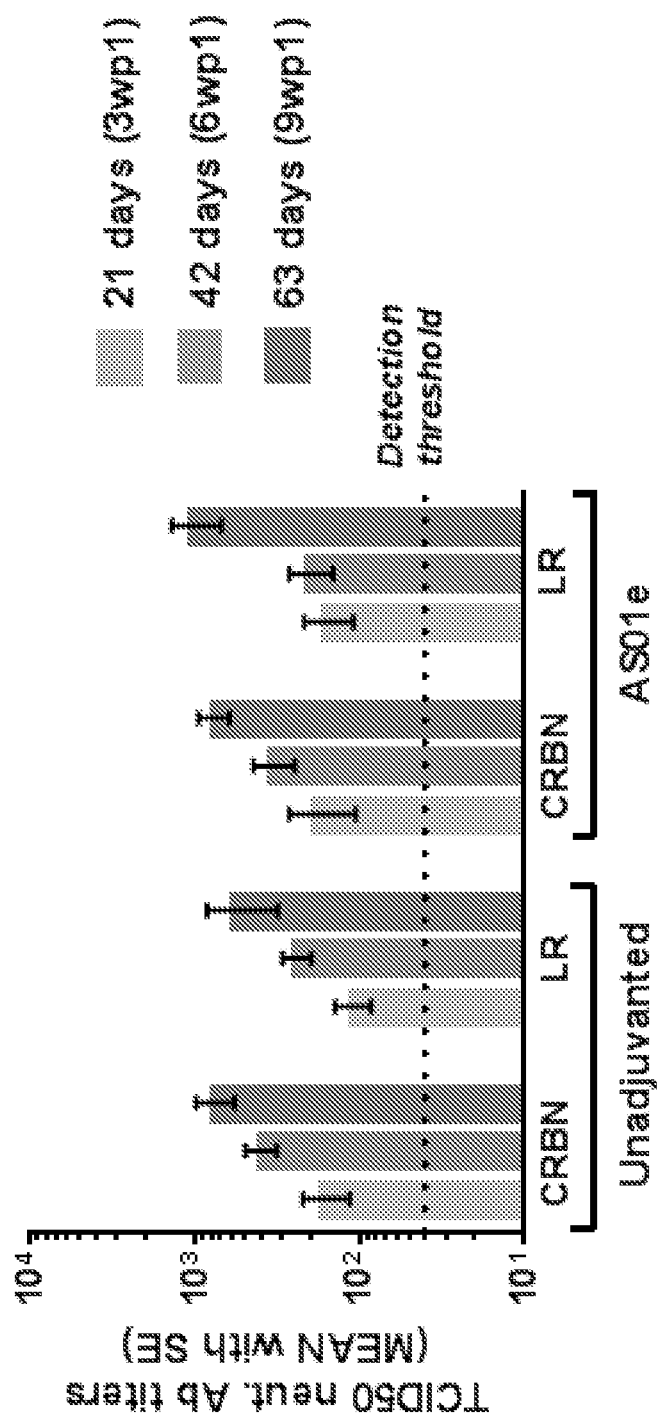
FIG. 11: Durability of ChAd155-CHIKV immunogenicity in mice. A single dose of ChAd155-CHIKV ($5\times10^8$ viral particles, i.m.) elicited high and durable neutralizing antibody (nAb) titers, expressed as 50% Tissue culture Infective Dose (TCID50). nAb titers above the detection threshold (dotted line) were observed at 3, 6 and 9 weeks postimmunization. In addition, antibodies elicited by the West-African CHIKV-based ChAd construct were capable of neutralizing both the La Reunion and Caribbean CHIKV strains. No difference was observed between the unadjuvanted and AS01E-adjuvanted groups.

As shown in FIG. 11, a single dose of ChAd155-CHIKV ($5\times10^8$ viral particles, i.m.) elicited high and durable neutralizing antibody titers. nAb titers above the detection threshold were observed at 3, 6 and 9 weeks post-immunization. In addition, antibodies elicited by the West-African CHIKV-based ChAd construct were capable of neutralizing both the La Reunion and Caribbean CHIKV strains. No difference was observed between the unadjuvanted and AS01E-adjuvanted groups.

Figure 12:
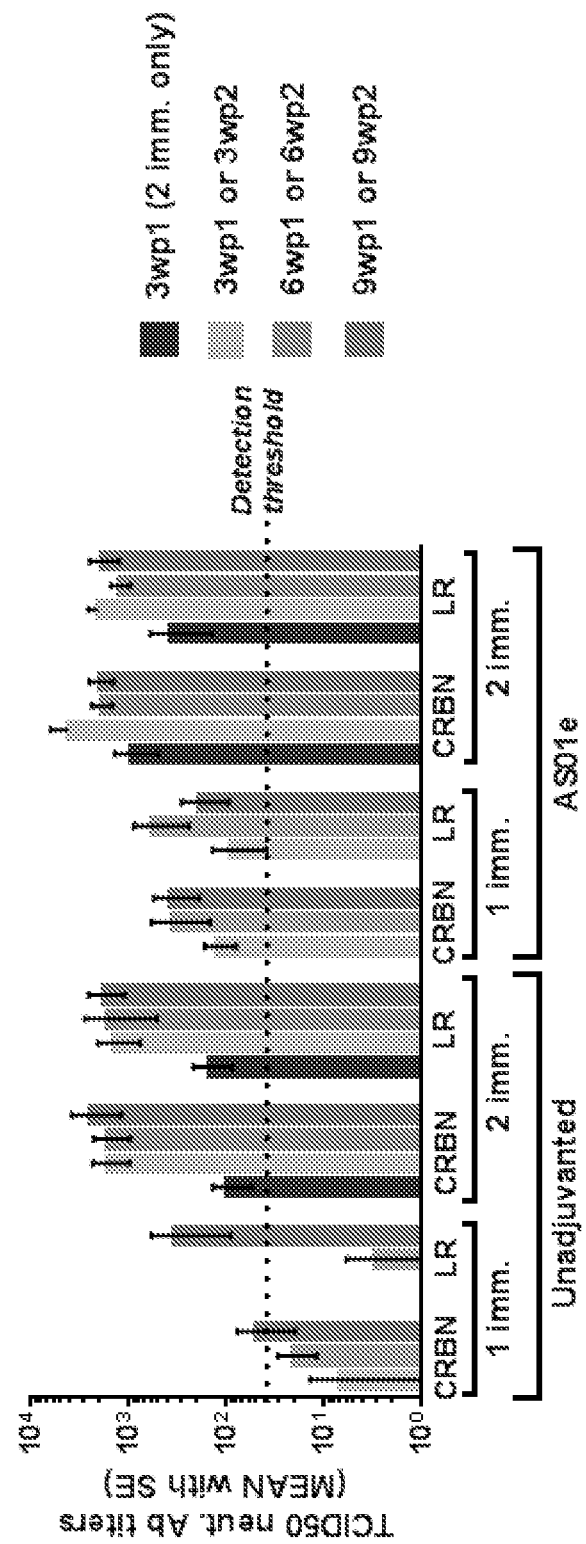
FIG. 12: Durability of CHIKV VLP immunogenicity in mice. CHIKV VLPs induced high nAb titers following 2 immunizations. The West-African CHIKV VLPs were capable of eliciting nAbs against the La Reunion (LR) and Caribbean (CRBN) CHIKV strains. Elevated nAb titers were observed 3, 6 and 9 weeks after the second immunization. A single immunization with CHIKV VLPs alone did not produce a robust nAb response, but an adjuvanting effect was observed for the single immunization combined with AS01E.

CHIKV VLPs induced high nAb titers following 2 immunizations, as shown in FIG. 12. As with the ChAd155-CHIKV construct, the West-African CHIKV VLPs were capable of eliciting nAbs against the La Reunion and Caribbean CHIKV strains. Elevated nAb titers were observed 3, 6 and 9 weeks after the second immunization. While a single immunization with CHIKV VLPs did not produce a robust nAb response, an adjuvanting effect was observed for the single immunization combined with AS01E.

These results demonstrate that a single immunization with ChAd155-CHIKV is capable of inducing CHIKV-specific neutralizing antibodies. Furthermore, immunization with the West African CHIKV strain elicited nAbs against the La Reunion and Caribbean CHIKV strains.

Example 6: Efficacy of ChAd155-CHIKV and VLP-CHIKV 10 weeks after the last immunization described in Example 4, animals were challenged with $1\times10^4$ $CCID_{50}$ of the La Reunion (LR) CHIKV strain subcutaneously into the side of each hind foot to assess the efficacy of the immunizations. CHIKV viremia was measured for 5 days post-challenge, and foot pad swelling (a correlate of CHIKV infection in mice) was measured for 13 days post-challenge.

Figure 13:
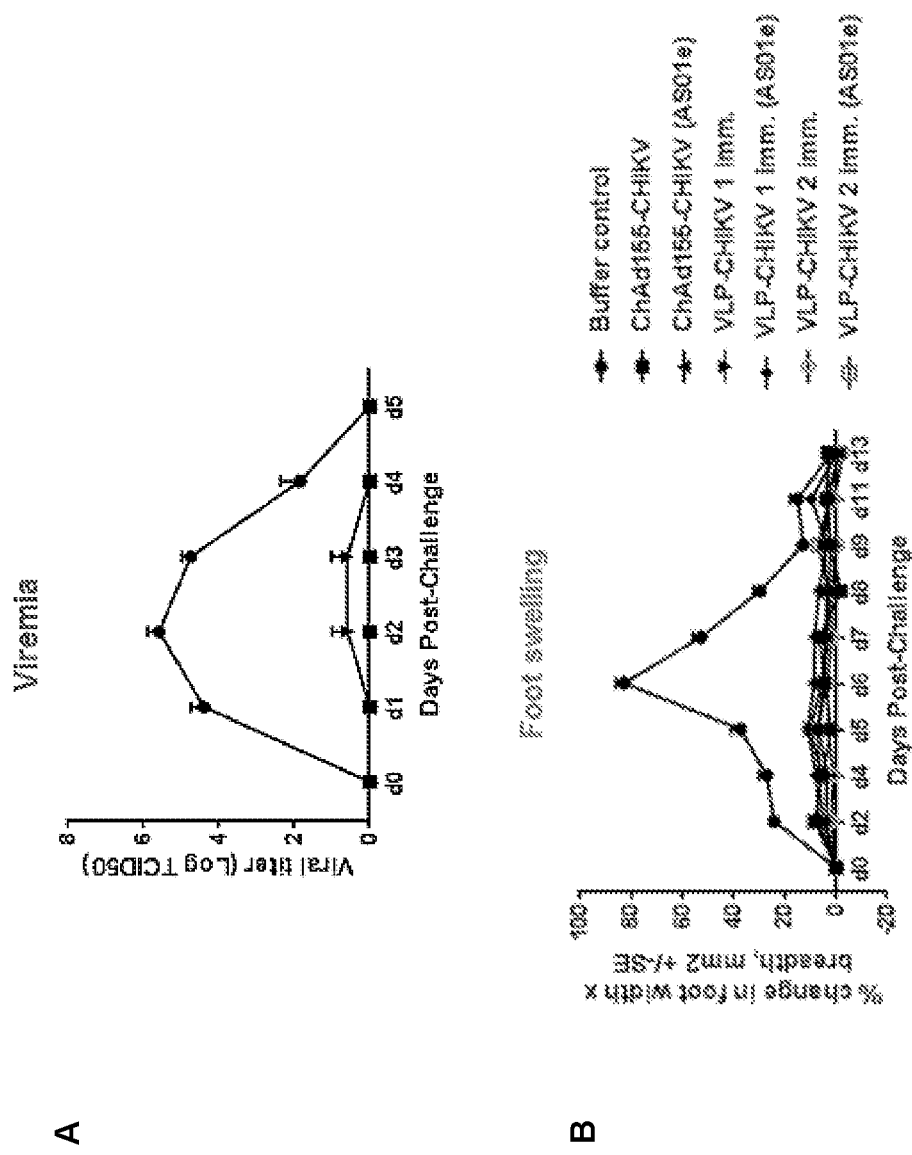
FIG. 13: Efficacy of ChAd155-CHIKV and CHIKV VLP in mice. (A) All immunized groups showed complete protection against CHIKV (LR strain) challenge, except the group receiving a single dose of CHIKV VLPs, which showed low levels of viremia at d2 and d3 post-challenge. Control animals exhibited CHIKV viremia peaking at d2. (B) All immunized groups showed complete protection from disease as measured by foot pad swelling. A small but not significant trend in foot pad swelling was noted at d2 post challenge in the group immunized with a single dose of CHIKV VLPs. Control animals exhibited foot pad swelling peaking at d6.

As shown in FIG. 13, all immunized groups showed complete protection, except the group receiving a single dose of CHIKV VLPs, which showed low levels of viremia at d2 and d3 post-challenge. Furthermore, all immunized groups showed complete protection from disease as measured by foot pad swelling. A small but not significant trend in foot pad swelling was noted at d2 post challenge in the group immunized with a single dose of CHIKV VLPs.

These results demonstrate that a single immunization with ChAd155-CHIKV is capable of preventing viremia and clinical symptoms caused by challenge with live Chikungunya virus. Furthermore, immunization with a West African CHIKV strain was protective against infection with the La Reunion strain.

The invention claimed is:

1. A recombinant adenovirus comprising a polynucleotide having a sequence at least 90% identical over its entire length identical to SEQ ID NO: 25.

2. A composition comprising the recombinant adenovirus according to claim 1, and a pharmaceutically acceptable excipient.

3. The adenovirus according to claim 1, wherein the nucleic acid sequence encodes a Chikungunya virus antigen comprising the amino acid sequence of SEQ ID NO: 23.

4. The adenovirus according to claim 1, wherein the recombinant adenovirus is replication-incompetent.

5. The adenovirus according to claim 1, wherein the Chikungunya virus antigen is derived from a Chikungunya virus genotype selected from West African, Asian and East/Central/South African (ECSA).

6. A method of inducing an immune response in a subject comprising administering the adenovirus according to claim 1 to the subject.

7. The adenovirus according to claim 1, comprising a polynucleotide having a sequence at least 95% identical over its entire length identical to SEQ ID NO: 25.

8. A method of prophylaxis of a disease caused by a Chikungunya virus infection, comprising administering the adenovirus according to claim 1 to a subject.

* * * * *

SEQUENCE LISTING

```
<160> NUMBER OF SEQ ID NOS: 25

<210> SEQ ID NO 1
<211> LENGTH: 578
<212> TYPE: PRT
<213> ORGANISM: Artificial Sequence
<220> FEATURE:
<223> OTHER INFORMATION: Polypeptide sequence of ChAd155 fiber

<400> SEQUENCE: 1

Met Lys Arg Thr Lys Thr Ser Asp Glu Ser Phe Asn Pro Val Tyr Pro
1               5                   10                  15
```

```
Tyr Asp Thr Glu Ser Gly Pro Pro Ser Val Pro Phe Leu Thr Pro Pro
         20                  25                  30

Phe Val Ser Pro Asp Gly Phe Gln Glu Ser Pro Pro Gly Val Leu Ser
         35                  40                  45

Leu Asn Leu Ala Glu Pro Leu Val Thr Ser His Gly Met Leu Ala Leu
 50                  55                  60

Lys Met Gly Ser Gly Leu Ser Leu Asp Asp Ala Gly Asn Leu Thr Ser
 65                  70                  75                  80

Gln Asp Ile Thr Thr Ala Ser Pro Pro Leu Lys Lys Thr Lys Thr Asn
                 85                  90                  95

Leu Ser Leu Glu Thr Ser Ser Pro Leu Thr Val Ser Thr Ser Gly Ala
             100                 105                 110

Leu Thr Val Ala Ala Ala Ala Pro Leu Ala Val Ala Gly Thr Ser Leu
             115                 120                 125

Thr Met Gln Ser Glu Ala Pro Leu Thr Val Gln Asp Ala Lys Leu Thr
130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
            195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
            260                 265                 270

Ala Tyr Pro Phe Asp Ala Gln Asn Asn Leu Ser Leu Arg Leu Gly Gln
            275                 280                 285

Gly Pro Leu Phe Val Asn Ser Ala His Asn Leu Asp Val Asn Tyr Asn
    290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Thr Ala Ile Ala
                325                 330                 335

Ile Asn Ala Gly Asp Gly Leu Gln Phe Asp Ser Gly Ser Asp Thr Asn
            340                 345                 350

Pro Leu Lys Thr Lys Leu Gly Leu Gly Leu Asp Tyr Asp Ser Ser Arg
            355                 360                 365

Ala Ile Ile Ala Lys Leu Gly Thr Gly Leu Ser Phe Asp Asn Thr Gly
            370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430
```

Val Ser Val Leu Ser Val Lys Gly Ser Leu Ala Pro Ile Ser Gly Thr
        435                 440                 445

Val Thr Ser Ala Gln Ile Val Leu Arg Phe Asp Glu Asn Gly Val Leu
    450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
                500                 505                 510

Ile Val Ser Gln Val Tyr Leu Asn Gly Asp Lys Ser Lys Pro Met Thr
            515                 520                 525

Leu Thr Ile Thr Leu Asn Gly Thr Asn Glu Thr Gly Asp Ala Thr Val
    530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 2
<211> LENGTH: 1734
<212> TYPE: DNA
<213> ORGANISM: Artificial Sequence
<220> FEATURE:
<223> OTHER INFORMATION: Polynucleotide sequence encoding ChAd155 fiber

<400> SEQUENCE: 2
atgaagcgca ccaaaacgtc tgacgagagc ttcaaccccg tgtaccccta tgacacggaa      60
agcggccctc cctccgtccc tttcctcacc cctcccttcg tgtctcccga tggattccaa     120
gaaagtcccc ccggggtcct gtctctgaac ctggccgagc cctggtcac ttccacggc     180 atgctcgccc tgaaaatggg aagtggcctc tccctggacg acgctggcaa cctcacctct     240
caagatatca ccaccgctag ccctcccctc aaaaaaacca agaccaacct cagcctagaa     300
acctcatccc ccctaactgt gagcacctca ggcgccctca ccgtagcagc cgccgctccc     360
ctggcggtgg ccggcacctc cctcaccatg caatcagagg cccccctgac agtacaggat     420
gcaaaactca ccctggccac caaaggcccc ctgaccgtgt ctgaaggcaa actggccttg     480
caaacatcgg ccccgctgac ggccgctgac agcagcaccc tcacagtcag tgccacacca     540
ccccttagca caagcaatgg cagcttgggt attgacatgc aagcccccat ttacaccacc     600
aatggaaaac taggacttaa ctttggcgct ccctgcatg tggtagacag cctaaatgca     660
ctgactgtag ttactggcca aggtcttacg ataaacggaa cagccctaca aactagagtc     720
tcaggtgccc tcaactatga cacatcagga acctagaat tgagagctgc aggggtatg     780 cgagttgatg caaatggtca acttatcctt gatgtagctt acccatttga tgcacaaaac     840
aatctcagcc ttaggcttgg acagggaccc ctgttttgta actctgccca caacttggat     900
gttaactaca acagaggcct ctacctgttc acatctggaa ataccaaaaa gctagaagtt     960
aatatcaaaa cagccaaggg tctcattat gatgacactg ctatagcaat caatgcgggt    1020
gatgggctac agtttgactc aggctcagat acaaatccat taaaaactaa acttggatta    1080
ggactggatt atgactccag cagagccata attgctaaac tgggaactgg cctaagcttt    1140
gacaacacag gtgccatcac agtaggcaac aaaaatgatg acaagcttac cttgtggacc    1200

-continued

```
acaccagacc catcccctaa ctgtagaatc tattcagaga aagatgctaa attcacactt    1260
gttttgacta aatgcggcag tcaggtgttg gccagcgttt ctgttttatc tgtaaaaggt    1320
agccttgcgc ccatcagtgg cacagtaact agtgctcaga ttgtcctcag atttgatgaa    1380
aatggagttc tactaagcaa ttcttccctt gaccctcaat actggaacta cagaaaaggt    1440
gaccttacag agggcactgc ataccaac gcagtgggat ttatgcccaa cctcacagca    1500
tacccaaaaa cacagagcca aactgctaaa agcaacattg taagtcaggt ttacttgaat    1560
ggggacaaat ccaaacccat gaccctcacc attaccctca atggaactaa tgaaacagga    1620
gatgccacag taagcactta ctccatgtca ttctcatgga actggaatgg aagtaattac    1680
attaatgaaa cgttccaaac caactccttc accttctcct acatcgccca agaa          1734
```

<210> SEQ ID NO 3
<211> LENGTH: 593
<212> TYPE: PRT
<213> ORGANISM: Artificial Sequence
<220> FEATURE:
<223> OTHER INFORMATION: Polypeptide sequence of ChAd155 penton

<400> SEQUENCE: 3

```
Met Arg Arg Ala Ala Met Tyr Gln Glu Gly Pro Pro Ser Tyr Glu
1               5                   10                  15

Ser Val Val Gly Ala Ala Ala Ala Pro Ser Ser Pro Phe Ala Ser
                20                  25                  30

Gln Leu Leu Glu Pro Pro Tyr Val Pro Pro Arg Tyr Leu Arg Pro Thr
            35                  40                  45

Gly Gly Arg Asn Ser Ile Arg Tyr Ser Glu Leu Ala Pro Leu Phe Asp
        50                  55                  60

Thr Thr Arg Val Tyr Leu Val Asp Asn Lys Ser Ala Asp Val Ala Ser
65                  70                  75                  80

Leu Asn Tyr Gln Asn Asp His Ser Asn Phe Leu Thr Thr Val Ile Gln
                85                  90                  95

Asn Asn Asp Tyr Ser Pro Ser Glu Ala Ser Thr Gln Thr Ile Asn Leu
            100                 105                 110

Asp Asp Arg Ser His Trp Gly Gly Asp Leu Lys Thr Ile Leu His Thr
        115                 120                 125

Asn Met Pro Asn Val Asn Glu Phe Met Phe Thr Asn Lys Phe Lys Ala
    130                 135                 140

Arg Val Met Val Ser Arg Ser His Thr Lys Glu Asp Arg Val Glu Leu
145                 150                 155                 160

Lys Tyr Glu Trp Val Glu Phe Glu Leu Pro Glu Gly Asn Tyr Ser Glu
                165                 170                 175

Thr Met Thr Ile Asp Leu Met Asn Asn Ala Ile Val Glu His Tyr Leu
            180                 185                 190

Lys Val Gly Arg Gln Asn Gly Val Leu Glu Ser Asp Ile Gly Val Lys
        195                 200                 205

Phe Asp Thr Arg Asn Phe Arg Leu Gly Leu Asp Pro Val Thr Gly Leu
    210                 215                 220

Val Met Pro Gly Val Tyr Thr Asn Glu Ala Phe His Pro Asp Ile Ile
225                 230                 235                 240

Leu Leu Pro Gly Cys Gly Val Asp Phe Thr Tyr Ser Arg Leu Ser Asn
                245                 250                 255

Leu Leu Gly Ile Arg Lys Arg Gln Pro Phe Gln Glu Gly Phe Arg Ile
            260                 265                 270
```

```
Thr Tyr Glu Asp Leu Glu Gly Gly Asn Ile Pro Ala Leu Leu Asp Val
            275                 280                 285

Glu Ala Tyr Gln Asp Ser Leu Lys Glu Asn Gly Ala Gly Gln Glu Asp
290                 295                 300

Thr Ala Pro Ala Ala Ser Ala Ala Ala Glu Gln Gly Glu Asp Ala Ala
305                 310                 315                 320

Asp Thr Ala Ala Ala Asp Gly Ala Glu Ala Asp Pro Ala Met Val Val
                325                 330                 335

Glu Ala Pro Glu Gln Glu Asp Met Asn Asp Ser Ala Val Arg Gly
            340                 345                 350

Asp Thr Phe Val Thr Arg Gly Glu Lys Gln Ala Glu Ala Glu Ala
            355                 360                 365

Ala Ala Glu Glu Lys Gln Leu Ala Ala Ala Ala Ala Ala Ala Leu
370                 375                 380

Ala Ala Ala Glu Ala Glu Ser Glu Gly Thr Lys Pro Ala Lys Glu Pro
385                 390                 395                 400

Val Ile Lys Pro Leu Thr Glu Asp Ser Lys Lys Arg Ser Tyr Asn Leu
                405                 410                 415

Leu Lys Asp Ser Thr Asn Thr Ala Tyr Arg Ser Trp Tyr Leu Ala Tyr
                420                 425                 430

Asn Tyr Gly Asp Pro Ser Thr Gly Val Arg Ser Trp Thr Leu Leu Cys
            435                 440                 445

Thr Pro Asp Val Thr Cys Gly Ser Glu Gln Val Tyr Trp Ser Leu Pro
            450                 455                 460

Asp Met Met Gln Asp Pro Val Thr Phe Arg Ser Thr Arg Gln Val Ser
465                 470                 475                 480

Asn Phe Pro Val Val Gly Ala Glu Leu Leu Pro Val His Ser Lys Ser
                485                 490                 495

Phe Tyr Asn Asp Gln Ala Val Tyr Ser Gln Leu Ile Arg Gln Phe Thr
                500                 505                 510

Ser Leu Thr His Val Phe Asn Arg Phe Pro Glu Asn Gln Ile Leu Ala
            515                 520                 525

Arg Pro Pro Ala Pro Thr Ile Thr Thr Val Ser Glu Asn Val Pro Ala
530                 535                 540

Leu Thr Asp His Gly Thr Leu Pro Leu Arg Asn Ser Ile Gly Gly Val
545                 550                 555                 560

Gln Arg Val Thr Val Thr Asp Ala Arg Arg Arg Thr Cys Pro Tyr Val
                565                 570                 575

Tyr Lys Ala Leu Gly Ile Val Ser Pro Arg Val Leu Ser Ser Arg Thr
            580                 585                 590

Phe
```

<210> SEQ ID NO 4
<211> LENGTH: 1779
<212> TYPE: DNA
<213> ORGANISM: Artificial Sequence
<220> FEATURE:
<223> OTHER INFORMATION: Polynucleotide sequence encoding ChAd155 penton

<400> SEQUENCE: 4

```
atgcggcgcg cggcgatgta ccaggaggga cctcctccct cttacgagag cgtggtgggc    60
gcggcggcgg cggcgccctc ttctcccttt gcgtcgcagc tgctggagcc gccgtacgtg   120
cctccgcgct acctgcggcc tacgggggga agaaacagca tccgttactc ggagctggcg   180
cccctgttcg acaccacccg ggtgtacctg gtggacaaca gtcggcgga cgtggcctcc   240
```

```
ctgaactacc agaacgacca cagcaatttt ttgaccacgg tcatccagaa caatgactac    300
agcccgagcg aggccagcac ccagaccatc aatctggatg accggtcgca ctggggcggc    360
gacctgaaaa ccatcctgca caccaacatg cccaacgtga acgagttcat gttcaccaat    420
aagttcaagg cgcgggtgat ggtgtcgcgc tcgcacacca aggaagaccg ggtggagctg    480
aagtacgagt gggtggagtt cgagctgcca gagggcaact actccgagac catgaccatt    540
gacctgatga caacgcgat cgtggagcac tatctgaaag tgggcaggca gaacggggtc     600
ctggagagcg acatcggggt caagttcgac accaggaact tccgcctggg gctggacccc    660
gtgaccgggc tggttatgcc cggggtgtac accaacgagg ccttccatcc cgacatcatc    720
ctgctgcccg gctgcggggt ggacttcact tacagccgcc tgagcaacct cctgggcatc    780
cgcaagcggc agcccttcca ggagggcttc aggatcacct acgaggacct ggagggggc    840 aacatccccg cgctcctcga tgtggaggcc taccaggata gcttgaagga aaatgaggcg    900
ggacaggagg ataccgcccc cgccgcctcc gccgccgccg agcagggcga ggatgctgct    960
gacaccgcgg ccgcggacgg ggcagaggcc gaccccgcta tggtggtgga ggctcccgag    1020
caggaggagg acatgaatga cagtgcggtg cgcggagaca ccttcgtcac ccgggggag     1080 gaaaagcaag cggaggccga ggccgcggcc gaggaaaagc aactggcggc agcagcggcg    1140
gcggcggcgt tggccgcggc ggaggctgag tctgagggga ccaagcccgc caaggagccc    1200
gtgattaagc ccctgaccga agatagcaag aagcgcagtt acaacctgct caaggacagc    1260
accaacaccg cgtaccgcag ctggtacctg gcctacaact acggcgaccc gtcgacgggg    1320
gtgcgctcct ggaccctgct gtgcacgccg gacgtgacct gcggctcgga gcaggtgtac    1380
tggtcgctgc ccgacatgat gcaagacccc gtgaccttcc gctccacgcg gcaggtcagc    1440
aacttcccgg tggtgggcgc cgagctgctg cccgtgcact ccaagagctt ctacaacgac    1500
caggccgtct actcccagct catccgccag ttcacctctc tgacccacgt gttcaatcgc    1560
tttcctgaga accagattct ggcgcgcccg cccgcccca ccatcaccac cgtcagtgaa     1620
aacgttcctg ctctcacaga tcacgggacg ctaccgctgc gcaacagcat cggaggagtc    1680
cagcgagtga ccgttactga cgccagacgc cgcacctgcc cctacgttta caaggccttg    1740
ggcatagtct cgccgcgcgt cctttccagc cgcactttt                           1779
```

<210> SEQ ID NO 5
<211> LENGTH: 964
<212> TYPE: PRT
<213> ORGANISM: Artificial Sequence
<220> FEATURE:
<223> OTHER INFORMATION: Polypeptide sequence of ChAd155 hexon

<400> SEQUENCE: 5

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Ser Tyr Phe Ser Leu Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
```

```
                    85                  90                  95
Ala Ser Thr Tyr Phe Asp Ile Arg Gly Val Leu Asp Arg Gly Pro Thr
                100                 105                 110

Phe Lys Pro Tyr Ser Gly Thr Ala Tyr Asn Ser Leu Ala Pro Lys Gly
            115                 120                 125

Ala Pro Asn Ser Cys Glu Trp Glu Gln Glu Glu Thr Gln Thr Ala Glu
130                 135                 140

Glu Ala Gln Asp Glu Glu Glu Asp Glu Ala Glu Ala Glu Glu Glu Met
145                 150                 155                 160

Pro Gln Glu Glu Gln Ala Pro Val Lys Lys Thr His Val Tyr Ala Gln
                165                 170                 175

Ala Pro Leu Ser Gly Glu Lys Ile Thr Lys Asp Gly Leu Gln Ile Gly
            180                 185                 190

Thr Asp Ala Thr Ala Thr Glu Gln Lys Pro Ile Tyr Ala Asp Pro Thr
        195                 200                 205

Phe Gln Pro Glu Pro Gln Ile Gly Glu Ser Gln Trp Asn Glu Ala Asp
    210                 215                 220

Ala Ser Val Ala Gly Gly Arg Val Leu Lys Lys Thr Thr Pro Met Lys
225                 230                 235                 240

Pro Cys Tyr Gly Ser Tyr Ala Arg Pro Thr Asn Ala Asn Gly Gly Gln
                245                 250                 255

Gly Val Leu Val Glu Lys Asp Gly Gly Lys Met Glu Ser Gln Val Asp
            260                 265                 270

Met Gln Phe Phe Ser Thr Ser Glu Asn Ala Arg Asn Glu Ala Asn Asn
        275                 280                 285

Ile Gln Pro Lys Leu Val Leu Tyr Ser Glu Asp Val His Met Glu Thr
    290                 295                 300

Pro Asp Thr His Ile Ser Tyr Lys Pro Ala Lys Ser Asp Asn Asn Ser
305                 310                 315                 320

Lys Val Met Leu Gly Gln Gln Ser Met Pro Asn Arg Pro Asn Tyr Ile
                325                 330                 335

Gly Phe Arg Asp Asn Phe Ile Gly Leu Met Tyr Tyr Asn Ser Thr Gly
            340                 345                 350

Asn Met Gly Val Leu Ala Gly Gln Ala Ser Gln Leu Asn Ala Val Val
        355                 360                 365

Asp Leu Gln Asp Arg Asn Thr Glu Leu Ser Tyr Gln Leu Leu Leu Asp
    370                 375                 380

Ser Met Gly Asp Arg Thr Arg Tyr Phe Ser Met Trp Asn Gln Ala Val
385                 390                 395                 400

Asp Ser Tyr Asp Pro Asp Val Arg Ile Ile Glu Asn His Gly Thr Glu
                405                 410                 415

Asp Glu Leu Pro Asn Tyr Cys Phe Pro Leu Gly Gly Ile Gly Val Thr
            420                 425                 430

Asp Thr Tyr Gln Ala Ile Lys Thr Asn Gly Asn Gly Asn Gly Gly Gly
        435                 440                 445

Asn Thr Thr Trp Thr Lys Asp Glu Thr Phe Ala Asp Arg Asn Glu Ile
    450                 455                 460

Gly Val Gly Asn Asn Phe Ala Met Glu Ile Asn Leu Ser Ala Asn Leu
465                 470                 475                 480

Trp Arg Asn Phe Leu Tyr Ser Asn Val Ala Leu Tyr Leu Pro Asp Lys
                485                 490                 495

Leu Lys Tyr Asn Pro Ser Asn Val Glu Ile Ser Asp Asn Pro Asn Thr
            500                 505                 510
```

```
Tyr Asp Tyr Met Asn Lys Arg Val Ala Pro Gly Leu Val Asp Cys
            515                 520                 525

Tyr Ile Asn Leu Gly Ala Arg Trp Ser Leu Asp Tyr Met Asp Asn Val
        530                 535                 540

Asn Pro Phe Asn His His Arg Asn Ala Gly Leu Arg Tyr Arg Ser Met
545                 550                 555                 560

Leu Leu Gly Asn Gly Arg Tyr Val Pro Phe His Ile Gln Val Pro Gln
                565                 570                 575

Lys Phe Phe Ala Ile Lys Asn Leu Leu Leu Pro Gly Ser Tyr Thr
            580                 585                 590

Tyr Glu Trp Asn Phe Arg Lys Asp Val Asn Met Val Leu Gln Ser Ser
            595                 600                 605

Leu Gly Asn Asp Leu Arg Val Asp Gly Ala Ser Ile Lys Phe Glu Ser
            610                 615                 620

Ile Cys Leu Tyr Ala Thr Phe Phe Pro Met Ala His Asn Thr Ala Ser
625                 630                 635                 640

Thr Leu Glu Ala Met Leu Arg Asn Asp Thr Asn Asp Gln Ser Phe Asn
                645                 650                 655

Asp Tyr Leu Ser Ala Ala Asn Met Leu Tyr Pro Ile Pro Ala Asn Ala
                660                 665                 670

Thr Asn Val Pro Ile Ser Ile Pro Ser Arg Asn Trp Ala Ala Phe Arg
            675                 680                 685

Gly Trp Ala Phe Thr Arg Leu Lys Thr Lys Glu Thr Pro Ser Leu Gly
        690                 695                 700

Ser Gly Phe Asp Pro Tyr Tyr Thr Tyr Ser Gly Ser Ile Pro Tyr Leu
705                 710                 715                 720

Asp Gly Thr Phe Tyr Leu Asn His Thr Phe Lys Lys Val Ser Val Thr
                725                 730                 735

Phe Asp Ser Ser Val Ser Trp Pro Gly Asn Asp Arg Leu Leu Thr Pro
            740                 745                 750

Asn Glu Phe Glu Ile Lys Arg Ser Val Asp Gly Glu Gly Tyr Asn Val
            755                 760                 765

Ala Gln Cys Asn Met Thr Lys Asp Trp Phe Leu Ile Gln Met Leu Ala
            770                 775                 780

Asn Tyr Asn Ile Gly Tyr Gln Gly Phe Tyr Ile Pro Glu Ser Tyr Lys
785                 790                 795                 800

Asp Arg Met Tyr Ser Phe Phe Arg Asn Phe Gln Pro Met Ser Arg Gln
                805                 810                 815

Val Val Asp Glu Thr Lys Tyr Lys Asp Tyr Gln Gln Val Gly Ile Ile
            820                 825                 830

His Gln His Asn Asn Ser Gly Phe Val Gly Tyr Leu Ala Pro Thr Met
            835                 840                 845

Arg Glu Gly Gln Ala Tyr Pro Ala Asn Phe Pro Tyr Pro Leu Ile Gly
        850                 855                 860

Lys Thr Ala Val Asp Ser Val Thr Gln Lys Lys Phe Leu Cys Asp Arg
865                 870                 875                 880

Thr Leu Trp Arg Ile Pro Phe Ser Ser Asn Phe Met Ser Met Gly Ala
                885                 890                 895

Leu Thr Asp Leu Gly Gln Asn Leu Leu Tyr Ala Asn Ser Ala His Ala
                900                 905                 910

Leu Asp Met Thr Phe Glu Val Asp Pro Met Asp Glu Pro Thr Leu Leu
            915                 920                 925
```

Tyr Val Leu Phe Glu Val Phe Asp Val Val Arg Val His Gln Pro His
    930                 935                 940

Arg Gly Val Ile Glu Thr Val Tyr Leu Arg Thr Pro Phe Ser Ala Gly
945                 950                 955                 960

Asn Ala Thr Thr

<210> SEQ ID NO 6
<211> LENGTH: 2880
<212> TYPE: DNA
<213> ORGANISM: Artificial Sequence
<220> FEATURE:
<223> OTHER INFORMATION: Polynucleotide sequence encoding ChAd155 hexon

<400> SEQUENCE: 6

| | | | | | |
|---|---|---|---|---|---|
| atggcgaccc | catcgatgat | gccgcagtgg | tcgtacatgc | acatctcggg | ccaggacgcc | 60 |
| tcggagtacc | tgagccccgg | gctggtgcag | ttcgcccgcg | ccaccgagag | ctacttcagc | 120 |
| ctgagtaaca | agtttaggaa | ccccacggtg | gcgcccacgc | acgatgtgac | caccgaccgg | 180 |
| tctcagcgcc | tgacgctgcg | gttcattccc | gtggaccgag | aggacaccgc | gtactcgtac | 240 |
| aaggcgcggt | tcaccctggc | cgtgggcgac | aaccgcgtgc | tggacatggc | ctccacctac | 300 |
| tttgacatcc | gcggggtgct | ggaccggggt | cccactttca | gccctactc | tggcaccgcc | 360 |
| tacaactccc | tggcccccaa | gggcgctccc | aactcctgcg | agtgggagca | agaggaaact | 420 |
| caggcagttg | aagaagcagc | agaagaggaa | gaagaagatg | ctgacggtca | agctgaggaa | 480 |
| gagcaagcag | ctaccaaaaa | gactcatgta | tatgctcagg | ctcccctttc | tggcgaaaaa | 540 |
| attagtaaag | atggtctgca | ataggaacg | gacgctacag | ctacagaaca | aaaacctatt | 600 |
| tatgcagacc | ctacattcca | gcccgaaccc | caaatcgggg | agtcccagtg | gaatgaggca | 660 |
| gatgctacag | tcgccggcgg | tagagtgcta | aagaaatcta | ctcccatgaa | accatgctat | 720 |
| ggttcctatg | caagacccac | aaatgctaat | ggaggtcagg | gtgtactaac | ggcaaatgcc | 780 |
| cagggacagc | tagaatctca | ggttgaaatg | caattctttt | caacttctga | aaacgcccgt | 840 |
| aacgaggcta | caacattca | gcccaaattg | gtgctgtata | gtgaggatgt | gcacatggag | 900 |
| accccggata | cgcaccttc | ttacaagccc | gcaaaaagcg | atgacaattc | aaaaatcatg | 960 |
| ctgggtcagc | agtccatgcc | aacagacct | aattacatcg | gcttcagaga | caacttatc | 1020 |
| ggcctcatgt | attacaatag | cactggcaac | atgggagtgc | ttgcaggtca | ggcctctcag | 1080 |
| ttgaatgcag | tggtggactt | gcaagacaga | aacacagaac | tgtcctacca | gctcttgctt | 1140 |
| gattccatgg | gtgacagaac | cagatacttt | tccatgtgga | atcaggcagt | ggacagttat | 1200 |
| gacccagatg | ttagaattat | tgaaaatcat | ggaactgaag | acgagctccc | caactattgt | 1260 |
| ttccctctgg | gtggcatagg | ggtaactgac | acttaccagg | ctgttaaaac | caacaatggc | 1320 |
| aataacgggg | gccaggtgac | ttggacaaaa | gatgaaactt | ttgcagatcg | caatgaaata | 1380 |
| ggggtgggaa | acaatttcgc | tatggagatc | aacctcagtg | ccaacctgtg | agaaacttc | 1440 |
| ctgtactcca | acgtggcgct | gtacctacca | gacaagctta | agtacaaccc | ctccaatgtg | 1500 |
| gacatctctg | acaaccccaa | cacctacgat | tacatgaaca | agcgagtggt | ggccccgggg | 1560 |
| ctggtggact | gctacatcaa | cctgggcgcg | cgctggtcgc | tggactacat | ggacaacgtc | 1620 |
| aaccccttca | accaccaccg | caatgcgggc | ctgcgctacc | gctccatgct | cctgggcaac | 1680 |
| gggcgctacg | tgcccttcca | catccaggtg | ccccagaagt | tctttgccat | caagaacctc | 1740 |
| ctcctcctgc | cgggctccta | cacctacgag | tggaacttca | ggaaggatgt | caacatggtc | 1800 |
| ctccagagct | ctctgggtaa | cgatctcagg | gtggacgggg | ccagcatcaa | gttcgagagc | 1860 |

```
atctgcctct acgccacctt cttccccatg gcccacaaca cggcctccac gctcgaggcc    1920
atgctcagga acgacaccaa cgaccagtcc ttcaatgact acctctccgc cgccaacatg    1980
ctctacccca tacccgccaa cgccaccaac gtccccatct ccatcccctc gcgcaactgg    2040
gcggccttcc gcggctgggc cttcacccgc tcaagacca aggagacccc ctccctgggc    2100
tcgggattcg accectacta cacctactcg ggctccattc cctacctgga cggcaccttc    2160
tacctcaacc acactttcaa gaaggtctcg gtcaccttcg actcctcggt cagctggccg    2220
ggcaacgacc gtctgctcac ccccaacgag ttcgagatca gcgctcggt cgacggggag    2280 ggctacaacg tggcccagtg caacatgacc aaggactggt tcctggtcca gatgctggcc    2340
aactacaaca tcggctacca gggcttctac atcccagaga gctacaagga caggatgtac    2400
tccttcttca ggaacttcca gcccatgagc cggcaggtgg tggaccagac caagtacaag    2460
gactaccagg aggtgggcat catccaccag cacaacaact cgggcttcgt gggctacctc    2520
gcccccacca tgcgcgaggg acaggcctac cccgccaact tcccctatcc gctcataggc    2580
aagaccgcgg tcgacagcat cacccagaaa aagttcctct gcgaccgcac cctctggcgc    2640
atccccttct ccagcaactt catgtccatg ggtgcgctct cggacctggg ccagaacttg    2700
ctctacgcca actccgccca cgccctcgac atgaccttcg aggtcgaccc catggacgag    2760
cccacccttc tctatgttct gttcgaagtc tttgacgtgg tccgggtcca ccagccgcac    2820
cgcggcgtca tcgagaccgt gtacctgcgt acgcccttct cggccggcaa cgccaccacc    2880

<210> SEQ ID NO 7
<211> LENGTH: 37912
<212> TYPE: DNA
<213> ORGANISM: Artificial Sequence
<220> FEATURE:
<223> OTHER INFORMATION: Polynucleotide sequence encoding ChAd155#1434
      backbone construct

<400> SEQUENCE: 7
catcatcaat aatataccct attttggatt gaagccaata tgataatgag atgggcggcg     60
cggggcgggg cgcggggcgg gaggcgggtt tggggcgggg ccggcgggcg gggcggtgtg    120
gcggaagtgg actttgtaag tgtggcggat gtgacttgct agtgccgggc gcggtaaaag    180
tgacgttttc cgtgcgcgac aacgcccccg ggaagtgaca ttttttcccgc ggttttttacc    240 ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg ggtcattag ttcatagccc    600 atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg    1020
```

-continued

```
gcaccaaaat caacgggact ttccaaaatg tcgtaacaac tccgccccat tgacgcaaat    1080
gggcggtagg cgtgtacggt gggaggtcta tataagcaga gctctcccta tcagtgatag    1140
agatctccct atcagtgata gagatcgtcg acgagctcgt ttagtgaacc gtcagatcgc    1200
ctggagacgc catccacgct gttttgacct ccatagaaga caccgggacc gatccagcct    1260
ccgcggccgg gaacggtgca ttggaacgcg gattccccgt gccaagagtg agatcttccg    1320
tttatctagg taccgggccc cccctcgagg tcgacggtat cgataagctt cacgctgccg    1380
caagcactca gggcgcaagg gctgctaaag gaagcggaac acgtagaaag ccagtccgca    1440
gaaacggtgc tgaccccgga tgaatgtcag ctactgggct atctggacaa gggaaaacgc    1500
aagcgcaaag agaaagcagg tagcttgcag tgggcttaca tggcgatagc tagactgggc    1560
ggttttatgg acagcaagcg aaccggaatt gccagctggg gcgccctctg taaggttgg     1620 gaagccctgc aaagtaaact ggatggcttt cttgccgcca aggatctgat ggcgcagggg    1680
atcaagatct aaccaggagc tatttaatgg caacagttaa ccagctggta cgcaaaccac    1740
gtgctcgcaa agttgcgaaa agcaacgtgc ctgcgctgga agcatgcccg caaaaacgtg    1800
gcgtatgtac tcgtgtatat actaccactc ctaaaaaacc gaactccgcg ctgcgtaaag    1860
tatgccgtgt tcgtctgact aacggtttcg aagtgacttc ctacatcggt ggtgaaggtc    1920
acaacctgca ggagcactcc gtgatcctga tccgtggcgg tcgtgttaaa gacctcccgg    1980
gtgttcgtta ccacaccgta cgtggtgcgc ttgactgctc cggcgttaaa gaccgtaagc    2040
aggctcgttc caagtatggc gtgaagcgtc ctaaggctta atggtagatc tgatcaagag    2100
acaggatgac ggtcgtttcg catgcttgaa caagatggat tgcacgcagg ttctccggcc    2160
gcttgggtgg agaggctatt cggctatgac tgggcacaac agacaatcgg ctgctctgat    2220
gccgccgtgt tccggctgtc agcgcagggg cgcccggttc ttttttgtcaa gaccgacctg    2280 tccggtgccc tgaatgaact gcaggacgag gcagcgcggc tatcgtggct ggccacgacg    2340
ggcgttcctt gcgcagctgt gctcgacgtt gtcactgaag cgggaaggga ctggctgcta    2400
ttgggcgaag tgccggggca ggatctcctg tcatctcacc ttgctcctgc cgagaaagta    2460
tccatcatgg ctgatgcaat gcggcggctg catacgcttg atccggctac ctgcccattc    2520
gaccaccaag cgaaacatcg catcgagcga gcacgtactc ggatggaagc cggtcttgtc    2580
gatcaggatg atctggacga agagcatcag gggctcgcgc cagccgaact gttcgccagg    2640
ctcaaggcgc gcatgcccga cggcgaggat ctcgtcgtga cccatggcga tgcctgcttg    2700
ccgaatatca tggtggaaaa tggccgcttt tctggattca tcgactgtgg ccggctgggt    2760
gtggcggacc gctatcagga catagcgttg gctacccgtg atattgctga agagcttggc    2820
ggcgaatggg ctgaccgctt cctcgtgctt tacggtatcg ccgctcccga ttcgcagcgc    2880
atcgccttct atcgccttct tgacgagttc ttctgagcgg actctgggg ttcgaaatga     2940 ccgaccaagc gacgcccaac ctgccatcac gagatttcga ttccaccgcc gccttctatg    3000
aaaggttggg cttcggaatc gttttccggg acgccggctg atgatcctc cagcgcgggg     3060 atctcatgct ggagttcttc gcccaccccg ggctcgatcc cctcgggggg aatcagaatt    3120
cagtcgacag cggccgcgat ctgctgtgcc ttctagttgc cagccatctg ttgtttgccc    3180
ctcccccgtg ccttccttga ccctggaagg tgccactccc actgtccttt cctaataaaa    3240
tgaggaaatt gcatcgcatt gtctgagtag gtgtcattct attctggggg gtggggtggg    3300
gcaggacagc aagggggagg attgggaaga caatagcagg catgctgggg atgcggtggg    3360
```

| | |
|---|---|
| ctctatggcc gatcagcgat cgctgaggtg ggtgagtggg cgtggcctgg ggtggtcatg | 3420 |
| aaaatatata agttgggggt cttagggtct ctttatttgt gttgcagaga ccgccggagc | 3480 |
| catgagcggg agcagcagca gcagcagtag cagcagcgcc ttggatggca gcatcgtgag | 3540 |
| cccttatttg acgacgcgga tgccccactg ggccggggtg cgtcagaatg tgatgggctc | 3600 |
| cagcatcgac ggccgacccg tcctgcccgc aaattccgcc acgctgacct atgcgaccgt | 3660 |
| cgcggggacg ccgttggacg ccaccgccgc cgccgccgcc accgcagccg cctcggccgt | 3720 |
| gcgcagcctg gccacggact ttgcattcct gggaccactg gcgacagggg ctacttctcg | 3780 |
| ggccgctgct gccgccgttc gcgatgacaa gctgaccgcc ctgctggcgc agttggatgc | 3840 |
| gcttactcgg gaactgggtg acctttctca gcaggtcatg gccctgcgcc agcaggtctc | 3900 |
| ctccctgcaa gctggcggga atgcttctcc cacaaatgcc gtttaagata aataaaacca | 3960 |
| gactctgttt ggattaaaga aaagtagcaa gtgcattgct ctctttattt cataattttc | 4020 |
| cgcgcgcgat aggccctaga ccagcgttct cggtcgttga gggtgcggtg tatcttctcc | 4080 |
| aggacgtggt agaggtggct ctggacgttg agatacatgg gcatgagccc gtcccggggg | 4140 |
| tggaggtagc accactgcag agcttcatgc tccggggtgg tgttgtagat gatccagtcg | 4200 |
| tagcaggagc gctgggcatg gtgcctaaaa atgtccttca gcagcaggcc gatggccagg | 4260 |
| gggaggccct tggtgtaagt gtttacaaaa cggttaagtt gggaagggtg cattcgggga | 4320 |
| gagatgatgt gcatcttgga ctgtattttt agattggcga tgtttccgcc cagatccctt | 4380 |
| ctgggattca tgttgtgcag gaccaccagt acagtgtatc cggtgcactt ggggaatttg | 4440 |
| tcatgcagct tagagggaaa agcgtggaag aacttggaga cgcctttgtg gcctcccaga | 4500 |
| ttttccatgc attcgtccat gatgatggca atgggcccgc gggaggcagc ttgggcaaag | 4560 |
| atatttctgg ggtcgctgac gtcgtagttg tgttccaggg tgaggtcgtc ataggccatt | 4620 |
| tttacaaagc gcgggcggag ggtgcccgac tgggggatga tggtcccctc tggccctggg | 4680 |
| gcgtagttgc cctcgcagat ctgcatttcc caggccttaa tctcggaggg gggaatcata | 4740 |
| tccacctgcg gggcgatgaa gaaaacggtt tccggagccg gggagattaa ctgggatgag | 4800 |
| agcaggtttc taagcagctg tgattttcca caaccggtgg gcccataaat aacacctata | 4860 |
| accggttgca gctggtagtt tagagagctg cagctgccgt cgtcccggag gagggggggcc | 4920 |
| acctcgttga gcatgtccct gacgcgcatg ttctccccga ccagatccgc cagaaggcgc | 4980 |
| tcgccgccca gggacagcag ctcttgcaag gaagcaaagt ttttcagcgg cttgaggccg | 5040 |
| tccgccgtgg gcatgttttt cagggtctgg ctcagcagct ccaggcggtc ccagagctcg | 5100 |
| gtgacgtgct ctacggcatc tctatccagc atatctcctc gtttcgcggg ttggggcgac | 5160 |
| tttcgctgta gggcaccaag cggtggtcgt ccagcggggc cagagtcatg tccttccatg | 5220 |
| ggcgcagggt cctcgtcagg gtggtctggg tcacggtgaa ggggtgcgct ccgggctgag | 5280 |
| cgcttgccaa ggtgcgcttg aggctggttc tgctggtgct gaagcgctgc cggtcttcgc | 5340 |
| cctgcgcgtc ggccaggtag catttgacca tggtgtcata gtccagcccc tccgcggcgt | 5400 |
| gtcccttggc gcgcagcttg cccttggagg tggcgccgca cgaggggcag agcaggctct | 5460 |
| tgagcgcgta gagcttgggg gcgaggaaga ccgattcggg ggagtaggcg tccgcgccgc | 5520 |
| agaccccgca cacggtctcg cactccacca gccaggtgag ctcggggcgc gccgggtcaa | 5580 |
| aaaccaggtt tccccatgc tttttgatgc gtttcttacc tcgggtctcc atgaggtggt | 5640 |
| gtccccgctc ggtgacgaag aggctgtccg tgtctccgta accgacttg aggggtcttt | 5700 |
| tctccagggg ggtccctcgg tcttcctcgt agaggaactc ggaccactct gagacgaagg | 5760 |

```
cccgcgtcca ggccaggacg aaggaggcta tgtgggaggg gtagcggtcg ttgtccacta    5820
gggggtccac cttctccaag gtgtgaagac acatgtcgcc ttcctcggcg tccaggaagg    5880
tgattggctt gtaggtgtag gccacgtgac cgggggttcc tgacgggggg gtataaaagg    5940
gggtgggggc gcgctcgtcg tcactctctt ccgcatcgct gtctgcgagg ccagctgct    6000 ggggtgagta ttccctctcg aaggcgggca tgacctccgc gctgaggttg tcagtttcca    6060
aaaacgagga ggatttgatg ttcacctgtc ccgaggtgat acctttgagg gtacccgcgt    6120
ccatctggtc agaaaacacg atcttttat tgtccagctt ggtggcgaac gacccgtaga    6180
gggcgttgga gagcagcttg gcgatggagc gcagggtctg gttcttgtcc ctgtcggcgc    6240
gctccttggc cgcgatgttg agctgcacgt actcgcgcgc gacgcagcgc cactcgggga    6300
agacggtggt gcgctcgtcg ggcaccaggc gcacgcgcca gccgcggttg tgcagggtga    6360
ccaggtccac gctggtggcg acctcgccgc gcaggcgctc gttggtccag cagagacggc    6420
cgcccttgcg cgagcagaag gggggcaggg ggtcgagctg ggtctcgtcc gggggggtccg   6480 cgtccacggt gaaaaccccg gggcgcaggc gcgcgtcgaa gtagtctatc ttgcaacctt    6540
gcatgtccag cgcctgctgc cagtcgcggg cggcgagcgc gcgctcgtag gggttgagcg    6600
gcgggcccca gggcatgggg tgggtgagtg cggaggcgta catgccgcag atgtcataga    6660
cgtagagggg ctcccgcagg accccgatgt aggtggggta gcagcggccg ccgcggatgc    6720
tggcgcgcac gtagtcatac agctcgtgcg aggggggcgag gaggtcgggg cccaggttgg    6780
tgcgggcggg gcgctccgcg cggaagacga tctgcctgaa gatggcatgc gagttggaag    6840
agatggtggg gcgctggaag acgttgaagc tggcgtcctg caggccgacg gcgtcgcgca    6900
cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttctttttcc    7020
acagctcgcg gttgaggaca aactcttcgc ggtctttcca gtactcttgg atcgggaaac    7080
cgtccggttc cgaacggtaa gagcctagca tgtagaactg gttgacggcc tggtaggcgc    7140
agcagccctt ctccacgggg agggcgtagg cctgcgcggc cttgcggagc gaggtgtggg    7200
tcagggcgaa ggtgtccctg accatgactt tgaggtactg gtgcttgaag tcggagtcgt    7260
cgcagccgcc ccgctcccag agcgagaagt cggtgcgctt cttggagcgg gggttgggca    7320
gagcgaaggt gacatcgttg aagaggattt tgcccgcgcg gggcatgaag ttgcgggtga    7380
tgcggaaggg ccccggcact tcagagcggt tgttgatgac ctgggcggcg agcacgatct    7440
cgtcgaagcc gttgatgttg tgcccacga tgtagagttc caggaagcgg ggccggccct    7500
ttacggtggg cagcttcttt agctcttcgt aggtgagctc ctcgggcgag gcgaggccgt    7560
gctcggccag ggcccagtcc gcgaggtgcg ggttgtctct gaggaaggac ttccagaggt    7620
cgcgggccag gagggtctgc aggcggtctc tgaaggtcct gaactggcgg cccacggcca    7680
ttttttcggg ggtgatgcag tagaaggtga gggggtcttg ctgccagcgg tcccagtcga    7740
gctgcagggc gaggtcgcgc gcggcggtga ccaggcgctc gtcgccccg aatttcatga    7800 ccagcatgaa gggcacgagc tgcttttccga aggcccccat ccaagtgtag gtctctacat    7860
cgtaggtgac aaagaggcgc tccgtgcgag gatgcgagcc gatcgggaag aactggatct    7920
cccgccacca gttggaggag tggctgttga tgtggtggaa gtagaagtcc cgtcgccggg    7980
ccgaacactc gtgctggctt ttgtaaaagc gagcgcagta ctggcagcgc tgcacgggct    8040
gtacctcatg cacgagatgc acctttcgcc cgcgcacgag gaagccgagg ggaaatctga    8100
```

```
gcccccccgcc tggctcgcgg catggctggt tctcttctac tttggatgcg tgtccgtctc   8160
cgtctggctc ctcgaggggt gttacggtgg agcggaccac cacgccgcgc gagccgcagg    8220
tccagatatc ggcgcgcggc ggtcggagtt tgatgacgac atcgcgcagc tgggagctgt   8280
ccatggtctg gagctcccgc ggcggcggca ggtcagccgg gagttcttgc aggttcacct   8340
cgcagagtcg ggccagggcg cggggcaggt ctaggtggta cctgatctct aggggcgtgt   8400
tggtggcggc gtcgatggct tgcaggagcc cgcagccccg gggggcgacg acggtgcccc   8460
gcggggtggt ggtggtggtg gcggtgcagc tcagaagcgg tgccgcgggc gggcccccgg   8520
aggtaggggg ggctccggtc ccgcgggcag gggcggcagc ggcacgtcgg cgtggagcgc   8580
gggcaggagt tggtgctgtg cccggaggtt gctggcgaag gcgacgacgc ggcggttgat   8640
ctcctggatc tggcgcctct gcgtgaagac gacgggcccg gtgagcttga acctgaaaga   8700
gagttcgaca gaatcaatct cggtgtcatt gaccgcggcc tggcgcagga tctcctgcac   8760
gtctcccgag ttgtcttggt aggcgatctc ggccatgaac tgctcgatct cttcctcctg   8820
gaggtctccg cgtccggcgc gttccacggt ggccgccagg tcgttggaga tgcgcccccat  8880 gagctgcgag aaggcgttga gtccgccctc gttccagact cggctgtaga ccacgccccc   8940
ctggtcatcg cgggcgcgca tgaccacctg cgcgaggttg agctccacgt gccgcgcgaa   9000
gacggcgtag ttgcgcagac gctggaagag gtagttgagg gtggtggcgg tgtgctcggc   9060
cacgaagaag ttcatgaccc agcggcgcaa cgtggattcg ttgatgtccc caaggcctc    9120 cagccgttcc atggcctcgt agaagtccac ggcgaagttg aaaaactggg agttgcgcgc   9180
cgacacggtc aactcctcct ccagaagacg gatgagctcg gcgacggtgt cgcgcacctc   9240
gcgctcgaag gctatgggga tctcttcctc cgctagcatc accacctcct cctcttcctc   9300
ctcttctggc acttccatga tggcttcctc ctcttcgggg ggtggcggcg gcggcggtgg   9360 gggaggggggc gctctgcgcc ggcggcggcg caccgggagg cggtccacga agcgcgcgat  9420
catctccccg cggcggcggc gcatggtctc ggtgacggcg cggccgttct cccggggccg   9480
cagttggaag acgccgccgg acatctggtg ctggggcggg tggccgtgag gcagcgagac   9540
ggcgctgacg atgcatctca acaattgctg cgtaggtacg ccgccgaggg acctgaggga   9600
gtccatatcc accggatccg aaaaccttc gaggaaggcg tctaaccagt cgcagtcgca    9660
aggtaggctg agcaccgtgg cgggcggcgg ggggtggggg gagtgtctgg cggaggtgct   9720
gctgatgatg taattgaagt aggcggactt gacacggcgg atggtcgaca ggagcaccat   9780
gtccttgggt ccggcctgct ggatgcgagg gcggtcggct atgccccagg cttcgttctg   9840
gcatcggcgc aggtccttgt agtagtcttg catgagcctt tccaccggca cctcttctcc   9900 ttcctctttct gcttcttcca tgtctgcttc ggccctgggg cggcgccgcg ccccctgcc   9960 ccccatgcgc gtgaccccga accccctgag cggttggagc agggccaggt cggcgacgac  10020
gcgctcggcc aggatggcct gctgcacctg cgtgagggtg gtttggaagt catccaagtc  10080
cacgaagcgg tggtaggcgc ccgtgttgat ggtgtaggtg cagttggcca tgacggacca  10140
gttgacggtc tggtggcccg gttgcgacat ctcggtgtac ctgagtcgcg agtaggcgcg  10200
ggagtcgaag acgtagtcgt tgcaagtccg caccaggtac tggtagccca ccaggaagtg  10260
cggcggcggc tggcggtaga ggggccagcg cagggtggcg ggggctccgg gggccaggtc  10320
ttccagcatg aggcggtggt aggcgtagat gtacctggac atccaggtga tacccgcggc  10380
ggtggtggag gcgcgcggga agtcgcgcac ccggttccag atgttgcgca ggggcagaaa  10440
gtgctccatg gtaggcgtgc tctgtccagt cagacgcgcg cagtcgttga tactctagac  10500
```

```
cagggaaaac gaaagccggt cagcgggcac tcttccgtgg tctggtgaat agatcgcaag   10560
ggtatcatgg cggagggcct cggttcgagc cccgggtccg ggccgacgg tccgccatga    10620 tccacgcggt taccgcccgc gtgtcgaacc caggtgtgcg acgtcagaca acggtggagt   10680
gttccttttg gcgttttctct ggccgggcgc cggcgccgcg taagagacta agccgcgaaa  10740
gcgaaagcag taagtggctc gctccccgta gccggaggga tccttgctaa gggttgcgtt   10800
gcggcgaacc ccggttcgaa tcccgtactc gggccggccg gacccgcggc taaggtgttg   10860
gattggcctc cccctcgtat aaagaccccg cttgcggatt gactccggac acggggacga   10920
gcccctttta tttttgcttt ccccagatgc atccggtgct gcggcagatg cgcccccgc    10980 cccagcagca gcaacaacac cagcaagagc ggcagcaaca gcagcgggag tcatgcaggg   11040 cccccctcacc caccctcggc gggccggcca cctcggcgtc cgcggccgtg tctggcgcct  11100
gcggcggcgg cgggggggccg gctgacgacc ccgaggagcc cccgcggcgc agggccagac   11160
actacctgga cctggaggag ggcgagggcc tggcgcggct gggggcgccg tctcccgagc   11220
gccacccgcg ggtgcagctg aagcgcgact cgcgcgaggc gtacgtgcct cggcagaacc   11280
tgttcaggga ccgcgcgggc gaggagcccg aggagatgcg ggacaggagg ttcagcgcag   11340
ggcgggagct gcggcagggg ctgaaccgcg agcggctgct gcgcgaggag gactttgagc   11400
ccgacgcgcg gacggggatc agcccgcgcg gcgcgcacgt ggcggccgcc gacctggtga   11460
cggcgtacga gcagacggtg aaccaggaga tcaacttcca aaagagtttc aacaaccacg   11520
tgcgcacgct ggtggcgcgc gaggaggtga ccatcgggct gatgcacctg tgggactttg   11580
taagcgcgct ggtgcagaac cccaacagca agcctctgac ggcgcagctg ttcctgatag   11640
tgcagcacag cagggacaac gaggcgttta gggacgcgct gctgaacatc accgagcccg   11700
agggtcggtg gctgctggac ctgattaaca tcctgcagag catagtggtg caggagcgca   11760
gcctgagcct ggccgacaag gtggcggcca tcaactactc gatgctgagc ctgggcaagt   11820
tttacgcgcg caagatctac cagacgccgt acgtgcccat agacaaggag gtgaagatcg   11880 acggtttta catgcgcatg gcgctgaagg tgctcaccct gagcgacgac ctgggcgtgt    11940
accgcaacga gcgcatccac aaggccgtga gcgtgagccg gcggcgcgag ctgagcgacc   12000
gcgagctgat gcacagcctg cagcgggcgc tggcgggcgc cggcagcggc gacagggagg   12060
cggagtccta cttcgatgcg ggggcggacc tgcgctgggc gccagccgg cgggccctgg    12120 aggccgcggg ggtccgcgag gactatgacg aggacggcga ggaggatgag gagtacgagc   12180
tagaggaggg cgagtacctg gactaaaccg cgggtggtgt ttccggtaga tgcaagaccc   12240
gaacgtggtg gacccggcgc tgcgggcggc tctgcagagc cagccgtccg gccttaactc   12300
ctcagacgac tggcgacagg tcatggaccg catcatgtcg ctgacggcgc gtaacccgga   12360
cgcgttccgg cagcagccgc aggccaacag gctctccgcc atcctggagg cggtggtgcc   12420
tgcgcgctcg aaccccacgc acgagaaggt gctggccata gtgaacgcgc tggccgagaa   12480
cagggccatc cgcccggacg aggccgggct ggtgtacgac gcgctgctgc agcgcgtggc   12540
ccgctacaac agcggcaacg tgcagaccaa cctggaccgg ctggtggggg acgtgcgcga   12600
ggcggtggcg cagcgcgagc gcgcggatcg gcagggcaac ctgggctcca tggtggcgct   12660
gaatgccttc ctgagcacgc agccggccaa cgtgccgcgg gggcaggaag actacaccaa   12720
ctttgtgagc gcgctgcggc tgatggtgac cgagaccccc cagagcgagg tgtaccagtc   12780
gggcccggac tacttcttcc agaccagcag acagggcctg cagacggtga acctgagcca   12840
```

```
ggctttcaag aacctgcggg ggctgtgggg cgtgaaggcg cccaccggcg accgggcgac    12900
ggtgtccagc ctgctgacgc ccaactcgcg cctgctgctg ctgctgatcg cgccgttcac    12960
ggacagcggc agcgtgtccc gggacaccta cctggggcac ctgctgaccc tgtaccgcga    13020
ggccatcggg caggcgcagg tggacgagca caccttccag gagatcacca gcgtgagccg    13080
cgcgctgggg caggaggaca cgagcagcct ggaggcgact ctgaactacc tgctgaccaa    13140
ccggcggcag aagattccct cgctgcacag cctgacctcc gaggaggagc gcatcttgcg    13200
ctacgtgcag cagagcgtga gcctgaacct gatgcgcgac ggggtgacgc ccagcgtggc    13260
gctggacatg accgcgcgca acatggaacc gggcatgtac gccgcgcacc ggccttacat    13320
caaccgcctg atggactacc tgcatcgcgc ggcggccgtg aaccccgagt actttaccaa    13380
cgccatcctg aacccgcact ggctcccgcc gcccgggttc tacagcgggg gcttcgaggt    13440
cccggagacc aacgatggct tcctgtggga cgacatggac gacagcgtgt tctccccgcg    13500
gccgcaggcg ctggcggaag cgtccctgct gcgtcccaag aaggaggagg aggaggaggc    13560
gagtcgccgc cgcggcagca gcggcgtggc ttctctgtcc gagctggggg cggcagccgc    13620
cgcgcgcccc gggtccctgg gcggcagccc cttccgagc ctggtggggt ctctgcacag    13680
cgagcgcacc acccgccctc ggctgctggg cgaggacgag tacctgaata actccctgct    13740
gcagccggtg cgggagaaaa acctgcctcc cgccttcccc aacaacggga tagagagcct    13800
ggtggacaag atgagcagat ggaagaccta tgcgcaggag cacagggacg cgcctgcgct    13860
ccggccgccc acgcggcgcc agcgccacga ccggcagcgg gggctggtgt gggatgacga    13920
ggactccgcg gacgatagca gcgtgctgga cctgggaggg agcggcaacc cgttcgcgca    13980
cctgcgcccc cgcctgggga ggatgtttta aaaaaaaaaa aaaaaagcaa gaagcatgat    14040
gcaaaaatta aataaaactc accaaggcca tggcgaccga gcgttggttt cttgtgttcc    14100
cttcagtatg cggcgcgcgg cgatgtacca ggagggacct cctccctctt acgagagcgt    14160
ggtgggcgcg gcggcggcgg cgccctcttc tccctttgcg tcgcagctgc tggagccgcc    14220
gtacgtgcct ccgcgctacc tgcggcctac gggggggaga aacagcatcc gttactcgga    14280
gctggcgccc ctgttcgaca ccacccgggt gtacctggtg gacaacaagt cggcggacgt    14340
ggcctccctg aactaccaga acgaccacag caatttttg accacggtca tccagaacaa    14400
tgactacagc ccgagcgagg ccagcaccca gaccatcaat ctggatgacc ggtcgcactg    14460
gggcggcgac ctgaaaacca tcctgcacac caacatgccc aacgtgaacg agttcatgtt    14520
caccaataag ttcaaggcgc gggtgatggt gtcgcgctcg cacaccaagg aagaccgggt    14580
ggagctgaag tacgagtggg tggagttcga gctgccagag ggcaactact ccgagaccat    14640
gaccattgac ctgatgaaca acgcgatcgt ggagcactat ctgaaagtgg gcaggcagaa    14700 cgggggtcctg gagagcgaca tcggggtcaa gttcgacacc aggaacttcc gcctggggct    14760
ggaccccgtg accgggctgg ttatgcccgg ggtgtacacc aacgaggcct tccatcccga    14820
catcatcctg ctgcccggct gcgggtgga cttcacttac agccgcctga gcaacctcct    14880
gggcatccgc aagcggcagc ccttccagga gggcttcagg atcacctacg aggacctgga    14940 gggggggcaac atccccgcgc tcctcgatgt ggaggcctac caggatagct tgaaggaaaa    15000
tgaggcggga caggaggata ccgcccccgc cgcctccgcc gccgccgagc agggcgagga    15060
tgctgctgac accgcggccg cggacggggc agaggccgac cccgctatgg tggtggaggc    15120 tccccgagcag gaggaggaca tgaatgacag tgccggtgcgc ggagacacct tcgtcacccg    15180
gggggaggaa aagcaagcgg aggccgaggc cgcggccgag gaaaagcaac tggcggcagc    15240
```

```
agcggcggcg gcggcgttgg ccgcggcgga ggctgagtct gagggggacca agcccgccaa    15300 ggagcccgtg attaagcccc tgaccgaaga tagcaagaag cgcagttaca acctgctcaa    15360
ggacagcacc aacaccgcgt accgcagctg gtacctggcc tacaactacg gcgacccgtc    15420 gacggggtg cgctcctgga ccctgctgtg cacgccggac gtgacctgcg gctcggagca     15480
ggtgtactgg tcgctgcccg acatgatgca agaccccgtg accttccgct ccacgcggca    15540
ggtcagcaac ttcccggtgg tgggcgccga gctgctgccc gtgcactcca agagcttcta    15600
caacgaccag gccgtctact cccagctcat ccgccagttc acctctctga cccacgtgtt    15660
caatcgcttt cctgagaacc agattctggc gcgcccgccc gccccacca tcaccaccgt     15720 cagtgaaaac gttcctgctc tcacagatca cgggacgcta ccgctgcgca acagcatcgg    15780
aggagtccag cgagtgaccg ttactgacgc cagacgccgc acctgcccct acgtttacaa    15840
ggccttgggc atagtctcgc cgcgcgtcct ttccagccgc acttttgag caacaccacc     15900 atcatgtcca tcctgatctc acccagcaat aactccggct ggggactgct gcgcgcgccc    15960
agcaagatgt tcggaggggc gaggaagcgt tccgagcagc accccgtgcg cgtgcgcggg    16020
cacttccgcg cccctgggg agcgcacaaa cgcggccgcg cggggcgcac caccgtggac     16080
gacgccatcg actcggtggt ggagcaggcg cgcaactaca ggcccgcggt ctctaccgtg    16140
gacgcggcca tccagaccgt ggtgcgggcg cgcggcggt acgccaagct gaagagccgc     16200
cggaagcgcg tggcccgccg ccaccgccgc cgacccgggg ccgccgccaa acgcgccgcc    16260 gcggcccctgc ttcgccgggc caagcgcacg ggccgccgcg ccgccatgag ggccgcgcgc    16320
cgcttggccg ccggcatcac cgccgccacc atggccccc gtacccgaag acgcgcggcc    16380
gccgccgccg ccgccgccat cagtgacatg ccagcaggc gccggggcaa cgtgtactgg    16440
gtgcgcgact cggtgaccgg cacgcgcgtg cccgtgcgct tccgcccccc gcggacttga    16500
gatgatgtga aaaacaaca ctgagtctcc tgctgttgtg tgtatcccag cggcggcggc     16560
gcgcgcagcg tcatgtccaa gcgcaaaatc aaagaagaga tgctccaggt cgtcgcgccg    16620
gagatctatg gccccccgaa gaaggaagag caggattcga agccccgcaa gataaagcgg    16680
gtcaaaaaga aaagaaaga tgatgacgat gccgatgggg aggtggagtt cctgcgcgcc    16740
acggcgccca ggcgcccggt gcagtggaag ggccggcgcg taaagcgcgt cctgcgcccc    16800
ggcaccgcgg tggtcttcac gcccggcgag cgctccaccc ggactttcaa gcgcgtctat    16860
gacgaggtgt acggcgacga agacctgctg gagcaggcca acgagcgctt cggagagttt    16920
gcttacggga agcgtcagcg ggcgctgggg aaggaggacc tgctggcgct gccgctggac    16980
cagggcaacc ccacccccag tctgaagccc gtgaccctgc agcaggtgct gccgagcagc    17040
gcaccctccg aggcgaagcg gggtctgaag cgcgagggcg gcgacctggc gccaccgtg    17100 cagctcatgg tgcccaagcg gcagaggctg gaggatgtgc tggagaaaat gaaagtagac    17160
cccggtctgc agccggacat cagggtccgc cccatcaagc aggtggcgcc gggcctcggc    17220
gtgcagaccg tggacgtggt catccccacc ggcaactccc ccgccgccgc caccactacc    17280
gctgcctcca cggacatgga gacacagacc gatcccgccg cagccgcagc cgcagccgcc    17340
gccgcgacct cctcggcgga ggtgcagacg gaccctggc tgccgccggc gatgtcagct    17400
ccccgcgcgc gtcgcgggcg caggaagtac ggcgccgcca acgcgctcct gcccgagtac    17460
gccttgcatc cttccatcgc gcccacccc ggctaccgag gctataccta ccgcccgcga    17520
agagccaagg gttccacccg ccgtcccgc cgacgcgccg ccgccaccac ccgccgccgc    17580
```

```
cgccgcagac gccagcccgc actggctcca gtctccgtga ggaaagtggc gcgcgacgga    17640
cacaccctgg tgctgcccag ggcgcgctac caccccagca tcgtttaaaa gcctgttgtg    17700
gttcttgcag atatggccct cacttgccgc ctccgtttcc cggtgccggg ataccgagga    17760
ggaagatcgc gccgcaggag gggtctggcc ggccgcggcc tgagcggagg cagccgccgc    17820
gcgcaccggc ggcgacgcgc caccagccga cgcatgcgcg gcggggtgct gcccctgtta    17880 atcccctga tcgccgcggc gatcggcgcc gtgcccggga tcgcctccgt ggccttgcaa     17940
gcgtcccaga ggcattgaca gacttgcaaa cttgcaaata tggaaaaaaa aaccccaata    18000
aaaaagtcta gactctcacg ctcgcttggt cctgtgacta ttttgtagaa tggaagacat    18060
caactttgcg tcgctggccc cgcgtcacgg ctcgcgcccg ttcctgggac actggaacga    18120
tatcggcacc agcaacatga gcggtggcgc cttcagttgg ggctctctgt ggagcggcat    18180
taaaagtatc gggtctgccg ttaaaaatta cggctcccgg gcctggaaca gcagcacggg    18240
ccagatgttg agagacaagt tgaaagagca gaacttccag cagaaggtgg tggagggcct    18300
ggcctccggc atcaacgggg tggtggacct ggccaaccag gccgtgcaga ataagatcaa    18360
cagcagactg gaccccggc cgccggtgga ggaggtgccg ccggcgctgg agacggtgtc     18420
ccccgatggg cgtggcgaga gcgcccgcg gcccgatagg gaagagacca ctctggtcac     18480
gcagaccgat gagccgcccc cgtatgagga ggccctgaag caaggtctgc ccaccacgcg    18540
gcccatcgcg cccatggcca ccggggtggt gggccgccac accccgcca cgctggactt     18600 gcctccgccc gccgatgtgc cgcagcagca gaaggcggca cagccgggcc cgcccgcgac    18660
cgcctcccgt tcctccgccg gtcctctgcg ccgcgcggcc agcggccccc gcggggggt     18720 cgcgaggcac ggcaactggc agagcacgct gaacagcatc gtgggtctgg gggtgcggtc    18780
cgtgaagcgc cgccgatgct actgaatagc ttagctaacg tgttgtatgt gtgtatgcgc    18840
cctatgtcgc cgccagagga gctgctgagt cgccgccgtt cgcgcgccca ccaccaccgc    18900
cactccgccc ctcaagatgg cgaccccatc gatgatgccg cagtggtcgt acatgcacat    18960
ctcgggccag gacgcctcgg agtacctgag ccccgggctg gtgcagttcg cccgcgccac    19020
cgagagctac ttcagcctga gtaacaagtt taggaacccc acggtggcgc ccacgcacga    19080
tgtgaccacc gaccggtctc agcgcctgac gctgcggttc attcccgtgg accgcgagga    19140
caccgcgtac tcgtacaagg cgcggttcac cctggccgtg ggcgacaacc gcgtgctgga    19200
catggcctcc acctactttg acatccgcgg ggtgctggac cggggtccca cttttcaagcc   19260 ctactctggc accgcctaca actccctggc ccccaagggc gctcccaact cctgcgagtg    19320
ggagcaagag gaaactcagg cagttgaaga agcagcagaa gaggaagaag aagatgctga    19380
cggtcaagct gaggaagagc aagcagctac caaaaagact catgtatatg ctcaggctcc    19440
cctttctggc gaaaaaatta gtaaagatgg tctgcaaata ggaacggacg ctacagctac    19500
agaacaaaaa cctatttatg cagaccctac attccagccc gaaccccaaa tcggggagtc    19560
ccagtggaat gaggcagatg ctacagtcgc cggcggtaga gtgctaaaga aatctactcc    19620
catgaaacca tgctatggtt cctatgcaag acccacaaat gctaatggag gtcagggtgt    19680
actaacggca aatgcccagg acagctagaa atctcaggtt gaaatgcaat tcttttcaac    19740
ttctgaaaac gcccgtaacg aggctaacaa cattcagccc aaattggtgc tgtatagtga    19800
ggatgtgcac atggagaccc cggatacgca cctttcttac aagcccgcaa aaagcgatga    19860
caattcaaaa atcatgctgg gtcagcagtc catgcccaac agacctaatt acatcggctt    19920
cagagacaac tttatcggcc tcatgtatta caatagcact ggcaacatgg gagtgcttgc    19980
```

```
aggtcaggcc tctcagttga atgcagtggt ggacttgcaa gacagaaaca cagaactgtc   20040
ctaccagctc ttgcttgatt ccatgggtga cagaaccaga tacttttcca tgtggaatca   20100
ggcagtggac agttatgacc cagatgttag aattattgaa aatcatggaa ctgaagacga   20160
gctccccaac tattgtttcc ctctgggtgg cataggggta actgacactt accaggctgt   20220
taaaaccaac aatggcaata acggggccca ggtgacttgg acaaaagatg aaacttttgc   20280
agatcgcaat gaaatagggg tgggaaacaa tttcgctatg gagatcaacc tcagtgccaa   20340
cctgtggaga aacttcctgt actccaacgt ggcgctgtac ctaccagaca agcttaagta   20400
caacccctcc aatgtggaca tctctgacaa ccccaacacc tacgattaca tgaacaagcg   20460
agtggtggcc ccggggctgg tggactgcta catcaacctg ggcgcgcgct ggtcgctgga   20520
ctacatggac aacgtcaacc ccttcaacca ccaccgcaat gcgggcctgc gctaccgctc   20580
catgctcctg ggcaacgggc gctacgtgcc cttccacatc caggtgcccc agaagttctt   20640
tgccatcaag aacctcctcc tcctgccggg ctcctacacc tacgagtgga acttcaggaa   20700
ggatgtcaac atggtcctcc agagctctct gggtaacgat ctcagggtgg acggggccag   20760
catcaagttc gagagcatct gcctctacgc caccttcttc cccatggccc acaacacggc   20820
ctccacgctc gaggccatgc tcaggaacga caccaacgac cagtccttca atgactacct   20880
ctccgccgcc aacatgctct accccatacc cgccaacgcc accaacgtcc ccatctccat   20940
cccctcgcgc aactgggcgg ccttccgcgg ctgggccttc acccgcctca gaccaaggga   21000
gaccccctcc ctgggctcgg gattcgaccc ctactacacc tactcgggct ccattcccta   21060
cctggacggc accttctacc tcaaccacac tttcaagaag gtctcggtca ccttcgactc   21120
ctcggtcagc tggccgggca acgaccgtct gctcaccccc aacgagttcg agatcaagcg   21180
ctcggtcgac ggggagggct acaacgtggc ccagtgcaac atgaccaagg actggttcct   21240
ggtccagatg ctggccaact acaacatcgg ctaccagggc ttctacatcc cagagagcta   21300
caaggacagg atgtactcct tcttcaggaa cttccagccc atgagccggc aggtggtgga   21360
ccagaccaag tacaaggact accaggaggt gggcatcatc accagcacaa caactcgggg   21420
cttcgtgggc tacctcgccc ccaccatgcg cgagggacag gcctacccg ccaacttccc   21480 ctatccgctc ataggcaaga ccgcggtcga cagcatcacc cagaaaaagt tcctctgcga   21540
ccgcacccct ggcgcatcc ccttctccag caacttcatg tccatgggtg cgctctcgga   21600
cctgggccag aacttgctct acgccaactc cgcccacgcc ctcgacatga ccttcgaggt   21660
cgaccccatg gacgagccca cccttctcta tgttctgttc gaagtctttg acgtggtccg   21720
ggtccaccag ccgcaccgcg gcgtcatcga ccgtgtac ctgcgtacgc ccttctcggc   21780
cggcaacgcc accacctaaa gaagcaagcc gcagtcatcg ccgcctgcat gccgtcgggt   21840
tccaccgagc aagagctcag ggccatcgtc agagacctgg gatgcgggcc ctattttttg   21900
ggcaccttcg acaagcgctt ccctggcttt gtctccccac acaagctggc ctgcgccatc   21960
gtcaacacgg ccggccgcga gaccgggggc gtgcactggc tggccttcgc ctggaacccg   22020
cgctccaaaa catgcttcct ctttgacccc ttcggctttt cggaccagcg gctcaagcaa   22080
atctacgagt tcgagtacga gggcttgctg cgtcgcagcg ccatcgcctc ctcgcccgac   22140
cgctgcgtca cctcgaaaa gtccacccag accgtgcagg ggcccgactc ggccgcctgc   22200
ggtctcttct gctgcatgtt tctgcacgcc tttgtgcact ggcctcagag tcccatggac   22260 cgcaaccccca ccatgaactt gctgacgggg gtgcccaact ccatgctcca gagcccccag   22320
```

```
gtcgagccca ccctgcgccg caaccaggag cagctctaca gcttcctgga gcgccactcg    22380
ccttacttcc gccgccacag cgcacagatc aggagggcca cctccttctg ccacttgcaa    22440
gagatgcaag aagggtaata acgatgtaca cactttttt ctcaataaat ggcatctttt     22500
tatttataca agctctctgg ggtattcatt tcccaccacc acccgccgtt gtcgccatct    22560
ggctctattt agaaatcgaa agggttctgc cgggagtcgc cgtgcgccac gggcagggac    22620
acgttgcgat actggtagcg ggtgccccac ttgaactcgg gcaccaccag gcgaggcagc    22680
tcggggaagt tttcgctcca caggctgcgg gtcagcacca gcgcgttcat caggtcgggc    22740
gccgagatct tgaagtcgca gttggggccg ccgccctgcg cgcgcgagtt gcggtacacc    22800
gggttgcagc actggaacac caacagcgcc gggtgcttca cgctggccag cacgctgcgg    22860
tcggagatca gctcggcgtc caggtcctcc gcgttgctca gcgcgaacgg ggtcatcttg    22920
ggcacttgcc gccccaggaa gggcgcgtgc cccggtttcg agttgcagtc gcagcgcagc    22980
gggatcagca ggtgcccgtg cccggactcg gcgttggggt acagcgcgcg catgaaggcc    23040
tgcatctggc ggaaggccat ctgggccttg gcgccctccg agaagaacat gccgcaggac    23100
ttgcccgaga actggtttgc ggggcagctg cgtcgtgca ggcagcagcg cgcgtcggtg      23160
ttggcgatct gcaccacgtt gcgccccac cggttcttca cgatcttggc cttggacgat     23220
tgctccttca gcgcgcgctg cccgttctcg ctggtcacat ccatctcgat cacatgttcc    23280
ttgttcacca tgctgctgcc gtgcagacac ttcagctcgc cctccgtctc ggtgcagcgg    23340
tgctgccaca gcgcgcagcc cgtgggctcg aaagacttgt aggtcacctc gcgaaggac     23400 tgcaggtacc cctgcaaaaa gcggcccatc atggtcacga aggtcttgtt gctgctgaag    23460
gtcagctgca gccgcggtg ctcctcgttc agccaggtct tgcacacggc cgccagcgcc     23520
tccacctggt cgggcagcat cttgaagttc accttcagct cattctccac gtggtacttg    23580
tccatcagcg tgcgcgccgc ctccatgccc ttctcccagg ccgacaccag cggcaggctc    23640
acggggttct tcaccatcac cgtggccgcc gcctccgccg cgctttcgct ttccgccccg    23700
ctgttctctt cctcttcctc ctcttcctcg ccgccgccca ctcgcagccc ccgcaccacg    23760
gggtcgtctt cctgcaggcg ctgcaccttg cgcttgccgt tgcgcccctg cttgatgcgc    23820 acggcgggt tgctgaagcc caccatcacc agcgcggcct cttcttgctc gtcctcgctg      23880
tccagaatga cctccgggga ggggggttg gtcatcctca gtaccgaggc acgcttcttt      23940
ttcttcctgg gggcgttcgc cagctccgcg gctgcggccg ctgccgaggt cgaaggccga    24000
gggctgggcg tgcgcggcac cagcgcgtcc tgcgagccgt cctcgtcctc ctcggactcg    24060
agacggaggc gggcccgctt cttcggggc gcgcggggcg gcggaggcgg cggcggcgac      24120
ggagacgggg acgagacatc gtccaggtg ggtggacggc gggccgcgcc gcgtccgcgc      24180
tcgggggtgg tctcgcgctg gtcctcttcc cgactggcca tctcccactg ctccttctcc    24240
tataggcaga aagagatcat ggagtctctc atgcgagtcg agaaggagga ggacagccta    24300 accgcccct ctgagccctc caccaccgcc gccaccaccg ccaatgccgc cgcggacgac      24360
gcgcccaccg agaccaccgc cagtaccacc ctccccagcg acgcacccc gctcgagaat      24420 gaagtgctga tcgagcagga cccgggtttt gtgagcggag aggaggatga ggtggatgag    24480
aaggagaagg aggaggtcgc cgcctcagtg ccaaaagagg ataaaaagca agaccaggac    24540
gacgcagata aggatgagac agcagtcggg cggggaacg gaagccatga tgctgatgac     24600
ggctacctag acgtgggaga cgacgtgctg cttaagcacc tgcaccgcca gtgcgtcatc    24660
gtctgcgacg cgctgcagga gcgctgcgaa gtgcccctgg acgtggcgga ggtcagccgc    24720
```

```
gcctacgagc ggcacctctt cgcgccgcac gtgcccccca agcgccggga gaacggcacc    24780
tgcgagccca acccgcgtct caacttctac ccggtcttcg cggtacccga ggtgctggcc    24840
acctaccaca tctttttcca aaactgcaag atcccctct cctgccgcgc caaccgcacc     24900
cgcgccgaca aaaccctgac cctgcggcag ggcgcccaca tacctgatat cgcctctctg    24960
gaggaagtgc ccaagatctt cgagggtctc ggtcgcgacg agaaacgggc ggcgaacgct    25020
ctgcacggag acagcgaaaa cgagagtcac tcggggggtgc tggtggagct cgagggcgac   25080
aacgcgcgcc tggccgtact caagcgcagc atagaggtca cccactttgc ctacccggcg    25140
ctcaacctgc cccccaaggt catgagtgtg gtcatgggcg agctcatcat cgcgccgcgc    25200
cagcccctgg ccgcggatgc aaacttgcaa gagtcctccg aggaaggcct gcccgcggtc    25260
agcgacgagc agctggcgcg ctggctggag acccgcgacc ccgcgcagct ggaggagcgg    25320
cgcaagctca tgatggccgc ggtgctggtc accgtggagc tcgagtgtct gcagcgcttc    25380
ttcgcggacc ccgagatgca gcgcaagctc gaggagaccc tgcactacac cttccgccag    25440
ggctacgtgc gccaggcctg caagatctcc aacgtggagc tctgcaacct ggtctcctac    25500
ctgggcatcc tgcacgagaa ccgcctcggg cagaacgtcc tgcactccac cctcaaaggg    25560
gaggcgcgcc gcgactacat ccgcgactgc gcctacctct tcctctgcta cacctggcag    25620
acggccatgg gggtctggca gcagtgcctg gaggagcgca acctcaagga gctgaaaaag    25680
ctcctcaagc gcaccctcag ggacctctgg acgggcttca cgagcgctc ggtggccgcc     25740 gcgctggcgg acatcatctt tcccgagcgc ctgctcaaga ccctgcagca gggcctgccc    25800
gacttcacca gccagagcat gctgcagaac ttcaggactt tcatcctgga gcgctcgggc    25860
atcctgccgg ccacttgctg cgcgctgccc agcgacttcg tgcccatcaa gtacagggag    25920
tgcccgccgc cgctctgggg ccactgctac ctcttccagc tggccaacta cctcgcctac    25980
cactcggacc tcatggaaga cgtgagcggc gagggcctgc tcgagtgcca ctgccgctgc    26040
aacctctgca cgccccaccg ctctctagtc tgcaacccgc agctgctcag cgagagtcag    26100
attatcggta ccttcgagct gcagggtccc tcgcctgacg agaagtccgc ggctccaggg    26160
ctgaaactca ctccggggct gtggacttcc gcctacctac gcaaatttgt acctgaggac    26220
taccacgccc acgagatcag gttctacgaa gaccaatccc gcccgcccaa ggcggagctc    26280
accgcctgcg tcatcaccca ggggcacatc ctgggccaat tgcaagccat caacaaagcc    26340
cgccgagagt tcttgctgaa aaagggtcgg ggggtgtacc tggacccca gtccggcgag     26400 gagctaaacc cgctaccccc gccgccgcc cagcagcggg accttgcttc ccaggatggc     26460
acccagaaag aagcagcagc cgccgccgcc gccgcagcca tacatgcttc tggaggaaga    26520
ggaggaggac tgggacagtc aggcagagga ggtttcggac gaggagcagg aggagatgat    26580
ggaagactgg gaggaggaca gcagcctaga cgaggaagct tcagaggccg aagaggtggc    26640
agacgcaaca ccatcgccct cggtcgcagc ccctcgccg gggcccctga aatcctccga     26700
acccagcacc agcgctataa cctccgctcc tccggcgccg gcgccacccg cccgcagacc    26760
caaccgtaga tgggacacca caggaaccgg ggtcggtaag tccaagtgcc cgccgccgcc    26820
accgcagcag cagcagcagc agcgccaggg ctaccgctcg tggcgcgggc acaagaacgc    26880
catagtcgcc tgcttgcaag actgcggggg caacatctct ttcgcccgcc gcttcctgct    26940
attccaccac ggggtcgcct ttccccgcaa tgtcctgcat tactaccgtc atctctacag    27000
cccctactgc agcggcgacc cagaggcggc agcggcagcc acagcggcga ccaccaccta    27060
```

```
ggaagatatc ctccgcgggc aagacagcgg cagcagcggc caggagaccc gcggcagcag    27120
cggcggggag ggtgggcgca ctgcgcctct cgcccaacga acccctctcg acccgggagc    27180
tcagacacag gatcttcccc actttgtatg ccatcttcca acagagcaga ggccaggagc    27240
aggagctgaa aataaaaaac agatctctgc gctccctcac ccgcagctgt ctgtatcaca    27300
aaagcgaaga tcagcttcgg cgcacgctgg aggacgcgga ggcactcttc agcaaatact    27360
gcgcgctcac tcttaaagac tagctccgcg cccttctcga atttaggcgg gagaaaacta    27420
cgtcatcgcc ggccgccgcc cagcccgccc agccgagatg agcaaagaga ttcccacgcc    27480
atacatgtgg agctaccagc cgcagatggg actcgcggcg ggagcggccc aggactactc    27540
cacccgcatg aactacatga gcgcgggacc ccacatgatc tcacaggtca acgggatccg    27600
cgcccagcga aaccaaatac tgctggaaca ggcggccatc accgccacgc ccgccataa    27660 tctcaacccc cgaaattggc ccgccgccct cgtgtaccag gaaacccct ccgccaccac    27720 cgtactactt ccgcgtgacg cccaggccga agtccagatg actaactcag gggcgcagct    27780
cgcgggcggc tttcgtcacg gggcgcggcc gctccgacca ggtataagac acctgatgat    27840
cagaggccga ggtatccagc tcaacgacga gtcggtgagc tcttcgctcg gtctccgtcc    27900
ggacggaact ttccagctcg ccggatccgg ccgctcttcg ttcacgcccc gccaggcgta    27960
cctgactctg cagacctcgt cctcggagcc ccgctccggc ggcatcggaa ccctccagtt    28020
cgtggaggag ttcgtgccct cggtctactt caacccctc tcgggacctc ccggacgcta    28080
ccccgaccag ttcattccga actttgacgc ggtgaaggac tcggcggacg gctacgactg    28140
aatgtcaggt gtcgaggcag agcagcttcg cctgagacac ctcgagcact gccgccgcca    28200
caagtgcttc gcccgcggtt ctggtgagtt ctgctacttt cagctacccg aggagcatac    28260
cgaggggccg gcgcacggcg tccgcctgac cacccagggc gaggttacct gttccctcat    28320
ccgggagttt accctccgtc ccctgctagt ggagcgggag cggggtccct gtgtcctaac    28380
tatcgcctgc aactgcccta accctggatt acatcaagat ctttgctgtc atctctgtgc    28440
tgagtttaat aaacgctgag atcagaatct actggggctc ctgtcgccat cctgtgaacg    28500
ccaccgtctt cacccacccc gaccaggccc aggcgaacct cacctgcggt ctgcatcgga    28560
gggccaagaa gtacctcacc tggtacttca acggcacccc ctttgtggtt acaacagct    28620 tcgacgggga cggagtctcc ctgaaagacc agctctccgg tctcagctac tccatccaca    28680
agaacaccac cctccaactc ttccctccct acctgccggg aacctacgag tgcgtcaccg    28740
gccgctgcac ccacctcacc cgcctgatcg taaaccagag cttccgggga acagataact    28800
ccctcttccc cagaacagga ggtgagctca ggaaactccc cggggaccag ggcggagacg    28860
taccttcgac ccttgtgggg ttaggatttt ttattaccgg gttgctggct cttttaatca    28920
aagtttcctt gagatttgtt ctttccttct acgtgtatga acacctcaac ctccaataac    28980
tctacccttt cttcggaatc aggtgacttc tctgaaatcg ggcttggtgt gctgcttact    29040
ctgttgattt ttttccttat catactcagc cttctgtgcc tcaggctcgc cgcctgctgc    29100
gcacacatct atatctactg ctggttgctc aagtgcaggg gtcgccaccc aagatgaaca    29160
ggtacatggt cctatcgatc ctaggcctgc tggccctggc ggcctgcagc gccgccaaaa    29220
aagagattac ctttgaggag cccgcttgca atgtaacttt caagcccgag ggtgaccaat    29280
gcaccaccct cgtcaaatgc gttaccaatc atgagaggct gcgcatcgac tacaaaaaca    29340
aaactggcca gttgcggtc tatagtgtgt ttacgcccgg agacccctct aactactctg    29400
tcaccgtctt ccagggcgga cagtctaaga tattcaatta cactttccct ttttatgagt    29460
```

```
tatgcgatgc ggtcatgtac atgtcaaaac agtacaacct gtggcctccc tctccccagg   29520
cgtgtgtgga aaatactggg tcttactgct gtatggcttt cgcaatcact acgctcgctc   29580
taatctgcac ggtgctatac ataaaattca ggcagaggcg aatctttatc gatgaaaaga   29640
aaatgccttg atcgctaaca ccggctttct atctgcagaa tgaatgcaat cacctcccta   29700
ctaatcacca ccaccctcct tgcgattgcc catgggttga cacgaatcga agtgccagtg   29760
gggtccaatg tcaccatggt gggccccgcc ggcaattcca ccctcatgtg ggaaaaattt   29820
gtccgcaatc aatgggttca tttctgctct aaccgaatca gtatcaagcc cagagccatc   29880
tgcgatgggc aaaatctaac tctgatcaat gtgcaaatga tggatgctgg gtactattac   29940
gggcagcggg gagaaatcat taattactgg cgaccccaca aggactacat gctgcatgta   30000
gtcgaggcac ttcccactac cacccccact accacctctc ccaccaccac caccactact   30060
actactacta ctactactac tactactacc actaccgctg cccgccatac ccgcaaaagc   30120
accatgatta gcacaaagcc ccctcgtgct cactcccacg ccggcgggcc catcggtgcg   30180
acctcagaaa ccaccgagct ttgcttctgc caatgcacta acgccagcgc tcatgaactg   30240
ttcgacctgg agaatgagga tgtccagcag agctccgctt gcctgaccca ggaggctgtg   30300
gagcccgttg ccctgaagca gatcggtgat tcaataattg actcttcttc ttttgccact   30360
cccgaatacc ctcccgattc tactttccac atcacgggta ccaaagaccc taacctctct   30420
ttctacctga tgctgctgct ctgtatctct gtggtctctt ccgcgctgat gttactgggg   30480
atgttctgct gcctgatctg ccgcagaaag agaaaagctc gctctcaggg ccaaccactg   30540
atgcccttcc cctacccccc ggattttgca gataacaaga tatgagctcg ctgctgacac   30600
taaccgcttt actagcctgc gctctaaccc ttgtcgcttg cgactcgaga ttccacaatg   30660
tcacagctgt ggcaggagaa aatgttactt tcaactccac ggccgatacc cagtggtcgt   30720
ggagtggctc aggtagctac ttaactatct gcaatagctc cacttccccc ggcatatccc   30780
caaccaagta ccaatgcaat gccagcctgt tcaccctcat caacgcttcc accctggaca   30840
atggactcta tgtaggctat gtacccttg tgggcaagg aaagacccac gcttacaacc   30900
tggaagttcg ccagcccaga accactaccc aagcttctcc caccaccacc accaccacca   30960
ccatcaccag cagcagcagc agcagcagcc acagcagcag cagcagatta ttgactttgg   31020
ttttggccag ctcatctgcc gctacccagg ccatctacag ctctgtgccc gaaaccactc   31080
agatccaccg cccagaaacg accaccgcca cccctaca cacctccagc gatcagatgc   31140
cgaccaacat caccccttg gctcttcaaa tgggacttac aagcccccact ccaaaaccag   31200 tggatgcggc cgaggtctcc gccctcgtca atgactgggc ggggctggga atgtggtggt   31260
tcgccatagg catgatggcg ctctgcctgc ttctgctctg gctcatctgc tgcctccacc   31320
gcaggcgagc cagacccccc atctatagac ccatcattgt cctgaacccc gataatgatg   31380
ggatccatag attggatggc ctgaaaaacc tacttttttc ttttacagta tgataaaattg   31440 agacatgcct cgcattttct tgtacatgtt ccttctccca ccttttctgg ggtgttctac   31500
gctggccgct gtgtctcacc tggaggtaga ctgcctctca cccttcactg tctacctgct   31560
ttacggattg gtcaccctca ctctcatctg cagcctaatc acagtaatca tcgccttcat   31620
ccagtgcatt gattacatct gtgtgcgcct cgcatacttc agacaccacc cgcagtaccg   31680
agacaggaac attgcccaac ttctaagact gctctaatca tgcataagac tgtgatctgc   31740
cttctgatcc tctgcatcct gcccaccctc acctcctgcc agtacaccac aaaatctccg   31800
```

```
cgcaaaagac atgcctcctg ccgcttcacc caactgtgga atatacccaa atgctacaac    31860
gaaaagagcg agctctccga agcttggctg tatggggtca tctgtgtctt agttttctgc    31920
agcactgtct ttgccctcat aatctacccc tactttgatt tgggatggaa cgcgatcgat    31980
gccatgaatt accccacctt tcccgcaccc gagataattc cactgcgaca agttgtaccc    32040
gttgtcgtta atcaacgccc cccatcccct acgcccactg aaatcagcta ctttaaccta    32100
acaggcggag atgactgacg ccctagatct agaaatggac ggcatcagta ccgagcagcg    32160
tctcctagag aggcgcaggc aggcggctga gcaagagcgc ctcaatcagg agctccgaga    32220
tctcgttaac ctgcaccagt gcaaagagg catcttttgt ctggtaaagc aggccaaagt    32280
cacctacgag aagaccggca acagccaccg cctcagttac aaaattgccca cccagcgcca    32340 gaagctggtg ctcatggtgg gtgagaatcc catcaccgtc acccagcact cggtagagac    32400 cgagggggtgt ctgcactccc cctgtcgggg tccagaagac ctctgcaccc tggtaaagac    32460
cctgtgcggt ctcagagatt tagtccccctt taactaatca aacactggaa tcaataaaaa    32520
gaatcactta cttaaaatca gacagcaggt ctctgtccag tttattcagc agcacctcct    32580 tccccctcctc ccaactctgg tactccaaac gccttctggc ggcaaacttc ctccacaccc    32640
tgaagggaat gtcagattct tgctcctgtc cctccgcacc cactatcttc atgttgttgc    32700
agatgaagcg caccaaaacg tctgacgaga gcttcaaccc cgtgtacccc tatgacacgg    32760
aaagcggccc tccctccgtc cctttcctca ccccctcccctt cgtgtctccc gatggattcc    32820
aagaaagtcc cccccggggtc ctgtctctga acctggccga gccctggtc acttcccacg    32880 gcatgctcgc cctgaaaatg ggaagtggcc tctccctgga cgacgctggc aacctcacct    32940
ctcaagatat caccaccgct agccctcccc tcaaaaaaac caagaccaac ctcagcctag    33000
aaacctcatc cccctaact gtgagcacct caggcgccct caccgtagca gccgccgctc    33060
ccctggcggt ggccggcacc tccctcacca tgcaatcaga ggccccctg acagtacagg    33120 atgcaaaact caccctggcc accaaaggcc ccctgaccgt gtctgaaggc aaactggcct    33180
tgcaaacatc ggccccgctg acggccgctg acagcagcac cctcacagtc agtgccacac    33240
caccccttag cacaagcaat ggcagcttgg gtattgacat gcaagccccc atttacacca    33300
ccaatggaaa actaggactt aactttggcg ctcccctgca tgtggtagac agcctaaatg    33360
cactgactgt agttactggc caaggtctta cgataaacgg aacagcccta caaactagag    33420
tctcaggtgc cctcaactat gacacatcag gaaacctaga attgagagct gcaggggta    33480 tgcgagttga tgcaaatggt caacttatcc ttgatgtagc ttacccatttt gatgcacaaa    33540 acaatctcag ccttaggctt ggacagggac ccctgtttgt taactctgcc cacaacttgg    33600
atgttaacta caacagaggc ctctacctgt tcacatctgg aaataccaaa aagctagaag    33660
ttaatatcaa aacagccaag ggtctcattt atgatgacac tgctatagca atcaatgcgg    33720
gtgatgggct acagtttgac tcaggctcag atacaaatcc attaaaaact aaacttggat    33780
taggactgga ttatgactcc agcagagcca taattgctaa actgggaact ggcctaagct    33840
ttgacaacac aggtgccatc acagtaggca acaaaaatga tgacaagctt accttgtgga    33900
ccacaccaga cccatcccct aactgtagaa tctattcaga gaaagatgct aaattcacac    33960
ttgttttgac taaatgcggc agtcaggtgt tggccagcgt ttctgtttta tctgtaaaag    34020
gtagccttgc gcccatcagt ggcacagtaa ctagtgctca gattgtcctc agatttgatg    34080
aaaatggagt tctactaagc aattcttccc ttgcccctca atactggaac tacagaaaag    34140
gtgaccttac agagggcact gcatatacca acgcagtggg atttatgccc aacctcacag    34200
```

```
catacccaaa aacacagagc caaactgcta aaagcaacat tgtaagtcag gtttacttga    34260
atggggacaa atccaaaccc atgaccctca ccattaccct caatggaact aatgaaacag    34320
gagatgccac agtaagcact tactccatgt cattctcatg gaactggaat ggaagtaatt    34380
acattaatga aacgttccaa accaactcct tcaccttctc ctacatcgcc caagaataaa    34440
aagcatgacg ctgttgattt gattcaatgt gtttctgttt tattttcaag cacaacaaaa    34500
tcattcaagt cattcttcca tcttagctta atagacacag tagcttaata gacccagtag    34560
tgcaaagccc cattctagct tataactagt ggagaagtac tcgcctacat gggggtagag    34620
tcataatcgt gcatcaggat agggcggtgg tgctgcagca gcgcgcgaat aaactgctgc    34680
cgccgccgct ccgtcctgca ggaatacaac atggcagtgg tctcctcagc gatgattcgc    34740
accgcccgca gcataaggcg ccttgtcctc cgggcacagc agcgcaccct gatctcactt    34800
aaatcagcac agtaactgca gcacagcacc acaatattgt tcaaaatccc acagtgcaag    34860
gcgctgtatc caaagctcat ggcggggacc acagaaccca cgtggccatc ataccacaag    34920
cgcaggtaga ttaagtggcg accctcata aacacgctgg acataaacat tacctctttt    34980
ggcatgttgt aattcaccac ctcccggtac catataaacc tctgattaaa catggcgcca    35040
tccaccacca tcctaaacca gctggccaaa acctgcccgc cggctataca ctgcagggaa    35100
ccgggactgg aacaatgaca gtggagagcc caggactcgt aaccatggat catcatgctc    35160
gtcatgatat caatgttggc acaacacagg cacacgtgca tacacttcct caggattaca    35220
agctcctccc gcgttagaac catatcccag ggaacaaccc attcctgaat cagcgtaaat    35280
cccacactgc agggaagacc tcgcacgtaa ctcacgttgt gcattgtcaa agtgttacat    35340 tcggcagca gcggatgatc ctccagtatg gtagcgcggg tttctgtctc aaaaggaggt    35400
agacgatccc tactgtacgg agtgcgccga gacaaccgag atcgtgttgg tcgtagtgtc    35460
atgccaaatg gaacgccgga cgtagtcata tttcctgaag tcttagatct ctcaacgcag    35520
caccagcacc aacacttcgc agtgtaaaag gccaagtgcc gagagagtat atataggaat    35580
aaaaagtgac gtaaacgggc aaagtccaaa aaacgcccag aaaaaccgca cgcgaaccta    35640
cgccccgaaa cgaaagccaa aaaacactag acactccctt ccggcgtcaa cttccgcttt    35700
cccacgctac gtcacttgcc ccagtcaaac aaactacata tcccgaactt ccaagtcgcc    35760
acgcccaaaa caccgcctac acctcccccgc ccgccggccc gccccaaaac ccgcctcccg    35820
ccccgcgccc cgccccgcgc cgcccatctc attatcatat tggcttcaat ccaaaataag    35880
gtatattatt gatgatggtt taaacggatc caattcttga agacgaaagg gcctcgtgat    35940
acgcctattt ttataggtta atgtcatgat aataatggtt tcttagacgt caggtggcac    36000
ttttcgggga aatgtgcgcg gaaccccctat ttgtttattt ttctaaatac attcaaatat    36060
gtatccgctc atgagacaat aaccctgata aatgcttcaa taatattgaa aaaggaagag    36120
tatgagtatt caacatttcc gtgtcgccct tattcccttt tttgcggcat tttgccttcc    36180 tgttttttgct cacccagaaa cgctggtgaa agtaaaagat gctgaagatc agttgggtgc    36240
acgagtgggt tacatcgaac tggatctcaa cagcggtaag atccttgaga gttttcgccc    36300
cgaagaacgt tttccaatga tgagcacttt taaagttctg ctatgtggcg cggtattatc    36360
ccgtgttgac gccgggcaag agcaactcgg tcgccgcata cactattctc agaatgactt    36420
ggttgagtac tcaccagtca cagaaaagca tcttacggat ggcatgacag taagagaatt    36480
atgcagtgct gccataacca tgagtgataa cactgcggcc aacttacttc tgacaacgat    36540
```

-continued

| | |
|---|---|
| cggaggaccg aaggagctaa ccgctttttt gcacaacatg ggggatcatg taactcgcct | 36600 |
| tgatcgttgg gaaccggagc tgaatgaagc cataccaaac gacgagcgtg acaccacgat | 36660 |
| gcctgtagca atggcaacaa cgttgcgcaa actattaact ggcgaactac ttactctagc | 36720 |
| ttcccggcaa caattaatag actggatgga ggcggataaa gttgcaggac cacttctgcg | 36780 |
| ctcggccctt ccggctggct ggtttattgc tgataaatct ggagccggtg agcgtgggtc | 36840 |
| tcgcggtatc attgcagcac tggggccaga tggtaagccc tcccgtatcg tagttatcta | 36900 |
| cacgacgggg agtcaggcaa ctatggatga acgaaataga cagatcgctg agataggtgc | 36960 |
| ctcactgatt aagcattggt aactgtcaga ccaagtttac tcatatatac tttagattga | 37020 |
| tttaaaagga tctaggtgaa gatcctttt gataatctca tgaccaaaat cccttaacgt | 37080 |
| gagttttcgt tccactgagc gtcagacccc gtagaaaaga tcaaaggatc ttcttgagat | 37140 |
| cctttttttc tgcgcgtaat ctgctgcttg caaacaaaaa aaccaccgct accagcggtg | 37200 |
| gtttgtttgc cggatcaaga gctaccaact cttttccga aggtaactgg cttcagcaga | 37260 |
| gcgcagatac caaatactgt ccttctagtg tagccgtagt taggccacca cttcaagaac | 37320 |
| tctgtagcac cgcctacata cctcgctctg ctaatcctgt taccagtggc tgctgccagt | 37380 |
| ggcgataagt cgtgtcttac cgggttggac tcaagacgat agttaccgga taaggcgcag | 37440 |
| cggtcgggct gaacggggggg ttcgtgcaca cagcccagct tggagcgaac gacctacacc | 37500 |
| gaactgagat acctacagcg tgagctatga gaaagcgcca cgcttcccga agggagaaag | 37560 |
| gcggacaggt atccggtaag cggcagggtc ggaacaggag agcgcacgag ggagcttcca | 37620 |
| gggggaaacg cctggtatct ttatagtcct gtcgggtttc gccacctctg acttgagcgt | 37680 |
| cgatttttgt gatgctcgtc agggggcgg agcctatgga aaaacgccag caacgcggcc | 37740 |
| ttttttacggt tcctggcctt ttgctggcct tgaagctgtc cctgatggtc gtcatctacc | 37800 |
| tgcctggaca gcatggcctg caacgcgggc atcccgatgc cgccggaagc gagaagaatc | 37860 |
| ataatgggga aggccatcca gcctcgcgtc gcagatccga attcgtttaa ac | 37912 |

<210> SEQ ID NO 8
<211> LENGTH: 43428
<212> TYPE: DNA
<213> ORGANISM: Artificial Sequence
<220> FEATURE:
<223> OTHER INFORMATION: Polynucleotide sequence encoding ChAd155#1390
      backbone construct

<400> SEQUENCE: 8

| | |
|---|---|
| catcatcaat aatataccttt attttggatt gaagccaata tgataatgag atgggcggcg | 60 |
| cggggcgggg cgcggggcgg gaggcgggtt tggggcgggg ccggcgggcg ggcggtgtg | 120 |
| gcggaagtgg actttgtaag tgtggcggat gtgacttgct agtgccgggc gcggtaaaag | 180 |
| tgacgttttc cgtgcgcgac aacgccccg ggaagtgaca ttttccgc ggttttacc | 240 |
| ggatgttgta gtgaatttgg gcgtaaccaa gtaagatttg gccattttcg cgggaaaact | 300 |
| gaaacgggga agtgaaatct gattaatttt gcgttagtca taccgcgtaa tatttgtcta | 360 |
| gggccgaggg actttggccg attacgtgga ggactcgccc aggtgttttt tgaggtgaat | 420 |
| ttccgcgttc cgggtcaaag tctgcgtttt attattatag gatatcccat tgcatacgtt | 480 |
| gtatccatat cataatatgt acatttatat tggctcatgt ccaacattac cgccatgttg | 540 |
| acattgatta ttgactagtt attaatagta atcaattacg ggtcattag ttcatagccc | 600 |
| atatatggag ttccgcgtta cataacttac ggtaaatggc ccgcctggct gaccgcccaa | 660 |

```
cgaccccgc  ccattgacgt  caataatgac  gtatgttccc  atagtaacgc  caatagggac    720
tttccattga  cgtcaatggg  tggagtattt  acggtaaact  gcccacttgg  cagtacatca    780
agtgtatcat  atgccaagta  cgcccctat   tgacgtcaat  gacggtaaat  ggcccgcctg    840
gcattatgcc  cagtacatga  ccttatggga  ctttcctact  tggcagtaca  tctacgtatt    900
agtcatcgct  attaccatgg  tgatgcggtt  ttggcagtac  atcaatgggc  gtggatagcg    960
gtttgactca  cggggatttc  caagtctcca  ccccattgac  gtcaatggga  gtttgttttg   1020
gcaccaaaat  caacgggact  ttccaaaatg  tcgtaacaac  tccgccccat  tgacgcaaat   1080
gggcggtagg  cgtgtacggt  gggaggtcta  tataagcaga  gctctcccta  tcagtgatag   1140
agatctccct  atcagtgata  gagatcgtcg  acgagctcgt  ttagtgaacc  gtcagatcgc   1200
ctggagacgc  catccacgct  gttttgacct  ccatagaaga  caccgggacc  gatccagcct   1260
ccgcggccgg  gaacggtgca  ttggaacgcg  gattccccgt  gccaagagtg  agatcttccg   1320
tttatctagg  taccgggccc  ccctcgaggt  cgacggtat   cgataagctt  cacgctgccg   1380
caagcactca  gggcgcaagg  gctgctaaag  gaagcggaac  acgtagaaag  ccagtccgca   1440
gaaacggtgc  tgaccccgga  tgaatgtcag  ctactgggct  atctggacaa  gggaaaacgc   1500
aagcgcaaag  agaaagcagg  tagccttgcag  tgggcttaca  tggcgatagc  tagactgggc   1560
ggttttatgg  acagcaagcg  aaccggaatt  gccagctggg  gcgccctctg  gtaaggttgg   1620
gaagccctgc  aaagtaaact  ggatggcttt  cttgccgcca  aggatctgat  ggcgcagggg   1680
atcaagatct  aaccaggagc  tatttaatgg  caacagttaa  ccagctggta  cgcaaaccac   1740
gtgctcgcaa  agttgcgaaa  agcaacgtgc  ctgcgctgga  agcatgcccg  caaaaacgtg   1800
gcgtatgtac  tcgtgtatat  actaccactc  ctaaaaaacc  gaactccgcg  ctgcgtaaag   1860
tatgccgtgt  tcgtctgact  aacggtttcg  aagtgacttc  ctacatcggt  ggtgaaggtc   1920
acaacctgca  ggagcactcc  gtgatcctga  tccgtggcgg  tcgtgttaaa  gacctcccgg   1980
gtgttcgtta  ccacaccgta  cgtggtgcgc  ttgactgctc  cggcgttaaa  gaccgtaagc   2040
aggctcgttc  caagtatggc  gtgaagcgtc  ctaaggctta  atggtagatc  tgatcaagag   2100
acaggatgac  ggtcgtttcg  catgcttgaa  caagatggat  tgcacgcagg  ttctccggcc   2160
gcttgggtgg  agaggctatt  cggctatgac  tgggcacaac  agacaatcgg  ctgctctgat   2220
gccgccgtgt  tccggctgtc  agcgcagggg  cgcccggttc  tttttgtcaa  gaccgacctg   2280
tccggtgccc  tgaatgaact  gcaggacgag  gcagcgcggc  tatcgtggct  ggccacgacg   2340
ggcgttcctt  gcgcagctgt  gctcgacgtt  gtcactgaag  cgggaaggga  ctggctgcta   2400
ttgggcgaag  tgccggggca  ggatctcctg  tcatctcacc  ttgctcctgc  cgagaaagta   2460
tccatcatgg  ctgatgcaat  gcggcggctg  catacgcttg  atccggctac  ctgcccattc   2520
gaccaccaag  cgaaacatcg  catcgagcga  gcacgtactc  ggatggaagc  cggtcttgtc   2580
gatcaggatg  atctggacga  agagcatcag  gggctcgcgc  cagccgaact  gttcgccagg   2640
ctcaaggcgc  gcatgcccga  cggcgaggat  ctcgtcgtga  cccatggcga  tgcctgcttg   2700
ccgaatatca  tggtggaaaa  tggccgcttt  tctggattca  tcgactgtgg  ccggctgggt   2760
gtggcggacc  gctatcagga  catagcgttg  gctacccgtg  atattgctga  agagcttggc   2820
ggcgaatggg  ctgaccgctt  cctcgtgctt  tacggtatcg  ccgctcccga  ttcgcagcgc   2880
atcgccttct  atcgccttct  tgacgagttc  ttctgagcgg  gactctgggg  ttcgaaatga   2940
ccgaccaagc  gacgcccaac  ctgccatcac  gagatttcga  ttccaccgcc  gccttctatg   3000
aaaggttggg  cttcggaatc  gttttccggg  acgccggctg  gatgatcctc  cagcgcgggg   3060
```

| | |
|---|---|
| atctcatgct ggagttcttc gcccaccccg ggctcgatcc cctcgggggg aatcagaatt | 3120 |
| cagtcgacag cggccgcgat ctgctgtgcc ttctagttgc cagccatctg ttgtttgccc | 3180 |
| ctcccccgtg ccttccttga ccctggaagg tgccactccc actgtccttt cctaataaaa | 3240 |
| tgaggaaatt gcatcgcatt gtctgagtag gtgtcattct attctggggg gtggggtggg | 3300 |
| gcaggacagc aaggggagg attgggaaga caatagcagg catgctgggg atgcggtggg | 3360 |
| ctctatggcc gatcagcgat cgctgagtg ggtgagtggg cgtggcctgg ggtggtcatg | 3420 |
| aaaatatata agttgggggt cttagggtct ctttatttgt gttgcagaga ccgccggagc | 3480 |
| catgagcgga agcagcagca gcagcagtag cagcagcgcc ttggatggca gcatcgtgag | 3540 |
| cccttatttg acgacgcgga tgccccactg gccggggtg cgtcagaatg tgatgggctc | 3600 |
| cagcatcgac ggccgacccg tcctgcccgc aaattccgcc acgctgacct atgcgaccgt | 3660 |
| cgcggggacg ccgttggacg ccaccgccgc cgccgccgcc accgcagccg cctcggccgt | 3720 |
| gcgcagcctg gccacggact ttgcattcct gggaccactg gcgacagggg ctacttctcg | 3780 |
| ggccgctgct gccgccgttc gcgatgacaa gctgaccgcc ctgctggcgc agttggatgc | 3840 |
| gcttactcgg gaactgggtg acctttctca gcaggtcatg gccctgcgcc agcaggtctc | 3900 |
| ctccctgcaa gctggcggga atgcttctcc cacaaatgcc gtttaagata aataaaacca | 3960 |
| gactctgttt ggattaaaga aaagtagcaa gtgcattgct ctctttattt cataattttc | 4020 |
| cgcgcgcgat aggccctaga ccagcgttct cggtcgttga gggtgcggtg tatcttctcc | 4080 |
| aggacgtggt agaggtggct ctggacgttg agatacatgg gcatgagccc gtcccggggg | 4140 |
| tggaggtagc accactgcag agcttcatgc tccggggtgg tgttgtagat gatccagtcg | 4200 |
| tagcaggagc gctgggcatg gtgcctaaaa atgtccttca gcagcaggcc gatggccagg | 4260 |
| gggaggccct tggtgtaagt gtttacaaaa cggttaagtt gggaagggtg cattcgggga | 4320 |
| gagatgatgt gcatcttgga ctgtattttt agattggcga tgtttccgcc cagatccctt | 4380 |
| ctgggattca tgttgtgcag gaccaccagt acagtgtatc cggtgcactt ggggaatttg | 4440 |
| tcatgcagct tagagggaaa agcgtggaag aacttggaga cgcctttgtg gcctcccaga | 4500 |
| ttttccatgc attcgtccat gatgatggca atggccccgc ggaggcagc ttgggcaaag | 4560 |
| atatttctgg ggtcgctgac gtcgtagttg tgttccaggg tgaggtcgtc ataggccatt | 4620 |
| tttacaaagc gcgggcggag ggtgcccgac tgggggatga tggtcccctc tggccctggg | 4680 |
| gcgtagttgc cctcgcagat ctgcatttcc caggccttaa tctcggaggg gggaatcata | 4740 |
| tccacctgcg gggcgatgaa gaaaacggtt tccggagccg gggagattaa ctgggatgag | 4800 |
| agcaggtttc taagcagctg tgattttcca caaccggtgg gcccataaat aacacctata | 4860 |
| accggttgca gctggtagtt tagagagctg cagctgccgt cgtcccggag gagggggcc | 4920 |
| acctcgttga gcatgtccct gacgcgcatg ttctccccga ccagatccgc cagaaggcgc | 4980 |
| tcgccgccca gggacagcag ctcttgcaag gaagcaaagt ttttcagcgg cttgaggccg | 5040 |
| tccgccgtgg gcatgttttt cagggtctgg ctcagcagct ccaggcggtc ccagagctcg | 5100 |
| gtgacgtgct ctacggcatc tctatccagc atatctcctc gtttcgcggg ttggggcgac | 5160 |
| tttcgctgta gggcaccaag cggtggtcgt ccagcggggc cagagtcatg tccttccatg | 5220 |
| ggcgcagggt cctcgtcagg gtggtctggg tcacggtgaa ggggtgcgct ccgggctgag | 5280 |
| cgcttgccaa ggtgcgcttg aggctggttc tgctggtgct gaagcgctgc cggtcttcgc | 5340 |
| cctgcgcgtc ggccaggtag catttgacca tggtgtcata gtccagcccc tccgcggcgt | 5400 |

-continued

```
gtcccttggc gcgcagcttg cccttggagg tggcgccgca cgaggggcag agcaggctct    5460
tgagcgcgta gagcttgggg gcgaggaaga ccgattcggg ggagtaggcg tccgcgccgc    5520
agaccccgca cacggtctcg cactccacca gccaggtgag ctcggggcgc gccgggtcaa    5580
aaaccaggtt tccccatgc tttttgatgc gtttcttacc tcgggtctcc atgaggtggt    5640
gtccccgctc ggtgacgaag aggctgtccg tgtctccgta gaccgacttg aggggtcttt    5700
tctccagggg ggtccctcgg tcttcctcgt agaggaactc ggaccactct gagacgaagg    5760
cccgcgtcca ggccaggacg aaggaggcta tgtgggaggg gtagcggtcg ttgtccacta    5820
gggggtccac cttctccaag gtgtgaagac acatgtcgcc ttcctcggcg tccaggaagg    5880
tgattggctt gtaggtgtag gccacgtgac cgggggttcc tgacgggggg gtataaaagg    5940
gggtgggggc gcgctcgtcg tcactctctt ccgcatcgct gtctgcgagg gccagctgct    6000
ggggtgagta ttccctctcg aaggcgggca tgacctccgc gctgaggttg tcagtttcca    6060
aaaacgagga ggatttgatg ttcacctgtc ccgaggtgat acctttgagg gtacccgcgt    6120
ccatctggtc agaaaacacg atctttttat tgtccagctt ggtggcgaac gacccgtaga    6180
gggcgttgga gagcagcttg gcgatggagc gcagggtctg gttcttgtcc ctgtcggcgc    6240
gctccttggc cgcgatgttg agctgcacgt actcgcgcgc gacgcagcgc cactcgggga    6300
agacggtggt gcgctcgtcg ggcaccaggc gcacgcgcca gccgcggttg tgcagggtga    6360
ccaggtccac gctggtggcg acctcgccgc gcaggcgctc gttggtccag cagagacggc    6420
cgcccttgcg cgagcagaag gggggcaggg ggtcgagctg ggtctcgtcc gggggggtccg    6480
cgtccacggt gaaaaccccg gggcgcaggc gcgcgtcgaa gtagtctatc ttgcaacctt    6540
gcatgtccag cgcctgctgc cagtcgcggg cggcgagcgc gcgctcgtag gggttgagcg    6600
gcgggccccca gggcatgggg tgggtgagtg cggaggcgta catgccgcag atgtcataga    6660
cgtagagggg ctcccgcagg accccgatgt aggtggggta gcagcggccg ccgcggatgc    6720
tggcgcgcac gtagtcatac agctcgtgcg aggggggcgag gaggtcgggg cccaggttgg    6780
tgcgggcggg gcgctccgcg cggaagacga tctgcctgaa gatggcatgc gagttggaag    6840
agatggtggg gcgctggaag acgttgaagc tggcgtcctg caggccgacg gcgtcgcgca    6900
cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttcttttttcc    7020
acagctcgcg gttgaggaca aactcttcgc ggtctttcca gtactcttgg atcgggaaac    7080
cgtccggttc cgaacggtaa gagcctagca tgtagaactg gttgacggcc tggtaggcgc    7140
agcagcccctt ctccacgggg agggcgtagg cctgcgcggc cttgcggagc gaggtgtggg    7200
tcagggcgaa ggtgtccctg accatgactt tgaggtactg gtgcttgaag tcggagtcgt    7260
cgcagccgcc ccgctcccag agcgagaagt cggtgcgctt cttggagcgg gggttgggca    7320
gagcgaaggt gacatcgttg aagaggattt tgcccgcgcg gggcatgaag ttgcgggtga    7380
tgcggaaggg ccccggcact tcagagcggt tgttgatgac ctgggcggcg agcacgatct    7440
cgtcgaagcc gttgatgttg tgcccacga tgtagagttc caggaagcgg ggccggccct    7500
ttacggtggg cagcttcttt agctcttcgt aggtgagctc ctcgggcgag gcgaggccgt    7560
gctcggccag ggcccagtcc gcgaggtgcg ggttgtctct gaggaaggac ttccagaggt    7620
cgcgggccag gagggtctgc aggcggtctc tgaaggtcct gaactggcgg cccacggcca    7680
ttttttcggg ggtgatgcag tagaaggtga ggggtcttg ctgccagcgg tcccagtcga    7740
gctgcagggc gaggtcgcgc gcggcggtga ccaggcgctc gtcgcccccg aatttcatga    7800
```

```
ccagcatgaa gggcacgagc tgctttccga aggcccccat ccaagtgtag gtctctacat    7860
cgtaggtgac aaagaggcgc tccgtgcgag gatgcgagcc gatcgggaag aactggatct    7920
cccgccacca gttggaggag tggctgttga tgtggtggaa gtagaagtcc cgtcgccggg    7980
ccgaacactc gtgctggctt ttgtaaaagc gagcgcagta ctggcagcgc tgcacgggct    8040
gtacctcatg cacgagatgc accttttcgcc cgcgcacgag gaagccgagg ggaaatctga   8100 gcccccgcc tggctcgcgg catgctggt tctcttctac tttggatgcg tgtccgtctc      8160
cgtctggctc ctcgagggt gttacggtgg agcggaccac cacgccgcgc gagccgcagg     8220
tccagatatc ggcgcgcggc ggtcggagtt tgatgacgac atcgcgcagc tgggagctgt    8280
ccatggtctg gagctcccgc ggcggcggca ggtcagccgg gagttcttgc aggttcacct    8340
cgcagagtcg ggccagggcg cggggcaggt ctaggtggta cctgatctct aggggcgtgt    8400
tggtggcggc gtcgatggct tgcaggagcc cgcagccccg gggggcgacg acggtgcccc    8460
gcggggtggt ggtggtggtg gcggtgcagc tcagaagcgg tgccgcgggc gggccccgg     8520 aggtaggggg ggctccggtc ccgcgggcag gggcggcagc ggcacgtcgg cgtggagcgc    8580
gggcaggagt tggtgctgtg cccggaggtt gctggcgaag gcgacgacgc ggcggttgat    8640
ctcctggatc tggcgcctct gcgtgaagac gacgggcccg gtgagcttga acctgaaaga    8700
gagttcgaca gaatcaatct cggtgtcatt gaccgcggcc tggcgcagga tctcctgcac    8760
gtctcccgag ttgtcttggt aggcgatctc ggccatgaac tgctcgatct cttcctcctg    8820
gaggtctccg cgtccggcgc gttccacggt ggccgccagg tcgttggaga tgcgccccat    8880
gagctgcgag aaggcgttga gtccgccctc gttccagact cggctgtaga ccacgccccc    8940
ctggtcatcg cgggcgcgca tgaccacctg cgcgaggttg agctccacgt gccgcgcgaa    9000
gacggcgtag ttgcgcagac gctggaagag gtagttgagg gtggtggcgg tgtgctcggc    9060
cacgaagaag ttcatgaccc agcggcgcaa cgtggattcg ttgatgtccc caaggcctc    9120 cagccgttcc atggcctcgt agaagtccac ggcgaagttg aaaaactggg agttgcgcgc    9180
cgacacggtc aactcctcct ccagaagacg gatgagctcg gcgacggtgt cgcgcacctc    9240
gcgctcgaag gctatgggga tctcttcctc cgctagcatc accacctcct cctcttcctc    9300
ctcttctggc acttccatga tggcttcctc ctcttcgggg ggtggcggcg gcggcggtgg    9360
gggagggggc gctctgcgcc ggcggcggcg caccggagg cggtccacga agcgcgcgat     9420
catctccccg cggcggcggc gcatggtctc ggtgacggcg cggccgttct cccgggggcg    9480
cagttggaag acgccgccgg acatctggtg ctggggcggg tggccgtgag gcagcgagac    9540
ggcgctgacg atgcatctca acaattgctg cgtaggtacg ccgccgaggg acctgaggga    9600
gtccatatcc accggatccg aaaacctttc gaggaaggcg tctaaccagt cgcagtcgca    9660
aggtaggctg agcaccgtgg cgggcggcgg ggggtggggg gagtgtctgg cggaggtgct    9720
gctgatgatg taattgaagt aggcggactt gacacggcgg atggtcgaca ggagcaccat    9780
gtccttgggt ccggcctgct ggatgcggag gcggtcggct atgcccagg cttcgttctg     9840 gcatcggcgc aggtccttgt agtagtcttg catgagcctt tccaccggca cctcttctcc    9900
ttcctcttct gcttcttcca tgtctgcttc ggccctgggg cggcgccgcg ccccctgcc    9960 ccccatgcgc gtgaccccga acccctgag cggttggagc agggccaggt cggcgacgac    10020
gcgctcggcc aggatggcct gctgcacctg cgtgagggtg gtttggaagt catccaagtc   10080
cacgaagcgg tggtaggcgc ccgtgttgat ggtgtaggtg cagttggcca tgacggacca   10140
```

-continued

```
gttgacggtc tggtggcccg gttgcgacat ctcggtgtac ctgagtcgcg agtaggcgcg    10200
ggagtcgaag acgtagtcgt tgcaagtccg caccaggtac tggtagccca ccaggaagtg    10260
cggcggcggc tggcggtaga ggggccagcg cagggtggcg ggggctccgg gggccaggtc    10320
ttccagcatg aggcggtggt aggcgtagat gtacctggac atccaggtga tacccgcggc    10380
ggtggtggag gcgcgcggga agtcgcgcac ccggttccag atgttgcgca ggggcagaaa    10440
gtgctccatg gtaggcgtgc tctgtccagt cagacgcgcg cagtcgttga tactctagac    10500
cagggaaaac gaaagccggt cagcgggcac tcttccgtgg tctggtgaat agatcgcaag    10560
ggtatcatgg cggagggcct cggttcgagc cccgggtccg ggccgacgg tccgccatga     10620
tccacgcggt taccgcccgc gtgtcgaacc caggtgtgcg acgtcagaca acggtggagt    10680
gttccttttg gcgttttcct ggccgggcgc cggcgccgcg taagagacta agccgcgaaa    10740
gcgaaagcag taagtggctc gctccccgta gccggaggga tccttgctaa gggttgcgtt    10800
gcggcgaacc ccggttcgaa tcccgtactc gggccggccg gacccgcggc taaggtgttg    10860
gattggcctc cccctcgtat aaagaccccg cttgcggatt gactccggac acggggacga    10920
gccccttta tttttgcttt ccccagatgc atccggtgct gcggcagatg cgcccccgc      10980
cccagcagca gcaacaacac cagcaagagc ggcagcaaca gcagcgggag tcatgcaggg    11040
cccctcacc caccctcggc gggcggcca cctcggcgtc cgcggccgtg tctggcgcct       11100
gcggcggcgg cggggggccg gctgacgacc ccgaggagcc cccgcggcgc agggccagac    11160
actacctgga cctggaggag ggcgagggcc tggcgcggct gggggcgccg tctcccgagc    11220
gccacccgcg ggtgcagctg aagcgcgact cgcgcgaggc gtacgtgcct cggcagaacc    11280
tgttcaggga ccgcgcgggc gaggagcccg aggagatgcg ggacaggagg ttcagcgcag    11340
ggcgggagct gcggcagggg ctgaaccgcg agcggctgct gcgcgaggag gactttgagc    11400
ccgacgcgcg gacggggatc agccccgcgc gcgcgcacgt ggcggccgcc gacctggtga    11460
cggcgtacga gcagcggtg aaccaggaga tcaacttcca aaagagtttc aacaaccacg      11520
tgcgcacgct ggtggcgcgc gaggaggtga ccatcgggct gatgcacctg tgggactttg    11580
taagcgcgct ggtgcagaac cccaacagca agcctctgac ggcgcagctg ttcctgatag    11640
tgcagcacag caggacaac gaggcgtttta gggacgcgct gctgaacatc accgagcccg     11700
agggtcggtg gctgctggac ctgattaaca tcctgcagag catagtggtg caggagcgca    11760
gcctgagcct ggccgacaag gtggcggcca tcaactactc gatgctgagc ctgggcaagt    11820
tttacgcgcg caagatctac cagacgccgt acgtgcccat agacaaggag gtgaagatcg    11880
acggttttta catgcgcatg gcgctgaagg tgctcaccct gagcgacgac ctgggcgtgt    11940
accgcaacga gcgcatccac aaggccgtga gcgtgagccg gcggcgcgag ctgagcgacc    12000
gcgagctgat gcacagcctg cagcgggcgc tggcgggcgc cggcagcggc gacagggagg    12060
cggagtccta cttcgatgcg ggggcggacc tgcgctgggc gccagccgg cgggccctgg      12120
aggccgcggg ggtccgcgag gactatgacg aggacggcga ggaggatgag gagtacgagc    12180
tagaggaggg cgagtacctg gactaaaccg cgggtggtgt ttccggtaga tgcaagaccc    12240
gaacgtggtg gacccggcgc tgcggcggc tctgcagagc cagccgtccg gccttaactc      12300
ctcagacgac tggcgacagg tcatggaccg catcatgtcg ctgacggcgc gtaacccgga    12360
cgcgttccgg cagcagccgc aggccaacag gctctccgcc atcctggagg cggtggtgcc    12420
tgcgcgctcg aaccccacgc acgagaaggt gctggcccta tgtaacgcgc tggcgagaaa    12480
cagggccatc cgcccggacg aggccgggct ggtgtacgac gcgctgctgc agcgcgtggc    12540
```

```
ccgctacaac agcggcaacg tgcagaccaa cctggaccgg ctggtggggg acgtgcgcga   12600
ggcggtggcg cagcgcgagc gcgcggatcg gcagggcaac ctgggctcca tggtggcgct   12660
gaatgccttc ctgagcacgc agccggccaa cgtgccgcgg gggcaggaag actacaccaa   12720
ctttgtgagc gcgctgcggc tgatggtgac cgagaccccc cagagcgagg tgtaccagtc   12780
gggcccggac tacttcttcc agaccagcag acagggcctg cagacggtga acctgagcca   12840
ggctttcaag aacctgcggg gctgtgggg cgtgaaggcg cccaccggcg accgggcgac   12900
ggtgtccagc ctgctgacgc ccaactcgcg cctgctgctg ctgctgatcg cgccgttcac   12960
ggacagcggc agcgtgtccc gggacaccta cctggggcac ctgctgaccc tgtaccgcga   13020
ggccatcggg caggcgcagg tggacgagca ccttccag gagatcacca gcgtgagccg   13080
cgcgctgggg caggaggaca cgagcagcct ggaggcgact ctgaactacc tgctgaccaa   13140
ccggcggcag aagattccct cgctgcacag cctgacctcc gaggaggagc gcatcttgcg   13200
ctacgtgcag cagagcgtga gcctgaacct gatgcgcgac ggggtgacgc ccagcgtggc   13260
gctggacatg accgcgcgca acatggaacc gggcatgtac gccgcgcacc ggccttacat   13320
caaccgcctg atggactacc tgcatcgcgc ggcggccgtg aaccccgagt actttaccaa   13380
cgccatcctg aacccgcact ggctcccgcc gcccgggttc tacagcgggg gcttcgaggt   13440
cccggagacc aacgatggct tcctgtggga cgacatggac gacagcgtgt tctccccgcg   13500
gccgcaggcg ctggcggaag cgtccctgct gcgtcccaag aaggaggagg aggaggaggc   13560
gagtcgccgc cgcggcagca gcggcgtggc ttctctgtcc gagctggggg cggcagccgc   13620
cgcgcgcccc gggtccctgg gcggcagccc cttccgagc ctggtgggt ctctgcacag   13680
cgagcgcacc acccgccctc ggctgctggg cgaggacgag tacctgaata actcccctgct   13740
gcagccggtg cgggagaaaa acctgcctcc cgccttcccc aacaacggga tagagagcct   13800
ggtggacaag atgagcagat ggaagaccta tgcgcaggag cacagggacg cgcctgcgct   13860
ccggccgccc acgcggcgcc agcgccacga ccggcagcgg gggctggtgt gggatgacga   13920
ggactccgcg gacgatagca gcgtgctgga cctgggaggg agcggcaacc cgttcgcgca   13980
cctgcgcccc cgcctgggga ggatgtttta aaaaaaaaaa aaaaaagcaa gaagcatgat   14040
gcaaaaatta aataaaactc accaaggcca tggcgaccga gcgttggttt cttgtgttcc   14100
cttcagtatg cggcgcgcgg cgatgtacca ggagggacct cctccctctt acgagagcgt   14160
ggtgggcgcg gcggcggcgg cgccctcttc tccctttgcg tcgcagctgc tggagccgcc   14220
gtacgtgcct ccgcgctacc tgcggcctac ggggggggaga acagcatcc gttactcgga   14280
gctggcgccc ctgttcgaca ccaccccggt gtacctggtg gacaacaagt cggcggacgt   14340
ggcctcccctg aactaccaga acgaccacag caattttttg accacggtca tccagaacaa   14400
tgactacagc ccgagcgagg ccagcaccca gaccatcaat ctggatgacc ggtcgcactg   14460
gggcggcgac ctgaaaaccca tcctgcacac caacatgccc aacgtgaacg agttcatgtt   14520
caccaataag ttcaaggcgc gggtgatggt gtcgcgctcg cacaccaagg aagaccgggt   14580
ggagctgaag tacgagtggg tggagttcga gctgccagag ggcaactact ccgagaccat   14640
gaccattgac ctgatgaaca acgcgatcgt ggagcactat ctgaaagtgg gcaggcagaa   14700
cggggtcctg gagagcgaca tcggggtcaa gttcgacacc aggaacttcc gcctggggct   14760
ggaccccgtg accgggctgg ttatgccgg ggtgtacacc aacgaggcct tccatcccga   14820
catcatcctg ctgcccggct gcggggtgga cttcacttac agccgcctga gcaacctcct   14880
```

```
gggcatccgc aagcggcagc ccttccagga gggcttcagg atcacctacg aggacctgga    14940
gggggggcaac atccccgcgc tcctcgatgt ggaggcctac caggatagct tgaaggaaaa   15000
tgaggcggga caggaggata ccgccccgc cgcctccgcc gccgccgagc agggcgagga    15060
tgctgctgac accgcggccg cggacggggc agaggccgac cccgctatgg tggtggaggc    15120
tcccgagcag gaggaggaca tgaatgacag tgcggtgcgc ggagacacct tcgtcacccg    15180
ggggggaggaa aagcaagcgg aggccgaggc gcggccgag gaaaagcaac tggcggcagc     15240
agcggcggcg gcggcgttgg ccgcggcgga ggctgagtct gaggggacca agcccgccaa    15300
ggagcccgtg attaagcccc tgaccgaaga tagcaagaag cgcagttaca acctgctcaa    15360
ggacagcacc aacaccgcgt accgcagctg gtacctggcc tacaactacg cgacccgtc     15420
gacggggtg cgctcctgga ccctgctgtg cacgccggac gtgacctgcg gctcggagca    15480
ggtgtactgg tcgctgcccg acatgatgca agaccccgtg accttccgct ccacgcggca    15540
ggtcagcaac ttcccggtgg tgggcgccga gctgctgccc gtgcactcca agagcttcta    15600
caacgaccag gccgtctact cccagctcat ccgccagttc acctctctga cccacgtgtt    15660
caatcgcttt cctgagaacc agattctggc gcgcccgccc gccccacca tcaccaccgt     15720
cagtgaaaac gttcctgctc tcacagatca cgggacgcta ccgctgcgca acagcatcgg    15780
aggagtccag cgagtgaccg ttactgacgc cagacgccgc acctgcccct acgtttacaa    15840
ggccttgggc atagtctcgc cgcgcgtcct ttccagccgc acttttttgag caacaccacc   15900
atcatgtcca tcctgatctc acccagcaat aactccggct ggggactgct gcgcgcgccc    15960
agcaagatgt tcgagggggc gaggaagcgt tccgagcagc accccgtgcg cgtgcgcggg    16020
cacttccgcg cccccctgggg agcgcacaaa cgcggccgcg cggggcgcac caccgtggac    16080
gacgccatcg actcggtggt ggagcaggcg cgcaactaca ggcccgcggt ctctaccgtg    16140
gacgcggcca tccagaccgt ggtgcggggc gcgcggcggt acgccaagct gaagagccgc    16200
cggaagcgcg tggcccgccg ccaccgccgc cgacccgggg ccgccgccaa acgcgccgcc    16260
gcggccctgc ttcgccgggc caagcgcacg gccgccgcg ccgccatgag gccgcgcgc     16320
cgcttggccg ccggcatcac cgccgccacc atggcccccc gtacccgaag acgcgcggcc    16380
gccgccgccg ccgccgccat cagtgacatg ccagcaggc gccggggcaa cgtgtactgg    16440
gtgcgcgact cggtgaccgg cacgcgcgtg cccgtgcgct tccgcccccc gcggacttga    16500
gatgatgtga aaaacaaca ctgagtctcc tgctgttgtg tgtatcccag cggcggcggc     16560
gcgcgcagc tcatgtccaa gcgcaaaatc aaagaagaga tgctccaggt cgtcgcgccg     16620
gagatctatg ggcccccgaa gaaggaagag caggattcga agccccgcaa gataaagcgg    16680
gtcaaaaaga aaagaaaga tgatgacgat gccgatgggg aggtggagtt cctgcgcgcc     16740
acggcgccca ggcgcccggt gcagtggaag ggccggcgcg taaagcgcgt cctgcgcccc    16800
ggcaccgcg tggtcttcac gcccggcgag cgctccaccc ggactttcaa gcgcgtctat    16860
gacgaggtgt acgcgacga agacctgctg gagcaggcca acgagcgctt cggagagttt     16920
gcttacggga agcgtcagcg ggcgctgggg aaggaggacc tgctggcgct gccgctggac    16980
cagggcaacc ccacccccag tctgaagccc gtgaccctgc agcaggtgct gccgagcagc    17040
gcaccctccg aggcgaagcg gggtctgaag cgcgagggcg cgacctggc gcccaccgtg    17100
cagctcatgg tgcccaagcg gcagaggctg gaggatgtgc tggagaaaat gaaagtagac    17160
cccggtctgc agcggacat cagggtccgc cccatcaagc aggtggcgcc gggcctcggc    17220
gtgcagaccg tggacgtggt catccccacc ggcaactccc ccgccgccgc caccactacc   17280
```

```
gctgcctcca cggacatgga gacacagacc gatcccgccg cagccgcagc cgcagccgcc   17340
gccgcgacct cctcggcgga ggtgcagacg gaccccctggc tgccgccggc gatgtcagct   17400
ccccgcgcgc gtcgcgggcg caggaagtac ggcgccgcca acgcgctcct gcccgagtac   17460
gccttgcatc cttccatcgc gcccaccccc ggctaccgag gctataccta ccgcccgcga   17520
agagccaagg gttccacccg ccgtccccgc cgacgcgccg ccgccaccac ccgccgccgc   17580
cgccgcagac gccagcccgc actggctcca gtctccgtga ggaaagtggc gcgcgacgga   17640
cacaccctgg tgctgcccag ggcgcgctac caccccagca tcgtttaaaa gcctgttgtg   17700
gttcttgcag atatggccct cacttgccgc ctccgtttcc cggtgccggg ataccgagga   17760
ggaagatcgc gccgcaggag gggtctggcc ggccgcggcc tgagcggagg cagccgccgc   17820
gcgcaccggc ggcgacgcgc caccagccga cgcatgcgcg gcggggtgct gcccctgtta   17880
atccccctga tcgccgcggc gatcggcgcc gtgcccggga tcgcctccgt ggccttgcaa   17940
gcgtcccaga ggcattgaca gacttgcaaa cttgcaaata tggaaaaaaa aaccccaata   18000
aaaaagtcta gactctcacg ctcgcttggt cctgtgacta ttttgtagaa tggaagacat   18060
caactttgcg tcgctggccc cgcgtcacgg ctcgcgcccg ttcctgggac actggaacga   18120
tatcggcacc agcaacatga gcggtggcgc cttcagttgg ggctctctgt ggagcggcat   18180
taaaagtatc gggtctgccg ttaaaaatta cggctcccgg gcctggaaca gcagcacggg   18240
ccagatgttg agagacaagt tgaaagagca gaacttccag cagaaggtgg tggagggcct   18300
ggcctccggc atcaacgggg tggtggacct ggccaaccag gccgtgcaga ataagatcaa   18360
cagcagactg gaccccccggc cgccggtgga ggaggtgccg ccggcgctgg agacggtgtc   18420
ccccgatggg cgtggcgaga agcgcccgcg gcccgatagg gaagagacca ctctggtcac   18480
gcagaccgat gagccgcccc cgtatgagga ggccctgaag caaggtctgc ccaccacgcg   18540
gcccatcgcg cccatggcca ccggggtggt gggccgccac accccgcca cgctggactt   18600 gcctccgccc gccgatgtgc cgcagcagca gaaggcggca cagccgggcc cgcccgcgac   18660
cgcctcccgt tcctccgccg gtcctctgcg ccgcgcggcc agcggccccc gcgggggggt   18720
cgcgaggcac ggcaactggc agagcacgct gaacagcatc gtgggtctgg gggtgcggtc   18780
cgtgaagcgc cgccgatgct actgaatagc ttagctaacg tgttgtatgt gtgtatgcgc   18840
cctatgtcgc cgccagagga gctgctgagt cgccgccgtt cgcgcgccca ccaccaccgc   18900
cactccgccc ctcaagatgg cgaccccatc gatgatgccg cagtggtcgt acatgcacat   18960
ctcgggccag gacgcctcgg agtacctgag ccccgggctg gtgcagttcg cccgcgcac   19020 cgagagctac ttcagcctga gtaacaagtt taggaacccc acggtggcgc ccacgcacga   19080
tgtgaccacc gaccggtctc agcgcctgac gctgcggttc attcccgtgg accgcgagga   19140
caccgcgtac tcgtacaagg cgcggttcac cctggccgtg ggcgacaacc gcgtgctgga   19200
catggcctcc acctactttg acatccgcgg ggtgctggac cggggtccca ctttcaagcc   19260
ctactctggc accgcctaca actccctggc ccccaagggc gctcccaact cctgcgagtg   19320
ggagcaagag gaaactcagg cagttgaaga agcagcagaa gaggaagaag aagatgctga   19380
cggtcaagct gaggaagagc aagcagctac caaaagact catgtatatg ctcaggctcc   19440
cctttctggc gaaaaaatta gtaaagatgg tctgcaaata ggaacggacg ctacagctac   19500
agaacaaaaa cctatttatg cagacccctac attccagccc gaaccccaaa tcgggagtc   19560 ccagtggaat gaggcagatg ctacagtcgc cggcggtaga gtgctaaaga aatctactcc   19620
```

-continued

```
catgaaacca tgctatggtt cctatgcaag acccacaaat gctaatggag gtcagggtgt   19680
actaacggca aatgcccagg gacagctaga atctcaggtt gaaatgcaat tcttttcaac   19740
ttctgaaaac gcccgtaacg aggctaacaa cattcagccc aaattggtgc tgtatagtga   19800
ggatgtgcac atggagaccc cggatacgca ccttctctac aagcccgcaa aaagcgatga   19860
caattcaaaa atcatgctgg gtcagcagtc catgcccaac agacctaatt acatcggctt   19920
cagagacaac tttatcggcc tcatgtatta caatagcact ggcaacatgg gagtgcttgc   19980
aggtcaggcc tctcagttga atgcagtggt ggacttgcaa gacagaaaca cagaactgtc   20040
ctaccagctc ttgcttgatt ccatgggtga cagaaccaga tacttttcca tgtggaatca   20100
ggcagtggac agttatgacc cagatgttag aattattgaa aatcatggaa ctgaagacga   20160
gctccccaac tattgtttcc ctctgggtgg catagggggta actgacactt accaggctgt   20220
taaaaccaac aatggcaata acgggggcca ggtgacttgg acaaaagatg aaacttttgc   20280
agatcgcaat gaaataggggg tgggaaacaa tttcgctatg gagatcaacc tcagtgccaa   20340
cctgtggaga aacttcctgt actccaacgt ggcgctgtac ctaccagaca agcttaagta   20400 caaccctcc aatgtggaca tctctgacaa ccccaacacc tacgattaca tgaacaagcg   20460
agtggtggcc ccggggctgg tggactgcta catcaacctg ggcgcgcgct ggtcgctgga   20520
ctacatggac aacgtcaacc ccttcaacca ccaccgcaat gcgggcctgc gctaccgctc   20580
catgctcctg ggcaacgggc gctacgtgcc cttccacatc caggtgcccc agaagttctt   20640
tgccatcaag aacctcctcc tcctgccggg ctcctacacc tacgagtgga acttcaggaa   20700
ggatgtcaac atggtcctcc agagctctct gggtaacgat tcagggtgg acggggccag   20760 catcaagttc gagagcatct gcctctacgc caccttcttc cccatggccc acaacacggc   20820
ctccacgctc gaggccatgc tcaggaacga caccaacgac cagtccttca atgactacct   20880
ctccgccgcc aacatgctct accccatacc cgccaacgcc accaacgtcc ccatctccat   20940
cccctcgcgc aactgggcgg ccttccgcgc ctgggcctte acccgcctca agaccaagga   21000 gacccctcc ctgggctcgg gattcgaccc ctactacacc tactcgggct ccattcccta   21060
cctggacggc accttctacc tcaaccacac tttcaagaag gtctcggtca ccttcgactc   21120
ctcggtcagc tggccgggca cgaccgtct gctcaccccc aacgagttcg agatcaagcg   21180
ctcggtcgac ggggagggct acaacgtggc ccagtgcaac atgaccaagg actggttcct   21240
ggtccagatg ctggccaact acaacatcgg ctaccagggc ttctacatcc cagagagcta   21300
caaggacagg atgtactcct tcttcaggaa cttccagccc atgagccggc aggtggtgga   21360
ccagaccaag tacaaggact accaggaggt gggcatcatc caccagcaca acaactcggg   21420
cttcgtgggc tacctcgccc ccaccatgcg cgagggacag gcctacccg ccaacttccc   21480 ctatccgctc ataggcaaga ccgcggtcga cagcatcacc cagaaaaagt tcctctgcga   21540
ccgcaccctc tggcgcatcc ccttctccag caacttcatg tccatggggt cgctctcgga   21600
cctgggccag aacttgctct acgccaactc cgcccacgcc ctcgacatga ccttcgaggt   21660
cgaccccatg gacgagccca cccttctcta tgttctgttc gaagtctttg acgtggtccg   21720
ggtccaccag ccgcaccgcg gcgtcatcga ccgtgtac ctgcgtacgc ccttctcggc   21780
cggcaacgcc accacctaaa gaagcaagcc gcagtcatcg ccgcctgcat gccgtcgggt   21840
tccaccgagc aagagctcag ggccatcgtc agagacctgg gatgcgggcc ctattttttg   21900
ggcaccttcg acaagcgctt ccctggcttt gtctccccac acaagctggc ctgcgccatc   21960
gtcaacacgg ccggccgcga gaccgggggc gtgcactggc tggccttcgc ctggaacccg   22020
```

```
cgctccaaaa catgcttcct ctttgacccc ttcggctttt cggaccagcg gctcaagcaa   22080
atctacgagt tcgagtacga gggcttgctg cgtcgcagcg ccatcgcctc ctcgcccgac   22140
cgctgcgtca ccctcgaaaa gtccacccag accgtgcagg ggcccgactc ggccgcctgc   22200
ggtctcttct gctgcatgtt tctgcacgcc tttgtgcact ggcctcagag tcccatggac   22260
cgcaaccccc ccatgaactt gctgacgggg gtgcccaact ccatgctcca gagcccccag   22320
gtcgagccca ccctgcgccg caaccaggag cagctctaca gcttcctgga cgccactcg   22380
ccttacttcc gccgccacag cgcacagatc aggagggcca cctccttctg ccacttgcaa   22440
gagatgcaag aagggtaata acgatgtaca cacttttttt ctcaataaat ggcatctttt   22500
tatttataca agctctctgg ggtattcatt tcccaccacc accgccgtt gtcgccatct    22560
ggctctattt agaaatcgaa agggttctgc cgggagtcgc cgtgcgccac gggcagggac   22620
acgttgcgat actggtagcg ggtgccccac ttgaactcgg gcaccaccag gcgaggcagc   22680
tcggggaagt tttcgctcca caggctgcgg gtcagcacca gcgcgttcat caggtcgggc   22740
gccgagatct tgaagtcgca gttggggccg ccgccctgcg cgcgcgagtt gcggtacacc   22800
gggttgcagc actggaacac caacagcgcc gggtgcttca cgctggccag cacgctgcgg   22860
tcggagatca gctcggcgtc caggtcctcc gcgttgctca gcgcgaacgg ggtcatcttg   22920
ggcacttgcc gccccaggaa gggcgcgtgc cccggtttcg agttgcagtc gcagcgcagc   22980
gggatcagca ggtgcccgtg cccggactcg gcgttggggt acagcgcgcg catgaaggcc   23040
tgcatctggc ggaaggccat ctgggccttg gcgccctccg agaagaacat gccgcaggac   23100
ttgcccgaga actggtttgc ggggcagctg gcgtcgtgca ggcagcagcg cgcgtcggtg   23160
ttggcgatct gcaccacgtt gcgccccac cggttcttca cgatcttggc cttggacgat   23220
tgctccttca gcgcgcgctg cccgttctcg ctggtcacat ccatctcgat cacatgttcc   23280
ttgttcacca tgctgctgcc gtgcagacac ttcagctcgc cctccgtctc ggtgcagcgg   23340
tgctgccaca gcgcgcagcc cgtgggctcg aaagacttgt aggtcacctc cgcgaaggac   23400
tgcaggtacc cctgcaaaaa gcggcccatc atggtcacga aggtcttgtt gctgctgaag   23460
gtcagctgca gcccgcggtg ctcctcgttc agccaggtct tgcacacggc cgccagcgcc   23520
tccacctggt cgggcagcat cttgaagttc accttcagct cattctccac gtggtacttg   23580
tccatcagcg tgcgcgccgc ctccatgccc ttctcccagg ccgacaccag cggcaggctc   23640
acggggttct tcaccatcac cgtggccgcc gcctccgccg cgctttcgct ttccgccccg   23700
ctgttctctt cctcttcctc ctcttcctcg ccgccgccca ctcgcagccc ccgcaccacg   23760
gggtcgtctt cctgcaggcg ctgcaccttg cgcttgccgt tgcgcccctg cttgatgcgc   23820
acgggcgggt tgctgaagcc caccatcacc agcgcggcct cttcttgctc gtcctcgctg   23880
tccagaatga cctccgggga gggggggttg gtcatcctca gtaccgaggc acgcttcttt   23940
ttcttcctgg gggcgttcgc cagctccgcg gctgcggccg ctgccgaggt cgaaggccga   24000
gggctgggcg tgcgcggcac cagcgcgtcc tgcgagccgt cctcgtcctc ctcggactcg   24060
agacggaggc gggcccgctt cttcggggc gcgcggggcg gcggaggcgg cggcggcgac   24120
ggagacgggg acgagacatc gtccaggtg ggtggacggc gggccgcgcc gcgtccgcgc   24180
tcggggtgg tctcgcgctg gtcctcttcc cgactggcca tctcccactg ctccttctcc   24240
tataggcaga aagagatcat ggagtctctc atgcgagtcg agaaggagga ggacagccta   24300
accgcccct ctgagccctc caccaccgcc gccaccaccg ccaatgccgc cgcggacgac    24360
```

```
gcgcccaccg agaccaccgc cagtaccacc ctccccagcg acgcacccccc gctcgagaat    24420 gaagtgctga tcgagcagga cccgggtttt gtgagcggag aggaggatga ggtggatgag    24480
aaggagaagg aggaggtcgc cgcctcagtg ccaaaagagg ataaaaagca agaccaggac    24540
gacgcagata aggatgagac agcagtcggg cggggaacg gaagccatga tgctgatgac    24600
ggctacctag acgtgggaga cgacgtgctg cttaagcacc tgcaccgcca gtgcgtcatc    24660
gtctgcgacg cgctgcagga gcgctgcgaa gtgcccctgg acgtggcgga ggtcagccgc    24720
gcctacgagc ggcacctctt cgcgccgcac gtgccccccaa agcgccggga gaacggcacc    24780
tgcgagccca cccgcgtct caacttctac ccggtcttcg cggtacccga ggtgctggcc    24840
acctaccaca tctttttcca aaactgcaag atccccctct cctgccgcgc caaccgcacc    24900
cgcgccgaca aaaccctgac cctgcggcag ggcgcccaca tacctgatat cgcctctctg    24960
gaggaagtgc ccaagatctt cgagggtctc ggtcgcgacg agaaacgggc ggcgaacgct    25020
ctgcacggag acagcgaaaa cgagagtcac tcggggggtgc tggtggagct cgagggcgac    25080
aacgcgcgcc tggccgtact caagcgcagc atagaggtca cccactttgc ctacccggcg    25140
ctcaacctgc cccccaaggt catgagtgtg gtcatgggcg agctcatcat gcgccgcgcc    25200 cagccccctgg ccgcggatgc aaacttgcaa gagtcctccg aggaaggcct gcccgcggtc    25260
agcgacgagc agctggcgcg ctggctggag acccgcgacc ccgcgcagct ggaggagcgg    25320
cgcaagctca tgatggccgc ggtgctggtc accgtgagc tcgagtgtct gcagcgcttc    25380
ttcgcggacc ccgagatgca gcgcaagctc gaggagaccc tgcactacac cttccgccag    25440
ggctacgtgc gccaggcctg caagatctcc aacgtgagc tctgcaacct ggtctcctac    25500
ctgggcatcc tgcacgagaa ccgcctcggg cagaacgtcc tgcactccac cctcaaaggg    25560
gaggcgcgcc gcgactacat ccgcgactgc gcctacctct tcctctgcta cacctggcag    25620
acggccatgg gggtctggca gcagtgcctg gaggagcgca acctcaagga gctggaaaag    25680
ctcctcaagc gcacccctcag ggacctctgg acgggcttca acgagcgctc ggtggccgcc    25740
gcgctggcgg acatcatctt tcccgagcgc ctgctcaaga ccctgcagca gggcctgccc    25800
gacttcacca gccagagcat gctgcagaac ttcaggactt tcatcctgga gcgctcgggc    25860
atcctgccgg ccacttgctg cgcgctgccc agcgacttcg tgcccatcaa gtacagggag    25920 tgccgccgc cgctctgggg ccactgctac ctcttccagc tggccaacta cctgcctac    25980 cactcggacc tcatggaaga cgtgagcggc gagggcctgc tcgagtgcca ctgccgctgc    26040
aacctctgca cgcccaccg ctctctagtc tgcaacccgc agctgctcag cgagagtcag    26100
attatcggta ccttcgagct gcagggtccc tcgcctgacg agaagtccgc ggctccaggg    26160
ctgaaactca ctccgggggct gtggacttcc gcctacctac gcaaatttgt acctgaggac    26220
taccacgccc acgagatcag gttctacgaa gaccaatccc gcccgcccaa ggcggagctc    26280
accgcctgcg tcatcaccca ggggcacatc ctgggccaat tgcaagccat caacaaagcc    26340
cgccgagagt tcttgctgaa aaagggtcgg ggggtgtacc tggacccca gtccggcgag    26400 gagctaaacc cgctaccccc gccgccgccc cagcagcggg accttgcttc ccaggatggc    26460
acccagaaag aagcagcagc cgccgccgcc gccgcagcca tacatgcttc tggaggaaga    26520
ggaggaggac tgggacagtc aggcagagga ggtttcggac gaggagcagg aggagatgat    26580
ggaagactgg gaggaggaca gcagcctaga cgaggaagct tcagaggccg aagaggtggc    26640
agacgcaaca ccatcgccct cggtcgcagc ccctcgccg gggccctga aatcctccga    26700 acccagcacc agcgctataa cctccgctcc tccggcgccg gcgccacccg cccgcagacc    26760
```

```
caaccgtaga tgggacacca caggaaccgg ggtcggtaag tccaagtgcc cgccgccgcc   26820
accgcagcag cagcagcagc agcgccaggg ctaccgctcg tggcgcgggc acaagaacgc   26880
catagtcgcc tgcttgcaag actgcggggg caacatctct ttcgcccgcc gcttcctgct   26940
attccaccac ggggtcgcct ttccccgcaa tgtcctgcat tactaccgtc atctctacag   27000
cccctactgc agcggcgacc cagaggcggc agcggcagcc acagcggcga ccaccaccta   27060
ggaagatatc ctccgcgggc aagacagcgg cagcagcggc caggagaccc gcggcagcag   27120
cggcgggagc ggtgggcgca ctgcgcctct cgcccaacga accctctcg acccgggagc    27180 tcagacacag gatcttcccc actttgtatg ccatcttcca acagagcaga ggccaggagc   27240
aggagctgaa aataaaaaac agatctctgc gctccctcac ccgcagctgt ctgtatcaca   27300
aaagcgaaga tcagcttcgg cgcacgctgg aggacgcgga ggcactcttc agcaaatact   27360
gcgcgctcac tcttaaagac tagctccgcg cccttctcga atttaggcgg gagaaaacta   27420
cgtcatcgcc ggccgccgcc cagcccgccc agcgagatg agcaaagaga ttcccacgcc     27480
atacatgtgg agctaccagc cgcagatggg actcgcggcg ggagcggccc aggactactc   27540
cacccgcatg aactacatga gcgcgggacc ccacatgatc tcacaggtca acgggatccg   27600
cgcccagcga aaccaaatac tgctggaaca ggcggccatc accgccacgc cccgccataa   27660
tctcaacccc cgaaattggc ccgccgcccct cgtgtaccag gaaaccccct ccgccaccac   27720
cgtactactt ccgcgtgacg cccaggccga agtccagatg actaactcag gggcgcagct   27780
cgcgggcggc tttcgtcacg gggcgcggcc gctccgacca ggtataagac acctgatgat   27840
cagaggccga ggtatccagc tcaacgacga gtcggtgagc tcttcgctcg gtctccgtcc   27900
ggacggaact ttccagctcg ccggatccgg ccgctcttcg ttcacgcccc gccaggcgta   27960
cctgactctg cagacctcgt cctcggagcc ccgctccggc ggcatcggaa ccctccagtt   28020
cgtggaggag ttcgtgccct cggtctactt caacccctt tcgggacctc ccggacgcta    28080 cccccgaccag ttcattccga actttgacgc ggtgaaggac tcggcggacg gctacgactg  28140
aatgtcaggt gtcgaggcag agcagcttcc cctgagacac ctcgagcact gccgccgcca   28200
caagtgcttc gcccgcggtt ctggtgagtt ctgctacttt cagctacccg aggagcatac   28260
cgaggggccg gcgcacggcg tccgcctgac cacccagggc gaggttacct gttccctcat   28320
ccgggagttt accctccgtc ccctgctagt ggagcgggag cggggtccct gtgtcctaac   28380
tatcgcctgc aactgcccta accctggatt acatcaagat ctttgctgtc atctctgtgc   28440
tgagtttaat aaacgctgag atcagaatct actggggctc ctgtcgccat cctgtgaacg   28500
ccaccgtctt cacccacccc gaccaggccc aggcgaacct cacctgcggt ctgcatcgga   28560
gggccaagaa gtacctcacc tggtacttca acggcacccc ctttgtggtt tacaacagct   28620
tcgacgggga cggagtctcc ctgaaagacc agctctccgg tctcagctac tccatccaca   28680
agaacaccac cctccaactc ttccctccct acctgccggg aacctacgag tgcgtcaccg   28740
gccgctgcac ccacctcacc cgcctgatcg taaaccagag ctttccggga acagataact   28800
ccctcttccc cagaacagga ggtgagctca ggaaactccc cggggaccag ggcggagacg   28860
taccttcgac ccttgtgggg ttaggatttt ttattaccgg gttgctggct ctttttaatca  28920 aagtttcctt gagatttgtt cttttccttct acgtgtatga acacctcaac ctccaataac   28980
tctacccttt cttcggaatc aggtgacttc tctgaaatcg ggcttggtgt gctgcttact   29040
ctgttgattt ttttccttat catactcagc cttctgtgcc tcaggctcgc cgcctgctgc    29100
```

```
gcacacatct atatctactg ctggttgctc aagtgcaggg gtcgccaccc aagatgaaca    29160
ggtacatggt cctatcgatc ctaggcctgc tggccctggc ggcctgcagc gccgccaaaa    29220
aagagattac ctttgaggag cccgcttgca atgtaacttt caagcccgag ggtgaccaat    29280
gcaccaccct cgtcaaatgc gttaccaatc atgagaggct cgcatcgac  tacaaaaaca    29340 aaactggcca gtttgcggtc tatagtgtgt ttacgcccgg agacccctct aactactctg    29400
tcaccgtctt ccagggcgga cagtctaaga tattcaatta cactttccct ttttatgagt    29460
tatgcgatgc ggtcatgtac atgtcaaaac agtacaacct gtggcctccc tctccccagg    29520
cgtgtgtgga aaatactggg tcttactgct gtatggcttt cgcaatcact acgctcgctc    29580
taatctgcac ggtgctatac ataaaattca ggcagaggcg aatctttatc gatgaaaaga    29640
aaatgccttg atcgctaaca ccggctttct atctgcagaa tgaatgcaat cacctcccta    29700
ctaatcacca ccaccctcct tgcgattgcc catgggttga cacgaatcga agtgccagtg    29760
gggtccaatg tcaccatggt gggcccegcc ggcaattcca ccctcatgtg ggaaaaattt    29820
gtccgcaatc aatgggttca tttctgctct aaccgaatca gtatcaagcc cagagccatc    29880
tgcgatgggc aaaatctaac tctgatcaat gtgcaaatga tggatgctgg gtactattac    29940
gggcagcggg gagaaatcat taattactgg cgaccccaca aggactacat gctgcatgta    30000
gtcgaggcac ttcccactac cacccccact accacctctc ccaccaccac caccactact    30060
actactacta ctactactac tactactacc actaccgctg cccgccatac ccgcaaaagc    30120
accatgatta gcacaaagcc ccctcgtgct cactcccacg ccggcgggcc catcggtgcg    30180
acctcagaaa ccaccgagct ttgcttctgc caatgcacta acgccagcgc tcatgaactg    30240
ttcgacctgg agaatgagga tgtccagcag agctccgctt gcctgaccca ggaggctgtg    30300
gagcccgttg ccctgaagca gatcggtgat tcaataattg actcttcttc ttttgccact    30360
cccgaatacc ctcccgattc tactttccac atcacgggta ccaaagaccc taacctctct    30420
ttctacctga tgctgctgct ctgtatctct gtggtctctt ccgcgctgat gttactgggg    30480
atgttctgct gcctgatctg ccgcagaaag agaaaagctc gctctcaggg ccaaccactg    30540
atgcccttcc cctaccccce ggattttgca gataacaaga tatgagctcg ctgctgacac    30600
taaccgcttt actagcctgc gctctaaccc ttgtcgcttg cgactcgaga ttccacaatg    30660
tcacagctgt ggcaggagaa aatgttactt caactccac ggccgatacc cagtggtcgt    30720
ggagtggctc aggtagctac ttaactatct gcaatagctc cacttccccc ggcatatccc    30780
caaccaagta ccaatgcaat gccagcctgt tcaccctcat caacgcttcc accctggaca    30840
atggactcta tgtaggctat gtacccttg gtgggcaagg aaagacccac gcttacaacc    30900
tggaagttcg ccagcccaga accactaccc aagcttctcc caccaccacc accaccacca    30960
ccatcaccag cagcagcagc agcagcagcc acagcagcag cagcagatta ttgactttgg    31020
ttttggccag ctcatctgcc gctacccagg ccatctacag ctctgtgccc gaaaccactc    31080
agatccaccg cccagaaacg accaccgcca ccaccctaca cacctccagc gatcagatgc    31140
cgaccaacat cacccccttg gctcttcaaa tgggacttac aagcccact  ccaaaaccag    31200 tggatgcggc cgaggtctcc gccctcgtca atgactgggc ggggctggga atgtggtggt    31260
tcgccatagg catgatggcg ctctgcctgc ttctgctctg gctcatctgc tgcctccacc    31320
gcaggcgagc cagacccccc atctatagac ccatcattgt cctgaacccc gataatgatg    31380
ggatccatag attggatggc ctgaaaaacc tacttttttc ttttacagta tgataaattg    31440
agacatgcct cgcattttct tgtacatgtt ccttctccca ccttttctgg ggtgttctac    31500
```

```
gctggccgct gtgtctcacc tggaggtaga ctgcctctca cccttcactg tctacctgct    31560
ttacggattg gtcaccctca ctctcatctg cagcctaatc acagtaatca tcgccttcat    31620
ccagtgcatt gattacatct gtgtgcgcct cgcatacttc agacaccacc cgcagtaccg    31680
agacaggaac attgcccaac ttctaagact gctctaatca tgcataagac tgtgatctgc    31740
cttctgatcc tctgcatcct gcccaccctc acctcctgcc agtacaccac aaaatctccg    31800
cgcaaaagac atgcctcctg ccgcttcacc caactgtgga atatacccaa atgctacaac    31860
gaaaagagcg agctctccga agcttggctg tatggggtca tctgtgtctt agttttctgc    31920
agcactgtct ttgccctcat aatctacccc tactttgatt tgggatggaa cgcgatcgat    31980
gccatgaatt accccacctt tcccgcaccc gagataattc cactgcgaca agttgtaccc    32040
gttgtcgtta atcaacgccc cccatcccct acgcccactg aaatcagcta ctttaaccta    32100
acaggcggag atgactgacg ccctagatct agaaatggac ggcatcagta ccgagcagcg    32160
tctcctagag aggcgcaggc aggcggctga gcaagagcgc tcaatcagg agctccgaga    32220
tctcgttaac ctgcaccagt gcaaaagagg catctttgt ctggtaaagc aggccaaagt    32280
cacctacgaa aagaccggca acagccaccg cctcagttac aaattgccca cccagcgcca    32340
gaagctggtg ctcatggtgg gtgagaatcc catcaccgtc acccagcact cggtagagac    32400
cgaggggtgt ctgcactccc cctgtcgggg tccagaagac ctctgcaccc tggtaaagac    32460
cctgtgcggt ctcagagatt tagtcccctt taactaatca aacactggaa tcaataaaaa    32520
gaatcactta cttaaaatca gacagcaggt ctctgtccag tttattcagc agcacctcct    32580
tcccctcctc ccaactctgg tactccaaac gccttctggc ggcaaacttc ctccacaccc    32640
tgaagggaat gtcagattct tgctcctgtc cctccgcacc cactatcttc atgttgttgc    32700
agatgaagcg caccaaaacg tctgacgaga gcttcaaccc cgtgtacccc tatgacacgg    32760
aaagcggccc tccctccgtc cctttcctca cccctccctt cgtgtctccc gatggattcc    32820
aagaaagtcc cccggggtc ctgtctctga acctggccga gccctggtc acttcccacg    32880
gcatgctcgc cctgaaaatg ggaagtggcc tctcccttgga cgacgctggc aacctcacct    32940
ctcaagatat caccaccgct agccctcccc tcaaaaaaac caagaccaac ctcagcctag    33000
aaacctcatc cccctaact gtgagcacct caggcgccct caccgtagca gccgccgctc    33060
ccctggcggt ggccggcacc tccctcacca tgcaatcaga ggccccctg acagtacagg    33120
atgcaaaact caccctggcc accaaaggcc ccctgaccgt gtctgaaggc aaactggcct    33180
tgcaaacatc ggccccgctg acggccgctg acagcagcac cctcacagtc agtgccacac    33240
caccccttag cacaagcaat ggcagcttgg gtattgacat gcaagccccc atttacacca    33300
ccaatggaaa actaggactt aactttggcg ctcccctgca tgtggtagac agcctaaatg    33360
cactgactgt agttactggc caaggtctta cgataaacgg aacagcccta caaactagag    33420
tctcaggtgc cctcaactat gacacatcag gaaacctaga attgagagct gcaggggta    33480
tgcgagttga tgcaaatggt caacttatcc ttgatgtagc ttacccattt gatgcacaaa    33540
acaatctcag cctttaggctt ggacagggac ccctgtttgt taactctgcc cacaacttgg    33600
atgttaacta caacagaggc ctctacctgt tcacatctgg aaataccaaa aagctagaag    33660
ttaatatcaa aacagccaag ggtctcattt atgatgacac tgctatagca atcaatgcgg    33720
gtgatgggct acagtttgac tcaggctcag atacaaatcc attaaaaact aaacttggat    33780
taggactgga ttatgactcc agcagagcca taattgctaa actgggaact ggcctaagct    33840
```

```
ttgacaacac aggtgccatc acagtaggca acaaaaatga tgacaagctt accttgtgga   33900
ccacaccaga cccatcccct aactgtagaa tctattcaga gaaagatgct aaattcacac   33960
ttgtttgac  taaatgcggc agtcaggtgt tggccagcgt ttctgtttta tctgtaaaag   34020
gtagccttgc gcccatcagt ggcacagtaa ctagtgctca gattgtcctc agatttgatg   34080
aaaatggagt tctactaagc aattcttccc ttgaccctca atactggaac tacagaaaag   34140
gtgaccttac agagggcact gcatatacca acgcagtggg atttatgccc aacctcacag   34200
catacccaaa aacacagagc caaactgcta aaagcaacat tgtaagtcag gtttacttga   34260
atggggacaa atccaaaccc atgaccctca ccattaccct caatgaaact aatgaaacag   34320
gagatgccac agtaagcact tactccatgt cattctcatg gaactggaat ggaagtaatt   34380
acattaatga aacgttccaa accaactcct tcaccttctc ctacatcgcc caagaataaa   34440
aagcatgacg ctgttgattt gattcaatgt gtttctgttt tattttcaag cacaacaaaa   34500
tcattcaagt cattcttcca tcttagctta atagacacag tagcttaata gacccagtag   34560
tgcaaagccc cattctagct tataactagt ggagaagtac tcgcctacat gggggtagag   34620
tcataatcgt gcatcaggat agggcggtgg tgctgcagca gcgcgcgaat aaactgctgc   34680
cgccgccgct ccgtcctgca ggaatacaac atggcagtgg tctcctcagc gatgattcgc   34740
accgcccgca gcataaggcg ccttgtcctc cgggcacagc agcgcaccct gatctcactt   34800
aaatcagcac agtaactgca gcacagcacc acaatattgt tcaaaatccc acagtgcaag   34860
gcgctgtatc caaagctcat ggcggggacc acagaaccca cgtggccatc ataccacaag   34920
cgcaggtaga ttaagtggcg acccctcata aacacgctgg acataaacat tacctctttt   34980
ggcatgttgt aattcaccac ctcccggtac catataaacc tctgattaaa catggcgcca   35040
tccaccacca tcctaaacca gctggccaaa acctgcccgc cggctataca ctgcagggaa   35100
ccgggactgg aacaatgaca gtggagagcc caggactcgt aaccatggat catcatgctc   35160
gtcatgatat caatgttggc acaacacagg cacacgtgca tacacttcct caggattaca   35220
agctcctccc gcgttagaac catatcccag ggaacaaccc attcctgaat cagcgtaaat   35280
cccacactgc agggaagacc tcgcacgtaa ctcacgttgt gcattgtcaa agtgttacat   35340
tcgggcagca gcggatgatc ctccagtatg gtagcgcggg tttctgtctc aaaaggaggt   35400
agacgatccc tactgtacgg agtgcgccga gacaaccgag atcgtgttgg tcgtagtgtc   35460
atgccaaatg gaacgccgga cgtagtcata tttcctgaag tcttagatct ctcaacgcag   35520
caccagcacc aacacttcgc agtgtaaaag gccaagtgcc gagagagtat atataggaat   35580
aaaaagtgac gtaaacgggc aaagtccaaa aaacgcccag aaaaaccgca cgcgaaccta   35640
cgccccgaaa cgaaagccaa aaaacactag acactcccct tccggcgtcaa cttccgcttt   35700
cccacgctac gtcacttgcc ccagtcaaac aaactacata tcccgaactt ccaagtcgcc   35760
acgcccaaaa caccgcctac acctccccgc ccgccggccc gccccaaac  ccgcctcccg   35820
ccccgcgccc cgccccgcgc cgcccatctc attatcatat tggcttcaat ccaaaataag   35880
gtatattatt gatgatggtt taaacggatc ctctagagtc gacctgcagg catgcaagct   35940
tgagtattct atagtgtcac ctaaatagct tggcgtaatc atggtcatag ctgtttcctg   36000
tgtgaaattg ttatccgctc acaattccac acaacatacg agccggaagc ataaagtgta   36060
aagcctgggg tgcctaatga gtgagctaac tcacattaat tgcgttgcgc tcactgcccg   36120
ctttccagtc gggaaacctg tcgtgccagc tgcattaatg aatcggccaa cgcgaacccc   36180
ttgcggccgc ccgggccgtc gaccaattct catgtttgac agcttatcat cgaatttctg   36240
```

```
ccattcatcc gcttattatc acttattcag gcgtagcaac caggcgttta agggcaccaa   36300
taactgcctt aaaaaaatta cgccccgccc tgccactcat cgcagtactg ttgtaattca   36360
ttaagcattc tgccgacatg gaagccatca caaacggcat gatgaacctg aatcgccagc   36420
ggcatcagca ccttgtcgcc ttgcgtataa tatttgccca tggtgaaaac gggggcgaag   36480
aagttgtcca tattggccac gtttaaatca aaactggtga aactcaccca gggattggct   36540
gagacgaaaa acatattctc aataaaccct ttagggaaat aggccaggtt ttcaccgtaa   36600
cacgccacat cttgcgaata tatgtgtaga aactgccgga aatcgtcgtg gtattcactc   36660
cagagcgatg aaaacgtttc agtttgctca tggaaaacgg tgtaacaagg gtgaacacta   36720
tcccatatca ccagctcacc gtctttcatt gccatacgga attccggatg agcattcatc   36780
aggcgggcaa gaatgtgaat aaaggccgga taaaacttgt gcttattttt ctttacggtc   36840
tttaaaaagg ccgtaatatc cagctgaacg gtctggttat aggtacattg agcaactgac   36900
tgaaatgcct caaaatgttc tttacgatgc cattgggata tatcaacggt ggtatatcca   36960 gtgattttt tctccatttt agcttcctta gctcctgaaa atctcgataa ctcaaaaaat   37020
acgcccggta gtgatcttat ttcattatgg tgaaagttgg aacctcttac gtgccgatca   37080
acgtctcatt ttcgccaaaa gttggcccag gcttccgg tatcaacagg acaccagga   37140 tttatttatt ctgcgaagtg atcttccgtc acaggtattt attcgcgata agctcatgga   37200
gcggcgtaac cgtcgcacag gaaggacaga gaaagcgcgg atctgggaag tgacggacag   37260
aacggtcagg acctggattg gggaggcggt tgccgccgct gctgctgacg gtgtgacgtt   37320
ctctgttccg gtcacaccac atacgttccg ccattcctat gcgatgcaca tgctgtatgc   37380
cggtataccg ctgaaagttc tgcaaagcct gatgggacat aagtccatca gttcaacgga   37440
agtctacacg aaggtttttg cgctggatgt ggctgcccgg caccgggtgc agtttgcgat   37500
gccggagtct gatgcggttg cgatgctgaa acaattatcc tgagaataaa tgccttggcc   37560
tttatatgga aatgtggaac tgagtggata tgctgttttt gtctgttaaa cagagaagct   37620
ggctgttatc cactgagaag cgaacgaaac agtcggaaaa atctcccatt atcgtagaga   37680
tccgcattat taatctcagg agcctgtgta gcgtttatag gaagtagtgt tctgtcatga   37740
tgcctgcaag cggtaacgaa aacgatttga atatgccttc aggaacaata gaaatcttcg   37800
tgcggtgtta cgttgaagtg gagcggatta tgtcagcaat ggacagaaca acctaatgaa   37860
cacagaacca tgatgtggtc tgtcctttta cagccagtag tgctcgccgc agtcgagcga   37920
cagggcgaag ccctcgagtg agcgaggaag caccagggaa cagcacttat atattctgct   37980
tacacacgat gcctgaaaaa acttcccttg gggttatcca cttatccacg gggatatttt   38040
tataattatt tttttatag ttttagatc ttctttttta gagcgccttg taggccttta   38100
tccatgctgg ttctagagaa ggtgttgtga caaattgccc tttcagtgtg acaaatcacc   38160
ctcaaatgac agtcctgtct gtgacaaatt gcccttaacc ctgtgacaaa ttgccctcag   38220
aagaagctgt ttttcacaa agttatccct gcttattgac tctttttat ttagtgtgac   38280 aatctaaaaa cttgtcacac ttcacatgga tctgtcatgg cggaaacagc ggttatcaat   38340
cacaagaaac gtaaaatag cccgcgaatc gtccagtcaa acgacctcac tgaggcggca   38400
tatagtctct cccgggatca aaaacgtatg ctgtatctgt tcgttgacca gatcagaaaa   38460
tctgatggca ccctacagga acatgacggt atctgcgaga tccatgttgc taaatatgct   38520
gaaatattcg gattgacctc tgcggaagcc agtaaggata tacggcaggc attgaagagt   38580
```

```
ttcgcgggga aggaagtggt tttttatcgc cctgaagagg atgccggcga tgaaaaaggc    38640
tatgaatctt ttccttggtt tatcaaacgt gcgcacagtc catccagagg gctttacagt    38700
gtacatatca acccatatct cattcccttc tttatcgggt tacagaaccg gtttacgcag    38760
tttcggctta gtgaaacaaa agaaatcacc aatccgtatg ccatgcgttt atacgaatcc    38820
ctgtgtcagt atcgtaagcc ggatggctca ggcatcgtct ctctgaaaat cgactggatc    38880
atagagcgtt accagctgcc tcaaagttac cagcgtatgc ctgacttccg ccgccgcttc    38940
ctgcaggtct gtgttaatga gatcaacagc agaactccaa tgcgcctctc atacattgag    39000
aaaaagaaag gccgccagac gactcatatc gtattttcct tccgcgatat cacttccatg    39060
acgacaggat agtctgaggg ttatctgtca cagatttgag ggtggttcgt cacatttgtt    39120
ctgacctact gagggtaatt tgtcacagtt ttgctgtttc cttcagcctg catggatttt    39180
ctcatacttt ttgaactgta attttaagg aagccaaatt tgagggcagt tgtcacagt    39240 tgatttcctt ctcttccct tcgtcatgtg acctgatatc gggggttagt tcgtcatcat    39300
tgatgagggt tgattatcac agtttattac tctgaattgg ctatccgcgt gtgtacctct    39360
acctggagtt tttcccacgg tggatatttc ttcttgcgct gagcgtaaga gctatctgac    39420
agaacagttc ttctttgctt cctcgccagt tcgctcgcta tgctcggtta cacggctgcg    39480
gcgagcgcta gtgataataa gtgactgagg tatgtgctct tcttatctcc ttttgtagtg    39540
ttgctcttat tttaaacaac tttgcggttt tttgatgact ttgcgatttt gttgttgctt    39600
tgcagtaaat tgcaagattt aataaaaaaa cgcaaagcaa tgattaaagg atgttcagaa    39660
tgaaactcat ggaaacactt aaccagtgca taaacgctgg tcatgaaatg acgaaggcta    39720
tcgccattgc acagtttaat gatgacagcc cggaagcgag gaaaataacc cggcgctgga    39780
gaataggtga agcagcggat ttagttgggg tttcttctca ggctatcaga gatgccgaga    39840
aagcagggcg actaccgcac ccggatatgg aaattcgagg acgggttgag caacgtgttg    39900
gttatacaat tgaacaaatt aatcatatgc gtgatgtgtt tggtacgcga ttgcgacgtg    39960
ctgaagacgt atttccaccg gtgatcgggg ttgctgccca taaggtggc gtttacaaaa    40020 cctcagtttc tgttcatctt gctcaggatc tggctctgaa ggggctacgt gttttgctcg    40080
tggaaggtaa cgacccccag ggaacagcct caatgtatca cggatgggta ccagatcttc    40140
atattcatgc agaagacact ctcctgcctt tctatcttgg ggaaaaggac gatgtcactt    40200
atgcaataaa gcccacttgc tggccggggc ttgacattat tccttcctgt ctggctctgc    40260
accgtattga aactgagtta atgggcaaat ttgatgaagg taaactgccc accgatccac    40320
acctgatgct ccgactggcc attgaaactg ttgctcatga ctatgatgtc atagttattg    40380
acagcgcgcc taacctgggt atcggcacga ttaatgtcgt atgtgctgct gatgtgctga    40440 tgttcccac gcctgctgag ttgtttgact acacctccgc actgcagttt ttcgatatgc    40500
ttcgtgatct gctcaagaac gttgatctta aaggggttcga gcctgatgta cgtattttgc    40560
ttaccaaata cagcaatagt aatggctctc agtccccgtg gatggaggag caaattcggg    40620
atgcctgggg aagcatggtt ctaaaaaatg ttgtacgtga aacggatgaa gttggtaaag    40680
gtcagatccg gatgagaact gttttttgaac aggccattga tcaacgctct tcaactggtg    40740
cctggagaaa tgctctttct atttgggaac ctgtctgcaa tgaaattttc gatcgtctga    40800
ttaaaccacg ctgggagatt agataatgaa gcgtgcgcct gttattccaa aacatacgct    40860
caatactcaa ccggttgaag atacttcgtt atcgacacca gctgccccga tggtggattc    40920
gttaattgcg cgcgtaggag taatggctcg cggtaatgcc attactttgc ctgtatgtgg    40980
```

```
tcgggatgtg aagtttactc ttgaagtgct ccggggtgat agtgttgaga agacctctcg   41040
ggtatggtca ggtaatgaac gtgaccagga gctgcttact gaggacgcac tggatgatct   41100
catcccttct tttctactga ctggtcaaca gacaccggcg ttcggtcgaa gagtatctgg   41160
tgtcatagaa attgccgatg ggagtcgccg tcgtaaagct gctgcactta ccgaaagtga   41220
ttatcgtgtt ctggttggcg agctggatga tgagcagatg gctgcattat ccagattggg   41280
taacgattat cgcccaacaa gtgcttatga acgtggtcag cgttatgcaa gccgattgca   41340
gaatgaattt gctggaaata tttctgcgct ggctgatgcg gaaaatattt cacgtaagat   41400
tattacccgc tgtatcaaca ccgccaaatt gcctaaatca gttgttgctc tttttttctca  41460
ccccggtgaa ctatctgccc ggtcaggtga tgcacttcaa aaagccttta cagataaaga   41520
ggaattactt aagcagcagg catctaacct tcatgagcga aaaaaagctg gggtgatatt   41580
tgaagctgaa gaagttatca ctcttttaac ttctgtgctt aaaacgtcat ctgcatcaag   41640
aactagttta agctcacgac atcagtttgc tcctggagcg acagtattgt taagggcga   41700
taaaatggtg cttaacctgg acaggtctcg tgttccaact gagtgtatag agaaaattga   41760
ggccattctt aaggaacttg aaaagccagc accctgatgc gaccacgttt tagtctacgt   41820
ttatctgtct ttacttaatg tccttttgtta caggccagaa agcataactg gcctgaatat  41880
tctctctggg cccactgttc cacttgtatc gtcggtctga taatcagact gggaccacgg   41940
tcccactcgt atcgtcggtc tgattattag tctgggacca cggtcccact cgtatcgtcg   42000
gtctgattat tagtctggga ccacggtccc actcgtatcg tcggtctgat aatcagactg   42060
ggaccacggt cccactcgta tcgtcggtct gattattagt ctgggaccat ggtcccactc   42120
gtatcgtcgg tctgattatt agtctgggac cacggtccca ctcgtatcgt cggtctgatt   42180
attagtctgg aaccacggtc ccactcgtat cgtcggtctg attattagtc tgggaccacg   42240
gtcccactcg tatcgtcggt ctgattatta gtctgggacc acgatcccac tcgtgttgtc   42300
ggtctgatta tcggtctggg accacggtcc cacttgtatt gtcgatcaga ctatcagcgt   42360
gagactacga ttccatcaat gcctgtcaag ggcaagtatt gacatgtcgt cgtaacctgt   42420
agaacggagt aacctcggtg tgcggttgta tgcctgctgt ggattgctgc tgtgtcctgc   42480
ttatccacaa cattttgcgc acggttatgt ggacaaaata cctggttacc caggccgtgc   42540
cggcacgtta accgggctgc atccgatgca agtgtgtcgc tgtcgacgag ctcgcgagct   42600
cggacatgag gttgccccgt attcagtgtc gctgatttgt attgtctgaa gttgttttta   42660
cgttaagttg atgcagatca attaatacga tacctgcgtc ataattgatt atttgacgtg   42720
gtttgatggc ctccacgcac gttgtgatat gtagatgata atcattatca ctttacgggt   42780
cctttccggt gatccgacag gttacggggc ggcgacctcg cgggttttcg ctatttatga   42840
aaattttccg gtttaaggcg tttccgttct tcttcgtcat aacttaatgt ttttatttaa   42900
aataccctct gaaaagaaag gaaacgacag gtgctgaaag cgagcttttt ggcctctgtc   42960
gtttcctttc tctgttttttg tccgtggaat gaacaatgga agtccgagct catcgctaat   43020
aacttcgtat agcatacatt atacgaagtt atattcgatg cggccgcaag gggttcgcgt   43080
cagcgggtgt tggcgggtgt cggggctggc ttaactatgc ggcatcagag cagattgtac   43140
tgagagtgca ccatatgcgg tgtgaaatac cgcacagatg cgtaaggaga aataccgca   43200
tcaggcgcca ttcgccattc aggctgcgca actgttggga agggcgatcg gtgcgggcct   43260
cttcgctatt acgccagctg gcgaaagggg gatgtgctgc aaggcgatta agttgggtaa   43320
```

| cgccagggtt tcccagtca cgacgttgta aaacgacggc cagtgaattg taatacgact | 43380 |
| cactataggg cgaattcgag ctcggtaccc ggggatcctc gtttaaac | 43428 |

<210> SEQ ID NO 9
<211> LENGTH: 45227
<212> TYPE: DNA
<213> ORGANISM: Artificial Sequence
<220> FEATURE:
<223> OTHER INFORMATION: Polynucleotide sequence encoding ChAd155#1375
      backbone construct

<400> SEQUENCE: 9

| catcatcaat aatatacctt attttggatt gaagccaata tgataatgag atgggcggcg | 60 |
| cggggcgggg cgcggggcgg gaggcgggtt tgggggcggg ccggcgggcg gggcggtgtg | 120 |
| gcggaagtgg actttgtaag tgtggcggat gtgacttgct agtgccgggc gcggtaaaag | 180 |
| tgacgttttc cgtgcgcgac aacgcccccg ggaagtgaca ttttccccgc ggttttacc | 240 |
| ggatgttgta gtgaatttgg gcgtaaccaa gtaagatttg gccattttcg cgggaaaact | 300 |
| gaaacgggga agtgaaatct gattaatttt gcgttagtca taccgcgtaa tatttgtcta | 360 |
| gggccgaggg actttggccg attacgtgga ggactcgccc aggtgttttt tgaggtgaat | 420 |
| ttccgcgttc cgggtcaaag tctgcgtttt attattatag gatatcccat tgcatacgtt | 480 |
| gtatccatat cataatatgt acatttatat tggctcatgt ccaacattac cgccatgttg | 540 |
| acattgatta ttgactagtt attaatagta atcaattacg gggtcattag ttcatagccc | 600 |
| atatatggag ttccgcgtta cataacttac ggtaaatggc ccgcctggct gaccgcccaa | 660 |
| cgacccccgc ccattgacgt caataatgac gtatgttccc atagtaacgc caatagggac | 720 |
| tttccattga cgtcaatggg tggagtattt acggtaaact gcccacttgg cagtacatca | 780 |
| agtgtatcat atgccaagta cgccccctat tgacgtcaat gacggtaaat ggcccgcctg | 840 |
| gcattatgcc cagtacatga ccttatggga ctttcctact tggcagtaca tctacgtatt | 900 |
| agtcatcgct attaccatgg tgatgcggtt ttggcagtac atcaatgggc gtggatagcg | 960 |
| gtttgactca cggggatttc caagtctcca ccccattgac gtcaatggga gtttgttttg | 1020 |
| gcaccaaaat caacgggact ttccaaaatg tcgtaacaac tccgccccat tgacgcaaat | 1080 |
| gggcggtagg cgtgtacggt gggaggtcta tataagcaga gctctcccta tcagtgatag | 1140 |
| agatctccct atcagtgata gagatcgtcg acgagctcgt ttagtgaacc gtcagatcgc | 1200 |
| ctggagacgc catccacgct gttttgacct ccatagaaga caccgggacc gatccagcct | 1260 |
| ccgcggccgg gaacggtgca ttggaacgcg gattccccgt gccaagagtg agatcttccg | 1320 |
| tttatctagg taccgggccc cccctcgagg tcgacggtat cgataagctt cacgctgccg | 1380 |
| caagcactca gggcgcaagg gctgctaaag gaagcggaac acgtagaaag ccagtccgca | 1440 |
| gaaacggtgc tgaccccgga tgaatgtcag ctactgggct atctggacaa gggaaaacgc | 1500 |
| aagcgcaaag agaaagcagg tagcttgcag tgggcttaca tggcgatagc tagactgggc | 1560 |
| ggttttatgg acagcaagcg aaccggaatt gccagctggg gcgccctctg gtaaggttgg | 1620 |
| gaagccctgc aaagtaaact ggatggcttt cttgccgcca aggatctgat ggcgcagggg | 1680 |
| atcaagatct aaccaggagc tatttaatgg caacagttaa ccagctggta cgcaaaccac | 1740 |
| gtgctcgcaa agttgcgaaa agcaacgtgc tgcgctgga agcatgcccg caaaaacgtg | 1800 |
| gcgtatgtac tcgtgtatat actaccactc taaaaaaacc gaactccgcg ctgcgtaaag | 1860 |
| tatgccgtgt tcgtctgact aacggtttcg aagtgacttc ctacatcggt ggtgaaggtc | 1920 |

-continued

```
acaacctgca ggagcactcc gtgatcctga tccgtggcgg tcgtgttaaa gacctcccgg    1980
gtgttcgtta ccacaccgta cgtggtgcgc ttgactgctc cggcgttaaa gaccgtaagc    2040
aggctcgttc caagtatggc gtgaagcgtc ctaaggctta atggtagatc tgatcaagag    2100
acaggatgac ggtcgtttcg catgcttgaa caagatggat tgcacgcagg ttctccggcc    2160
gcttgggtgg agaggctatt cggctatgac tgggcacaac agacaatcgg ctgctctgat    2220
gccgccgtgt tccggctgtc agcgcagggg cgcccggttc tttttgtcaa gaccgacctg    2280
tccggtgccc tgaatgaact gcaggacgag gcagcgcggc tatcgtggct ggccacgacg    2340
ggcgttcctt gcgcagctgt gctcgacgtt gtcactgaag cgggaaggga ctggctgcta    2400
ttgggcgaag tgccggggca ggatctcctg tcatctcacc ttgctcctgc cgagaaagta    2460
tccatcatgg ctgatgcaat gcggcggctg catacgcttg atccggctac ctgcccattc    2520
gaccaccaag cgaaacatcg catcgagcga gcacgtactc ggatggaagc cggtcttgtc    2580
gatcaggatg atctggacga agagcatcag gggctcgcgc cagccgaact gttcgccagg    2640
ctcaaggcgc gcatgcccga cggcgaggat ctcgtcgtga cccatggcga tgcctgcttg    2700
ccgaatatca tggtggaaaa tggccgcttt tctggattca tcgactgtgg ccggctgggt    2760
gtggcggacc gctatcagga catagcgttg gctacccgtg atattgctga agagcttggc    2820
ggcgaatggg ctgaccgctt cctcgtgctt tacggtatcg ccgctcccga ttcgcagcgc    2880
atcgccttct atcgccttct tgacgagttc ttctgagcgg gactctgggg ttcgaaatga    2940
ccgaccaagc gacgcccaac ctgccatcac gagatttcga ttccaccgcc gccttctatg    3000
aaaggttggg cttcggaatc gttttccggg acgccggctg atgatcctc cagcgcgggg    3060
atctcatgct ggagttcttc gcccaccccg ggctcgatcc cctcggggg aatcagaatt    3120
cagtcgacag cggccgcgat ctgctgtgcc ttctagttgc cagccatctg ttgtttgccc    3180
ctcccccgtg ccttccttga ccctggaagg tgccactccc actgtccttt cctaataaaa    3240
tgaggaaatt gcatcgcatt gtctgagtag tgtgcattct attctggggg gtgggtggg    3300
gcaggacagc aaggggggagg attgggaaga caatagcagg catgctgggg atgcggtggg    3360
ctctatggcc gatcagcgat cgctgaggtg ggtgagtggg cgtggcctgg ggtggtcatg    3420
aaaatatata agttgggggt cttagggtct ctttatttgt gttgcagaga ccgccggagc    3480
catgagcggg agcagcagca gcagcagtag cagcagcgcc ttggatggca gcatcgtgag    3540
cccttatttg acgacgcgga tgccccactg ggccggggtg cgtcagaatg tgatgggctc    3600
cagcatcgac ggccgacccg tcctgcccgc aaattccgcc acgctgacct atgcgaccgt    3660
cgcggggacg ccgttggacg ccaccgccgc cgccgccgcc accgcagccg cctcggccgt    3720
gcgcagcctg gccacggact ttgcattcct gggaccactg cgacaggggc tacttctcg    3780
ggccgctgct gccgccgttc gcgatgacaa gctgaccgcc ctgctggcgc agttggatgc    3840
gcttactcgg gaactgggtg acctttctca gcaggtcatg gccctgcgcc agcaggtctc    3900
ctccctgcaa gctggcggga atgcttctcc cacaaatgcc gtttaagata aataaaacca    3960
gactctgttt ggattaaaga aaagtagcaa gtgcattgct ctctttattt cataattttc    4020
cgcgcgcgat aggccctaga ccagcgttct cggtcgttga gggtgcggtg tatcttctcc    4080
aggacgtggt agaggtggct ctggacgttg agatacatgg gcatgagccc gtcccggggg    4140
tggaggtagc accactgcag agcttcatgc tccggggtgg tgttgtagat gatccagtcg    4200
tagcaggagc gctgggcatg gtgcctaaaa atgtccttca gcagcaggcc gatggccagg    4260
gggaggccct tggtgtaagt gtttacaaaa cggttaagtt gggaagggtg cattcgggga    4320
```

```
gagatgatgt gcatcttgga ctgtattttt agattggcga tgtttccgcc cagatccctt   4380
ctgggattca tgttgtgcag gaccaccagt acagtgtatc cggtgcactt ggggaatttg   4440
tcatgcagct tagagggaaa agcgtggaag aacttggaga cgcctttgtg gcctcccaga   4500
ttttccatgc attcgtccat gatgatgcaa atgggcccgc gggaggcagc ttgggcaaag   4560
atatttctgg ggtcgctgac gtcgtagttg tgttccaggg tgaggtcgtc ataggccatt   4620
tttacaaagc gcgggcggag ggtgcccgac tgggggatga tggtcccctc tggccctggg   4680
gcgtagttgc cctcgcagat ctgcatttcc caggccttaa tctcggaggg gggaatcata   4740
tccacctgcg gggcgatgaa gaaaacggtt tccggagccg gggagattaa ctgggatgag   4800
agcaggtttc taagcagctg tgattttcca caaccggtgg gcccataaat aacacctata   4860
accggttgca gctggtagtt tagagagctg cagctgccgt cgtcccggag gagggggcc    4920 acctcgttga gcatgtccct gacgcgcatg ttctccccga ccagatccgc cagaaggcgc   4980
tcgccgccca gggacagcag ctcttgcaag gaagcaaagt ttttcagcgg cttgaggccg   5040
tccgccgtgg gcatgttttt cagggtctgg ctcagcagct ccaggcggtc ccagagctcg   5100
gtgacgtgct ctacggcatc tctatccagc atatctcctc gtttcgcggg ttggggcgac   5160
tttcgctgta gggcaccaag cggtggtcgt ccagcggggc cagagtcatg tccttccatg   5220
ggcgcagggt cctcgtcagg gtggtctggg tcacggtgaa ggggtgcgct ccgggctgag   5280
cgcttgccaa ggtgcgcttg aggctggttc tgctggtgct gaagcgctgc cggtcttcgc   5340
cctgcgcgtc ggccaggtag catttgacca tggtgtcata gtccagcccc tccgcggcgt   5400
gtcccttggc gcgcagcttg cccttggagg tggcgccgca cgaggggcag agcaggctct   5460
tgagcgcgta gagcttgggg gcgaggaaga ccgattcggg ggagtaggcg tccgcgccgc   5520
agaccccgca cacggtctcg cactccacca gccaggtgag ctcggggcgc gccgggtcaa   5580
aaaccaggtt tccccatgc tttttgatgc gtttcttacc tcgggtctcc atgaggtggt    5640
gtccccgctc ggtgacgaag aggctgtccg tgtctccgta gaccgacttg aggggtcttt   5700
tctccagggg ggtccctcgg tcttcctcgt agaggaactc ggaccactct gagacgaagg   5760
cccgcgtcca ggccaggacg aaggaggcta tgtgggaggg gtagcggtcg ttgtccacta   5820
gggggtccac cttctccaag gtgtgaagac acatgtcgcc ttcctcggcg tccaggaagg   5880
tgattggctt gtaggtgtag gccacgtgac cgggggttcc tgacgggggg gtataaaagg   5940
gggtgggggc gcgctcgtcg tcactctctt ccgcatcgct gtctgcgagg gccagctgct   6000
ggggtgagta ttccctctcg aaggcgggca tgacctccgc gctgaggttg tcagtttcca   6060
aaaacgagga ggatttgatg ttcacctgtc ccgaggtgat acctttgagg gtacccgcgt   6120
ccatctggtc agaaaacacg atcttttat tgtccagctt ggtggcgaac gacccgtaga    6180
gggcgttgga gagcagcttg gcgatggagc gcagggtctg gttcttgtcc ctgtcggcgc   6240
gctccttggc cgcgatgttg agctgcacgt actcgcgcgc gacgcagcgc cactcgggga   6300
agacggtggt gcgctcgtcg ggcaccaggc gcacgcgcca gccgcggttg tgcagggtga   6360
ccaggtccac gctggtggcg acctcgccgc gcaggcgctc gttggtccag cagagacggc   6420
cgcccttgcg cgagcagaag gggggcaggg ggtcgagctg ggtctcgtcc gggggtccg    6480 cgtccacggt gaaaaccccg gggcgcaggc gcgcgtcgaa gtagtctatc ttgcaacctt   6540
gcatgtccag cgcctgctgc cagtcgcggg cggcgagcgc gcgctcgtag gggttgagcg   6600 gcgggccca gggcatgggg tgggtgagtg cggaggcgta catgccgcag atgtcataga    6660
```

```
cgtagagggg ctcccgcagg accccgatgt aggtggggta gcagcggccg ccgcggatgc    6720
tggcgcgcac gtagtcatac agctcgtgcg aggggggcgag gaggtcgggg cccaggttgg    6780
tgcgggcggg gcgctccgcg cggaagacga tctgcctgaa gatggcatgc gagttggaag    6840
agatggtggg gcgctggaag acgttgaagc tggcgtcctg caggccgacg gcgtcgcgca    6900
cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttcttttttcc    7020 acagctcgcg gttgaggaca aactcttcgc ggtctttcca gtactcttgg atcgggaaac    7080
cgtccggttc cgaacggtaa gagcctagca tgtagaactg gttgacggcc tggtaggcgc    7140
agcagccctt ctccacgggg agggcgtagg cctgcgcggc cttgcggagc gaggtgtggg    7200
tcagggcgaa ggtgtccctg accatgactt tgaggtactg gtgcttgaag tcggagtcgt    7260
cgcagccgcc ccgctcccag agcgagaagt cggtgcgctt cttggagcgg gggttgggca    7320
gagcgaaggt gacatcgttg aagaggattt tgcccgcgcg gggcatgaag ttgcgggtga    7380
tgcggaaggg ccccggcact tcagagcggt tgttgatgac ctgggcggcg agcacgatct    7440
cgtcgaagcc gttgatgttg tggcccacga tgtagagttc caggaagcgg ggccggccct    7500
ttacggtggg cagcttcttt agctcttcgt aggtgagctc ctcgggcgag gcgaggccgt    7560
gctcggccag ggcccagtcc gcgaggtgcg ggttgtctct gaggaaggac ttccagaggt    7620
cgcgggccag gagggtctgc aggcggtctc tgaaggtcct gaactggcgg cccacggcca    7680 tttttttcggg ggtgatgcag tagaaggtga gggggtcttg ctgccagcgg tcccagtcga    7740
gctgcagggc gaggtcgcgc gcggcggtga ccaggcgctc gtcgccccg aatttcatga    7800 ccagcatgaa gggcacgagc tgctttccga aggcccccat ccaagtgtag gtctctacat    7860
cgtaggtgac aaagaggcgc tccgtgcgag gatgcgagcc gatcgggaag aactggatct    7920
cccgccacca gttggaggag tggctgttga tgtggtggaa gtagaagtcc cgtcgccggg    7980
ccgaacactc gtgctggctt ttgtaaaagc gagcgcagta ctggcagcgc tgcacgggct    8040
gtacctcatg cacgagatgc acctttcgcc cgcgcacgag gaagccgagg ggaaatctga    8100
gccccccgcc tggctcgcgg catggctggt tctcttctac tttggatgcg tgtccgtctc    8160
cgtctggctc ctcgagggggt gttacggtgg agcggaccac cacgccgcgc gagccgcagg    8220
tccagatatc ggcgcgcggc ggtcggagtt tgatgacgac atcgcgcagc tgggagctgt    8280
ccatggtctg gagctcccgc ggcggcggca ggtcagccgg gagttcttgc aggttcacct    8340
cgcagagtcg ggccagggcg cggggcaggt ctaggtggta cctgatctct aggggcgtgt    8400
tggtggcggc gtcgatggct tgcaggagcc cgcagccccg ggggggcgacg acggtgcccc    8460 gcggggtggt ggtggtggtg gcggtgcagc tcagaagcgg tgccgcgggc gggcccccgg    8520
aggtaggggg ggctccggtc ccgcgggcag gggcggcagc ggcacgtcgg cgtggagcgc    8580
gggcaggagt tggtgctgtg cccggaggtt gctggcgaag gcgacgacgc ggcggttgat    8640
ctcctggatc tggcgcctct gcgtgaagac gacgggcccg gtgagcttga acctgaaaga    8700
gagttcgaca gaatcaatct cggtgtcatt gaccgcggcc tggcgcagga tctcctgcac    8760
gtctcccgag ttgtcttggt aggcgatctc ggccatgaac tgctcgatct cttcctcctg    8820
gaggtctccg cgtccggcgc gttccacggt ggccgccagg tcgttggaga tgcgcccat    8880 gagctgcgag aaggcgttga gtccgccctc gttccagact cggctgtaga ccacgccccc    8940
ctggtcatcg cgggcgcgca tgaccacctg cgcgaggttg agctccacgt gccgcgcgaa    9000
gacggcgtag ttgcgcagac gctggaagag gtagttgagg gtggtggcgg tgtgctcggc    9060
```

```
cacgaagaag ttcatgaccc agcggcgcaa cgtggattcg ttgatgtccc ccaaggcctc   9120
cagccgttcc atggcctcgt agaagtccac ggcgaagttg aaaaactggg agttgcgcgc   9180
cgacacggtc aactcctcct ccagaagacg gatgagctcg gcgacggtgt cgcgcacctc   9240
gcgctcgaag gctatgggga tctcttcctc cgctagcatc accacctcct cctcttcctc   9300
ctcttctggc acttccatga tggcttcctc ctcttcgggg ggtggcggcg gcggcggtgg   9360 gggaggggggc gctctgcgcc ggcggcggcg caccgggagg cggtccacga agcgcgcgat   9420
catctccccg cggcggcggc gcatggtctc ggtgacggcg cggccgttct cccggggggcg   9480 cagttggaag acgccgccgg acatctggtg ctggggcggg tggccgtgag gcagcgagac   9540
ggcgctgacg atgcatctca acaattgctg cgtaggtacg ccgccgaggg acctgaggga   9600
gtccatatcc accggatccg aaaacctttc gaggaaggcg tctaaccagt cgcagtcgca   9660
aggtaggctg agcaccgtgg cgggcggcgg ggggtggggg gagtgtctgg cggaggtgct   9720
gctgatgatg taattgaagt aggcggactt gacacggcgg atggtcgaca ggagcaccat   9780
gtccttgggt ccggcctgct ggatgcggag gcggtcggct atgccccagg cttcgttctg   9840
gcatcggcgc aggtccttgt agtagtcttg catgagcctt ccaccggcca cctcttctcc   9900
ttcctcttct gcttcttcca tgtctgcttc ggccctgggg cggcgccgcg ccccccctgcc   9960 ccccatgcgc gtgaccccga acccctgag cggttggagc agggccaggt cggcgacgac  10020
gcgctcggcc aggatggcct gctgcacctg cgtgagggtg gtttggaagt catccaagtc  10080
cacgaagcgg tggtaggcgc ccgtgttgat ggtgtaggtg cagttggcca tgacggacca  10140
gttgacggtc tggtggcccg gttgcgacat ctcggtgtac ctgagtcgcg agtaggcgcg  10200
ggagtcgaag acgtagtcgt tgcaagtccg caccaggtac tggtagccca ccaggaagtg  10260
cggcggcggc tggcggtaga ggggccagcg cagggtggcg ggggctccgg gggccaggtc  10320
ttccagcatg aggcggtggt aggcgtagat gtacctggac atccaggtga tacccgcggc  10380
ggtggtggag gcgcgcggga agtcgcgcac ccggttccag atgttgcgca ggggcagaaa  10440
gtgctccatg gtaggcgtgc tctgtccagt cagacgcgcg cagtcgttga tactctagac  10500
cagggaaaac gaaagccggt cagcgggcac tcttccgtgg tctggtgaat agatcgcaag  10560
ggtatcatgg cggagggcct cggttcgagc cccgggtccg ggccggacgg tccgccatga  10620
tccacgcggt taccgcccgc gtgtcgaacc caggtgtgcg acgtcagaca acggtggagt  10680
gttccttttg gcgttttttct ggccgggcgc cggcgccgcg taagagacta agccgcgaaa  10740
gcgaaagcag taagtggctc gctccccgta gccgagggga tccttgctaa gggttgcgtt  10800
gcggcgaacc ccggttcgaa tcccgtactc gggccggccg gacccgcggc taaggtgttg  10860
gattggcctc cccctcgtat aaagaccccg cttgcggatt gactccggac acggggacga  10920 gccccttttta tttttgcttt cccccagatgc atccggtgct gcggcagatg cgcccccccgc  10980 cccagcagca gcaacaacac cagcaagagc ggcagcaaca gcagcgggag tcatgcaggg  11040
ccccctcacc caccctcggc gggccggcca cctcggcgtc cgcggccgtg tctggcgcct  11100
gcggcggcgg cgggggggccg gctgacgacc ccgaggagcc cccgcggcgc agggccagac  11160
actacctgga cctggaggag ggcgagggcc tggcgcggct gggggcgccg tctcccgagc  11220 gccaccgcg ggtgcagctg aagcgcgact cgcgcgaggc gtacgtgcct cggcagaacc  11280
tgttcaggga ccgcgcgggc gaggagcccg aggagatgcg ggacaggagg ttcagcgcag  11340
ggcgggagct gcggcagggg ctgaaccgcg agcggctgct gcgcgaggag gactttgagc  11400
```

```
ccgacgcgcg gacgggatc  agcccgcgc  gcgcgcacgt ggcggccgcc gacctggtga  11460
cggcgtacga gcagacggtg aaccaggaga tcaacttcca aaagagtttc aacaaccacg  11520
tgcgcacgct ggtggcgcgc gaggaggtga ccatcgggct gatgcacctg tgggactttg  11580
taagcgcgct ggtgcagaac cccaacagca agcctctgac ggcgcagctg ttcctgatag  11640
tgcagcacag cagggacaac gaggcgttta gggacgcgct gctgaacatc accgagcccg  11700
agggtcggtg gctgctggac ctgattaaca tcctgcagag catagtggtg caggagcgca  11760
gcctgagcct ggccgacaag gtggcggcca tcaactactc gatgctgagc ctgggcaagt  11820
tttacgcgcg caagatctac cagacgccgt acgtgcccat agacaaggag gtgaagatcg  11880
acggtttta  catgcgcatg gcgctgaagg tgctcaccct gagcgacgac ctgggcgtgt  11940
accgcaacga gcgcatccac aaggccgtga gcgtgagccg gcggcgcgag ctgagcgacc  12000
gcgagctgat gcacagcctg cagcgggcgc tggcgggcgc cggcagcggc gacagggagg  12060
cggagtccta cttcgatgcg ggggcggacc tgcgctgggc gcccagccgg cgggccctgg  12120
aggccgcggg ggtccgcgag gactatgacg aggacgcgca ggaggatgag gagtacgagc  12180
tagaggaggg cgagtacctg gactaaaccg cgggtggtgt ttccggtaga tgcaagaccc  12240
gaacgtggtg gacccggcgc tgcgggcggc tctgcagagc cagccgtccg gccttaactc  12300
ctcagacgac tggcgacagg tcatggaccg catcatgtcg ctgacggcgc gtaacccgga  12360
cgcgttccgg cagcagccgc aggccaacag gctctccgcc atcctggagg cggtggtgcc  12420
tgcgcgctcg aaccccacgc acgagaaggt gctggccata gtgaacgcgc tggccgagaa  12480
cagggccatc cgcccggacg aggccgggct ggtgtacgac gcgctgctgc agcgcgtggc  12540
ccgctacaac agcggcaacg tgcagaccaa cctggaccgg ctggtggggg acgtgcgcga  12600
ggcggtggcg cagcgcgagc gcgcggatcg gcagggcaac ctgggctcca tggtggcgct  12660
gaatgccttc ctgagcacgc agccggccaa cgtgccgcgg gggcaggaag actacaccaa  12720
ctttgtgagc gcgctgcggc tgatggtgac cgagaccccc cagagcgagg tgtaccagtc  12780
gggcccggac tacttcttcc agaccagcag acagggcctg cagacggtga acctgagcca  12840
ggctttcaag aacctgcggg ggctgtgggg cgtgaaggcg cccaccggcg accgggcgac  12900
ggtgtccagc ctgctgacgc ccaactcgcg cctgctgctg ctgctgatcg cgccgttcac  12960
ggacagcgga agcgtgtccc gggacaccta cctggggcac ctgctgaccc tgtaccgcga  13020
ggccatcggg caggcgcagg tggacgagca caccttccag gagatcacca gcgtgagccg  13080
cgcgctgggg caggaggaca cgagcagcct ggaggcgact ctgaactacc tgctgaccaa  13140
ccggcggcag aagattccct cgctgcacag cctgacctcc gaggaggagc gcatcttgcg  13200
ctacgtgcag cagagcgtga gcctgaacct gatgcgcgac ggggtgacgc ccagcgtggc  13260
gctggacatg accgcgcgca acatggaacc gggcatgtac gccgcgcacc ggccttacat  13320
caaccgcctg atggactacc tgcatcgcgc ggcggccgtg aaccccgagt actttaccaa  13380
cgccatcctg aacccgcact ggctcccgcc gcccgggttc tacagcgggg gcttcgaggt  13440
cccggagacc aacgatggct tcctgtggga cgacatggac gacagcgtgt ctccccgcg  13500
gccgcaggcg ctggcggaag cgtccctgct gcgtcccaag aaggaggagg aggaggagc  13560
gagtcgccgc cgcggcagca gcggcgtggc ttctctgtcc gagctggggg cggcagccgc  13620
cgcgcgcccc gggtccctgg gcggcagccc ctttccgagc ctggtgggt  ctctgcacag  13680
cgagcgcacc acccgccctc ggctgctggg cgaggacgag tacctgaata actccctgct  13740
gcagccggtg cgggagaaaa acctgcctcc cgccttcccc aacaacggga tagagagcct  13800
```

```
ggtggacaag atgagcagat ggaagaccta tgcgcaggag cacagggacg cgcctgcgct   13860
ccggccgccc acgcggcgcc agcgccacga ccggcagcgg gggctggtgt gggatgacga   13920
ggactccgcg gacgatagca gcgtgctgga cctgggaggg agcggcaacc cgttcgcgca   13980
cctgcgcccc cgcctgggga ggatgtttta aaaaaaaaa aaaaagcaa gaagcatgat     14040 gcaaaaatta aataaaactc accaaggcca tggcgaccga gcgttggttt cttgtgttcc   14100
cttcagtatg cggcgcgcgg cgatgtacca ggagggacct cctccctctt acgagagcgt   14160
ggtgggcgcg gcggcggcgg cgccctcttc tccctttgcg tcgcagctgc tggagccgcc   14220
gtacgtgcct ccgcgctacc tgcggcctac ggggggagaa aacagcatcc gttactcgga   14280
gctggcgccc ctgttcgaca ccacccgggt gtacctggtg gacaacaagt cggcggacgt   14340
ggcctccctg aactaccaga acgaccacag caatttttg accacggtca tccagaacaa    14400
tgactacagc ccgagcgagg ccagcaccca gaccatcaat ctggatgacc ggtcgcactg   14460
gggcggcgac ctgaaaacca tcctgcacac caacatgccc aacgtgaacg agttcatgtt   14520
caccaataag ttcaaggcgc gggtgatggt gtcgcgctcg cacaccaagg aagaccgggt   14580
ggagctgaag tacgagtggg tggagttcga gctgccagag ggcaactact ccgagaccat   14640
gaccattgac ctgatgaaca acgcgatcgt ggagcactat ctgaaagtgg gcaggcagaa   14700
cggggtcctg gagagcgaca tcggggtcaa gttcgacacc aggaacttcc gcctggggct   14760
ggaccccgtg accgggctgg ttatgcccgg ggtgtacacc aacgaggcct ccatcccga    14820 catcatcctg ctgcccggct gcggggtgga cttcacttac agccgcctga gcaacctcct   14880
gggcatccgc aagcggcagc ccttccagga gggcttcagg atcacctacg aggacctgga   14940 gggggcaac atccccgcgc tcctcgatgt ggaggcctac caggatagct tgaaggaaaa    15000
tgaggcggga caggaggata ccgccccgc cgcctccgcc gccgccgagc agggcgagga    15060
tgctgctgac accgcggccg cggacggggc agaggccgac cccgctatgg tggtggaggc   15120
tcccgagcag gaggaggaca tgaatgacag tgcggtgcgc ggagacacct tcgtcacccg   15180
gggggaggaa aagcaagcgg aggccgaggc cgcggccgag gaaaagcaac tggcggcagc   15240
agcggcggcg gcggcgttgg ccgcggcgga ggctgagtct gaggggacca agcccgccaa   15300
ggagcccgtg attaagcccc tgaccgaaga tagcaagaag cgcagttaca acctgctcaa   15360
ggacagcacc aacaccgcgt accgcagctg gtacctggcc tacaactacg cgacccgtc    15420 gacggggtg cgctcctgga ccctgctgtg cacgccggac gtgacctgcg gctcggagca    15480
ggtgtactgt tcgctgcccg acatgatgca agaccccgtg accttccgct ccacgcggca   15540
ggtcagcaac ttcccggtgg tgggcgccga gctgctgccc gtgcactcca agagcttcta   15600
caacgaccag gccgtctact cccagctcat ccgccagttc acctctctga cccacgtgtt   15660
caatcgcttt cctgagaacc agattctggc gcgcccgccc gccccacca tcaccaccgt    15720 cagtgaaaac gttcctgctc tcacagatca cgggacgcta ccgctgcgca acagcatcgg   15780
aggagtccag cgagtgaccg ttactgacgc cagacgccgc acctgccct acgtttacaa    15840 ggccttgggc atagtctcgc cgcgcgtcct ttccagccgc actttttgag caacaccacc   15900
atcatgtcca tcctgatctc acccagcaat aactccggct ggggactgct gcgcgcgccc   15960
agcaagatgt tcggaggggc gaggaagcgt tccgagcagc accccgtgcg cgtgcgcggg   16020
cacttccgcg cccctgggg agcgcacaaa cgcggccgcg cggggcgcac caccgtggac   16080
gacgccatcg actcggtggt ggagcaggcg cgcaactaca ggcccgcggt ctctaccgtg    16140
```

```
gacgcggcca tccagaccgt ggtgcgggc gcgcggcggt acgccaagct gaagagccgc    16200
cggaagcgcg tggcccgccg ccaccgccgc cgacccgggg ccgccgccaa acgcgccgcc    16260
gcggccctgc ttcgccgggc caagcgcacg ggccgccgcg ccgccatgag ggccgcgcgc    16320
cgcttggccg ccggcatcac cgccgccacc atggcccccc gtacccgaag acgcgcggcc    16380
gccgccgccg ccgccgccat cagtgacatg gccagcaggc gccggggcaa cgtgtactgg    16440
gtgcgcgact cggtgaccgg cacgcgcgtg cccgtgcgct tccgccccc  gcggacttga    16500 gatgatgtga aaaacaaca ctgagtctcc tgctgttgtg tgtatcccag cggcggcggc    16560
gcgcgcagcg tcatgtccaa gcgcaaaatc aaagaagaga tgctccaggt cgtcgcgccg    16620
gagatctatg ggcccccgaa gaaggaagag caggattcga agccccgcaa gataaagcgg    16680
gtcaaaaaga aaagaaaga tgatgacgat gccgatgggg aggtggagtt cctgcgcgcc    16740
acggcgccca ggcgcccggt gcagtggaag ggccggcgcg taaagcgcgt cctgcgcccc    16800
ggcaccgcgg tggtcttcac gcccggcgag cgctccaccc ggactttcaa gcgcgtctat    16860
gacgaggtgt acgcgacga agacctgctg gagcaggcca acgagcgctt cggagagttt    16920
gcttacggga agcgtcagcg ggcgctgggg aaggaggacc tgctggcgct gccgctggac    16980
cagggcaacc ccaccccag tctgaagccc gtgaccctgc agcaggtgct gccgagcagc    17040
gcaccctccg aggcgaagcg gggtctgaag cgcgagggcg gcgacctggc gcccaccgtg    17100
cagctcatgg tgcccaagcg gcagaggctg gaggatgtgc tggagaaaat gaaagtagac    17160
cccggtctgc agccggacat cagggtccgc cccatcaagc aggtggcgcc gggcctcggc    17220
gtgcagaccg tggacgtggt catccccacc ggcaactccc ccgccgccgc caccactacc    17280
gctgcctcca cggacatgga gacacagacc gatcccgccg cagccgcagc cgcagccgcc    17340
gccgcgacct cctcggcgga ggtgcagacg gacccctggc tgccgccggc gatgtcagct    17400
ccccgcgcgc gtcgcgggcg caggaagtac ggcgccgcca acgcgctcct gcccgagtac    17460
gccttgcatc cttccatcgc gcccaccccc ggctaccgag gctataccta ccgcccgcga    17520
agagccaagg gttccacccg ccgtccccgc cgacgcgccg ccgccaccac ccgccgccgc    17580
cgccgcagac gccagcccgc actggctcca gtctccgtga ggaaagtggc gcgcgacgga    17640
cacaccctgg tgctgcccag ggcgcgctac caccccagca tcgtttaaaa gcctgttgtg    17700
gttcttgcag atatggccct cacttgccgc ctccgtttcc cggtgccggg ataccgagga    17760
ggaagatcgc gccgcaggag gggtctggcc ggccgcggcc tgagcggagg cagccgccgc    17820
gcgcaccggc ggcgacgcgc caccagccga cgcatgcgcg gcgggtgct  gcccctgtta    17880 atccccctga tcgccgcggc gatcggcgcc gtgcccggga tcgcctccgt ggccttgcaa    17940
gcgtcccaga ggcattgaca gacttgcaaa cttgcaaata tggaaaaaaa accccaata     18000 aaaaagtcta gactctcacg ctcgcttggt cctgtgacta ttttgtagaa tggaagacat    18060
caactttgcg tcgctggccc cgcgtcacgg ctcgcgcccg ttcctgggac actgggaacga    18120 tatcggcacc agcaacatga gcggtggcgc cttcagttgg ggctctctgt ggagcggcat    18180
taaaagtatc gggtctgccg ttaaaaatta cggctcccgg gcctggaaca gcagcacggg    18240
ccagatgttg agagacaagt tgaaagagca gaacttccag cagaaggtgg tggagggcct    18300
ggcctccggc atcaacgggg tggtggacct ggccaaccag gccgtgcaga ataagatcaa    18360
cagcagactg gaccccggc cgccggtgga ggaggtgccg ccggcgctgg agacggtgtc    18420
ccccgatggg cgtggcgaga agcgcccgcg gcccgatagg gaagagacca ctctggtcac    18480
gcagaccgat gagccgcccc cgtatgagga ggccctgaag caaggtctgc ccaccacgcg    18540
```

```
gcccatcgcg cccatggcca ccggggtggt gggccgccac accccgcca cgctggactt    18600 gcctccgccc gccgatgtgc cgcagcagca gaaggcggca cagccgggcc cgcccgcgac    18660
cgcctcccgt tcctccgccg gtcctctgcg ccgcgcggcc agcggccccc gcggggggt    18720 cgcgaggcac ggcaactggc agagcacgct gaacagcatc gtgggtctgg gggtgcggtc    18780
cgtgaagcgc cgccgatgct actgaatagc ttagctaacg tgttgtatgt gtgtatgcgc    18840
cctatgtcgc cgccagagga gctgctgagt cgccgccgtt cgcgcgccca ccaccaccgc    18900
cactccgccc ctcaagatgg cgaccccatc gatgatgccg cagtggtcgt acatgcacat    18960
ctcgggccag gacgcctcgg agtacctgag ccccgggctg gtgcagttcg cccgcgccac    19020
cgagagctac ttcagcctga gtaacaagtt taggaacccc acggtggcgc ccacgcacga    19080
tgtgaccacc gaccggtctc agcgcctgac gctgcggttc attcccgtgg accgcgagga    19140
caccgcgtac tcgtacaagg cgcggttcac cctggccgtg ggcgacaacc gcgtgctgga    19200
catgccctcc acctactttg acatccgcgg ggtgctggac cggggtccca ctttcaagcc    19260
ctactctggc accgcctaca actccctggc ccccaagggc gctcccaact cctgcgagtg    19320
ggagcaagag gaaactcagg cagttgaaga agcagcagaa gaggaagaag aagatgctga    19380
cggtcaagct gaggaagagc aagcagctac caaaaagact catgtatatg ctcaggctcc    19440
cctttctggc gaaaaaatta gtaaagatgg tctgcaaata ggaacggacg ctacagctac    19500
agaacaaaaa cctatttatg cagaccctac attccagccc gaaccccaaa tcggggagtc    19560
ccagtggaat gaggcagatg ctacagtcgc cggcggtaga gtgctaaaga aatctactcc    19620
catgaaacca tgctatggtt cctatgcaag acccacaaat gctaatggag gtcagggtgt    19680
actaacggca aatgcccagg acagctagaa tctcaggtt gaaatgcaat tcttttcaac    19740
ttctgaaaac gcccgtaacg aggctaacaa cattcagccc aaattggtgc tgtatagtga    19800
ggatgtgcac atggagaccc cggatacgca cctttcttac aagcccgcaa aaagcgatga    19860
caattcaaaa atcatgctgg gtcagcagtc catgcccaac agacctaatt acatcggctt    19920
cagagacaac tttatcggcc tcatgtatta caatagcact ggcaacatgg gagtgccttgc    19980 aggtcaggcc tctcagttga atgcagtggt ggacttgcaa gacagaaaca cagaactgtc    20040
ctaccagctc ttgcttgatt ccatgggtga cagaaccaga tacttttcca tgtggaatca    20100
ggcagtggac agttatgacc cagatgttag aattattgaa aatcatgaa ctgaagacga    20160 gctccccaac tattgtttcc ctctgggtgg catagggggta actgacactt accaggctgt    20220
taaaaccaac aatggcaata acgggggcca ggtgacttgg acaaaagatg aaactttttgc    20280 agatcgcaat gaaatagggg tgggaaacaa tttcgctatg gagatcaacc tcagtgccaa    20340
cctgtggaga aacttcctgt actccaacgt ggcgctgtac ctaccagaca agcttaagta    20400 caaccctcc aatgtggaca tctctgacaa ccccaacacc tacgattaca tgaacaagcg    20460
agtggtggcc ccggggctgg tggactgcta catcaacctg ggcgcgcgct ggtcgctgga    20520
ctacatggac aacgtcaacc ccttcaacca ccaccgcaat gcgggcctgc gctaccgctc    20580
catgctcctg ggcaacgggc gctacgtgcc cttccacatc caggtgcccc agaagttctt    20640
tgccatcaag aacctcctcc tcctgccggg ctcctacacc tacgagtgga cttcaggaa    20700 ggatgtcaac atggtcctcc agagctctct gggtaacgat ctcagggtgg acgggggccag    20760 catcaagttc gagagcatct gcctctacgc caccttcttc cccatggccc acaacacggc    20820
ctccacgctc gaggccatgc tcaggaacga caccaacgac cagtccttca tgactacct    20880
```

```
ctccgccgcc aacatgctct accccatacc cgccaacgcc accaacgtcc ccatctccat    20940
cccctcgcgc aactgggcgg ccttccgcgg ctgggccttc acccgcctca agaccaagga    21000
gaccccctcc ctgggctcgg gattcgaccc ctactacacc tactcgggct ccattcccta    21060
cctggacggc accttctacc tcaaccacac tttcaagaag gtctcggtca ccttcgactc    21120
ctcggtcagc tggccgggca acgaccgtct gctcaccccc aacgagttcg agatcaagcg    21180
ctcggtcgac ggggagggct acaacgtggc ccagtgcaac atgaccaagg actggttcct    21240
ggtccagatg ctggccaact acaacatcgg ctaccagggc ttctacatcc cagagagcta    21300
caaggacagg atgtactcct tcttcaggaa cttccagccc atgagccggc aggtggtgga    21360
ccagaccaag tacaaggact accaggaggt gggcatcatc caccagcaca caactcggg    21420 cttcgtgggc tacctcgccc ccaccatgcg cgagggacag gcctaccccg ccaacttccc    21480
ctatccgctc ataggcaaga ccgcggtcga cagcatcacc cagaaaaagt tcctctgcga    21540
ccgcaccctc tggcgcatcc ccttctccag caacttcatg tccatgggtg cgctctcgga    21600
cctgggccag aacttgctct acgccaactc cgcccacgcc ctcgacatga ccttcgaggt    21660
cgaccccatg gacgagccca cccttctcta tgttctgttc gaagtctttg acgtggtccg    21720
ggtccaccag ccgcaccgcg cgtcatcga accgtgtac ctgcgtacgc ccttctcggc    21780
cggcaacgcc accacctaaa gaagcaagcc gcagtcatcg ccgcctgcat gccgtcgggt    21840
tccaccgagc aagagctcag ggccatcgtc agagacctgg gatgcgggcc ctattttttg    21900
ggcaccttcg acaagcgctt ccctggcttt gtctccccac acaagctggc ctgcgccatc    21960
gtcaacacgg ccgccgcga accgggggc gtgcactggc tggccttcgc ctggaacccg    22020
cgctccaaaa catgcttcct cttgaccc ttcggctttt cggaccagcg gctcaagcaa    22080
atctacgagt tcgagtacga gggcttgctg cgtcgcagcg ccatcgcctc ctcgcccgac    22140
cgctgcgtca ccctcgaaaa gtccacccag accgtgcagg ggcccgactc ggccgcctgc    22200
ggtctcttct gctgcatgtt tctgcacgcc tttgtgcact ggcctcagag tcccatggac    22260 cgcaaccca ccatgaactt gctgacgggg gtgcccaact ccatgctcca gagccccag    22320 gtcgagccca ccctgcgccg caaccaggag cagctctaca gcttcctgga cgccactcg    22380 ccttacttcc gccgccacag cgcacagatc aggagggcca cctccttctg ccacttgcaa    22440
gagatgcaag aagggtaata acgatgtaca cactttttt ctcaataaat ggcatctttt    22500
tatttataca agctctctgg ggtattcatt tcccaccacc acccgccgtt gtcgccatct    22560
ggctctattt agaaatcgaa agggttctgc cgggagtcgc cgtgcgccac gggcagggac    22620
acgttgcgat actggtagcg ggtgccccac ttgaactcgg gcaccaccag gcgaggcagc    22680
tcggggaagt tttcgctcca caggctgcgg gtcagcacca gcgcgttcat caggtcgggc    22740
gccgagatct tgaagtcgca gttggggccg ccgccctgcg cgcgcgagtt gcggtacacc    22800
gggttgcagc actggaacac caacagcgcc gggtgcttca cgctggccag cacgctgcgg    22860
tcggagatca gctcggcgtc caggtcctcc gcgttgctca gcgcgaacgg ggtcatcttg    22920
ggcacttgcc gccccaggaa gggcgcgtgc cccggtttcg agttgcagtc gcagcgcagc    22980
gggatcagca ggtgcccgtg cccggactcg gcgttgggt acagcgcgcg catgaaggcc    23040
tgcatctggc ggaaggccat ctgggccttg gcgccctccg agaagaacat gccgcaggac    23100
ttgcccgaga actggtttgc ggggcagctg gcgtcgtgca ggcagcagcg cgcgtcggtg    23160
ttggcgatct gcaccacgtt gcgccccac cggttcttca cgatcttggc cttggacgat    23220
tgctccttca gcgcgcgctg cccgttctcg ctggtcacat ccatctcgat cacatgttcc    23280
```

```
ttgttcacca tgctgctgcc gtgcagacac ttcagctcgc cctccgtctc ggtgcagcgg   23340
tgctgccaca gcgcgcagcc cgtgggctcg aaagacttgt aggtcacctc cgcgaaggac   23400
tgcaggtacc cctgcaaaaa gcggcccatc atggtcacga aggtcttgtt gctgctgaag   23460
gtcagctgca gcccgcggtg ctcctcgttc agccaggtct tgcacacggc cgccagcgcc   23520
tccacctggt cgggcagcat cttgaagttc accttcagct cattctccac gtggtacttg   23580
tccatcagcg tgcgcgccgc ctccatgccc ttctcccagg ccgacaccag cggcaggctc   23640
acggggttct tcaccatcac cgtggccgcc gcctccgccg cgctttcgct ttccgccccg   23700
ctgttctctt cctcttcctc ctcttcctcg ccgccgccca ctcgcagccc ccgcaccacg   23760
gggtcgtctt cctgcaggcg ctgcaccttg cgcttgccgt tgcgcccctg cttgatgcgc   23820
acgggcgggt tgctgaagcc caccatcacc agcgcggcct cttcttgctc gtcctcgctg   23880
tccagaatga cctccgggga gggggggttg gtcatcctca gtaccgaggc acgcttcttt   23940
ttcttcctgg gggcgttcgc cagctccgcg gctgcggccg ctgccgaggt cgaaggccga   24000
gggctgggcg tgcgcggcac cagcgcgtcc tgcgagccgt cctcgtcctc ctcggactcg   24060
agacggaggc gggcccgctt cttcgggggc gcgcggggcg gcgaggcgg cggcggcgac   24120 ggagacgggg acgagacatc gtccagggtg ggtggacggc gggccgcgcc gcgtccgcgc   24180 tcggggggtgg tctcgcgctg gtcctcttcc cgactggcca tctcccactg ctccttctcc   24240
tataggcaga aagagatcat ggagtctctc atgcgagtcg agaaggagga ggacagccta   24300
accgccccct ctgagccctc caccaccgcc gccaccaccg ccaatgccgc cgcggacgac   24360
gcgcccaccg agaccaccgc cagtaccacc ctccccagcg acgcaccccc gctcgagaat   24420
gaagtgctga tcgagcagga cccgggtttt gtgagcggag aggaggatga ggtggatgag   24480
aaggagaagg aggaggtcgc cgcctcagtg ccaaaagagg ataaaaagca agaccaggac   24540
gacgcagata aggatgagac agcagtcggg cggggggaacg gaagccatga tgctgatgac   24600
ggctacctag acgtgggaga cgacgtgctg cttaagcacc tgcaccgcca gtgcgtcatc   24660
gtctgcgacg cgctgcagga gcgctgcgaa gtgcccctgg acgtggcgga ggtcagccgc   24720
gcctacgagc ggcacctctt cgcgccgcac gtgccccccca agcgccggga gaacggcacc   24780
tgcgagccca cccgcgtct caacttctac ccggtcttcg cggtacccga ggtgctggcc   24840
acctaccaca tcttttttcca aaactgcaag atccccctct cctgccgcgc caaccgcacc   24900
cgcgccgaca aaaccctgac cctgcggcag ggcgcccaca tacctgatat cgcctctctg   24960
gaggaagtgc ccaagatctt cgagggtctc ggtcgcgacg agaaacgggc ggcgaacgct   25020
ctgcacggag acagcgaaaa cgagagtcac tcgggggtgc tggtggagct cgagggcgac   25080
aacgcgcgcc tggccgtact caagcgcagc atagaggtca cccactttgc ctacccggcg   25140
ctcaacctgc cccccaaggt catgagtgtg gtcatgggcg agctcatcat cgccgcgcc   25200 cagcccctgg ccgcggatgc aaacttgcaa gagtcctccg aggaaggcct gcccgcggtc   25260
agcgacgagc agctggcgcg ctggctggag accgcgacc ccgcgcagct ggaggagcgg   25320
cgcaagctca tgatggccgc ggtgctggtc accgtggagc tcgagtgtct gcagcgcttc   25380
ttcgcggacc ccgagatgca gcgcaagctc gaggagaccc tgcactacac cttccgccag   25440
ggctacgtgc gccaggcctg caagatctcc aacgtggagc tctgcaacct ggtctcctac   25500
ctgggcatcc tgcacgagaa ccgctcgggg cagaacgtcc tgcactccac cctcaaaggg   25560
gaggcgcgcc gcgactacat ccgcgactgc gcctacctct tcctctgcta cacctggcag   25620
```

```
acggccatgg gggtctggca gcagtgcctg gaggagcgca acctcaagga gctggaaaag   25680
ctcctcaagc gcaccctcag ggacctctgg acgggcttca acgagcgctc ggtggccgcc   25740
gcgctggcgg acatcatctt tcccgagcgc ctgctcaaga ccctgcagca gggcctgccc   25800
gacttcacca gccagagcat gctgcagaac ttcaggactt tcatcctgga gcgctcgggc   25860
atcctgccgg ccacttgctg cgcgctgccc agcgacttcg tgcccatcaa gtacagggag   25920
tgcccgccgc cgctctgggg ccactgctac ctcttccagc tggccaacta cctcgcctac   25980
cactcggacc tcatggaaga cgtgagcggc gagggcctgc tcgagtgcca ctgccgctgc   26040
aacctctgca cgccccaccg ctctctagtc tgcaacccgc agctgctcag cgagagtcag   26100
attatcggta ccttcgagct gcagggtccc tcgcctgacg agaagtccgc ggctccaggg   26160
ctgaaactca ctccggggct gtggacttcc gcctacctac gcaaatttgt acctgaggac   26220
taccacgccc acgagatcag gttctacgaa gaccaatccc gcccgcccaa ggcggagctc   26280
accgcctgcg tcatcaccca ggggcacatc ctgggccaat tgcaagccat caacaaagcc   26340
cgccgagagt tcttgctgaa aaagggtcgg ggggtgtacc tggaccccca gtccggcgag   26400
gagctaaacc cgctaccccc gccgccgccc cagcagcggg accttgcttc ccaggatggc   26460
acccagaaag aagcagcagc cgccgccgcc gccgcagcca tacatgcttc tggaggaaga   26520
ggaggaggac tgggacagtc aggcagagga ggtttcggac gaggagcagg aggagatgat   26580
ggaagactgg gaggaggaca gcagcctaga cgaggaagct tcagaggccg aagaggtggc   26640
agacgcaaca ccatcgccct cggtcgcagc ccccctcgccg gggcccctga atcctccga   26700 acccagcacc agcgctataa cctccgctcc tccggcgccg cgccacccg cccgcagacc   26760 caaccgtaga tgggacacca caggaaccgg ggtcggtaag tccaagtgcc cgccgccgcc   26820
accgcagcag cagcagcagc agcgccaggg ctaccgctcg tggcgcgggc acaagaacgc   26880
catagtcgcc tgcttgcaag actgcggggg caacatctct ttcgcccgcc gcttcctgct   26940
attccaccac ggggtcgcct ttccccgcaa tgtcctgcat tactaccgtc atctctacag   27000
cccctactgc agcggcgacc cagaggcggc agcggcagcc acagcggcga ccaccaccta   27060
ggaagatatc ctccgcgggc aagacagcgg cagcagcggc caggagaccc gcggcagcag   27120
cggcgggagc ggtgggcgca ctgcgcctct cgcccaacga ccctctcg acccgggagc   27180 tcagacacag gatcttcccc actttgtatg ccatcttcca acagagcaga ggccaggagc   27240
aggagctgaa aataaaaaac agatctctgc gctccctcac ccgcagctgt ctgtatcaca   27300
aaagcgaaga tcagcttcgg cgcacgctgg aggacgcgga ggcactcttc agcaaatact   27360
gcgcgctcac tcttaaagac tagctccgcg cccttctcga atttaggcgg gagaaaacta   27420
cgtcatcgcc ggccgccgcc cagcccgccc agcgagatg agcaaagaga ttcccacgcc   27480
atacatgtgg agctaccagc cgcagatggg actcgcggcg ggagcggccc aggactactc   27540
cacccgcatg aactacatga gcgcgggacc ccacatgatc tcacaggtca acgggatccg   27600
cgcccagcga aaccaaatac tgctggaaca ggcggccatc accgccacgc cccgccataa   27660 tctcaaccccc cgaaattggc ccgccgccct cgtgtaccag gaaaccccct ccgccaccac   27720
cgtactactt ccgcgtgacg cccaggccga agtccagatg actaactcag gggcgcagct   27780
cgcgggcggc tttcgtcacg gggcgcggcc gctccgacca ggtataagac acctgatgat   27840
cagaggccga ggtatccagc tcaacgacga gtcggtgagc tcttcgctcg gtctccgtcc   27900
ggacggaact ttccagctcg ccggatccgg ccgctcttcg ttcacgcccc gccaggcgta   27960
cctgactctg cagacctcgt cctcggagcc ccgctccggc ggcatcggaa ccctccagtt   28020
```

```
cgtggaggag ttcgtgccct cggtctactt caaccccttc tcgggacctc ccggacgcta   28080
ccccgaccag ttcattccga actttgacgc ggtgaaggac tcggcggacg gctacgactg   28140
aatgtcaggt gtcgaggcag agcagcttcg cctgagacac ctcgagcact gccgccgcca   28200
caagtgcttc gcccgcggtt ctggtgagtt ctgctacttt cagctacccg aggagcatac   28260
cgagggccg gcgcacggcg tccgcctgac cacccagggc gaggttacct gttccctcat   28320
ccgggagttt accctccgtc ccctgctagt ggagcgggag cggggtccct gtgtcctaac   28380
tatcgcctgc aactgcccta accctggatt acatcaagat ctttgctgtc atctctgtgc   28440
tgagtttaat aaacgctgag atcagaatct actgggctc ctgtcgccat cctgtgaacg   28500
ccaccgtctt cacccacccc gaccaggccc aggcgaacct cacctgcggt ctgcatcgga   28560
gggccaagaa gtacctcacc tggtacttca acggcacccc ctttgtggtt tacaacagct   28620
tcgacgggga cggagtctcc ctgaaagacc agctctccgg tctcagctac tccatccaca   28680
agaacaccac cctccaactc ttccctccct acctgccggg aacctacgag tgcgtcaccg   28740
gccgctgcac ccacctcacc cgcctgatcg taaaccagag cttccgggga acagataact   28800
ccctcttccc cagaacagga ggtgagctca ggaaactccc cggggaccag ggcggagacg   28860
taccttcgac ccttgtgggg ttaggatttt ttattaccgg gttgctggct cttttaatca   28920
aagtttcctt gagatttgtt ctttccttct acgtgtatga acacctcaac ctccaataac   28980
tctacccttt cttcggaatc aggtgacttc tctgaaatcg ggcttggtgt gctgcttact   29040
ctgttgattt ttttccttat catactcagc cttctgtgcc tcaggctcgc cgcctgctgc   29100
gcacacatct atatctactg ctggttgctc aagtgcaggg gtcgccaccc aagatgaaca   29160
ggtacatggt cctatcgatc ctaggcctgc tggccctggc ggcctgcagc gccgccaaaa   29220
aagagattac ctttgaggag cccgcttgca atgtaacttt caagcccgag ggtgaccaat   29280
gcaccaccct cgtcaaatgc gttaccaatc atgagaggct gcgcatcgac tacaaaaaca   29340
aaactggcca gtttgcggtc tatagtgtgt ttacgcccgg agacccctct aactactctg   29400
tcaccgtctt ccagggcgga cagtctaaga tattcaatta cactttccct ttttatgagt   29460
tatgcgatgc ggtcatgtac atgtcaaaac agtacaacct gtggcctccc tctccccagg   29520
cgtgtgtgga aaatactggg tcttactgct gtatggcttt cgcaatcact acgctcgctc   29580
taatctgcac ggtgctatac ataaaattca ggcagaggcg aatctttatc gatgaaaaga   29640
aaatgccttg atcgctaaca ccggcttttct atctgcagaa tgaatgcaat cacctcccta   29700
ctaatcacca ccaccctcct tgcgattgcc catgggttga cacgaatcga agtgccagtg   29760
gggtccaatg tcaccatggt gggccccgcc ggcaattcca ccctcatgtg ggaaaaattt   29820
gtccgcaatc aatgggttca tttctgctct aaccgaatca gtatcaagcc cagagccatc   29880
tgcgatgggc aaaatctaac tctgatcaat gtgcaaatga tggatgctgg gtactattac   29940
gggcagcggg gagaaatcat taattactgg cgacccaca aggactacat gctgcatgta   30000
gtcgaggcac ttcccactac cacccccact accacctctc ccaccaccac caccactact   30060
actactacta ctactactac tactactacc actaccgctg cccgccatac ccgcaaaagc   30120
accatgatta gcacaaagcc ccctcgtgct cactcccacg ccggcgggcc catcggtgcg   30180
acctcagaaa ccaccgagct ttgcttctgc caatgcacta acgccagcgc tcatgaactg   30240
ttcgacctgg agaatgagga tgtccagcag agctccgctt gcctgaccca ggaggctgtg   30300
gagcccgttg ccctgaagca gatcggtgat tcaataattg actcttcttc ttttgccact   30360
```

```
cccgaatacc ctcccgattc tactttccac atcacgggta ccaaagaccc taacctctct   30420
ttctacctga tgctgctgct ctgtatctct gtggtctctt ccgcgctgat gttactgggg   30480
atgttctgct gcctgatctg ccgcagaaag agaaaagctc gctctcaggg ccaaccactg   30540
atgcccttcc cctacccccc ggattttgca gataacaaga tatgagctcg ctgctgacac   30600
taaccgcttt actagcctgc gctctaaccc ttgtcgcttg cgactcgaga ttccacaatg   30660
tcacagctgt ggcaggagaa aatgttactt tcaactccac ggccgatacc cagtggtcgt   30720
ggagtggctc aggtagctac ttaactatct gcaatagctc cacttccccc ggcatatccc   30780
caaccaagta ccaatgcaat gccagcctgt tcaccctcat caacgcttcc accctggaca   30840
atggactcta tgtaggctat gtacccttttg gtgggcaagg aaagacccac gcttacaacc   30900
tggaagttcg ccagcccaga accactaccc aagcttctcc caccaccacc accaccacca   30960
ccatcaccag cagcagcagc agcagcagcc acagcagcag cagcagatta ttgactttgg   31020
ttttggccag ctcatctgcc gctacccagg ccatctacag ctctgtgccc gaaaccactc   31080
agatccaccg cccagaaacg accaccgcca ccaccctaca cacctccagc gatcagatgc   31140
cgaccaacat caccccccttg gctcttcaaa tgggacttac aagcccccact ccaaaaccag   31200
tggatgcggc cgaggtctcc gccctcgtca atgactgggc ggggctggga atgtggtggt   31260
tcgccatagg catgatggcg ctctgcctgc ttctgctctg gctcatctgc tgcctccacc   31320
gcaggcgagc cagacccccc atctatagac ccatcattgt cctgaacccc gataatgatg   31380
ggatccatag attggatggc ctgaaaaacc tactttttc ttttacagta tgataaattg   31440
agacatgcct cgcattttct tgtacatgtt ccttctccca ccttttctgg ggtgttctac   31500
gctggccgct gtgtctcacc tggaggtaga ctgcctctca cccttcactg tctacctgct   31560
ttacggattg gtcacccctca ctctcatctg cagcctaatc acagtaatca tcgccttcat   31620
ccagtgcatt gattacatct gtgtgcgcct cgcatacttc agacaccacc cgcagtaccg   31680
agacaggaac attgcccaac ttctaagact gctctaatca tgcataagac tgtgatctgc   31740
cttctgatcc tctgcatcct gcccaccctc acctcctgcc agtacaccac aaaatctccg   31800
cgcaaaagac atgcctcctg ccgcttcacc caactgtgga atatacccaa atgctacaac   31860
gaaaagagcg agctctccga agcttggctg tatggggtca tctgtgtctt agttttctgc   31920
agcactgtct ttgccctcat aatctacccc tactttgatt tgggatggaa cgcgatcgat   31980
gccatgaatt acccccacctt tcccgcaccc gagataattc cactgcgaca agttgtaccc   32040
gttgtcgtta atcaacgccc cccatcccct acgcccactg aaatcagcta ctttaaccta   32100
acaggcggag atgactgacg ccctagatct agaaatggac ggcatcagta ccgagcagcg   32160
tctcctagag aggcgcaggc aggcggctga gcaagagcgc ctcaatcagg agctccgaga   32220
tctcgttaac ctgcaccagt gcaaaagagg catctttttgt ctggtaaagc aggccaaagt   32280
cacctacgag aagaccggca acagccaccg cctcagttac aaattgccca cccagcgcca   32340
gaagctggtg ctcatggtgg gtgagaatcc catcaccgtc acccagcact cggtagagac   32400
cgaggggtgt ctgcactccc cctgtcgggg tccagaagac ctctgcaccc tggtaaagac   32460
cctgtgcggt ctcagagatt tagtcccctt taactaatca aacactggaa tcaataaaaa   32520
gaatcactta cttaaaatca gacagcaggt ctctgtccag tttattcagc agcacctcct   32580
tccctcctc ccaactctgg tactccaaac gccttctggc ggcaaacttc ctccacaccc   32640
tgaagggaat gtcagattct tgctcctgtc cctccgcacc cactatcttc atgttgttgc   32700
agatgaagcg caccaaaacg tctgacgaga gcttcaaccc cgtgtacccc tatgacacgg   32760
```

```
aaagcggccc tccctccgtc cctttcctca cccctcccct cgtgtctccc gatggattcc   32820
aagaaagtcc ccccggggtc ctgtctctga acctggccga gccctggtc acttcccacg    32880 gcatgctcgc cctgaaaatg ggaagtggcc tctccctgga cgacgctggc aacctcacct   32940
ctcaagatat caccaccgct agccctcccc tcaaaaaaac caagaccaac ctcagcctag   33000
aaacctcatc ccccctaact gtgagcacct caggcgccct caccgtagca gccgccgctc   33060
ccctggcggt ggccggcacc tccctcacca tgcaatcaga ggccccctg acagtacagg    33120 atgcaaaact caccctggcc accaaaggcc ccctgaccgt gtctgaaggc aaactggcct   33180
tgcaaacatc ggccccgctg acggccgctg acagcagcac cctcacagtc agtgccacac   33240
caccccttag cacaagcaat ggcagcttgg gtattgacat gcaagccccc atttacacca   33300
ccaatggaaa actaggactt aactttggcg ctcccctgca tgtggtagac agcctaaatg   33360
cactgactgt agttactggc caaggtctta cgataaacgg aacagcccta caaactagag   33420
tctcaggtgc cctcaactat gacacatcag gaaacctaga attgagagct gcaggggta    33480 tgcgagttga tgcaaatggt caacttatcc ttgatgtagc ttacccattt gatgcacaaa   33540
acaatctcag ccttaggctt ggacagggac ccctgtttgt taactctgcc cacaacttgg   33600
atgttaacta caacagaggc ctctacctgt tcacatctgg aaataccaaa aagctagaag   33660
ttaatatcaa aacagccaag ggtctcattt atgatgacac tgctatagca atcaatgcgg   33720
gtgatgggct acagtttgac tcaggctcag atacaaatcc attaaaaact aaacttggat   33780
taggactgga ttatgactcc agcagagcca taattgctaa actgggaact ggcctaagct   33840
ttgacaacac aggtgccatc acagtaggca acaaaaatga tgacaagctt accttgtgga   33900
ccacaccaga cccatcccct aactgtagaa tctattcaga gaaagatgct aaattcacac   33960
ttgttttgac taaatgcggc agtcaggtgt tggccagcgt ttctgttta tctgtaaaag    34020 gtagccttgc gcccatcagt ggcacagtaa ctagtgctca gattgtcctc agatttgatg   34080
aaaatggagt tctactaagc aattcttccc ttgaccctca atactggaac tacagaaaag   34140
gtgaccttac agagggcact gcatatacca acgcagtggg attttatgccc aacctcacag   34200 catacccaaa aacacagagc caaactgcta aaagcaaacat tgtaagtcag gtttacttga   34260
atggggacaa atccaaaccc atgaccctca ccattaccct caatggaact aatgaaacag   34320
gagatgccac agtaagcact tactccatgt cattctcatg gaactggaat ggaagtaatt   34380
acattaatga aacgttccaa accaactcct tcaccttctc ctacatcgcc caagaataaa   34440
aagcatgacg ctgttgattt gattcaatgt gtttctgttt tatttccaag cacaacaaaa   34500
tcattcaagt cattcttcca tcttagctta atagacacag tagcttaata gacccagtag   34560
tgcaaagccc cattctagct tatagatcag acagtgataa ttaaccacca ccaccaccat   34620
accttttgat tcaggaaatc atgatcatca caggatccta gtcttcaggc cgcccctcc    34680 ctcccaagac acagaataca cagtcctctc ccccgactg gctttaaata acaccatctg    34740
gttggtcaca gacatgttct taggggttat attccacacg gtctcctgcc gcgccaggcg   34800
ctcgtcggtg atgttgataa actctcccgg cagctcgctc aagttcacgt cgctgtccag   34860
cggctgaacc tccggctgac gcgataactg tgcgaccggc tgctggacga acggaggccg   34920
cgcctacaag ggggtagagt cataatcctc ggtcaggata gggcggtgat gcagcagcag   34980
cgagcgaaac atctgctgcc gccgccgctc cgtccgcag gaaaacaaca cgccggtggt    35040
ctcctccgcg ataatccgca ccgcccgcag catcagcttc ctcgttctcc gcgcgcagca   35100
```

```
cctcacccttatctcgctcaaatcggcgcagtaggtacagcacagcaccacgatgttatt   35160
catgatcccacagtgcagggcgctgtatccaaagctcatgccgggaaccaccgcccccac   35220
gtggccatcgtaccacaagcgcacgtaaatcaagtgtcgaccccctcatgaacgcgctgga  35280
cacaaacattacttccttgggcatgttgtaattcaccacctcccggtaccagataaacct   35340
ctggttgaacagggcaccttccaccaccatcctgaaccaagaggccagaacctgcccacc   35400
ggctatgcactgcagggaaccgggttggaacaatgacaatgcagactccaaggctcgta    35460
accgtggatcatccggctgctgaaggcatcgatgttggcaacacagacacacgtgcat     35520
gcactttctcatgattagcagctcttccctcgtcaggatcatatcccaaggaataaccca   35580
ttcttgaatcaacgtaaaacccacacagcagggaaggcctcgcacataactcacgttgtg   35640
catggtcagcgtgttgcattccggaaacagcggatgatcctccagtatcgaggcgcgggt   35700
ctccttctcacagggaggtaaagggtccctgctgtacggactgcgccgggacgaccgaga   35760
tcgtgttgagcgtagtgtcatggaaaagggaacgccggacgtggtcatacttcttgaagc   35820
agaaccaggttcgcgcgtggcaggcctcctgtgcgtctgcggtctcgccgtctagctcgct  35880
ccgtgtgatagttgtagtacagccactcccgcagagcgtcgaggcgcaccctggcttccg   35940
gatctatgtagactccgtctgtgcaccgcgccctgataatatccaccaccgtagaataag   36000
caacacccagccaagcaatacactcgctctgcgagcggcagacaggaggagcgggcagag   36060
atgggagaacatgataaaaaacttttttttaaagaatatttccaattcttcgaaagtaa     36120
gatctatcaagtggcagcgctccctccactggcgcggtcaaactctacggccaaagcac   36180
agacaacggcatttctaagatgttccttaatggcgtccaaaagacacaccgctctcaagt   36240
tgcagtaaactatgaatgaaaacccatccggctgatttcaatatagacgcgccggcag    36300
cgtccaccaaacccagataattttcttctctccagcggtttacgatctgtctaagcaaat   36360
cccttatatcaagtccgaccatgccaaaaatctgctcaagagcgccctccaccttcatgt   36420
acaagcagcgcatcatgattgcaaaaattcaggttcttcagagacctgtataagattcaa   36480
aatgggaacattaacaaaaattcctctgtcgcgcagatcccttcgcagggcaagctgaac   36540
ataatcagacaggtccgaacggaccagtgaggccaaatccccaccaggaaccagatccag   36600
agaccctatactgattatgacgcgcatactcggggctatgctgaccagcgtagcgccgat   36660
gtaggcgtgctgcatgggcggcgagataaaaatgcaaagtgctggttaaaaatcaggcaa   36720
agcctcgcgcaaaaaagctaacacatcataatcatgctcatgcaggtagttgcaggtaag   36780
ctcaggaaccaaaacggaataacacacgatttttcctctcaaacatgacttcgcggatact  36840
gcgtaaaacaaaaattataaataaaaattaattaaatactaaacattggaagcctg      36900
tctcacaacaggaaaaaccactttaatcaacataagacggccacgggcatgccggcata    36960
gccgtaaaaaaattggtccccgtgattaacaagtaccacagacagctcccggtcatgtc    37020
gggggtcatcatgtgagactctgtatacagtctggattgtgaacatcagacaaacaaag    37080
aaatcgagccacgtagcccggaggtataatcacccgcaggcggaggtacagcaaaacgac  37140
ccccataggaggaatcacaaaattagtaggagaaaaaaatacataaacaccagaaaaacc   37200
ctgttgctgaggcaaaatagcgccctcccgatccaaaacaacataaagcgcttccacagg  37260
agcagccataacaaagacccgagtcttaccagtaaaagaaaaagatctctcaacgcagc   37320
accagcaccaacacttcgcagtgtaaaaggccaagtgccgagagagtatatataggaata    37380
aaaagtgacgtaaacgggcaaagtccaaaaacgcccagaaaaaccgcacgcgaacctac   37440
gccccgaaacgaaagccaaaaaaacactagacactcccttccggcgtcaacttccgctttc 37500
```

```
ccacgctacg tcacttgccc cagtcaaaca aactacatat cccgaacttc caagtcgcca   37560
cgcccaaaac accgcctaca cctccccgcc cgccggcccg cccccaaacc cgcctcccgc   37620
cccgcgcccc gccccgcgcc gcccatctca ttatcatatt ggcttcaatc caaaataagg   37680
tatattattg atgatggttt aaacggatcc tctagagtcg acctgcaggc atgcaagctt   37740
gagtattcta tagtgtcacc taaatagctt ggcgtaatca tggtcatagc tgtttcctgt   37800
gtgaaattgt tatccgctca caattccaca acatacga gccggaagca taagtgtaa   37860 agcctggggt gcctaatgag tgagctaact cacattaatt gcgttgcgct cactgcccgc   37920
tttccagtcg ggaaacctgt cgtgccagct gcattaatga atcggccaac gcgaacccct   37980
tgcggccgcc cgggccgtcg accaattctc atgtttgaca gcttatcatc gaatttctgc   38040
cattcatccg cttattatca cttattcagg cgtagcaacc aggcgtttaa gggcaccaat   38100
aactgcctta aaaaaattac gccccgccct gccactcatc gcagtactgt tgtaattcat   38160
taagcattct gccgacatgg aagccatcac aaacggcatg atgaacctga atcgccagcg   38220
gcatcagcac cttgtcgcct tgcgtataat atttgcccat ggtgaaaacg ggggcgaaga   38280
agttgtccat attggccacg tttaaatcaa aactggtgaa actcacccag ggattggctg   38340
agacgaaaaa catattctca ataaacccrtt tagggaaata ggccaggttt tcaccgtaac   38400
acgccacatc ttgcgaatat atgtgtagaa actgccggaa atcgtcgtgg tattcactcc   38460
agagcgatga aaacgtttca gtttgctcat ggaaaacggt gtaacaaggg tgaacactat   38520
cccatatcac cagctcaccg tctttcattg ccatacggaa ttccggatga gcattcatca   38580
ggcgggcaag aatgtgaata aaggccggat aaaacttgtg cttattttc tttacggtct   38640 ttaaaaggc cgtaatatcc agctgaacgg tctggttata ggtacattga gcaactgact   38700
gaaatgcctc aaaatgttct ttacgatgcc attgggata tcaacggtg gtatatccag   38760 tgatttttt ctccatttta gcttccttag ctcctgaaaa tctcgataac tcaaaaaata   38820
cgcccggtag tgatcttatt tcattatggt gaaagttgga acctcttacg tgccgatcaa   38880
cgtctcattt tcgccaaaag ttggcccagg cttcccggt atcaacaggg acaccaggat   38940
ttatttattc tgcgaagtga tcttccgtca caggtattta ttcgcgataa gctcatggag   39000
cggcgtaacc gtcgcacagg aaggacagag aaagcgcgga tctgggaagt gacggacaga   39060
acggtcagga cctggattgg ggaggcggtt gccgccgctg ctgctgacgg tgtgacgttc   39120
tctgttccgg tcacaccaca tacgttccgc cattcctatg cgatgcacat gctgtatgcc   39180
ggtataccgc tgaaagttct gcaaagcctg atgggacata agtccatcag ttcaacggaa   39240
gtctacacga aggttttgc gctggatgtg gctgcccggc accgggtgca gtttgcgatg   39300
ccggagtctg atgcggttgc gatgctgaaa caattatcct gagaataaat gccttggcct   39360
ttatatggaa atgtggaact gagtggatat gctgttttg tctgttaaac agagaagctg   39420
gctgttatcc actgagaagc gaacgaaaca gtcgggaaaa tctcccatta tcgtagagat   39480
ccgcattatt aatctcagga gcctgtgtag cgtttatagg aagtagtgtt ctgtcatgat   39540
gcctgcaagc ggtaacgaaa acgatttgaa tatgccttca ggaacaatag aaatcttcgt   39600
gcggtgttac gttgaagtgg agcggattat gtcagcaatg acagaacaa cctaatgaac   39660 acagaaccat gatgtggtct gtccttttac agccagtagt gctcgccgca gtcgagcgac   39720
agggcgaagc cctcgagtga gcgaggaagc accaggaac agcacttata tattctgctt   39780
acacacgatg cctgaaaaaa cttcccttgg ggttatccac ttatccacgg ggatattttt   39840
```

```
ataattattt tttttatagt ttttagatct tctttttag agcgccttgt aggcctttat    39900
ccatgctggt tctagagaag gtgttgtgac aaattgccct ttcagtgtga caaatcaccc    39960
tcaaatgaca gtcctgtctg tgacaaattg cccttaaccc tgtgacaaat tgccctcaga    40020
agaagctgtt ttttcacaaa gttatccctg cttattgact cttttttatt tagtgtgaca    40080
atctaaaaac ttgtcacact tcacatggat ctgtcatggc ggaaacagcg gttatcaatc    40140
acaagaaacg taaaaatagc ccgcgaatcg tccagtcaaa cgacctcact gaggcggcat    40200
atagtctctc ccgggatcaa aaacgtatgc tgtatctgtt cgttgaccag atcagaaaat    40260
ctgatggcac cctacaggaa catgacggta tctgcgagat ccatgttgct aaatatgctg    40320
aaatattcgg attgacctct gcggaagcca gtaaggatat acggcaggca ttgaagagtt    40380
tcgcggggaa ggaagtggtt ttttatcgcc ctgaagagga tgccggcgat gaaaaaggct    40440
atgaatcttt tccttggttt atcaaacgtg cgcacagtcc atccagaggg ctttacagtg    40500
tacatatcaa cccatatctc attcccttct ttatcgggtt acagaaccgg tttacgcagt    40560
ttcggcttag tgaaacaaaa gaaatcacca atccgtatgc catgcgttta tacgaatccc    40620
tgtgtcagta tcgtaagccg gatggctcag gcatcgtctc tctgaaaatc gactggatca    40680
tagagcgtta ccagctgcct caaagttacc agcgtatgcc tgacttccgc cgccgcttcc    40740
tgcaggtctg tgttaatgag atcaacagca gaactccaat gcgcctctca tacattgaga    40800
aaaagaaagg ccgccagacg actcatatcg tatttccctt ccgcgatatc acttccatga    40860
cgacaggata gtctgagggt tatctgtcac agatttgagg gtggttcgtc acatttgttc    40920
tgacctactg agggtaattt gtcacagttt tgctgtttcc ttcagcctgc atggattttc    40980
tcatactttt tgaactgtaa tttttaagga agccaaattt gagggcagtt tgtcacagtt    41040
gatttccttc tctttcccctt cgtcatgtga cctgatatcg ggggttagtt cgtcatcatt    41100
gatgagggtt gattatcaca gtttattact ctgaattggc tatccgcgtg tgtacctcta    41160
cctggagttt ttcccacggt ggatatttct tcttgcgctg agcgtaagag ctatctgaca    41220
gaacagttct tctttgcttc ctcgccagtt cgctcgctat gctcggttac acggctgcgg    41280
cgagcgctag tgataataag tgactgaggt atgtgctctt cttatctcct tttgtagtgt    41340
tgctcttatt ttaaacaact ttgcggtttt ttgatgactt tgcgattttg ttgttgcttt    41400
gcagtaaatt gcaagattta ataaaaaaac gcaaagcaat gattaaagga tgttcagaat    41460
gaaactcatg gaaacactta accagtgcat aaacgctggt catgaaatga cgaaggctat    41520
cgccattgca cagtttaatg atgacagccc ggaagcgagg aaaataaccc ggcgctggag    41580
aataggtgaa gcagcggatt tagttggggt ttcttctcag gctatcagag atgccgagaa    41640
agcagggcga ctaccgcacc cggatatgga aattcgagga cgggttgagc aacgtgttgg    41700
ttatacaatt gaacaaatta atcatatgcg tgatgtgttt ggtacgcgat tgcgacgtgc    41760
tgaagacgta tttccaccgg tgatcggggt tgctgcccat aaaggtggcg tttacaaaac    41820
ctcagtttct gttcatcttg ctcaggatct ggctctgaag gggctacgtg ttttgctcgt    41880
ggaaggtaac gaccccagg gaacagcctc aatgtatcac ggatgggtac cagatcttca    41940
tattcatgca gaagacactc tcctgccttt ctatcttggg gaaaaggacg atgtcactta    42000
tgcaataaag cccacttgct ggccgggct tgacattatt ccttcctgtc tggctctgca    42060
ccgtattgaa actgagttaa tgggcaaatt tgatgaaggt aaactgccca ccgatccaca    42120
cctgatgctc cgactggcca ttgaaactgt tgctcatgac tatgatgtca tagttattga    42180
cagcgcgcct aacctgggta tcggcacgat taatgtcgta tgtgctgctg atgtgctgat    42240
```

```
tgttcccacg cctgctgagt tgtttgacta cacctccgca ctgcagtttt tcgatatgct   42300
tcgtgatctg ctcaagaacg ttgatcttaa agggttcgag cctgatgtac gtattttgct   42360
taccaaatac agcaatagta atggctctca gtccccgtgg atggaggagc aaattcggga   42420
tgcctgggga agcatggttc taaaaaatgt tgtacgtgaa acggatgaag ttggtaaagg   42480
tcagatccgg atgagaactg tttttgaaca ggccattgat caacgctctt caactggtgc   42540
ctggagaaat gctcttctta tttgggaacc tgtctgcaat gaaattttcg atcgtctgat   42600
taaaccacgc tgggagatta gataatgaag cgtgcgcctg ttattccaaa acatacgctc   42660
aatactcaac cggttgaaga tacttcgtta tcgacaccag ctgccccgat ggtggattcg   42720
ttaattgcgc gcgtaggagt aatggctcgc ggtaatgcca ttactttgcc tgtatgtggt   42780
cgggatgtga agtttactct tgaagtgctc cggggtgata tgttgagaa gacctctcgg   42840 gtatggtcag gtaatgaacg tgaccaggag ctgcttactg aggacgcact ggatgatctc   42900
atcccttctt ttctactgac tggtcaacag acaccggcgt tcggtcgaag agtatctggt   42960
gtcatagaaa ttgccgatgg gagtcgccgt cgtaaagctg ctgcacttac cgaaagtgat   43020
tatcgtgttc tggttggcga gctggatgat gagcagatgg ctgcattatc cagattgggt   43080
aacgattatc gcccaacaag tgcttatgaa cgtggtcagc gttatgcaag ccgattgcag   43140
aatgaatttg ctggaaatat ttctgcgctg gctgatgcgg aaaatatttc acgtaagatt   43200
attacccgct gtatcaacac cgccaaattg cctaaatcag ttgttgctct ttttctcac   43260 cccggtgaac tatctgcccg gtcaggtgat gcacttcaaa aagcctttac agataaagag   43320
gaattactta agcagcaggc atctaacctt catgagcaga aaaaagctgg ggtgatattt   43380
gaagctgaag aagttatcac tcttttaact tctgtgctta aaacgtcatc tgcatcaaga   43440
actagtttaa gctcacgaca tcagtttgct cctggagcga cagtattgta aagggcgat   43500 aaaatggtgc ttaacctgga caggtctcgt gttccaactg agtgtataga gaaaattgag   43560
gccattctta aggaacttga aaagccagca ccctgatgcg accacgtttt agtctacgtt   43620
tatctgtctt tacttaatgt cctttgttac aggccagaaa gcataactgg cctgaatatt   43680
ctctctgggc ccactgttcc acttgtatcg tcggtctgat aatcagactg ggaccacggt   43740
cccactcgta tcgtcggtct gattattagt ctgggaccac ggtcccactc gtatcgtcgg   43800
tctgattatt agtctgggac cacggtccca ctcgtatcgt cggtctgata atcagactgg   43860
gaccacggtc ccactcgtat cgtcggtctg attattagtc tgggaccatg gtcccactcg   43920
tatcgtcggt ctgattatta gtctgggacc acggtcccac tcgtatcgtc ggtctgatta   43980
ttagtctgga accacggtcc cactcgtatc gtcggtctga ttattagtct gggaccacgg   44040
tcccactcgt atcgtcggtc tgattattag tctgggacca cgatcccact cgtgttgtcg   44100
gtctgattat cggtctggga ccacggtccc acttgtattg tcgatcagac tatcagcgtg   44160
agactacgat tccatcaatg cctgtcaagg gcaagtattg acatgtcgtc gtaacctgta   44220
gaacggagta acctcggtgt gcggttgtat gcctgctgtg gattgctgct gtgtcctgct   44280
tatccacaac atttttgcgca cggttatgtg gacaaaatac ctggttaccc aggccgtgcc   44340
ggcacgttaa ccgggctgca tccgatgcaa gtgtgtcgct gtcgacgagc tcgcgagctc   44400
ggacatgagg ttgccccgta ttcagtgtcg ctgatttgta ttgtctgaag ttgttttttac   44460 gttaagttga tgcagatcaa ttaatacgat acctgcgtca taattgatta tttgacgtgg   44520
tttgatggcc tccacgcacg ttgtgatatg tagatgataa tcattatcac tttacgggtc   44580
```

```
ctttccggtg atccgacagg ttacggggcg gcgacctcgc gggttttcgc tatttatgaa   44640
aattttccgg tttaaggcgt ttccgttctt cttcgtcata acttaatgtt tttatttaaa   44700
ataccctctg aaaagaaagg aaacgacagg tgctgaaagc gagcttttg gcctctgtcg    44760 tttcctttct ctgttttgt ccgtggaatg aacaatggaa gtccgagctc atcgctaata    44820
acttcgtata gcatacatta tacgaagtta tattcgatgc ggccgcaagg ggttcgcgtc   44880
agcgggtgtt ggcgggtgtc ggggctggct taactatgcg gcatcagagc agattgtact   44940
gagagtgcac catatgcggt gtgaaatacc gcacagatgc gtaaggagaa aataccgcat   45000
caggcgccat cgccattca ggctgcgcaa ctgttgggaa gggcgatcgg tgcgggcctc    45060
ttcgctatta cgccagctgg cgaaagggg atgtgctgca aggcgattaa gttgggtaac    45120
gccagggttt tcccagtcac gacgttgtaa aacgacggcc agtgaattgt aatacgactc   45180
actatagggc gaattcgagc tcggtacccg gggatcctcg tttaaac                  45227

<210> SEQ ID NO 10
<211> LENGTH: 37830
<212> TYPE: DNA
<213> ORGANISM: Artificial Sequence
<220> FEATURE:
<223> OTHER INFORMATION: Polynucleotide sequence encoding wild type
      ChAd155

<400> SEQUENCE: 10
catcatcaat aatataccct attttggatt gaagccaata tgataatgag atgggcggcg     60
cggggcggga ggcgggtccg ggggcgggcc ggcgggcggg gcggtgtggc ggaagtggac    120
tttgtaagtg tggcggatgt gacttgctag tgccgggcgc ggtaaaagtg acgttttccg    180
tgcgcgacaa cgcccacggg aagtgacatt tttcccgcgg tttttaccgg atgttgtagt    240
gaatttgggc gtaaccaagt aagatttggc cattttcgcg ggaaaactga acggggaag    300 tgaaatctga ttaatttcgc gttagtcata ccgcgtaata tttgtcgagg ccgagggac    360 tttggccgat tacgtggagg actcgcccag gtgttttttg aggtgaattt ccgcgttccg   420
ggtcaaagtc tccgttttat tattatagtc agctgacgcg gagtgtattt ataccctctg   480
atctcgtcaa gtggccactc ttgagtgcca gcgagtagag ttttctcctc tgccgctctc    540
cgctccgctc cgctcggctc tgacaccggg gaaaaaatga gacatttcac ctacgatggc    600
ggtgtgctca ccggccagct ggctgctgaa gtcctggaca ccctgatcga ggaggtattg   660
gccgataatt atcctcccctc gactccttttt gagccaccta cacttcacga actctacgat   720 ctggatgtg tggggcccag cgatccgaac gagcaggcg tttccagttt ttttccagag     780
tccatgttgt tggccagcca ggaggggtc gaacttgaga cccctcctcc gatcgtggat     840
tcccccgatc cgccgcagct gactaggcag cccgagcgct gtgcgggacc tgagactatg    900
ccccagctgc tacctgaggt gatcgatctc acctgtaatg agtctggttt tccacccagc    960
gaggatgagg acgaagaggg tgagcagttt gtgttagatt ctgtgaaca acccgggcga   1020 ggatgcaggt cttgtcaata tcaccggaaa aacacaggag actcccagat tatgtgttct   1080
ctgtgttata tgaagatgac ctgtatgttt atttacagta agtttatcat ctgtgggcag   1140
gtgggctata gtgtgggtgg tggtctttgg ggggttttt aatatatgtc aggggttatg    1200
ctgaagactt ttattgtg atttttaag gtccagtgtc tgagcccgag caagaacctg      1260
aaccggagcc tgagccttct cgccccagga gaaagcctgt aatcttaact agacccagcg   1320
caccggtagc gagaggcctc agcagcgcgg agaccaccga ctccggtgct tcctcatcac   1380
```

```
ccccggagat tcacccccctg gtgcccctgt gtcccgttaa gcccgttgcc gtgagagtca    1440
gtgggcggcg gtctgctgtg gagtgcattg aggacttgct ttttgattca caggaacctt    1500
tggacttgag cttgaaacgc cccaggcatt aaacctggtc acctggactg aatgagttga    1560
cgcctatgtt tgcttttgaa tgacttaatg tgtatagata taaagagtg agataatgtt     1620 ttaattgcat ggtgtgttta acttgggcgg agtctgctgg gtatataagc ttccctgggc    1680
taaacttggt tacacttgac ctcatggagg cctgggagtg tttggagaac tttgccggag    1740
ttcgtgcctt gctggacgag agctctaaca atacctcttg gtggtggagg tatttgtggg    1800
gctctcccca gggcaagtta gtttgtagaa tcaaggagga ttacaagtgg gaatttgaag    1860
agcttttgaa atcctgtggt gagctattgg attctttgaa tctaggccac caggctctct    1920
tccaggagaa ggtcatcagg actttggatt ttttccacacc ggggcgcatt gcagccgcgg   1980
ttgcttttct agcttttttg aaggatagat ggagcgaaga gacccacttg agttcgggct    2040
acgtcctgga ttttctggcc atgcaactgt ggagagcatg gatcagacac aagaacaggc    2100
tgcaactgtt gtcttccgtc cgcccgttgc tgattccggc ggaggagcaa caggccgggt    2160
cagaggaccg ggcccgtcgg gatccggagg agagggcacc gaggccgggc gagaggagcg    2220
cgctgaacct gggaaccggg ctgagcggcc atccacatcg ggagtgaatg tcgggcaggt    2280
ggtggatctt tttccagaac tgcggcggat tttgactatt agggaggatg ggcaatttgt    2340
taagggtctt aagagggaga ggggggcttc tgagcataac gaggaggcca gtaatttagc    2400
ttttagcttg atgaccagac accgtccaga gtgcatcact tttcagcaga ttaaggacaa    2460
ttgtgccaat gagttggatc tgttgggtca gaagtatagc atagagcagc tgaccactta    2520
ctggctgcag ccgggtgatg atctggagga agctattagg gtgtatgcta aggtggccct    2580
gcggcccgat tgcaagtaca agctcaaggg gctggtgaat atcaggaatt gttgctacat    2640
ttctggcaac ggggcggagg tggagataga gaccgaagac agggtggctt tcagatgcag    2700
catgatgaat atgtggccgg gggtgctggg catggacggg gtggtgatta tgaatgtgag    2760
gttcacgggg cccaacttta acggcacggt gttttttgggg aacaccaacc tggtcctgca    2820
cggggtgagc ttctatgggt ttaacaacac ctgtgtggag gcctggaccg atgtgaaggt    2880
ccgcggttgc gccttttatg gatgttggaa ggccatagtg agccgcccta agagcaggag    2940
ttccattaag aaatgcttgt ttgagaggtg caccttgggg atcctggccg agggcaactg    3000
cagggtgcgc cacaatgtgg cctccgagtg cggttgcttc atgctagtca gagagcgtggc    3060 ggtaatcaag cataatatgg tgtgcggcaa cagcgaggac aaggcctcac agatgctgac    3120
ctgcacggat ggcaactgcc acttgctgaa gaccatccat gtaaccagcc acagccggaa    3180
ggcctggccc gtgttcgagc acaacttgct gacccgctgc tccttgcatc tgggcaacag    3240 gcgggggggtg ttcctgccct atcaatgcaa ctttagtcac accaagatct tgctagagcc    3300
cgagagcatg tccaaggtga acttgaacgg ggtgtttgac atgaccatga agatctggaa    3360
ggtgctgagg tacgacgaga ccaggtcccg gtgcagaccc tgcgagtgcg ggggcaagca    3420
tatgaggaac cagcccgtga tgctggatgt gaccgaggag ctgaggacag accacttggt    3480
tctggcctgc accagggccg agtttggttc tagcgatgaa gacacagatt gaggtgggtg    3540
agtgggcgtg gcctgggggtg gtcatgaaaa tatataagtt gggggtctta gggtctcttt    3600
atttgtgttg cagagaccgc cggagccatg agcgggagca gcagcagcag cagtagcagc    3660
agcgccttgg atggcagcat cgtgagccct tatttgacga cgcggatgcc ccactgggcc    3720 gggggtgcgtc agaatgtgat gggctccagc atcgacggcc gacccgtcct gcccgcaaat    3780
```

```
tccgccacgc tgacctatgc gaccgtcgcg gggacgccgt tggacgccac cgccgccgcc    3840
gccgccaccg cagccgcctc ggccgtgcgc agcctggcca cggactttgc attcctggga    3900
ccactggcga caggggctac ttctcgggcc gctgctgccg ccgttcgcga tgacaagctg    3960
accgccctgc tggcgcagtt ggatgcgctt actcgggaac tgggtgacct ttctcagcag    4020
gtcatggccc tgcgccagca ggtctcctcc ctgcaagctg gcgggaatgc ttctcccaca    4080
aatgccgttt aagataaata aaccagact ctgtttggat taaagaaaag tagcaagtgc     4140
attgctctct ttatttcata attttccgcg cgcgataggc cctagaccag cgttctcggt    4200
cgttgagggt gcggtgtatc ttctccagga cgtggtagag gtggctctgg acgttgagat    4260
acatgggcat gagcccgtcc cggggtgga ggtagcacca ctgcagagct tcatgctccg     4320
gggtggtgtt gtagatgatc cagtcgtagc aggagcgctg ggcatggtgc ctaaaaatgt    4380
ccttcagcag caggccgatg ccaggggga ggcccttggt gtaagtgttt acaaaacggt     4440
taagttggga agggtgcatt cggggagaga tgatgtgcat cttggactgt attttagat     4500 tggcgatgtt tccgcccaga tcccttctgg gattcatgtt gtgcaggacc accagtacag    4560
tgtatccggt gcacttgggg aatttgtcat gcagcttaga gggaaaagcg tggaagaact    4620
tggagacgcc tttgtggcct cccagatttt ccatgcattc gtccatgatg atggcaatgg    4680
gcccgcggga ggcagcttgg gcaaagatat ttctggggtc gctgacgtcg tagttgtgtt    4740
ccagggtgag gtcgtcatag gccattttta caaagcgcgg gcggagggtg cccgactggg    4800
ggatgatggt cccctctggc cctggggcgt agttgccctc gcagatctgc atttcccagg    4860
ccttaatctc ggaggggga atcatatcca cctgcgggc gatgaagaaa acggtttccg      4920
gagccgggga gattaactgg gatgagagca ggtttctaag cagctgtgat tttccacaac    4980
cggtgggccc ataaataaca cctataaccg gttgcagctg gtagtttaga gagctgcagc    5040
tgccgtcgtc ccggaggagg ggggccacct cgttgagcat gtccctgacg cgcatgttct    5100
ccccgaccag atccgccaga aggcgctcgc cgcccaggga cagcagctct tgcaaggaag    5160
caaagttttt cagcggcttg aggccgtccg ccgtgggcat gttttttcagg tctggctca   5220 gcagctccag gcggtcccag agctcggtga cgtgctctac ggcatctcta tccagcatat    5280
ctcctcgttt cgcggggttgg ggcgactttc gctgtagggc accaagcggt ggtcgtccag   5340
cggggccaga gtcatgtcct tccatgggcg cagggtcctc gtcagggtgg tctgggtcac    5400
ggtgaagggg tgcgctccgg gctgagcgct tgccaaggtg cgcttgaggc tggttctgct    5460
ggtgctgaag cgctgccggt cttcgccctg cgcgtcggcc aggtagcatt tgaccatggt    5520
gtcatagtcc agcccctccg cggcgtgtcc cttggcgcgc agcttgccct tggaggtggc    5580
gccgcacgag gggcagagca ggctcttgag cgcgtagagc ttgggggcga ggaagaccga    5640 ttcggggag taggcgtccg cgccgcagac cccgcacacg gtctcgcact ccaccagcca     5700
ggtgagctcg gggcgcgccg ggtcaaaaac caggtttccc ccatgctttt tgatgcgttt    5760
cttacctcgg gtctccatga ggtggtgtcc ccgctcggtg acgaagaggc tgtccgtgtc    5820
tccgtagacc gacttgaggg gtcttttctc caggggggtc cctcggtctt cctcgtagag    5880
gaactcggac cactctgaga cgaaggcccg cgtccaggcc aggacgaagg aggctatgtg    5940
ggaggggtag cggtcgttgt ccactagggg gtccaccttc tccaaggtgt gaagacacat    6000
gtcgccttcc tcggcgtcca ggaaggtgat tggcttgtag gtgtaggcca cgtgaccggg    6060
ggttcctgac gggggggtat aaaaggggggt ggggcgcgc tcgtcgtcac tctcttccgc    6120
```

-continued

```
atcgctgtct gcgagggcca gctgctgggg tgagtattcc ctctcgaagg cgggcatgac    6180
ctccgcgctg aggttgtcag tttccaaaaa cgaggaggat ttgatgttca cctgtcccga    6240
ggtgatacct ttgagggtac ccgcgtccat ctggtcagaa aacacgatct ttttattgtc    6300
cagcttggtg gcgaacgacc cgtagagggc gttggagagc agcttggcga tggagcgcag    6360
ggtctggttc ttgtccctgt cggcgcgctc cttggccgcg atgttgagct gcacgtactc    6420
gcgcgcgacg cagcgccact cggggaagac ggtggtgcgc tcgtcgggca ccaggcgcac    6480
gcgccagccg cggttgtgca gggtgaccag gtccacgctg gtggcgacct cgccgcgcag    6540
gcgctcgttg gtccagcaga gacggccgcc cttgcgcgag cagaagggg gcagggggtc     6600 gagctgggtc tcgtccgggg ggtccgcgtc cacggtgaaa accccgggc gcaggcgcgc     6660 gtcgaagtag tctatcttgc aaccttgcat gtccagcgcc tgctgccagt cgcgggcggc    6720
gagcgcgcgc tcgtaggggt tgagcggcgg gccccagggc atggggtggg tgagtgcgga    6780
ggcgtacatg ccgcagatgt catagacgta gaggggctcc cgcaggaccc cgatgtaggt    6840
ggggtagcag cggccgccgc ggatgctggc gcgcacgtag tcatacagct cgtgcgaggg    6900
ggcgaggagg tcggggccca ggttggtgcg ggcggggcgc tccgcgcgga agacgatctg    6960
cctgaagatg gcatgcgagt tggaagagat ggtggggcgc tggaagacgt tgaagctggc    7020
gtcctgcagg ccgacggcgt cgcgcacgaa ggaggcgtag gagtcgcgca gcttgtgtac    7080
cagctcggcg gtgacctgca cgtcgagcgc gcagtagtcg agggtctcgc ggatgatgtc    7140
atatttagcc tgccccttct ttttccacag ctcgcggttg aggacaaact cttcgcggtc    7200
tttccagtac tcttggatcg ggaaaccgtc cggttccgaa cggtaagagc ctagcatgta    7260
gaactggttg acggcctggt aggcgcagca gcccttctcc acggggaggg cgtaggcctg    7320
cgcggccttg cggagcgagg tgtgggtcag ggcgaaggtg tccctgacca tgactttgag    7380
gtactggtgc ttgaagtcgg agtcgtcgca gccgccccgc tcccagagcg agaagtcggt    7440
gcgcttcttg gagcggggt tgggcagagc gaaggtgaca tcgttgaaga ggattttgcc     7500 cgcgcgggc atgaagttgc gggtgatgcg gaagggcccc ggcacttcag agcggttgtt     7560
gatgacctgg gcggcgagca cgatctcgtc gaagccgttg atgttgtggc ccacgatgta    7620
gagttccagg aagcggggcc ggcccttac ggtgggcagc ttctttagct cttcgtaggt     7680
gagctcctcg ggcgaggcga ggccgtgctc ggccagggcc cagtccgcga ggtgcgggtt    7740
gtctctgagg aaggacttcc agaggtcgcg ggccaggagg gtctgcaggc ggtctctgaa    7800
ggtcctgaac tggcggccca cggccattt ttcgggggtg atgcagtaga aggtgagggg     7860
gtcttgctgc cagcggtccc agtcgagctg cagggcgagg tcgcgcgcgg cggtgaccag    7920
gcgctcgtcg cccccgaatt tcatgaccag catgaagggc acgagctgct ttccgaaggc    7980
ccccatccaa gtgtaggtct ctacatcgta ggtgacaaag aggcgctccg tgcgaggatg    8040
cgagccgatc gggaagaact ggatctcccg ccaccagttg gaggagtggc tgttgatgtg    8100
gtggaagtag aagtcccgtc gccgggccga acactcgtgc tggcttttgt aaaagcgagc    8160
gcagtactgg cagcgctgca cgggctgtac ctcatgcacg agatgcacct ttcgcccgcg    8220
cacgaggaag ccgagggga atctgagccc cccgcctggc tcgcggcatg gctggttctc    8280
ttctactttg gatgcgtgtc cgtctccgtc tggctcctcg aggggtgtta cggtggagcg    8340
gaccaccacg ccgcgcgagc cgcaggtcca gatatcggcg cgcggcggtc ggagtttgat    8400
gacgacatcg cgcagctggg agctgtccat ggtctggagc tccgcggcg gcggcaggtc     8460 agccgggagt tcttgcaggt tcacctcgca gagtcgggcc agggcgcggg gcaggtctag    8520
```

```
gtggtacctg atctctaggg gcgtgttggt ggcggcgtcg atggcttgca ggagcccgca   8580
gccccggggg gcgacgacgg tgccccgcgg ggtggtggtg gtggtggcgg tgcagctcag   8640
aagcggtgcc gcgggcgggc ccccggaggt aggggggggct ccggtcccgc gggcaggggc   8700
ggcagcggca cgtcggcgtg gagcgcgggc aggagttggt gctgtgcccg gaggttgctg   8760
gcgaaggcga cgacgcggcg gttgatctcc tggatctggc gcctctgcgt gaagacgacg   8820
ggcccggtga gcttgaacct gaaagagagt tcgacagaat caatctcggt gtcattgacc   8880
gcggcctggc gcaggatctc ctgcacgtct cccgagttgt cttggtaggc gatctcggcc   8940
atgaactgct cgatctcttc ctcctggagg tctccgcgtc cggcgcgttc cacggtggcc   9000
gccaggtcgt tggagatgcg ccccatgagc tgcgagaagg cgttgagtcc gccctcgttc   9060
cagactcggc tgtagaccac gccccctgg tcatcgcggg cgcgcatgac cacctgcgcg   9120
aggttgagct ccacgtgccg cgcgaagacg gcgtagttgc gcagacgctg aagaggtag    9180 ttgagggtgg tggcggtgtg ctcggccacg aagaagttca tgacccagcg gcgcaacgtg   9240
gattcgttga tgtcccccaa ggcctccagc cgttccatgg cctcgtagaa gtccacggcg   9300
aagttgaaaa actgggagtt gcgcgccgac acggtcaact cctcctccag aagacggatg   9360
agctcggcga cggtgtcgcg cacctcgcgc tcgaaggcta tggggatctc ttcctccgct   9420
agcatcacca cctcctcctc ttcctcctct tctggcactt ccatgatggc ttcctcctct   9480 tcgggggtg gcggcggcgg cggtggggga gggggcgctc tgcgccggcg gcggcgcacc   9540
gggaggcggt ccacgaagcg cgcgatcatc tccccgcggc ggcggcgcat ggtctcggtg   9600
acggcgcggc cgttctcccg ggggcgcagt tggaagacgc cgccggacat ctggtgctgg   9660
ggcgggtggc cgtgaggcag cgagacggcg ctgacgatgc atctcaacaa ttgctgcgta   9720
ggtacgccgc cgagggacct gagggagtcc atatccaccg gatccgaaaa cctttcgagg   9780
aaggcgtcta accagtcgca gtcgcaaggt aggctgagca ccgtggcggg cggcggggg   9840 tgggggagt gtctggcgga ggtgctgctg atgatgtaat tgaagtaggc ggacttgaca   9900
cggcggatgg tcgacaggag caccatgtcc ttgggtccgg cctgctggat gcggaggcgg   9960
tcggctatgc cccaggcttc gttctggcat cggcgcaggt ccttgtagta gtcttgcatg  10020
agcctttcca ccggcacctc ttctccttcc tcttctgctt cttccatgtc tgcttcggcc  10080
ctggggcggc gccgcgcccc cctgcccccc atgcgcgtga ccccgaaccc cctgagcggt  10140
tggagcaggg ccaggtcggc gacgacgcgc tcggccagga tggcctgctg cacctgcgtg  10200
agggtggttt ggaagtcatc caagtccacg aagcggtggt aggcgcccgt gttgatggtg  10260
taggtgcagt tggccatgac ggaccagttg acggtctggt ggcccggttg cgacatctcg  10320
gtgtacctga gtcgcgagta ggcgcgggag tcgaagacgt agtcgttgca agtccgcacc  10380
aggtactggt agcccaccag gaagtgcggc ggcggctggc ggtagagggg ccagcgcagg  10440
gtggcggggg ctccggggc caggtcttcc agcatgagcc ggtggtaggc gtagatgtac  10500
ctggacatcc aggtgatacc cgcggcggtg gtggaggcgc gcgggaagtc gcgcacccgg  10560
ttccagatgt tgcgcagggg cagaaagtgc tccatggtag gcgtgctctg tccagtcaga  10620
cgcgcgcagt cgttgatact ctagaccagg gaaaacgaaa gccggtcagc gggcactctt  10680
ccgtggtctg gtgaatagat cgcaagggta tcatggcgga gggcctcggt tcgagccccg  10740
ggtccgggcc ggacggtccg ccatgatcca cgcggttacc gcccgcgtgt cgaacccagg  10800
tgtgcgacgt cagacaacgg tggagtgttc cttttggcgt ttttctggcc gggcgccggc  10860
```

```
gccgcgtaag agactaagcc gcgaaagcga aagcagtaag tggctcgctc cccgtagccg    10920
gagggatcct tgctaagggt tgcgttgcgg cgaaccccgg ttcgaatccc gtactcgggc    10980
cggccggacc cgcggctaag gtgttggatt ggcctccccc tcgtataaag accccgcttg    11040
cggattgact ccggacacgg ggacgagccc cttttatttt tgctttcccc agatgcatcc    11100
ggtgctgcgg cagatgcgcc ccccgcccca gcagcagcaa caacaccagc aagagcggca    11160
gcaacagcag cgggagtcat gcaggggccc ctcacccacc ctcggcgggc cggccacctc    11220
ggcgtccgcg gccgtgtctg gcgcctgcgg cggcggcggg gggccggctg acgacccga    11280
ggagccccg cggcgcaggg ccagacacta cctggacctg gaggagggcg agggcctggc    11340
gcggctgggg gcgccgtctc ccgagcgcca cccgcgggtg cagctgaagc gcgactcgcg    11400
cgaggcgtac gtgcctcggc agaacctgtt cagggaccgc gcgggcgagg agcccgagga    11460
gatgcgggac aggaggttca gcgcagggcg ggagctgcgg caggggctga accgcgagcg    11520
gctgctgcgc gaggaggact ttgagcccga cgcgcggacg gggatcagcc ccgcgcgcgc    11580
gcacgtggcg gccgccgacc tggtgacggc gtacgagcag acggtgaacc aggagatcaa    11640
cttccaaaag agtttcaaca accacgtgcg cacgctggtg gcgcgcgagg aggtgaccat    11700
cgggctgatg cacctgtggg actttgtaag gcgcgctggtg cagaacccca acagcaagcc    11760
tctgacggcg cagctgttcc tgatagtgca gcacagcagg gacaacgagg cgtttaggga    11820
cgcgctgctg aacatcaccg agcccgaggg tcggtggctg ctggacctga ttaacatcct    11880
gcagagcata gtggtgcagg agcgcagcct gagcctggcc gacaaggtgg cggccatcaa    11940
ctactcgatg ctgagcctgg gcaagtttta cgcgcgcaag atctaccaga cgccgtacgt    12000
gcccatagac aaggaggtga agatcgacgg ttttttacatg cgcatggcgc tgaaggtgct    12060
caccctgagc gacgacctgg gcgtgtaccg caacgagcgc atccacaagg ccgtgagcgt    12120
gagccggcgg cgcgagctga gcgaccgcga gctgatgcac agcctgcagc gggcgctggc    12180
gggcgccgga gcggcgaca gggaggcgga gtcctacttc gatgcggggg cggacctgcg    12240
ctgggcgccc agccggcggg ccctggaggc gcgggggtc cgcgaggact atgacgagga    12300
cggcgaggag gatgaggagt acgagctaga ggagggcgag tacctggact aaaccgcggg    12360
tggtgtttcc ggtagatgca agacccgaac gtggtggacc cggcgctgcg ggcggctctg    12420
cagagccagc cgtccggcct taactcctca gacgactggc gacaggtcat ggaccgcatc    12480
atgtcgctga cggcgcgtaa cccggacgcg ttccggcagc agccgcaggc caacaggctc    12540
tccgccatcc tggaggcggt ggtgcctgcg cgctcgaacc ccacgcacga aaggtgctg    12600
gccatagtga acgcgctggc cgagaacagg gccatccgcc cggacgaggc cgggctggtg    12660
tacgacgcgc tgctgcagcg cgtggcccgc tacaacagcg gcaacgtgca gaccaacctg    12720
gaccggctgg tgggggacgt gcgcgaggcg gtggcgcagc gcgagcgcgc ggatcggcag    12780
ggcaacctgg gctccatggt ggcgctgaat gccttcctga gcacgcagcc ggccaacgtg    12840
ccgcggggc aggaagacta caccaacttt gtgagcgcgc tgcggctgat ggtgaccgag    12900
acccccaga gcgaggtgta ccagtcgggc ccggactact tcttccagac cagcagacag    12960
ggcctgcaga cggtgaacct gagccaggct ttcaagaacc tgcgggggct gtggggcgtg    13020
aaggcgccca ccggcgaccg ggcgacggtg tccagcctgc tgacgcccaa ctcgcgcctg    13080
ctgctgctgc tgatcgcgcc gttcacggac agcggcagcg tgtcccggga cacctacctg    13140
gggcacctgc tgaccctgta ccgcgaggcc atcgggcagg cgcaggtgga cgagcacacc    13200
ttccaggaga tcaccagcgt gagccgcgcg ctggggcagg aggacacgag cagcctggag    13260
```

```
gcgactctga actacctgct gaccaaccgg cggcagaaga ttccctcgct gcacagcctg    13320
acctccgagg aggagcgcat cttgcgctac gtgcagcaga gcgtgagcct gaacctgatg    13380
cgcgacgggg tgacgcccag cgtggcgctg gacatgaccg cgcgcaacat ggaaccgggc    13440
atgtacgccg cgcaccggcc ttacatcaac cgcctgatgg actacctgca tcgcgcggcc    13500
gccgtgaacc ccgagtactt taccaacgcc atcctgaacc cgcactggct cccgccgccc    13560
gggttctaca gcgggggctt cgaggtcccg gagaccaacg atggcttcct gtgggacgac    13620
atggacgaca gcgtgttctc cccgcggccg caggcgctgg cggaagcgtc cctgctgcgt    13680
cccaagaagg aggaggagga ggaggcgagt cgccgccgcg gcagcagcgg cgtggcttct    13740
ctgtccgagc tgggggcggc agccgccgcg cgccccgggt ccctgggcgg cagccccttt    13800
ccgagcctgg tggggtctct gcacagcgag cgcaccaccc gccctcggct gctgggcgag    13860
gacgagtacc tgaataactc cctgctgcag ccggtgcggg agaaaaacct gcctcccgcc    13920
ttccccaaca acgggataga gagcctggtg gacaagatga gcagatggaa gacctatgcg    13980
caggagcaca gggacgcgcc tgcgctccgg ccgcccacgc ggcgccagcg ccacgaccgg    14040
cagcgggggc tggtgtggga tgacgaggac tccgcggacg atagcagcgt gctggacctg    14100
ggagggagcg gcaacccgtt cgcgcacctg cgcccccgcc tggggaggat gttttaaaaa    14160
aaaaaaaaaa aagcaagaag catgatgcaa aaattaaata aaactcacca aggccatggc    14220
gaccgagcgt tggtttcttg tgttcccttc agtatgcggc gcgcggcgat gtaccaggag    14280
ggacctcctc cctcttacga gagcgtggtg ggcgcggcgg cggcggcgcc ctcttctccc    14340
tttgcgtcgc agctgctgga gccgccgtac gtgcctccgc gctacctgcg gcctacgggg    14400
gggagaaaca gcatccgtta ctcggagctg gcgcccctgt tcgacaccac ccgggtgtac    14460
ctggtggaca acaagtcggc ggacgtggcc tccctgaact accagaacga ccacagcaat    14520
tttttgacca cggtcatcca gaacaatgac tacagcccga gcgaggccag cacccagacc    14580
atcaatctgg atgaccggtc gcactggggc ggcgacctga aaaccatcct gcacaccaac    14640
atgcccaacg tgaacgagtt catgttcacc aataagttca aggcgcgggt gatggtgtcg    14700
cgctcgcaca ccaaggaaga ccgggtggag ctgaagtacg agtgggtgga gttcgagctg    14760
ccagagggca actactccga gaccatgacc attgacctga tgaacaacgc gatcgtggag    14820
cactatctga aagtgggcag gcagaacggg gtcctggaga gcgacatcgg ggtcaagttc    14880
gacaccagga acttccgcct ggggctggac cccgtgaccg gctggttat gcccggggtg    14940
tacaccaacg aggccttcca tcccgacatc atcctgctgc ccggctgcgg ggtggacttc    15000
acttacagcc gcctgagcaa cctcctgggc atccgcaagc ggcagcccctt ccaggagggc    15060
ttcaggatca cctacgagga cctggagggg gcaacatcc ccgcgctcct cgatgtggag    15120
gcctaccagg atagcttgaa ggaaaatgag gcgggacagg aggataccgc ccccgccgcc    15180
tccgccgccg ccgagcaggg cgaggatgct gctgacaccg cggccgcgga cggggcagag    15240
gccgaccccg ctatggtggt ggaggctccc gagcaggagg aggacatgaa tgacagtgcg    15300
gtgcgcggag acaccttcgt cacccggggg gaggaaaagc aagcggaggc cgaggccgcg    15360
gccgaggaaa agcaactggc ggcagcagcg gcggcggcgc cgttggccgc ggcggaggct    15420
gagtctgagg ggaccaagcc cgccaaggag cccgtgatta agcccctgac cgaagatagc    15480
aagaagcgca gttacaacct gctcaaggac agcaccaaca ccgcgtaccg cagctggtac    15540
ctggcctaca actacggcga cccgtcgacg ggggtgcgct cctggaccct gctgtgcacg    15600
```

```
ccggacgtga cctgcggctc ggagcaggtg tactggtcgc tgcccgacat gatgcaagac    15660
cccgtgacct tccgctccac gcggcaggtc agcaacttcc cggtggtggg cgccgagctg    15720
ctgcccgtgc actccaagag cttctacaac gaccaggccg tctactccca gctcatccgc    15780
cagttcacct ctctgaccca cgtgttcaat cgctttcctg agaaccagat tctggcgcgc    15840
ccgcccgccc ccaccatcac caccgtcagt gaaaacgttc ctgctctcac agatcacggg    15900
acgctaccgc tgcgcaacag catcggagga gtccagcgag tgaccgttac tgacgccaga    15960
cgccgcacct gccctacgt ttacaaggcc ttgggcatag tctcgccgcg cgtcctttcc    16020
agccgcactt tttgagcaac accaccatca tgtccatcct gatctcaccc agcaataact    16080
ccggctgggg actgctgcgc gcgcccagca agatgttcgg aggggcgagg aagcgttccg    16140
agcagcaccc cgtgcgcgtg cgcgggcact tccgcgcccc ctggggagcg cacaaacgcg    16200
gccgcgcggg gcgcaccacc gtggacgacg ccatcgactc ggtggtggag caggcgcgca    16260
actacaggcc cgcggtctct accgtggacg cggccatcca gaccgtggtg cggggcgcgc    16320
ggcggtacgc caagctgaag agccgccgga agcgcgtggc ccgccgccac cgccgccgac    16380
ccggggccgc cgccaaacgc ccgccgcgg ccctgcttcg ccgggccaag cgcacgggcc    16440
gccgcgccgc catgagggcc gcgcgccgct ggccgccgg catcaccgcc gccaccatgg    16500 cccccccgtac ccgaagacgc gcggccgccg ccgccgccgc cgccatcagt gacatggcca    16560
gcaggcgccg gggcaacgtg tactgggtgc gcgactcggt gaccggcacg cgcgtgcccg    16620
tgcgcttccg ccccccgcgg acttgagatg atgtgaaaaa acaacactga gtctcctgct    16680
gttgtgtgta tccagcggc ggcggcgcgc gcagcgtcat gtccaagcgc aaaatcaaag    16740
aagagatgct ccaggtcgtc gcgccggaga tctatgggcc cccgaagaag gaagagcagg    16800
attcgaagcc ccgcaagata aagcgggtca aaaagaaaaa gaaagatgat gacgatgccg    16860
atggggaggt ggagttcctg cgcgccacgg cgcccaggcg cccggtgcag tggaagggcc    16920
ggcgcgtaaa gcgcgtcctg cgccccgca ccgcggtggt cttcacgccc ggcgagcgct    16980
ccacccggac tttcaagcgc gtctatgacg aggtgtacgg cgacgaagac ctgctggagc    17040
aggccaacga gcgcttcgga gagtttgctt acgggaagcg tcagcgggcg ctggggaagg    17100
aggacctgct ggcgctgccg ctggaccagg gcaaccccac ccccagtctg aagcccgtga    17160
ccctgcagca ggtgctgccg agcagcgcac cctccgaggc gaagcggggt ctgaagcgcg    17220
agggcggcga cctggcgccc accgtgcagc tcatggtgcc caagcggcag aggctggagg    17280
atgtgctgga gaaaatgaaa gtagacccg gtctgcagcc ggacatcagg gtccgcccca    17340
tcaagcaggt ggcgccgggc ctcggcgtgc agaccgtgga cgtggtcatc cccaccggca    17400
actcccccgc cgccgccacc actaccgctg cctccacgga catggagaca cagaccgatc    17460
ccgccgcagc cgcagccgca gccgccgccg cgacctcctc ggcggaggtg cagacggacc    17520
cctggctgcc gccggcgatg tcagctcccc gcgcgcgtcg cgggcgcagg aagtacggcg    17580
ccgccaacgc gctcctgccc gagtacgcct tgcatccttc catcgcgccc accccggct    17640 accgaggcta tacctaccgc ccgcgaagag ccaagggttc caccgccgt ccccgccgac    17700 gcgccgccgc caccacccgc cgccgccgcc gcagacgcca gccgcactg gctccagtct    17760 ccgtgaggaa agtggcgcgc gacggacaca ccctggtgct gcccagggcg cgctaccacc    17820
ccagcatcgt ttaaaagcct gttgtggttc ttgcagatat ggccctcact tgccgcctcc    17880
gtttcccggt gccgggatac cgaggaggaa gatcgcgccg caggaggggt ctggccggcc    17940
gcggcctgag cggaggcagc cgccgcgcgc accggcggcg acgcgccacc agccgacgca    18000
```

```
tgcgcggcgg ggtgctgccc ctgttaatcc ccctgatcgc cgcggcgatc ggcgccgtgc    18060
ccgggatcgc ctccgtggcc ttgcaagcgt cccagaggca ttgacagact tgcaaacttg    18120
caaatatgga aaaaaaaacc ccaataaaaa agtctagact ctcacgctcg cttggtcctg    18180
tgactatttt gtagaatgga agacatcaac tttgcgtcgc tggccccgcg tcacggctcg    18240
cgcccgttcc tgggacactg gaacgatatc ggcaccagca acatgagcgg tggcgccttc    18300
agttggggct ctctgtggag cggcattaaa agtatcgggt ctgccgttaa aaattacggc    18360
tcccgggcct ggaacagcag cacgggccag atgttgagag acaagttgaa agagcagaac    18420
ttccagcaga aggtggtgga gggcctggcc tccggcatca acggggtggt ggacctggcc    18480
aaccaggccg tgcagaataa gatcaacagc agactggacc cccggccgcc ggtggaggag    18540
gtgccgccgg cgctggagac ggtgtccccc gatgggcgtg gcgagaagcg cccgcggccc    18600
gatagggaag agaccactct ggtcacgcag accgatgagc cgccccgta tgaggaggcc    18660 ctgaagcaag gtctgcccac cacgcggccc atcgcgccca tggccaccgg ggtggtgggc    18720
cgccacaccc ccgccacgct ggacttgcct ccgcccgccg atgtgccgca gcagcagaag    18780
gcggcacagc cgggccccgcc cgcgaccgcc tcccgttcct ccgccggtcc tctgcgccgc    18840
gcggccagcg gcccccgcgg gggggtcgcg aggcacggca actggcagag cacgctgaac    18900
agcatcgtgg gtctggggt gcggtccgtg aagcgccgcc gatgctactg aatagcttag    18960
ctaacgtgtt gtatgtgtgt atgcgcccta tgtcgccgcc agaggagctg ctgagtcgcc    19020
gccgttcgcg cgcccaccac caccgccact ccgcccctca agatggcgac cccatcgatg    19080
atgccgcagt ggtcgtacat gcacatctcg ggccaggacg cctcggagta cctgagcccc    19140
gggctggtgc agttcgcccg cgccaccgag agctacttca gcctgagtaa caagtttagg    19200
aaccccacgg tggcgcccac gcacgatgtg accaccgacc ggtctcagcg cctgacgctg    19260
cggttcattc ccgtggaccg cgaggacacc gcgtactcgt acaaggcgcg gttcaccctg    19320
gccgtgggcg acaaccgcgt gctggacatg gcctccacct actttgacat ccgcgggtg    19380 ctggaccggg gtcccacttt caagccctac tctggcaccg cctacaactc cctggccccc    19440
aagggcgctc ccaactcctg cgagtgggag caagaggaaa ctcaggcagt tgaagaagca    19500
gcagaagagg aagaagaaga tgctgacggt caagctgagg aagagcaagc agctaccaaa    19560
aagactcatg tatatgctca ggctcccctt tctggcaaaa aaattagtaa agatggtctg    19620
caaataggaa cggacgctac agctacagaa caaaaaccta tttatgcaga ccctacattc    19680
cagcccgaac cccaaatcgg ggagtcccag tggaatgagg cagatgctac agtcgccggc    19740
ggtagagtgc taaagaaatc tactcccatg aaaccatgct atggttccta tgcaagaccc    19800
acaaatgcta atggaggtca gggtgtacta acggcaaatg cccagggaca gctagaatct    19860
caggttgaaa tgcaattctt ttcaacttct gaaaacgccc gtaacgaggc taacaacatt    19920
cagcccaaat tggtgctgta tagtgaggat gtgcacatgg agaccccgga tacgcacctt    19980
tcttacaagc ccgcaaaaag cgatgacaat tcaaaaatca tgctgggtca gcagtccatg    20040
cccaacagac ctaattacat cggcttcaga gacaacttta tcggcctcat gtattacaat    20100
agcactggca acatgggagt gcttgcaggt caggcctctc agttgaatgc agtggtggac    20160
ttgcaagaca gaaacacaga actgtcctac cagctcttgc ttgattccat gggtgacaga    20220
accagatact tttccatgtg gaatcaggca gtggacagtt atgacccaga tgttagaatt    20280
attgaaaatc atggaactga agacgagctc cccaactatt gtttccctct gggtggcata    20340
```

```
ggggtaactg acacttacca ggctgttaaa accaacaatg gcaataacgg gggccaggtg   20400
acttggacaa aagatgaaac ttttgcagat cgcaatgaaa tagggtgggg aaacaatttc   20460
gctatggaga tcaacctcag tgccaacctg tggagaaact tcctgtactc caacgtggcg   20520
ctgtacctac cagacaagct taagtacaac ccctccaatg tggacatctc tgacaacccc   20580
aacacctacg attacatgaa caagcgagtg gtggccccgg ggctggtgga ctgctacatc   20640
aacctgggcg cgcgctggtc gctggactac atggacaacg tcaaccccct caaccaccac   20700
cgcaatgcgg gcctgcgcta ccgctccatg ctcctgggca acgggcgcta cgtgcccttc   20760
cacatccagg tgccccagaa gttctttgcc atcaagaacc tcctcctcct gccgggctcc   20820
tacacctacg agtggaactt caggaaggat gtcaacatgg tcctccagag ctctctgggt   20880
aacgatctca gggtgacgg ggccagcatc aagttcgaga gcatctgcct ctacgccacc   20940
ttcttcccca tggcccacaa cacggcctcc acgctcgagg ccatgctcag gaacgacacc   21000
aacgaccagt ccttcaatga ctacctctcc gccgccaaca tgctctaccc catacccgcc   21060
aacgccacca acgtccccat ctccatcccc tcgcgcaact gggcggcctt ccgcggctgg   21120
gccttcaccc gcctcaagac caaggagacc ccctccctgg gctcgggatt cgacccctac   21180
tacacctact cgggctccat tccctacctg gacggcacct tctacctcaa ccacactttc   21240
aagaaggtct cggtcacctt cgactcctcg gtcagctggc cgggcaacga ccgtctgctc   21300 accccccaacg agttcgagat caagcgctcg gtcgacgggg agggctacaa cgtggcccag   21360
tgcaacatga ccaaggactg gttcctggtc cagatgctgg ccaactacaa catcggctac   21420
cagggcttct acatcccaga gagctacaag gacaggatgt actccttctt caggaacttc   21480
cagcccatga gccggcaggt ggtggaccag accaagtaca aggactacca ggaggtgggc   21540
atcatccacc agcacaacaa ctcgggcttc gtgggctacc tcgcccccac catgcgcgag   21600
ggacaggcct accccgccaa cttcccctat ccgctcatag gcaagaccgc ggtcgacagc   21660
atcacccaga aaaagttcct ctgcgaccgc accctctggc gcatcccctt ctccagcaac   21720
ttcatgtcca tgggtgcgct ctcggacctg ggccagaact tgctctacgc caactccgcc   21780
cacgccctcg acatgacctt cgaggtcgac cccatggacg agcccaccct tctctatgtt   21840
ctgttcgaag tctttgacgt ggtccgggtc caccagccgc accgcggcgt catcgagacc   21900
gtgtacctgc gtacgccctt ctcggccggc aacgccacca cctaaagaag caagccgcag   21960
tcatcgccgc ctgcatgccg tcgggttcca ccgagcaaga gctcagggcc atcgtcagag   22020
acctgggatg cgggccctat tttttgggca ccttcgacaa gcgcttccct ggctttgtct   22080
ccccacacaa gctggcctgc gccatcgtca acacggccgg ccgcgagacc gggggcgtgc   22140
actggctggc cttcgcctgg aacccgcgct ccaaaacatg cttcctcttt gaccccttcg   22200
gcttttcgga ccagcggctc aagcaaatct acgagttcga gtacgagggc ttgctgcgtc   22260
gcagcgccat cgcctcctcg cccgaccgct gcgtcaccct cgaaaagtcc acccagaccg   22320
tgcaggggcc cgactcggcc gcctgcggtc tcttctgctg catgtttctg cacgcctttg   22380
tgcactggcc tcagagtccc atggaccgca cccccaccat gaacttgctg acggggtgc    22440 ccaactccat gctccagagc ccccaggtcg agcccaccct cgccgcaac caggagcagc    22500 tctacagctt cctggagcgc cactcgcctt acttccgccg ccacagcgca cagatcagga    22560
gggccacctc cttctgccac ttgcaagaga tgcaagaagg gtaataacga tgtacacact    22620
ttttttctca ataaatggca tcttttattt tatacaagct ctctggggta ttcattccc    22680 accaccaccc gccgttgtcg ccatctggct ctatttagaa atcgaaaggg ttctgccggg    22740
```

```
agtcgccgtg cgccacgggc agggacacgt tgcgatactg gtagcgggtg ccccacttga   22800
actcgggcac caccaggcga ggcagctcgg ggaagttttc gctccacagg ctgcgggtca   22860
gcaccagcgc gttcatcagg tcgggcgccg agatcttgaa gtcgcagttg gggccgccgc   22920
cctgcgcgcg cgagttgcgg tacaccgggt tgcagcactg gaacaccaac agcgccgggt   22980
gcttcacgct ggccagcacg ctgcggtcgg agatcagctc ggcgtccagg tcctccgcgt   23040
tgctcagcgc gaacgggtc atcttgggca cttgccgccc caggaagggc gcgtgccccg    23100
gtttcgagtt gcagtcgcag cgcagcggga tcagcaggtg cccgtgcccg gactcggcgt   23160
tggggtacag cgcgcgcatg aaggcctgca tctggcggaa ggccatctgg gccttggcgc   23220
cctccgagaa gaacatgccg caggacttgc ccgagaactg gtttgcgggg cagctggcgt   23280
cgtgcaggca gcagcgcgcg tcggtgttgg cgatctgcac cacgttgcgc ccccaccggt   23340
tcttcacgat cttggccttg gacgattgct ccttcagcgc gcgctgcccg ttctcgctgg   23400
tcacatccat ctcgatcaca tgttccttgt tcaccatgct gctgccgtgc agacacttca   23460
gctcgccctc cgtctcggtg cagcggtgct gccacagcgc gcagcccgtg ggctcgaaag   23520
acttgtaggt cacctccgcg aaggactgca ggtaccctg caaaaagcgg cccatcatgg    23580
tcacgaaggt cttgttgctg ctgaaggtca gctgcagccc gcggtgctcc tcgttcagcc   23640
aggtcttgca cacggccgcc agcgcctcca cctggtcggg cagcatcttg aagttcacct   23700
tcagctcatt ctccacgtgg tacttgtcca tcagcgtgcg cgccgcctcc atgcccttct   23760
cccaggccga caccagcggc aggctcacgg ggttcttcac catcaccgtg gccgccgcct   23820
ccgccgcgct ttcgctttcc gccccgctgt tctcttcctc ttcctcctct tcctcgccgc   23880
cgcccactcg cagcccccgc accacggggt cgtcttcctg caggcgctgc accttgcgct   23940
tgccgttgcg cccctgcttg atgcgcacgg gcgggttgct gaagcccacc atcaccagcg   24000
cggcctcttc ttgctcgtcc tcgctgtcca gaatgacctc cggggagggg gggttggtca   24060
tcctcagtac cgaggcacgc ttcttttct tcctgggggc gttcgccagc tccgcggctg     24120
cggccgctgc cgaggtcgaa ggccgagggc tgggcgtgcg cggcaccagc gcgtcctgcg   24180
agccgtcctc gtcctcctcg gactcgagac ggaggcgggc ccgcttcttc ggggcgcgc    24240 ggggcggcgg aggcggcggc ggcgacggag acggggacga gacatcgtcc agggtgggtg   24300
gacggcgggc cgcgccgcgt ccgcgctcgg gggtggtctc gcgctggtcc tcttcccgac   24360
tggccatctc ccactgctcc ttctcctata ggcagaaaga gatcatggag tctctcatgc   24420
gagtcgagaa ggaggaggac agcctaaccg cccctctga gccctccacc accgccgcca    24480
ccaccgccaa tgccgccgcg gacgacgcgc ccaccgagac caccgccagt accaccctcc   24540
ccagcgacgc acccccgctc gagaatgaag tgctgatcga gcaggacccg ggttttgtga   24600
gcggagagga ggatgaggtg gatgagaagg agaaggagga ggtcgccgcc tcagtgccaa   24660
aagaggataa aaagcaagac caggacgacg cagataagga tgagacagca gtcgggcggg   24720
ggaacggaag ccatgatgct gatgacggct acctagacgt gggagacgac gtgctgctta   24780
agcacctgca ccgccagtgc gtcatcgtct gcgacgcgct gcaggagcgc tgcgaagtgc   24840
ccctggacgt ggcggaggtc agccgcgcct acgagcggca cctcttcgcg ccgcacgtgc   24900
cccccaagcg ccgggagaac ggcacctgcg agcccaaccc gcgtctcaac ttctacccgg   24960
tcttcgcggt acccgaggtg ctggccacct accacatctt tttccaaaac tgcaagatcc   25020
ccctctcctg ccgcgccaac cgcacccgcg ccgacaaaac cctgacctg cggcagggcg     25080
```

```
cccacatacc tgatatcgcc tctctggagg aagtgcccaa gatcttcgag ggtctcggtc    25140
gcgacgagaa acgggcggcg aacgctctgc acggagacag cgaaaacgag agtcactcgg    25200
gggtgctggt ggagctcgag ggcgacaacg cgcgcctggc cgtactcaag cgcagcatag    25260
aggtcaccca ctttgcctac ccggcgctca acctgcccc caaggtcatg agtgtggtca     25320
tgggcgagct catcatgcgc cgcgcccagc ccctggccgc ggatgcaaac ttgcaagagt    25380
cctccgagga aggcctgccc gcggtcagcg acgagcagct ggcgcgctgg ctggagaccc    25440
gcgaccccgc gcagctggag gagcggcgca agctcatgat ggccgcggtg ctggtcaccg    25500
tggagctcga gtgtctgcag cgcttcttcg cggaccccga gatgcagcgc aagctcgagg    25560
agaccctgca ctacaccttc cgccagggct acgtgcgcca ggcctgcaag atctccaacg    25620
tggagctctg caacctggtc tcctacctgg gcatcctgca cgagaaccgc ctcgggcaga    25680
acgtcctgca ctccaccctc aaggggagg cgcgccgcga ctacatccgc gactgcgcct     25740
acctcttcct ctgctacacc tggcagacgg ccatggggt ctggcagcag tgcctggagg     25800
agcgcaacct caaggagctg gaaaagctcc tcaagcgcac cctcagggac ctctggacgg    25860
gcttcaacga gcgctcggtg gccgccgcgc tggcggacat catctttccc gagcgcctgc    25920
tcaagaccct gcagcagggc ctgcccgact tcaccagcca gagcatgctg cagaacttca    25980
ggactttcat cctggagcgc tcgggcatcc tgccggccac ttgctgcgcg ctgcccagcg    26040
acttcgtgcc catcaagtac agggagtgcc cgccgccgct ctgggccac tgctacctct     26100
tccagctggc caactacctc gcctaccact cggacctcat ggaagacgtg agcggcgagg    26160
gcctgctcga gtgccactgc cgctgcaacc tctgcacgcc ccaccgctct ctagtctgca    26220
acccgcagct gctcagcgag agtcagatta tcggtacctt cgagctgcag ggtccctcgc    26280
ctgacgagaa gtccgcggct ccagggctga aactcactcc ggggctgtgg acttccgcct    26340
acctacgcaa atttgtacct gaggactacc acgcccacga gatcaggttc tacgaagacc    26400
aatcccgccc gcccaaggcg gagctcaccg cctgcgtcat cacccagggg cacatcctgg    26460
gccaattgca agccatcaac aaagcccgcc gagagttctt gctgaaaaag ggtcgggggg    26520
tgtacctgga ccccagtcc ggcgaggagc taaacccgct accccgccg ccgcccagc      26580
agcgggacct tgcttcccag gatggcaccc agaaagaagc agcagccgcc gccgccgccg    26640
cagccataca tgcttctgga ggaagaggag gaggactggg acagtcaggc agaggaggtt    26700
tcggacgagg agcaggagga gatgatggaa gactgggagg aggacagcag cctagacgag    26760
gaagcttcag aggccgaaga ggtggcagac gcaacaccat cgccctcggt cgcagccccc    26820
tcgccggggc ccctgaaatc ctccgaaccc agcaccagcg ctataacctc cgctcctccg    26880
gcgccggcgc cacccgcccg cagacccaac cgtagatggg acaccacagg aaccggggtc    26940
ggtaagtcca agtgcccgcc gccgccaccg cagcagcagc agcagcagcg ccagggctac    27000
cgctcgtggc gcgggcacaa gaacgccata gtcgcctgct gcaagactg cgggggcaac     27060
atctctttcg cccgccgctt cctgctattc caccacgggg tcgcctttcc ccgcaatgtc    27120
ctgcattact accgtcatct ctacagcccc tactgcagcg gcgacccaga ggcggcagcg    27180
gcagccacag cggcgaccac cacctaggaa gatatcctcc gcgggcaaga cagcggcagc    27240
agcggccagg agaccgcgg cagcagcggc gggagcggtg ggcgcactgc gcctctcgcc     27300
caacgaaccc ctctcgaccc gggagctcag acacaggatc ttccccactt tgtatgccat    27360
cttccaacag agcagaggcc aggagcagga gctgaaaata aaaaacagat ctctgcgctc    27420
cctcacccgc agctgtctgt atcacaaaag cgaagatcag cttcggcgca cgctggagga    27480
```

```
cgcggaggca ctcttcagca aatactgcgc gctcactctt aaagactagc tccgcgccct    27540
tctcgaattt aggcgggaga aaactacgtc atcgccggcc gccgcccagc ccgcccagcc    27600
gagatgagca aagagattcc cacgccatac atgtggagct accagccgca gatgggactc    27660
gcggcgggag cggcccagga ctactccacc cgcatgaact acatgagcgc gggaccccac    27720
atgatctcac aggtcaacgg gatccgcgcc cagcgaaacc aaatactgct ggaacaggcg    27780
gccatcaccg ccacgccccg ccataatctc aaccccgaa attggcccgc cgccctcgtg     27840
taccaggaaa cccctccgc caccaccgta ctacttccgc gtgacgccca ggccgaagtc     27900
cagatgacta actcaggggc gcagctcgcg ggcggctttc gtcacggggc gcggccgctc    27960
cgaccaggta taagacacct gatgatcaga ggccgaggta tccagctcaa cgacgagtcg    28020
gtgagctctt cgctcggtct ccgtccggac ggaactttcc agctcgccgg atccggccgc    28080
tcttcgttca cgccccgcca ggcgtacctg actctgcaga cctcgtcctc ggagccccgc    28140
tccggcggca tcggaaccct ccagttcgtg gaggagttcg tgccctcggt ctacttcaac    28200
cccttctcgg gacctcccgg acgctacccc gaccagttca ttccgaactt tgacgcggtg    28260
aaggactcgg cggacggcta cgactgaatg tcaggtgtcg aggcagagca gcttcgcctg    28320
agacacctcg agcactgccg ccgccacaag tgcttcgccc gcggttctgg tgagttctgc    28380
tactttcagc tacccgagga gcataccgag gggccggcgc acggcgtccg cctgaccacc    28440
cagggcgagg ttacctgttc cctcatccgg gagtttaccc tccgtcccct gctagtggag    28500
cgggagcggg gtccctgtgt cctaactatc gcctgcaact gccctaaccc tggattacat    28560
caagatcttt gctgtcatct ctgtgctgag tttaataaac gctgagatca gaatctactg    28620
gggctcctgt cgccatcctg tgaacgccac cgtcttcacc caccccgacc aggcccaggc    28680
gaacctcacc tgcggtctgc atcggagggc caagaagtac ctcacctggt acttcaacgg    28740
cacccccttt gtggtttaca acagcttcga cggggacgga gtctccctga agaccagct    28800 ctccggtctc agctactcca tccacaagaa caccaccctc caactcttcc ctccctacct    28860
gccgggaacc tacgagtgcg tcaccggccg ctgcacccac ctcacccgcc tgatcgtaaa    28920
ccagagcttt ccgggaacag ataactccct cttcccaga acaggaggtg agctcaggaa    28980
actccccggg gaccagggcg gagacgtacc ttcgaccctt gtggggttag gattttttat    29040 taccggggttg ctggctcttt taatcaaagt ttccttgaga tttgttcttt ccttctacgt    29100
gtatgaacac ctcaacctcc aataactcta ccctttcttc ggaatcaggt gacttctctg    29160
aaatcgggct tggtgtgctg cttactctgt tgatttttt ccttatcata ctcagccttc    29220
tgtgcctcag gctcgccgcc tgctgcgcac acatctatat ctactgctgg ttgctcaagt    29280
gcaggggtcg ccaccaaga tgaacaggta catggtccta tcgatcctag gcctgctggc    29340
cctggcggcc tgcagcgccg ccaaaaaaga gattaccttt gaggagcccg cttgcaatgt    29400
aactttcaag cccgagggtg accaatgcac caccctcgtc aaatgcgtta ccaatcatga    29460
gaggctgcgc atcgactaca aaaacaaaac tggccagttt gcggtctata gtgtgtttac    29520
gcccggagac ccctctaact actctgtcac cgtcttccag ggcggacagt ctaagatatt    29580
caattacact ttccctttt atgagttatg cgatgcggtc atgtacatgt caaaacagta    29640
caacctgtgg cctccctctc cccaggcgtg tgtggaaaat actgggtctt actgctgtat    29700
ggctttcgca atcactacgc tcgctctaat ctgcacggtg ctatacataa aattcaggca    29760
gaggcgaatc tttatcgatg aaaagaaaat gccttgatcg ctaacaccgg ctttctatct    29820
```

```
gcagaatgaa tgcaatcacc tccctactaa tcaccaccac cctccttgcg attgcccatg    29880
ggttgacacg aatcgaagtg ccagtggggt ccaatgtcac catggtgggc cccgccggca    29940
attccaccct catgtgggaa aaatttgtcc gcaatcaatg ggttcatttc tgctctaacc    30000
gaatcagtat caagcccaga gccatctgcg atgggcaaaa tctaactctg atcaatgtgc    30060
aaatgatgga tgctgggtac tattacgggc agcggggaga aatcattaat tactggcgac    30120
cccacaagga ctacatgctg catgtagtcg aggcacttcc cactaccacc cccactacca    30180
cctctcccac caccaccacc actactacta ctactactac tactactact actaccacta    30240
ccgctgcccg ccatcccgc aaaagcacca tgattagcac aaagcccct cgtgctcact    30300 cccacgccgg cgggcccatc ggtgcgacct cagaaaccac cgagctttgc ttctgccaat    30360
gcactaacgc cagcgctcat gaactgttcg acctggagaa tgaggatgtc cagcagagct    30420
ccgcttgcct gacccaggag gctgtggagc ccgttgccct gaagcagatc ggtgattcaa    30480
taattgactc ttcttctttt gccactcccg aataccctcc cgattctact ttccacatca    30540
cgggtaccaa agaccctaac ctctctttct acctgatgct gctgctctgt atctctgtgg    30600
tctcttccgc gctgatgtta ctggggatgt tctgctgcct gatctgccgc agaaagagaa    30660
aagctcgctc tcagggccaa ccactgatgc ccttcccccta cccccggat tttgcagata    30720 acaagatatg agctcgctgc tgacactaac cgctttacta gcctgcgctc taacccttgt    30780
cgcttgcgac tcgagattcc acaatgtcac agctgtggca ggagaaaatg ttactttcaa    30840
ctccacggcc gatacccagt ggtcgtggag tggctcaggt agctacttaa ctatctgcaa    30900
tagctccact tcccccggca tatccccaac caagtaccaa tgcaatgcca gcctgttcac    30960
cctcatcaac gcttccaccc tggacaatgg actctatgta ggctatgtac cctttggtgg    31020
gcaaggaaag acccacgctt acaacctgga agttcgccag cccagaacca ctacccaagc    31080
ttctcccacc accaccacca ccaccaccat caccagcagc agcagcagca gcagccacag    31140
cagcagcagc agattattga ctttggtttt ggccagctca tctgccgcta cccaggccat    31200
ctacagctct gtgcccgaaa ccactcagat ccaccgccca gaaacgacca ccgccaccac    31260
cctacacacc tccagcgatc agatgccgac caacatcacc cccttggctc ttcaaatggg    31320
acttacaagc cccactccaa aaccagtgga tgcggccgag gtctccgccc tcgtcaatga    31380
ctgggcgggg ctgggaatgt ggtggttcgc cataggcatg atggcgctct gcctgcttct    31440
gctctggctc atctgctgcc tccaccgcag gcgagccaga cccccccatct atagacccat    31500 cattgtcctg aaccccgata atgatgggat ccatagattg gatggcctga aaaacctact    31560 ttttctttt acagtatgat aaattgagac atgcctcgca ttttcttgta catgttcctt    31620
ctcccacctt ttctggggtg ttctacgctg gccgctgtgt ctcacctgga ggtagactgc    31680
ctctcaccct tcactgtcta cctgctttac ggattggtca ccctcactct catctgcagc    31740
ctaatcacag taatcatcgc cttcatccag tgcattgatt acatctgtgt gcgcctcgca    31800
tacttcagac accaccgca gtaccgagac aggaacattg cccaacttct aagactgctc    31860
taatcatgca taagactgtg atctgccttc tgatcctctg catcctgccc accctcacct    31920
cctgccagta caccacaaaa tctccgcgca aaagacatgc ctcctgccgc ttcacccaac    31980
tgtggaatat acccaaatgc tacaacgaaa agagcgagct ctccgaagct tggctgtatg    32040
gggtcatctg tgtcttagtt ttctgcagca ctgtctttgc cctcataatc taccctact    32100 ttgatttggg atggaacgcg atcgatgcca tgaattaccc cacctttccc gcacccgaga    32160
taattccact gcgacaagtt gtacccgttg tcgttaatca acgcccccca tcccctacgc    32220
```

```
ccactgaaat cagctacttt aacctaacag gcggagatga ctgacgccct agatctagaa   32280
atggacggca tcagtaccga gcagcgtctc ctagagaggc gcaggcaggc ggctgagcaa   32340
gagcgcctca atcaggagct ccgagatctc gttaacctgc accagtgcaa aagaggcatc   32400
ttttgtctgg taaagcaggc caaagtcacc tacgagaaga ccggcaacag ccaccgcctc   32460
agttacaaat tgcccaccca gcgccagaag ctggtgctca tggtgggtga aatcccatc   32520
accgtcaccc agcactcggt agagaccgag gggtgtctgc actcccctg tcggggtcca   32580
gaagacctct gcaccctggt aaagaccctg tgcggtctca gagatttagt cccctttaac   32640
taatcaaaca ctggaatcaa taaaagaat cacttactta aaatcagaca gcaggtctct   32700
gtccagttta ttcagcagca cctccttccc ctcctcccaa ctctggtact ccaaacgcct   32760
tctggcggca aacttcctcc acaccctgaa gggaatgtca gattcttgct cctgtccctc   32820
cgcacccact atcttcatgt tgttgcagat gaagcgcacc aaaacgtctg acgagagctt   32880
caaccccgtg tacccctatg acacggaaag cggccctccc tccgtccctt tcctcacccc   32940
tcccttcgtg tctcccgatg gattccaaga aagtcccccc ggggtcctgt ctctgaacct   33000
ggccgagccc ctggtcactt cccacggcat gctcgccctg aaaatgggaa gtggcctctc   33060
cctggacgac gctggcaacc tcacctctca agatatcacc accgctagcc ctccctcaa   33120
aaaaaccaag accaacctca gcctagaaac ctcatccccc ctaactgtga gcacctcagg   33180
cgccctcacc gtagcagccg ccgctcccct ggcggtggcc ggcacctccc tcaccatgca   33240
atcagaggcc cccctgacag tacaggatgc aaaactcacc ctggccacca aggcccccct   33300
gaccgtgtct gaaggcaaac tggccttgca acatcggcc ccgctgacgg ccgctgacag   33360
cagcaccctc acagtcagtg ccacaccacc ccttagcaca agcaatggca gcttgggtat   33420
tgacatgcaa gccccccattt acaccaccaa tggaaaacta ggacttaact ttggcgctcc   33480
cctgcatgtg gtagacagcc taaatgcact gactgtagtt actggccaag gtcttacgat   33540
aaacggaaca gccctacaaa ctagagtctc aggtgccctc aactatgaca catcaggaaa   33600
cctagaattg agagctgcag ggggtatgcg agttgatgca aatggtcaac ttatccttga   33660
tgtagcttac ccatttgatg cacaaaacaa tctcagcctt aggcttggac agggacccct   33720
gtttgttaac tctgcccaca acttggatgt taactacaac agaggcctct acctgttcac   33780
atctggaaat accaaaaagc tagaagttaa tatcaaaaca gccaagggtc tcatttatga   33840
tgacactgct atagcaatca atgcgggtga tgggctacag tttgactcag gctcagatac   33900
aaatccatta aaaactaaac ttggattagg actggattat gactccagca gagccataat   33960
tgctaaactg ggaactggcc taagctttga caacacaggt gccatcacag taggcaacaa   34020
aaatgatgac aagcttacct tgtgaccac accagaccca tccctaact gtagaatcta   34080
ttcagagaaa gatgctaaat tcacacttgt tttgactaaa tgcggcagtc aggtgttggc   34140
cagcgttttct gttttatctg taaaaggtag ccttgcgccc atcagtggca cagtaactag   34200
tgctcagatt gtcctcagat ttgatgaaaa tggagttcta ctaagcaatt cttcccttga   34260
ccctcaatac tggaactaca gaaaaggtga ccttacagag ggcactgcat ataccaacgc   34320
agtgggattt atgcccaacc tcacagcata cccaaaaaca cagagccaaa ctgctaaaag   34380
caacattgta agtcaggttt acttgaatgg ggacaaatcc aaacccatga ccctcaccat   34440
taccctcaat ggaactaatg aaacaggaga tgccacagta agcacttact ccatgtcatt   34500
ctcatggaac tggaatggaa gtaattacat taatgaaacg ttccaaacca actccttcac   34560
```

```
cttctcctac atcgcccaag aataaaaagc atgacgctgt tgatttgatt caatgtgttt    34620
ctgttttatt ttcaagcaca acaaaatcat tcaagtcatt cttccatctt agcttaatag    34680
acacagtagc ttaatagacc cagtagtgca aagccccatt ctagcttata gatcagacag    34740
tgataattaa ccaccaccac caccatacct tttgattcag gaaatcatga tcatcacagg    34800
atcctagtct tcaggccgcc ccctccctcc caagacacag aatacacagt cctctccccc    34860
cgactggctt taaataacac catctggttg gtcacagaca tgttcttagg ggttatattc    34920
cacacggtct cctgccgcgc caggcgctcg tcggtgatgt tgataaactc tcccggcagc    34980
tcgctcaagt tcacgtcgct gtccagcggc tgaacctccg gctgacgcga taactgtgcg    35040
accggctgct ggacgaacgg aggccgcgcc tacaaggggg tagagtcata atcctcggtc    35100
aggatagggc ggtgatgcag cagcagcgag cgaaacatct gctgccgccg ccgctccgtc    35160
cggcaggaaa acaacacgcc ggtggtctcc tccgcgataa tccgcaccgc ccgcagcatc    35220
agcttcctcg ttctccgcgc gcagcacctc acccttatct cgctcaaatc ggcgcagtag    35280
gtacagcaca gcaccacgat gttattcatg atcccacagt gcagggcgct gtatccaaag    35340
ctcatgccgg gaaccaccgc ccccacgtgg ccatcgtacc acaagcgcac gtaaatcaag    35400
tgtcgacccc tcatgaacgc gctggacaca aacattactt ccttgggcat gttgtaattc    35460
accacctccc ggtaccagat aaacctctgg ttgaacaggg caccttccac caccatcctg    35520
aaccaagagg ccagaacctg cccaccggct atgcactgca gggaacccgg gttggaacaa    35580
tgacaatgca gactccaagg ctcgtaaccg tggatcatcc ggctgctgaa ggcatcgatg    35640
ttggcacaac acagacacac gtgcatgcac tttctcatga ttagcagctc ttccctcgtc    35700
aggatcatat cccaaggaat aacccattct tgaatcaacg taaaacccac acagcaggga    35760
aggcctcgca cataactcac gttgtgcatg gtcagcgtgt tgcattccgg aaacagcgga    35820
tgatcctcca gtatcgaggc gcgggtctcc ttctcacagg gaggtaaagg gtccctgctg    35880
tacggactgc gccgggacga ccgagatcgt gttgagcgta gtgtcatgga aaagggaacg    35940
ccggacgtgg tcatacttct tgaagcagaa ccaggttcgc gcgtggcagg cctccttgcg    36000
tctgcggtct cgccgtctag ctcgctccgt gtgatagttg tagtacagcc actcccgcag    36060
agcgtcgagg cgcaccctgg cttccggatc tatgtagact ccgtcttgca ccgcggccct    36120
gataatatcc accaccgtag aataagcaac acccagccaa gcaatacact cgctctgcga    36180
gcggcagaca ggaggagcgg gcagagatgg gagaaccatg ataaaaaact ttttttaaag    36240
aatattttcc aattcttcga aagtaagatc tatcaagtgg cagcgctccc ctccactggc    36300
gcggtcaaac tctacggcca aagcacagac aacggcattt ctaagatgtt ccttaatggc    36360
gtccaaaaga cacaccgctc tcaagttgca gtaaactatg aatgaaaacc catccggctg    36420
attttccaat atagacgcgc cggcagcgtc caccaaaccc agataatttt cttctctcca    36480
gcggtttacg atctgtctaa gcaaatccct tatatcaagt ccgaccatgc caaaaatctg    36540
ctcaagagcg ccctccacct tcatgtacaa gcagcgcatc atgattgcaa aaattcaggt    36600
tcttcagaga cctgtataag attcaaaatg gaacattaa caaaaattcc tctgtcgcgc    36660
agatcccttc gcagggcaag ctgaacataa tcagacaggt ccgaacggac cagtgaggcc    36720
aaatccccac caggaaccag atccagagac cctatactga ttatgacgcg catactcggg    36780
gctatgctga ccagcgtagc gccgatgtag gcgtgctgca tgggcggcga gataaaatgc    36840
aaagtgctgg ttaaaaaatc aggcaaagcc tcgcgcaaaa aagctaacac atcataatca    36900
tgctcatgca ggtagttgca ggtaagctca ggaaccaaaa cggaataaca cacgatttc    36960
```

```
ctctcaaaca tgacttcgcg gatactgcgt aaaacaaaaa attataaata aaaaattaat    37020
taaataactt aaacattgga agcctgtctc acaacaggaa aaaccacttt aatcaacata    37080
agacgggcca cgggcatgcc ggcatagccg taaaaaaatt ggtccccgtg attaacaagt    37140
accacagaca gctccccggt catgtcgggg gtcatcatgt gagactctgt atacacgtct    37200
ggattgtgaa catcagacaa acaaagaaat cgagccacgt agcccggagg tataatcacc    37260
cgcaggcgga ggtacagcaa aacgaccccc ataggaggaa tcacaaaatt agtaggagaa    37320
aaaaatacat aaacaccaga aaaaccctgt tgctgaggca aaatagcgcc ctcccgatcc    37380
aaaacaacat aaagcgcttc cacaggagca gccataacaa agacccgagt cttaccagta    37440
aaagaaaaaa gatctctcaa cgcagcacca gcaccaacac ttcgcagtgt aaaaggccaa    37500
gtgccgagag agtatatata ggaataaaaa gtgacgtaaa cgggcaaagt ccaaaaaacg    37560
cccagaaaaa ccgcacgcga acctacgccc cgaaacgaaa gccaaaaaac actagacact    37620
cccttccggc gtcaacttcc gctttcccac gctacgtcac ttcccccggt caaacaaact    37680
acatatcccg aacttccaag tcgccacgcc caaaacaccg cctacacctc cccgcccgcc    37740
ggcccgcccc cggacccgcc tcccgccccg cgccgcccat ctcattatca tattggcttc    37800
aatccaaaat aaggtatatt attgatgatg                                    37830

<210> SEQ ID NO 11
<211> LENGTH: 543
<212> TYPE: PRT
<213> ORGANISM: Artificial Sequence
<220> FEATURE:
<223> OTHER INFORMATION: ChAd3 fiber amino acid sequence

<400> SEQUENCE: 11

Met Lys Arg Thr Lys Thr Ser Asp Glu Ser Phe Asn Pro Val Tyr Pro
 1               5                  10                  15

Tyr Asp Thr Glu Ser Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
        50                  55                  60

Lys Met Gly Ser Gly Leu Ser Leu Asp Asp Ala Gly Asn Leu Thr Ser
 65                  70                  75                  80

Gln Asp Ile Thr Thr Ala Ser Pro Pro Leu Lys Lys Thr Lys Thr Asn
                 85                  90                  95

Leu Ser Leu Glu Thr Ser Ser Pro Leu Thr Val Ser Thr Ser Gly Ala
            100                 105                 110

Leu Thr Val Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Leu Thr Val
                165                 170                 175

Ser Ala Thr Pro Pro Ile Asn Val Ser Ser Gly Ser Leu Gly Leu Asp
            180                 185                 190

Met Glu Asp Pro Met Tyr Thr His Asp Gly Lys Leu Gly Ile Arg Ile
        195                 200                 205
```

```
Gly Gly Pro Leu Arg Val Val Asp Ser Leu His Thr Leu Thr Val Val
        210                 215                 220

Thr Gly Asn Gly Leu Thr Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asn Val
            260                 265                 270

Ala Tyr Pro Phe Asp Ala Gln Asn Asn Leu Ser Leu Arg Leu Gly Gln
        275                 280                 285

Gly Pro Leu Tyr Ile Asn Thr Asp His Asn Leu Asp Leu Asn Cys Asn
    290                 295                 300

Arg Gly Leu Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
            340                 345                 350

Gly Asn Thr Gly Asp Asp Lys Leu Thr Leu Trp Thr Thr Pro Asp Pro
        355                 360                 365

Ser Pro Asn Cys Arg Ile His Ser Asp Lys Asp Cys Lys Phe Thr Leu
    370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ala Ser Val
                405                 410                 415

Thr Ile Phe Leu Arg Phe Asp Gln Asn Gly Val Leu Met Glu Asn Ser
            420                 425                 430

Ser Leu Asp Arg Gln Tyr Trp Asn Phe Arg Asn Gly Asn Ser Thr Asn
        435                 440                 445

Ala Ala Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540

<210> SEQ ID NO 12
<211> LENGTH: 541
<212> TYPE: PRT
<213> ORGANISM: Artificial Sequence
<220> FEATURE:
<223> OTHER INFORMATION: PanAd3 fiber amino acid sequence

<400> SEQUENCE: 12

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30
```

Phe Val Ser Pro Asp Gly Phe Gln Glu Ser Pro Gly Val Leu Ser
            35                  40                  45

Leu Arg Leu Ser Glu Pro Leu Val Thr Ser His Gly Met Leu Ala Leu
 50                  55                  60

Lys Met Gly Asn Gly Leu Ser Leu Asp Asp Ala Gly Asn Leu Thr Ser
 65                  70                  75                  80

Gln Asp Val Thr Thr Val Thr Pro Pro Leu Lys Lys Thr Lys Thr Asn
                    85                  90                  95

Leu Ser Leu Gln Thr Ser Ala Pro Leu Thr Val Ser Ser Gly Ser Leu
                100                 105                 110

Thr Val Ala Ala Ala Ala Pro Leu Ala Val Ala Gly Thr Ser Leu Thr
                115                 120                 125

Met Gln Ser Gln Ala Pro Leu Thr Val Gln Asp Ala Lys Leu Gly Leu
            130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Gly
                    165                 170                 175

Thr Thr Pro Pro Ile Ser Val Ser Ser Gly Ser Leu Gly Leu Asp Met
                180                 185                 190

Glu Asp Pro Met Tyr Thr His Asp Gly Lys Leu Gly Ile Arg Ile Gly
            195                 200                 205

Gly Pro Leu Gln Val Val Asp Ser Leu His Thr Leu Thr Val Val Thr
            210                 215                 220

Gly Asn Gly Ile Thr Val Ala Asn Asn Ala Leu Gln Thr Lys Val Ala
225                 230                 235                 240

Gly Ala Leu Gly Tyr Asp Ser Ser Gly Asn Leu Glu Leu Arg Ala Ala
                    245                 250                 255

Gly Gly Met Arg Ile Asn Thr Gly Gly Gln Leu Ile Leu Asp Val Ala
                260                 265                 270

Tyr Pro Phe Asp Ala Gln Asn Asn Leu Ser Leu Arg Leu Gly Gln Gly
            275                 280                 285

Pro Leu Tyr Val Asn Thr Asn His Asn Leu Asp Leu Asn Cys Asn Arg
            290                 295                 300

Gly Leu Thr Thr Thr Thr Ser Ser Asn Thr Thr Lys Leu Glu Thr Lys
305                 310                 315                 320

Ile Asp Ser Gly Leu Asp Tyr Asn Ala Asn Gly Ala Ile Ile Ala Lys
                    325                 330                 335

Leu Gly Thr Gly Leu Thr Phe Asp Asn Thr Gly Ala Ile Thr Val Gly
                340                 345                 350

Asn Thr Gly Asp Asp Lys Leu Thr Leu Trp Thr Thr Pro Asp Pro Ser
            355                 360                 365

Pro Asn Cys Arg Ile His Ala Asp Lys Asp Lys Phe Thr Leu Val Leu
            370                 375                 380

Thr Lys Cys Gly Ser Gln Ile Leu Ala Ser Val Ala Ala Leu Ala Val
385                 390                 395                 400

Ser Gly Asn Leu Ser Ser Met Thr Gly Thr Val Ser Ser Val Thr Ile
                    405                 410                 415

Phe Leu Arg Phe Asp Gln Asn Gly Val Leu Met Glu Asn Ser Ser Leu
                420                 425                 430

Asp Lys Glu Tyr Trp Asn Phe Arg Asn Gly Asn Ser Thr Asn Ala Thr
            435                 440                 445

```
Pro Tyr Thr Asn Ala Val Gly Phe Met Pro Asn Leu Ser Ala Tyr Pro
    450                 455                 460

Lys Thr Gln Ser Gln Thr Ala Lys Asn Asn Ile Val Ser Glu Val Tyr
465                 470                 475                 480

Leu His Gly Asp Lys Ser Lys Pro Met Ile Leu Thr Ile Thr Leu Asn
                485                 490                 495

Gly Thr Asn Glu Ser Ser Glu Thr Ser Gln Val Ser His Tyr Ser Met
                500                 505                 510

Ser Phe Thr Trp Ser Trp Asp Ser Gly Lys Tyr Ala Thr Glu Thr Phe
            515                 520                 525

Ala Thr Asn Ser Phe Thr Phe Ser Tyr Ile Ala Glu Gln
    530                 535                 540

<210> SEQ ID NO 13
<211> LENGTH: 543
<212> TYPE: PRT
<213> ORGANISM: Artificial Sequence
<220> FEATURE:
<223> OTHER INFORMATION: ChAd17 fiber amino acid sequence

<400> SEQUENCE: 13

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Ser Thr Thr Pro Pro Leu Lys Lys Thr Lys Thr Asn
                85                  90                  95

Leu Ser Leu Glu Thr Ser Ser Pro Leu Thr Val Ser Thr Ser Gly Ala
                100                 105                 110

Leu Thr Val Ala Ala Ala Ala Pro Leu Ala Val Ala Gly Thr Ser Leu
            115                 120                 125

Thr Met Gln Ser Glu Ala Pro Leu Ala Val Gln Asp Ala Lys Leu Thr
130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ser Thr Pro Pro Ile Ser Val Ser Ser Gly Ser Leu Gly Leu Asp
                180                 185                 190

Met Glu Asp Pro Met Tyr Thr His Asp Gly Lys Leu Gly Ile Arg Ile
            195                 200                 205

Gly Gly Pro Leu Arg Val Val Asp Ser Leu His Thr Leu Thr Val Val
    210                 215                 220

Thr Gly Asn Gly Leu Thr Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asp Val
                260                 265                 270
```

```
Ala Tyr Pro Phe Asp Ala Gln Asn Asn Leu Ser Leu Arg Leu Gly Gln
            275                 280                 285

Gly Pro Leu Tyr Val Asn Thr Asp His Asn Leu Asp Leu Asn Cys Asn
290                 295                 300

Arg Gly Leu Thr Thr Thr Thr Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
                340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ala Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
            435                 440                 445

Ala Ala Pro Tyr Thr Asn Ala Val Gly Phe Met Pro Asn Leu Ala Ala
            450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
            515                 520                 525

Thr Phe Ala Thr Asn Ser Phe Thr Phe Ser Tyr Ile Ala Glu Gln
            530                 535                 540

<210> SEQ ID NO 14
<211> LENGTH: 543
<212> TYPE: PRT
<213> ORGANISM: Artificial Sequence
<220> FEATURE:
<223> OTHER INFORMATION: ChAd19 fiber amino acid sequence

<400> SEQUENCE: 14

Met Lys Arg Thr Lys Thr Ser Asp Lys Ser Phe Asn Pro Val Tyr Pro
1               5                   10                  15

Tyr Asp Thr Glu Asn Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
50                  55                  60

Lys Met Gly Ser Gly Leu Ser Leu Asp Asp Ala Gly Asn Leu Thr Ser
65                  70                  75                  80

Gln Asp Val Thr Thr Thr Thr Pro Pro Leu Lys Lys Thr Lys Thr Asn
                85                  90                  95
```

```
Leu Ser Leu Glu Thr Ser Ala Pro Leu Thr Val Ser Thr Ser Gly Ala
                100                 105                 110

Leu Thr Leu Ala Ala Ala Ala Pro Leu Ala Val Ala Gly Thr Ser Leu
115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Ile Ser Val Ser Ser Gly Ser Leu Gly Leu Asp
                180                 185                 190

Met Glu Asp Pro Met Tyr Thr His Asp Gly Lys Leu Gly Ile Arg Ile
            195                 200                 205

Gly Gly Pro Leu Arg Val Val Asp Ser Leu His Thr Leu Thr Val Val
        210                 215                 220

Thr Gly Asn Gly Ile Ala Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asp Val
                260                 265                 270

Ala Tyr Pro Phe Asp Ala Gln Asn Asn Leu Ser Leu Arg Leu Gly Gln
                275                 280                 285

Gly Pro Leu Tyr Val Asn Thr Asp His Asn Leu Asp Leu Asn Cys Asn
        290                 295                 300

Arg Gly Leu Thr Thr Thr Thr Asn Asn Thr Lys Lys Leu Glu Thr
305                 310                 315                 320

Lys Ile Gly Ser Gly Leu Asp Tyr Asp Thr Asn Gly Ala Val Ile Ile
                325                 330                 335

Lys Leu Gly Thr Gly Val Ser Phe Asp Ser Thr Gly Ala Leu Ser Val
                340                 345                 350

Gly Asn Thr Gly Asp Asp Lys Leu Thr Leu Trp Thr Thr Pro Asp Pro
        355                 360                 365

Ser Pro Asn Cys Arg Ile His Ser Asp Lys Asp Cys Lys Phe Thr Leu
    370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ser Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
        435                 440                 445

Ala Thr Pro Tyr Thr Asn Ala Val Gly Phe Met Pro Asn Leu Ala Ala
            450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
```

```
              515                 520                 525
Thr Phe Ala Thr Asn Ser Phe Thr Phe Ser Tyr Ile Ala Glu Gln
    530                 535                 540
```

<210> SEQ ID NO 15
<211> LENGTH: 543
<212> TYPE: PRT
<213> ORGANISM: Artificial Sequence
<220> FEATURE:
<223> OTHER INFORMATION: ChAd24 fiber amino acid sequence

<400> SEQUENCE: 15

```
Met Lys Arg Thr Lys Thr Ser Asp Glu Ser Phe Asn Pro Val Tyr Pro
1               5                   10                  15

Tyr Asp Thr Glu Asn Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
        50                  55                  60

Lys Met Gly Ser Gly Leu Ser Leu Asp Asp Ala Gly Asn Leu Thr Ser
65                  70                  75                  80

Gln Asp Val Thr Thr Thr Pro Pro Leu Lys Lys Thr Lys Thr Asn
                85                  90                  95

Leu Ser Leu Glu Thr Ser Ala Pro Leu Thr Val Ser Thr Ser Gly Ala
                100                 105                 110

Leu Thr Leu Ala Ala Ala Pro Leu Ala Val Ala Gly Thr Ser Leu
            115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Ile Asn Val Ser Ser Gly Ser Leu Gly Leu Asp
            180                 185                 190

Met Glu Asn Pro Met Tyr Thr His Asp Gly Lys Leu Gly Ile Arg Ile
        195                 200                 205

Gly Gly Pro Leu Arg Val Val Asp Ser Leu His Thr Leu Thr Val Val
    210                 215                 220

Thr Gly Asn Gly Ile Ala Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Tyr Val Asn Thr Asp His Asn Leu Asp Leu Asn Cys Asn
    290                 295                 300

Arg Gly Leu Thr Thr Thr Thr Asn Asn Thr Lys Lys Leu Glu Thr
305                 310                 315                 320

Lys Ile Gly Ser Gly Leu Asp Tyr Asp Thr Asn Gly Ala Val Ile Ile
                325                 330                 335

Lys Leu Gly Thr Gly Val Ser Phe Asp Ser Thr Gly Ala Leu Ser Val
```

```
              340                 345                 350
Gly Asn Thr Gly Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
    370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ser Ser Val
            405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
            435                 440                 445

Ala Thr Pro Tyr Thr Asn Ala Val Gly Phe Met Pro Asn Leu Ala Ala
            450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Ile Leu Thr Ile Thr
            485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
            515                 520                 525

Thr Phe Ala Thr Asn Ser Phe Thr Phe Ser Tyr Ile Ala Glu Gln
            530                 535                 540

<210> SEQ ID NO 16
<211> LENGTH: 578
<212> TYPE: PRT
<213> ORGANISM: Artificial Sequence
<220> FEATURE:
<223> OTHER INFORMATION: ChAd11 fiber amino acid sequence

<400> SEQUENCE: 16

Met Lys Arg Thr Lys Thr Ser Asp Glu Ser Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
50                  55                  60

Lys Met Gly Ser Gly Leu Ser Leu Asp Asp Ala Gly Asn Leu Thr Ser
65                  70                  75                  80

Gln Asp Val Thr Thr Thr Thr Pro Leu Lys Lys Thr Lys Thr Asn
            85                  90                  95

Leu Ser Leu Glu Thr Ser Ala Pro Leu Thr Val Ser Ser Gly Ala
            100                 105                 110

Leu Thr Leu Ala Ala Ala Val Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Ile
```

-continued

```
                165                 170                 175
Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
            195                 200                 205

Gly Ala Pro Leu His Val Val Asp Ser Leu Asn Ala Leu Thr Val Val
            210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Ser Ser Gly Asn Leu Glu Leu Arg Ala
                245                 250                 255

Ala Gly Gly Met Arg Val Asp Ala Asn Gly Lys Leu Ile Leu Asp Val
            260                 265                 270

Ala Tyr Pro Phe Asp Ala Gln Asn Asn Leu Ser Leu Arg Leu Gly Gln
            275                 280                 285

Gly Pro Leu Phe Val Asn Ser Ala His Asn Leu Asp Val Asn Tyr Asn
            290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Thr Ala Ile Ala
                325                 330                 335

Ile Asn Pro Gly Asp Gly Leu Glu Phe Gly Ser Gly Ser Asp Thr Asn
            340                 345                 350

Pro Leu Lys Thr Lys Leu Gly Leu Gly Leu Glu Tyr Asp Ser Ser Arg
            355                 360                 365

Ala Ile Ile Ala Lys Leu Gly Thr Gly Leu Ser Phe Asp Asn Thr Gly
            370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
            435                 440                 445

Val Thr Ser Ala Gln Ile Ile Leu Arg Phe Asp Glu Asn Gly Val Leu
            450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Ile
            515                 520                 525

Leu Thr Ile Thr Leu Asn Gly Thr Asn Glu Thr Gly Asp Ala Thr Val
            530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu
```

<210> SEQ ID NO 17
<211> LENGTH: 578
<212> TYPE: PRT
<213> ORGANISM: Artificial Sequence
<220> FEATURE:
<223> OTHER INFORMATION: ChAd20 fiber amino acid sequence

<400> SEQUENCE: 17

```
Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
        195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Phe Val Asn Ser Ala His Asn Leu Asp Val Asn Tyr Asn
    290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
            340                 345                 350

Pro Leu Lys Thr Lys Leu Gly Leu Gly Leu Asp Tyr Asp Ser Ser Arg
        355                 360                 365
```

```
Ala Ile Ile Ala Lys Leu Gly Thr Gly Leu Ser Phe Asp Asn Thr Gly
        370                 375                 380

Ala Ile Thr Val Gly Asn Lys Asn Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
            435                 440                 445

Val Thr Ser Ala Gln Ile Val Leu Arg Phe Asp Glu Asn Gly Val Leu
        450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Thr
        515                 520                 525

Leu Thr Ile Thr Leu Asn Gly Thr Asn Glu Thr Gly Asp Ala Thr Val
        530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 18
<211> LENGTH: 578
<212> TYPE: PRT
<213> ORGANISM: Artificial Sequence
<220> FEATURE:
<223> OTHER INFORMATION: ChAd31 fiber amino acid sequence

<400> SEQUENCE: 18

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Pro Leu Ala Val Ala Gly Thr Ser Leu
            115                 120                 125

Thr Met Gln Ser Glu Ala Pro Leu Thr Val Gln Asp Ala Lys Leu Thr
        130                 135                 140

Leu Ala Thr Lys Gly Pro Leu Thr Val Ser Glu Gly Lys Leu Ala Leu
```

```
                145                 150                 155                 160
        Gln Thr Ser Ala Pro Leu Thr Ala Ala Asp Ser Ser Thr Leu Thr Val
                        165                 170                 175

Ser Ala Thr Pro Pro Leu Ser Thr Ser Asn Gly Ser Leu Gly Ile Asp
                        180                 185                 190

Met Gln Ala Pro Ile Tyr Thr Thr Asn Gly Lys Leu Gly Leu Asn Phe
                        195                 200                 205

Gly Ala Pro Leu His Val Val Asp Ser Leu Asn Ala Leu Thr Val Val
                210                 215                 220

Thr Gly Gln Gly Leu Thr Ile Asn Gly Thr Ala Leu Gln Thr Arg Val
        225                 230                 235                 240

Ser Gly Ala Leu Asn Tyr Asp Thr Ser Gly Asn Leu Glu Leu Arg Ala
                        245                 250                 255

Ala Gly Gly Met Arg Val Asp Ala Asn Gly Gln Leu Ile Leu Asp Val
                        260                 265                 270

Ala Tyr Pro Phe Asp Ala Gln Asn Asn Leu Ser Leu Arg Leu Gly Gln
                        275                 280                 285

Gly Pro Leu Phe Val Asn Ser Ala His Asn Leu Asp Val Asn Tyr Asn
                        290                 295                 300

Arg Gly Leu Tyr Leu Phe Thr Ser Gly Asn Thr Lys Lys Leu Glu Val
        305                 310                 315                 320

Asn Ile Lys Thr Ala Lys Gly Leu Ile Tyr Asp Asp Thr Ala Ile Ala
                        325                 330                 335

Ile Asn Ala Gly Asp Gly Leu Gln Phe Asp Ser Gly Ser Asp Thr Asn
                        340                 345                 350

Pro Leu Lys Thr Lys Leu Gly Leu Gly Leu Asp Tyr Asp Ser Ser Arg
                        355                 360                 365

Ala Ile Ile Ala Lys Leu Gly Thr Gly Leu Ser Phe Asp Asn Thr Gly
                        370                 375                 380

Ala Ile Thr Val Gly Asn Lys Asn Asp Lys Leu Thr Leu Trp Thr
        385                 390                 395                 400

Thr Pro Asp Pro Ser Pro Asn Cys Arg Ile Tyr Ser Glu Lys Asp Ala
                        405                 410                 415

Lys Phe Thr Leu Val Leu Thr Lys Cys Gly Ser Gln Val Leu Ala Ser
                        420                 425                 430

Val Ser Val Leu Ser Val Lys Gly Ser Leu Ala Pro Ile Ser Gly Thr
                        435                 440                 445

Val Thr Ser Ala Gln Ile Val Leu Arg Phe Asp Glu Asn Gly Val Leu
                        450                 455                 460

Leu Ser Asn Ser Ser Leu Asp Pro Gln Tyr Trp Asn Tyr Arg Lys Gly
        465                 470                 475                 480

Asp Leu Thr Glu Gly Thr Ala Tyr Thr Asn Ala Val Gly Phe Met Pro
                        485                 490                 495

Asn Leu Thr Ala Tyr Pro Lys Thr Gln Ser Gln Thr Ala Lys Ser Asn
                        500                 505                 510

Ile Val Ser Gln Val Tyr Leu Asn Gly Asp Lys Ser Lys Pro Met Thr
                        515                 520                 525

Leu Thr Ile Thr Leu Asn Gly Thr Asn Glu Thr Gly Asp Ala Thr Val
                        530                 535                 540

Ser Thr Tyr Ser Met Ser Phe Ser Trp Asn Trp Asn Gly Ser Asn Tyr
        545                 550                 555                 560

Ile Asn Glu Thr Phe Gln Thr Asn Ser Phe Thr Phe Ser Tyr Ile Ala
                        565                 570                 575
```

Gln Glu

<210> SEQ ID NO 19
<211> LENGTH: 577
<212> TYPE: PRT
<213> ORGANISM: Artificial Sequence
<220> FEATURE:
<223> OTHER INFORMATION: PanAd1 fiber amino acid sequence

<400> SEQUENCE: 19

```
Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Arg Leu Ser Glu Pro Leu Val Thr Ser His Gly Met Leu Ala Leu
        50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
        115                 120                 125

Met Gln Ser Gln Ala Pro Leu Thr Val Gln Asp Ala Lys Leu Gly Leu
    130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
                165                 170                 175

Ala Thr Pro Pro Leu Ser Thr Ser Asn Gly Ser Leu Ser Ile Asp Met
            180                 185                 190

Gln Ala Pro Ile Tyr Thr Thr Asn Gly Lys Leu Ala Leu Asn Ile Gly
        195                 200                 205

Ala Pro Leu His Val Val Asp Thr Leu Asn Ala Leu Thr Val Val Thr
    210                 215                 220

Gly Gln Gly Leu Thr Ile Asn Gly Arg Ala Leu Gln Thr Arg Val Thr
225                 230                 235                 240

Gly Ala Leu Ser Tyr Asp Thr Glu Gly Asn Ile Gln Leu Gln Ala Gly
                245                 250                 255

Gly Gly Met Arg Ile Asp Asn Asn Gly Gln Leu Ile Leu Asn Val Ala
            260                 265                 270

Tyr Pro Phe Asp Ala Gln Asn Asn Leu Ser Leu Arg Leu Gly Gln Gly
        275                 280                 285

Pro Leu Ile Val Asn Ser Ala His Asn Leu Asp Leu Asn Leu Asn Arg
    290                 295                 300

Gly Leu Tyr Leu Phe Thr Ser Gly Asn Thr Lys Lys Leu Glu Val Asn
305                 310                 315                 320

Ile Lys Thr Ala Lys Gly Leu Phe Tyr Asp Gly Thr Ala Ile Ala Ile
                325                 330                 335

Asn Ala Gly Asp Gly Leu Gln Phe Gly Ser Gly Ser Asp Thr Asn Pro
            340                 345                 350
```

Leu Gln Thr Lys Leu Gly Leu Gly Leu Glu Tyr Asp Ser Asn Lys Ala
         355                 360                 365

Ile Ile Thr Lys Leu Gly Thr Gly Leu Ser Phe Asp Asn Thr Gly Ala
370                 375                 380

Ile Thr Val Gly Asn Lys Asn Asp Lys Leu Thr Leu Trp Thr Thr
385                 390                 395                 400

Pro Asp Pro Ser Pro Asn Cys Arg Ile Asn Ser Glu Lys Asp Ala Lys
             405                 410                 415

Leu Thr Leu Val Leu Thr Lys Cys Gly Ser Gln Val Leu Ala Ser Val
             420                 425                 430

Ser Val Leu Ser Val Lys Gly Ser Leu Ala Pro Ile Ser Gly Thr Val
             435                 440                 445

Thr Ser Ala Gln Ile Val Leu Arg Phe Asp Glu Asn Gly Val Leu Leu
         450                 455                 460

Ser Asn Ser Ser Leu Asp Pro Gln Tyr Trp Asn Tyr Arg Lys Gly Asp
465                 470                 475                 480

Ser Thr Glu Gly Thr Ala Tyr Thr Asn Ala Val Gly Phe Met Pro Asn
             485                 490                 495

Leu Thr Ala Tyr Pro Lys Thr Gln Ser Gln Thr Ala Lys Ser Asn Ile
             500                 505                 510

Val Ser Gln Val Tyr Leu Asn Gly Asp Lys Thr Lys Pro Met Thr Leu
             515                 520                 525

Thr Ile Thr Leu Asn Gly Thr Asn Glu Thr Gly Asp Ala Thr Val Ser
             530                 535                 540

Thr Tyr Ser Met Ser Phe Ser Trp Asn Trp Gly Ser Asn Tyr Ile
545                 550                 555                 560

Asn Asp Thr Phe Gln Thr Asn Ser Phe Thr Phe Ser Tyr Ile Ala Gln
                 565                 570                 575

Glu

```
<210> SEQ ID NO 20
<211> LENGTH: 577
<212> TYPE: PRT
<213> ORGANISM: Artificial Sequence
<220> FEATURE:
<223> OTHER INFORMATION: PanAd2 fiber amino acid sequence

<400> SEQUENCE: 20
```

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
            35                  40                  45

Leu Arg Leu Ser Glu Pro Leu Val Thr Ser His Gly Met Leu Ala Leu
         50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
         115                 120                 125

Met Gln Ser Gln Ala Pro Leu Thr Val Gln Asp Ala Lys Leu Gly Leu

```
                130               135               140
Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
                165                 170                 175

Ala Thr Pro Pro Leu Ser Thr Ser Asn Gly Ser Leu Ser Ile Asp Met
            180                 185                 190

Gln Ala Pro Ile Tyr Thr Thr Asn Gly Lys Leu Ala Leu Asn Ile Gly
                195                 200                 205

Ala Pro Leu His Val Val Asp Thr Leu Asn Ala Leu Thr Val Val Thr
            210                 215                 220

Gly Gln Gly Leu Thr Ile Asn Gly Arg Ala Leu Gln Thr Arg Val Thr
225                 230                 235                 240

Gly Ala Leu Ser Tyr Asp Thr Glu Gly Asn Ile Gln Leu Gln Ala Gly
                245                 250                 255

Gly Gly Met Arg Ile Asp Asn Asn Gly Gln Leu Ile Leu Asn Val Ala
                260                 265                 270

Tyr Pro Phe Asp Ala Gln Asn Asn Leu Ser Leu Arg Leu Gly Gln Gly
            275                 280                 285

Pro Leu Ile Val Asn Ser Ala His Asn Leu Asp Leu Asn Leu Asn Arg
            290                 295                 300

Gly Leu Tyr Leu Phe Thr Ser Gly Asn Thr Lys Lys Leu Glu Val Asn
305                 310                 315                 320

Ile Lys Thr Ala Lys Gly Leu Phe Tyr Asp Gly Thr Ala Ile Ala Ile
                325                 330                 335

Asn Ala Gly Asp Gly Leu Gln Phe Gly Ser Gly Ser Asp Thr Asn Pro
                340                 345                 350

Leu Gln Thr Lys Leu Gly Leu Gly Leu Glu Tyr Asp Ser Asn Lys Ala
            355                 360                 365

Ile Ile Thr Lys Leu Gly Thr Gly Leu Ser Phe Asp Asn Thr Gly Ala
            370                 375                 380

Ile Thr Val Gly Asn Lys Asn Asp Asp Lys Leu Thr Leu Trp Thr Thr
385                 390                 395                 400

Pro Asp Pro Ser Pro Asn Cys Arg Ile Asn Ser Glu Lys Asp Ala Lys
                405                 410                 415

Leu Thr Leu Val Leu Thr Lys Cys Gly Ser Gln Val Leu Ala Ser Val
            420                 425                 430

Ser Val Leu Ser Val Lys Gly Ser Leu Ala Pro Ile Ser Gly Thr Val
            435                 440                 445

Thr Ser Ala Gln Ile Val Leu Arg Phe Asp Glu Asn Gly Val Leu Leu
450                 455                 460

Ser Asn Ser Ser Leu Asp Pro Gln Tyr Trp Asn Tyr Arg Lys Gly Asp
465                 470                 475                 480

Ser Thr Glu Gly Thr Ala Tyr Thr Asn Ala Val Gly Phe Met Pro Asn
                485                 490                 495

Leu Thr Ala Tyr Pro Lys Thr Gln Ser Gln Thr Ala Lys Ser Asn Ile
            500                 505                 510

Val Ser Gln Val Tyr Leu Asn Gly Asp Lys Thr Lys Pro Met Thr Leu
            515                 520                 525

Thr Ile Thr Leu Asn Gly Thr Asn Glu Thr Gly Asp Ala Thr Val Ser
            530                 535                 540

Thr Tyr Ser Met Ser Phe Ser Trp Asn Trp Asn Gly Ser Asn Tyr Ile
545                 550                 555                 560
```

Asn Asp Thr Phe Gln Thr Asn Ser Phe Thr Phe Ser Tyr Ile Ala Gln
            565                 570                 575

Glu

<210> SEQ ID NO 21
<211> LENGTH: 3747
<212> TYPE: DNA
<213> ORGANISM: Artificial Sequence
<220> FEATURE:
<223> OTHER INFORMATION: Nucleotide sequence for CHIKV structural
    polypeptide, strain #37997 (wild type, nts 7569-11315 of Genbank
    Accession No. EU224270)

<400> SEQUENCE: 21

```
atggagttca tcccgacgca aactttctat aacagaaggt accaaccccg accctgggcc      60
ccacgcccta caattcaagt aattagacct agaccacgtc cacagaggca ggctgggcaa     120
ctcgcccagc tgatctccgc agtcaacaaa ttgaccatgc gcgcggtacc tcaacagaag     180
cctcgcagaa atcggaaaaa caagaagcaa aggcagaaga gcaggcgcc gcaaaacgac      240 ccaaagcaaa agaagcaacc accacaaaag aagccggctc aaaagaagaa gaaaccaggc     300
cgtagggaga gaatgtgcat gaaaattgaa atgattgca tcttcgaagt caagcatgaa      360
ggcaaagtga tgggctacgc atgcctggtg ggggataaag taatgaaacc agcacatgtg     420
aagggaacta tcgacaatgc cgatctggct aaactggcct ttaagcggtc gtctaaatac     480
gatcttgaat gtgcacagat accggtgcac atgaagtctg atgcctcgaa gtttacccac     540
gagaaacccg aggggtacta taactggcat cacggagcag tgcagtattc aggaggccgg     600
ttcactatcc cgacgggtgc aggcaagccg ggagacagcg gcagaccgat cttcgacaac     660
aaaggacggg tggtggccat cgtcctagga ggggccaacg aaggtgcccg cacggccctc     720
tccgtggtga cgtggaacaa agacatcgtc acaaaaatta cccctgaggg agccgaagag     780
tggagcctcg ccctcccggt cttgtgcctg ttggcaaaca ctacattccc ctgctctcag     840
ccgccttgca caccctgctg ctacgaaaag gaaccggaaa gcaccttgcg catgcttgag     900
gacaacgtga tgagacccgg atactaccag ctactaaaag catcgctgac ttgctctccc     960
caccgccaaa gacgcagtac taaggacaat tttaatgtct ataaagccac aagaccatat    1020
ctagctcatt gtcctgactg cggagaaggg cattcgtgcc acagccctat cgcattggag    1080
cgcatcagaa atgaagcaac ggacggaacg ctgaaaatcc aggtctcttt gcagatcggg    1140
ataaagacag atgacagcca cgattggacc aagctgcgct atatggatag ccatacgcca    1200
gcggacgcgg agcgagccgg attgcttgta aggacttcag caccgtgcac gatcaccggg    1260
accatgggac actttattct cgcccgatgc ccgaaaggag agacgctgac agtgggattt    1320
acggacagca gaaagatcag ccacacatgc acacacccgt tccatcatga ccacctgtg     1380 ataggtaggg agaggttcca ctctcgacca caacatggta agagttacc ttgcagcacg     1440 tacgtgcaga gcaccgctgc cactgctgag agatagagg tgcatatgcc cccagatact     1500
cctgaccgca cgctgatgac gcagcagtct ggcaacgtga agatcacagt taatgggcag     1560
acggtgcggt acaagtgcaa ctgcggtggc tcaaacgagg gactgacaac cacagacaaa     1620
gtgatcaata actgcaaaat tgatcagtgc catgctgcag tcactaatca agaattgg      1680 caatacaact ccccttagt cccgcgcaac gctgaactcg gggaccgtaa aggaaagatc     1740
cacatcccat tccattggc aaacgtgact tgcagagtgc aaaagcaag aaaccctaca     1800 gtaacttacg gaaaaaacca agtcaccatg ctgctgtatc ctgaccatcc tgactcttg     1860
```

```
tcttaccgta acatgggaca ggaaccaaat taccacgagg agtgggtgac acacaagaag    1920
gaggttacct tgaccgtgcc tactgagggt ctggaggtca cttggggcaa caacgaacca    1980
tacaagtact ggccgcagat gtctacgaac ggtactgctc atggtcaccc acatgagata    2040
atcttgtact attatgagct gtaccccact atgactgtag tcattgtgtc ggtggcctcg    2100
ttcgtgcttc tgtcgatggt gggcacagca gtgggaatgt gtgtgtgcgc acggcgcaga    2160
tgcattacac catatgaatt aacaccagga gccactgttc ccttcctgct cagcctgcta    2220
tgctgcgtca gaacgaccaa ggcggccaca tattacgagg ctgcggcata tctatggaac    2280
gaacagcagc cctgttctg gttgcaggct cttatcccgc tggccgcctt gatcgtcctg     2340
tgcaactgtc tgaaactctt gccatgctgc tgtaagaccc tggctttttt agccgtaatg    2400
agcatcggtg cccacactgt gagcgcgtac gaacacgtaa cagtgatccc gaacacggtg    2460
ggagtaccgt ataagactct tgtcaacaga ccgggttaca gcccatggt gttggagatg     2520 gagctacaat cagtcacctt ggaaccaaca ctgtcacttg actacatcac gtgcgagtac    2580
aaaactgtca tcccctcccc gtacgtgaag tgctgtggta cagcagagtg caaggacaag    2640
agcctaccag actacagctg caaggtcttt actggagtct acccatttat gtggggcggc    2700
gcctactgct tttgcgacgc cgaaaatacg caattgagcg aggcacatgt agagaaatct    2760
gaatcttgca aaacagagtt tgcatcggcc tacagaccc acaccgcatc ggcgtcggcg     2820
aagctccgcg tccttaccta aggaaacaac attaccgtag ctgcctacgc taacggtgac    2880
catgccgtca cagtaaagga cgccaagttt gtcgtgggcc caatgtcctc cgcctggaca    2940
ccttttgaca caaaatcgt ggtgtacaaa ggcgacgtct acaacatgga ctacccacct     3000
tttggcgcag gaagaccagg acaatttggt gacattcaaa gtcgtacacc ggaaagtaaa    3060
gacgtttatg ccaacactca gttggtacta cagaggccag cagcaggcac ggtacatgta    3120
ccatactctc aggcaccatc tggcttcaag tattggctga aggaacgagg agcatcgcta    3180
cagcacacgg caccgttcgg ttgccagatt gcgacaaacc cggtaagagc tgtaaattgc    3240
gctgtgggga acataccaat ttccatcgac ataccggatg cggcctttac tagggttgtc    3300
gatgcaccct ctgtaacgga catgtcatgc gaagtaccag cctgcactca ctcctccgac    3360
tttgggggcg tcgccatcat caaatacaca gctagcaaga aggtaaatg tgcagtacat     3420 tcgatgacca acgccgttac cattcgagaa gccgactag aagtagaggg gaactcccag     3480
ctgcaaatat ccttctcaac agccctggca agcgccgagt tcgcgtgca agtgtgctcc     3540 acacaagtac actgcgcagc cgcatgccac cctccaaagg accacatagt caattaccca    3600
gcatcacaca ccaccccttgg ggtccaggat atatccacaa cggcaatgtc ttgggtgcag    3660
aagattacgg gaggagtagg attaattgtt gctgttgctg ccttaatttt aattgtggtg    3720
ctatgcgtgt cgtttagcag gcactaa                                        3747
```

<210> SEQ ID NO 22
<211> LENGTH: 3753
<212> TYPE: DNA
<213> ORGANISM: Artificial Sequence
<220> FEATURE:
<223> OTHER INFORMATION: Nucleotide sequence for CHIKV structural
      polypeptide, strain #37997 (codon optimized)

<400> SEQUENCE: 22
atggaattca tccccaccca gacattctac aacaggaggt accaacctag accctgggcc 60
cccaggccta caatccaggt catcaggcct aggcccagac ctcaaagaca ggctggccag 120

```
ctcgcccaac tgattagcgc tgtcaataaa ctcacaatga gggccgtccc ccagcagaag      180
cccaggagga ataggaaaaa taagaagcag aggcagaaaa agcaagcccc ccagaacgac      240
cccaagcaga agaagcaacc cccccaaaag aagcctgctc aaaaaaagaa gaagcccggc      300
aggagggaaa gaatgtgtat gaagatcgag aacgactgca tctttgaggt gaaacacgag      360
ggaaaagtga tgggatacgc ctgcctcgtg ggcgacaaag tgatgaaacc tgcccacgtc      420
aagggcacaa ttgacaatgc cgacctggct aagctggctt tcaaaaggag ctccaaatat      480
gacctggagt gtgcccagat ccccgtgcac atgaagtccg acgcctccaa gttcacccac      540
gaaaaacccg agggatacta caactggcat catggagccg tccagtacag cggcggaagg      600
ttcacaattc ctacaggcgc cggaaagccc ggagactccg gaaggcccat cttcgacaac      660
aaaggaagag tggtggccat cgtgctcggc ggagccaacg aaggcgctag accgccctg      720 tccgtggtga cctggaacaa agacatcgtg accaaaatca cccctgaggg agccgaagag      780
tggagcctcg ccctgccgt gctgtgtctg ctggccaata caaccttcc ttgcagccag      840 cctccttgca caccctgctg ctacgagaag gaacctgaaa gcaccctgag aatgctcgag      900
gacaacgtga tgaggcctgg ctattaccag ctgctgaagg cctccctgac ctgcagcct       960 cacaggcaaa ggaggagcac aaaggacaac ttcaacgtgt ataaagctac aaggccctac     1020
ctcgctcact gtcctgattg tggcgaggga cactcctgcc actcccctat tgccctggag     1080
aggatcagaa acgaggctac cgacggaacc ctgaagatcc aggtgtccct gcagattgga     1140
atcaagaccg atgacagcca cgattggaca aagctgaggt atatggacag ccacacccc     1200 gctgatgctg aaagggccgg cctgctggtg agaacctccg ccccttgcac catcaccgga     1260
accatgggcc acttcattct cgccaggtgt cccaaaggcg agaccctgac cgtgggcttt     1320
accgacagca gaaaaatcag ccacacatgc acccacccct tccatcacga gccccccgtg     1380
atcggcaggg aaaggtttca ctccaggccc cagcacggca agaactccc ctgcagcacc     1440 tacgtgcaat ccaccgccgc cacagccgag gaaattgagg tgcatatgcc tcctgatacc     1500
cccgacagaa cactcatgac acagcaaagc ggcaacgtca agattaccgt gaacggccag     1560
accgtgagat acaagtgcaa ctgtggagga agcaatgagg gcctgaccac aacagacaag     1620
gtgattaata actgtaaaat tgaccaatgc cacgccgctg tcaccaatca caagaattgg     1680
cagtacaata gccctctggt gcctagaaat gctgagctgg gcgacaggaa aggcaagatt     1740
cacattcctt tcccctggc caacgtgaca tgcagggtcc ccaaagccag gaaccccacc     1800
gtcacctacg gcaaaaatca ggtgaccatg ctgctctacc ccgatcaccc taccctcctc     1860
agctacagga atatgggcca ggaacccaac taccacgagg agtgggtgac ccacaagaag     1920
gaggtgacac tgacagtccc cacagaagga ctggaggtca cctggggcaa caatgagccc     1980
tacaaatact ggcctcagat gtccaccaac ggaaccgctc acggccatcc ccatgagatc     2040
atcctgtact actacgagct gtaccccaca atgacagtgg tcatcgtcag cgtcgcctcc     2100
tttgtgctgc tctccatggt cggcacagcc gtgggcatgt gtgtgtgtgc cagaaggagg     2160
tgcatcaccc cctatgaact gacccctggc gctacagtgc cttttctcct cagcctgctg     2220
tgttgcgtca gaaccaccaa agccgccacc tattatgagg ctgccgctta cctgtggaat     2280
gagcagcagc ctcgttctg gctccaggct ctgatccctc tcgctgccct catcgtgctg     2340
tgtaactgcc tcaagctgct gccctgctgt tgcaagacct agctttttt agctgtgatg     2400 agcattggcg ctcatacagt gtccgcctat gagcacgtga ccgtgatccc taacacagtg     2460
```
ggcgtgccct ataagaccct ggtgaatagg cccggatata gccccatggt gctcgaaatg 2520
gagctgcaga gcgtcaccct cgaacccacc ctgagcctgg actacatcac atgcgaatat 2580
aaaaccgtga tcccctcccc ctacgtgaag tgctgcggca ccgctgagtg taaggacaag 2640
agcctgcccg actatagctg caaggtgttt accggcgtgt atccctttat gtggggcggc 2700
gcttactgct tctgtgacgc tgaaaatacc cagctgagcg aggctcacgt ggagaagagc 2760
gaaagctgca agaccgagtt cgccagcgct tatagagctc acaccgccag cgctagcgcc 2820
aaactgagag tgctctacca gggcaacaat atcaccgtcg ctgcctacgc taatggcgac 2880
cacgccgtga ccgtgaagga cgccaaattc gtcgtcggac ccatgtcctc cgcttggacc 2940
ccctttgaca acaagatcgt ggtgtacaag ggagacgtgt acaacatgga ctaccctcct 3000
ttcggcgctg gcaggcctgg acagtttgga gacattcagt ccaggacccc cgaatccaag 3060
gacgtgtatg ccaacaccca actggtgctc cagagacccg ccgctggcac agtgcacgtg 3120
ccttacagcc aagcccccag cggatttaaa tactggctga aggagagagg cgccagcctg 3180
caacataccg ctccttttgg atgccagatt gccaccaacc ctgtgagggc cgtcaactgc 3240
gccgtcggca acattcccat cagcatcgac attcccgacg ccgcctttac cagggtggtg 3300
gacgccccca gcgtcacaga catgtcctgc gaggtgcccg cttgcaccca ctcctccgac 3360
ttcggaggag tggccatcat caaatacacc gccagcaaga agggcaagtg tgccgtgcac 3420
tccatgacca acgccgtcac catcagggag gccgacgtgg aggtcgaagg caactcccaa 3480
ctgcagatct ccttcagcac cgctctggct agcgccgagt tcagggtgca ggtgtgcagc 3540
acacaggtgc attgtgccgc cgcttgccat ccccctaaag accacatcgt gaattacccc 3600
gcctcccata ccaccctggg agtccaggac atcagcacca cagccatgtc ctgggtgcag 3660
aaaatcaccg gaggcgtggg cctgatcgtg gctgtggctg ccctgattct gatcgtcgtg 3720
ctctgcgtca gctttagcag gcactgatga tga 3753

<210> SEQ ID NO 23
<211> LENGTH: 1248
<212> TYPE: PRT
<213> ORGANISM: Artificial Sequence
<220> FEATURE:
<223> OTHER INFORMATION: Amino acid sequence for CHIKV structural polypeptide, strain #37997

<400> SEQUENCE: 23

Met Glu Phe Ile Pro Thr Gln Thr Phe Tyr Asn Arg Arg Tyr Gln Pro
1 5 10 15

Arg Pro Trp Ala Pro Arg Pro Thr Ile Gln Val Ile Arg Pro Arg Pro
20 25 30

Arg Pro Gln Arg Gln Ala Gly Gln Leu Ala Gln Leu Ile Ser Ala Val
35 40 45

Asn Lys Leu Thr Met Arg Ala Val Pro Gln Gln Lys Pro Arg Arg Asn
50 55 60

Arg Lys Asn Lys Lys Gln Arg Gln Lys Lys Gln Ala Pro Gln Asn Asp
65 70 75 80

Pro Lys Gln Lys Lys Gln Pro Pro Gln Lys Lys Pro Ala Gln Lys Lys
85 90 95

Lys Lys Pro Gly Arg Arg Glu Arg Met Cys Met Lys Ile Glu Asn Asp
100 105 110

Cys Ile Phe Glu Val Lys His Glu Gly Lys Val Met Gly Tyr Ala Cys
115 120 125

-continued

Leu Val Gly Asp Lys Val Met Lys Pro Ala His Val Lys Gly Thr Ile
130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
290                 295                 300

Arg Pro Gly Tyr Tyr Gln Leu Leu Lys Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
        370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
            405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
            435                 440                 445

Thr Cys Thr His Pro Phe His His Glu Pro Pro Val Ile Gly Arg Glu
        450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Ile Glu Val His Met
            485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
            515                 520                 525

Gly Gly Ser Asn Glu Gly Leu Thr Thr Thr Asp Lys Val Ile Asn Asn
        530                 535                 540

Cys Lys Ile Asp Gln Cys His Ala Ala Val Thr Asn His Lys Asn Trp

```
                545                 550                 555                 560
        Gln Tyr Asn Ser Pro Leu Val Pro Arg Asn Ala Glu Leu Gly Asp Arg
                        565                 570                 575

Lys Gly Lys Ile His Ile Pro Phe Pro Leu Ala Asn Val Thr Cys Arg
                        580                 585                 590

Val Pro Lys Ala Arg Asn Pro Thr Val Thr Tyr Gly Lys Asn Gln Val
                        595                 600                 605

Thr Met Leu Leu Tyr Pro Asp His Pro Thr Leu Leu Ser Tyr Arg Asn
                        610                 615                 620

Met Gly Gln Glu Pro Asn Tyr His Glu Glu Trp Val Thr His Lys Lys
        625                 630                 635                 640

Glu Val Thr Leu Thr Val Pro Thr Glu Leu Gly Leu Val Thr Trp Gly
                        645                 650                 655

Asn Asn Glu Pro Tyr Lys Tyr Trp Pro Gln Met Ser Thr Asn Gly Thr
                        660                 665                 670

Ala His Gly His Pro His Glu Ile Ile Leu Tyr Tyr Glu Leu Tyr
                        675                 680                 685

Pro Thr Met Thr Val Ile Val Ser Val Ala Ser Phe Val Leu Leu
                        690                 695                 700

Ser Met Val Gly Thr Ala Val Gly Met Cys Val Cys Ala Arg Arg Arg
        705                 710                 715                 720

Cys Ile Thr Pro Tyr Glu Leu Thr Pro Gly Ala Thr Val Pro Phe Leu
                        725                 730                 735

Leu Ser Leu Leu Cys Cys Val Arg Thr Thr Lys Ala Ala Thr Tyr Tyr
                        740                 745                 750

Glu Ala Ala Ala Tyr Leu Trp Asn Glu Gln Gln Pro Leu Phe Trp Leu
                        755                 760                 765

Gln Ala Leu Ile Pro Leu Ala Ala Leu Ile Val Leu Cys Asn Cys Leu
                        770                 775                 780

Lys Leu Leu Pro Cys Cys Cys Lys Thr Leu Ala Phe Leu Ala Val Met
        785                 790                 795                 800

Ser Ile Gly Ala His Thr Val Ser Ala Tyr Glu His Val Thr Val Ile
                        805                 810                 815

Pro Asn Thr Val Gly Val Pro Tyr Lys Thr Leu Val Asn Arg Pro Gly
                        820                 825                 830

Tyr Ser Pro Met Val Leu Glu Met Glu Leu Gln Ser Val Thr Leu Glu
                        835                 840                 845

Pro Thr Leu Ser Leu Asp Tyr Ile Thr Cys Glu Tyr Lys Thr Val Ile
                        850                 855                 860

Pro Ser Pro Tyr Val Lys Cys Cys Gly Thr Ala Glu Cys Lys Asp Lys
        865                 870                 875                 880

Ser Leu Pro Asp Tyr Ser Cys Lys Val Phe Thr Gly Val Tyr Pro Phe
                        885                 890                 895

Met Trp Gly Gly Ala Tyr Cys Phe Cys Asp Ala Glu Asn Thr Gln Leu
                        900                 905                 910

Ser Glu Ala His Val Glu Lys Ser Glu Ser Cys Lys Thr Glu Phe Ala
                        915                 920                 925

Ser Ala Tyr Arg Ala His Thr Ala Ser Ala Ser Ala Lys Leu Arg Val
                        930                 935                 940

Leu Tyr Gln Gly Asn Asn Ile Thr Val Ala Ala Tyr Ala Asn Gly Asp
        945                 950                 955                 960

His Ala Val Thr Val Lys Asp Ala Lys Phe Val Val Gly Pro Met Ser
                        965                 970                 975
```

```
Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
        995                1000                1005

Phe Gly Asp Ile Gln Ser Arg Thr Pro Glu Ser Lys Asp Val Tyr
   1010                1015                1020

Ala Asn Thr Gln Leu Val Leu Gln Arg Pro Ala Ala Gly Thr Val
   1025                1030                1035

His Val Pro Tyr Ser Gln Ala Pro Ser Gly Phe Lys Tyr Trp Leu
   1040                1045                1050

Lys Glu Arg Gly Ala Ser Leu Gln His Thr Ala Pro Phe Gly Cys
   1055                1060                1065

Gln Ile Ala Thr Asn Pro Val Arg Ala Val Asn Cys Ala Val Gly
   1070                1075                1080

Asn Ile Pro Ile Ser Ile Asp Ile Pro Asp Ala Ala Phe Thr Arg
   1085                1090                1095

Val Val Asp Ala Pro Ser Val Thr Asp Met Ser Cys Glu Val Pro
   1100                1105                1110

Ala Cys Thr His Ser Ser Asp Phe Gly Gly Val Ala Ile Ile Lys
   1115                1120                1125

Tyr Thr Ala Ser Lys Lys Gly Lys Cys Ala Val His Ser Met Thr
   1130                1135                1140

Asn Ala Val Thr Ile Arg Glu Ala Asp Val Glu Val Glu Gly Asn
   1145                1150                1155

Ser Gln Leu Gln Ile Ser Phe Ser Thr Ala Leu Ala Ser Ala Glu
   1160                1165                1170

Phe Arg Val Gln Val Cys Ser Thr Gln Val His Cys Ala Ala Ala
   1175                1180                1185

Cys His Pro Pro Lys Asp His Ile Val Asn Tyr Pro Ala Ser His
   1190                1195                1200

Thr Thr Leu Gly Val Gln Asp Ile Ser Thr Thr Ala Met Ser Trp
   1205                1210                1215

Val Gln Lys Ile Thr Gly Gly Val Gly Leu Ile Val Ala Val Ala
   1220                1225                1230

Ala Leu Ile Leu Ile Val Val Leu Cys Val Ser Phe Ser Arg His
   1235                1240                1245
```

<210> SEQ ID NO 24
<211> LENGTH: 7879
<212> TYPE: DNA
<213> ORGANISM: Artificial Sequence
<220> FEATURE:
<223> OTHER INFORMATION: Nucleotide sequence of plasmid pvjTetOhCMV
      CHIKV bghpolyA

<400> SEQUENCE: 24

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
```

```
cccgcctggc tgaccgccca acgaccccg cccattgacg tcaataatga cgtatgttcc      480
catagtaacg ccaataggga ctttccattg acgtcaatgg gtggagtatt tacggtaaac      540
tgcccacttg gcagtacatc aagtgtatca tatgccaagt acgccccta ttgacgtcaa       600
tgacggtaaa tggcccgcct ggcattatgc ccagtacatg accttatggg actttcctac      660
ttggcagtac atctacgtat tagtcatcgc tattaccatg gtgatgcggt tttggcagta      720
catcaatggg cgtggatagc ggtttgactc acggggattt ccaagtctcc accccattga      780
cgtcaatggg agtttgtttt ggaaccaaaa tcaacgggac tttccaaaat gtcgtaacaa      840
ctccgcccca ttgacgcaaa tgggcggtag gcgtgtacgg tgggaggtct atataagcag      900
agctctccct atcagtgata gagatctccc tatcagtgat agagatcgtc gacgagctcg      960
tttagtgaac cgtcagatcg cctggagacg ccatccacgc tgttttgacc tccatagaag     1020
acaccgggac cgatccagcc tccgcggccg ggaacggtgc attggaacgc ggattccccg     1080
tgccaagagt gagatcttcc gtttatctag gtaccagata tcgccaccat ggaattcatc     1140
cccacccaga cattctacaa caggaggtac caacctagac cctgggcccc caggcctaca     1200
atccaggtca tcaggcctag gcccagacct caaagacagg ctggccagct cgcccaactg     1260
attagcgctg tcaataaact cacaatgagg gccgtccccc agcagaagcc caggaggaat     1320
aggaaaaata agaagcagag gcagaaaaag caagcccccc agaacgaccc caagcagaag     1380
aagcaacccc cccaaaagaa gcctgctcaa aaaagaaga agcccggcag gagggaaga      1440
atgtgtatga agatcgagaa cgactgcatc tttgaggtga aacacgaggg aaagtgatg      1500
ggatacgcct gcctcgtggg cgacaaagtg atgaaacctg cccacgtcaa gggcacaatt     1560
gacaatgccg acctggctaa gctggctttc aaaaggagct ccaaatatga cctggagtgt     1620
gcccagatcc ccgtgcacat gaagtccgac gcctccaagt tcacccacga aaacccgag      1680
ggatactaca actggcatca tggagccgtc cagtacagcg gcggaaggtt cacaattcct     1740
acaggcgccg gaaagcccgg agactccgga aggcccatct tcgacaacaa ggaagagtg      1800
gtggccatcg tgctcggcgg agccaacgaa ggcgctagga ccgccctgtc cgtggtgacc     1860
tggaacaaag acatcgtgac caaaatcacc cctgagggag ccgaagagtg gagcctcgcc     1920
ctgcccgtgc tgtgtctgct ggccaataca acctttcctt gcagccagcc tccttgcaca     1980
ccctgctgct acgagaagga acctgaaagc accctgagaa tgctcgagga caacgtgatg     2040
aggcctggct attaccagct gctgaaggcc tccctgacct gcagccctca caggcaaagg     2100
aggagcacaa aggacaactt caacgtgtat aaagctacaa ggccctacct cgctcactgt     2160
cctgattgtg gcgagggaca ctcctgccac tcccctattg ccctggagag atcagaaac      2220
gaggctaccg acgaaccct gaagatccag gtgtccctgc agattggaat caagaccgat     2280
gacagccacg attggacaaa gctgaggtat atggacagcc acacccccgc tgatgctgaa     2340
agggccggcc tgctggtgag aacctccgcc ccttgcacca tcaccggaac catgggccac     2400
ttcattctcg ccaggtgtcc caaaggcgag accctgaccg tgggctttac cgacagcaga     2460
aaaatcagcc acacatgcac ccaccctttc catcacgagc ccccgtgat cggcagggaa     2520
aggtttcact ccaggcccca gcacggcaaa gaactcccct gcagcaccta cgtgcaatcc     2580
accgccgcca cagccgagga aattgaggtg catatgcctc ctgataccc cgacagaaca     2640
ctcatgacac agcaaagcgg caacgtcaag attaccgtga acggccagac cgtgagatac     2700
aagtgcaact gtggaggaag caatgagggc ctgaccacaa cagacaaggt gattaataac     2760
```

```
tgtaaaattg accaatgcca cgccgctgtc accaatcaca agaattggca gtacaatagc    2820
cctctggtgc ctagaaatgc tgagctgggc gacaggaaag gcaagattca cattcctttc    2880
cccctggcca acgtgacatg cagggtcccc aaagccagga accccaccgt cacctacggc    2940
aaaaatcagg tgaccatgct gctctacccc gatcaccsta ccctcctcag ctacaggaat    3000
atgggccagg aacccaacta ccacgaggag tgggtgaccc acaagaagga ggtgacactg    3060
acagtcccca cagaaggact ggaggtcacc tggggcaaca atgagcccta caaatactgg    3120
cctcagatgt ccaccaacgg aaccgctcac ggccatcccc atgagatcat cctgtactac    3180
tacgagctgt accccacaat gacagtggtc atcgtcagcg tcgcctcctt tgtgctgctc    3240
tccatggtcg gcacagccgt gggcatgtgt gtgtgtgcca gaaggaggtg catcaccccc    3300
tatgaactga cccctggcgc tacagtgcct tttctcctca gcctgctgtg ttgcgtcaga    3360
accaccaaag ccgccaccta ttatgaggct gccgcttacc tgtggaatga gcagcagcct    3420
ctgttctggc tccaggctct gatccctctc gctgccctca tcgtgctgtg taactgcctc    3480
aagctgctgc cctgctgttg caagacctta gcttttttag ctgtgatgag cattggcgct    3540
catacagtgt ccgcctatga gcacgtgacc gtgatcccta acacagtggg cgtgccctat    3600
aagaccctgg tgaataggcc cggatatagc cccatggtgc tcgaaatgga gctgcagagc    3660
gtcacccctg aacccaccct gagcctggac tacatcacat gcgaatataa aaccgtgatc    3720
ccctccccct acgtgaagtg ctgcggcacc gctgagtgta aggacaagag cctgcccgac    3780
tatagctgca aggtgtttac cggcgtgtat cccttttatgt ggggcggcgc ttactgcttc    3840
tgtgacgctg aaaatacccca gctgagcgag gctcacgtgg agaagagcga aagctgcaag    3900
accgagttcg ccagcgctta tagagctcac accgccagcg ctagcgccaa actgagagtg    3960
ctctaccagg gcaacaatat caccgtcgct gcctacgcta atggcgacca cgccgtgacc    4020
gtgaaggacg ccaaattcgt cgtcggaccc atgtcctccg cttggacccc ctttgacaac    4080
aagatcgtgt gtgtacaaggg agacgtgtac aacatggact accctccttt cggcgctggc    4140
aggcctggac agtttggaga cattcagtcc aggacccccg aatccaagga cgtgtatgcc    4200
aacacccaac tggtgctcca gagacccgcc gctggcacag tgcacgtgcc ttacagccaa    4260
gcccccagcg gatttaaata ctggctgaag gagagaggcg ccagcctgca acataccgct    4320
ccttttggat gccagattgc caccaaccct gtgagggccg tcaactgcgc cgtcggcaac    4380
attcccatca gcatcgacat tcccgacgcc gcctttacca gggtggtgga cgccccagc    4440 gtcacagaca tgtcctgcga ggtgcccgct tgcacccact cctccgactt cggaggagtg    4500
gccatcatca atacaccgc cagcaagaag ggcaagtgtg ccgtgcactc catgaccaac    4560
gccgtcacca tcagggaggc cgacgtggag gtcgaaggca actccaact gcagatctcc    4620 ttcagcaccg ctctggctag cgccgagttc agggtgcagg tgtgcagcac acaggtgcat    4680
tgtgccgccg cttgccatcc ccctaaagac cacatcgtga attacccgc ctcccatacc    4740 accctgggag tccaggacat cagcaccaca gccatgtcct gggtgcagaa aatcaccgga    4800
ggcgtgggcc tgatcgtggc tgtggctgcc ctgattctga tcgtcgtgct ctgcgtcagc    4860
tttagcaggc actgatgatg agcggccgcg atctgctgtg ccttctagtt gccagccatc    4920
tgttgtttgc cctcccccg tgccttcctt gaccctggaa ggtgccactc ccactgtcct    4980
ttcctaataa aatgaggaaa ttgcatcgca ttgtctgagt aggtgtcatt ctattctggg    5040
gggtggggtg gggcaggaca gcaagggga ggattgggaa gacaatagca ggcatgctgg    5100
ggatgcggtg ggctctatgg ccgctgcggc caggtgctga agaattgacc cggttcctcc    5160
```

```
tgggccagaa agaagcaggc acatcccctt ctctgtgaca caccctgtcc acgcccctgg   5220
ttcttagttc cagccccact cataggacac tcatagctca ggagggctcc gccttcaatc   5280
ccacccgcta aagtacttgg agcggtctct ccctccctca tcagcccacc aaaccaaacc   5340
tagcctccaa gagtgggaag aaattaaagc aagataggct attaagtgca gagggagaga   5400
aaatgcctcc aacatgtgag gaagtaatga gagaaatcat agaatttctt ccgcttcctc   5460
gctcactgac tcgctgcgct cggtcgttcg gctgcggcga gcggtatcag ctcactcaaa   5520
ggcggtaata cggttatcca cagaatcagg ggataacgca ggaaagaaca tgtgagcaaa   5580
aggccagcaa aaggccagga accgtaaaaa ggccgcgttg ctggcgtttt tccataggct   5640
ccgcccccct gacgagcatc acaaaaatcg acgctcaagt cagaggtggc gaaacccgac   5700
aggactataa agataccagg cgtttccccc tggaagctcc ctcgtgcgct ctcctgttcc   5760
gaccctgccg cttaccggat acctgtccgc ctttctccct tcgggaagcg tggcgctttc   5820
tcatagctca cgctgtaggt atctcagttc ggtgtaggtc gttcgctcca agctgggctg   5880
tgtgcacgaa ccccccgttc agcccgaccg ctgcgcctta tccggtaact atcgtcttga   5940
gtccaacccg gtaagacacg acttatcgcc actggcagca gccactggta acaggattag   6000
cagagcgagg tatgtaggcg gtgctacaga gttcttgaag tggtggccta actacggcta   6060
cactagaaga acagtatttg gtatctgcgc tctgctgaag ccagttacct tcggaaaaag   6120
agttggtagc tcttgatccg gcaaacaaac caccgctggt agcggtggtt tttttgtttg   6180
caagcagcag attacgcgca gaaaaaaagg atcctttga tcttttctac   6240 ggggtctgac gctcagtgga acgaaaactc acgttaaggg attttggtca tgagattatc   6300
aaaaaggatc ttcacctaga tccttttaaa ttaaaaatga agttttaaat caatctaaag   6360
tatatatgag taaacttggt ctgacagtta ccaatgctta atcagtgagg cacctatctc   6420
agcgatctgt ctatttcgtt catccatagt tgcctgactc ccccgggggg ggcgctgagg   6480
tctgcctcgt gaagaaggtg ttgctgactc ataccaggcc tgaatcgccc catcatccag   6540
ccagaaagtg agggagccac ggttgatgag agctttgttg taggtggacc agttggtgat   6600
tttgaacttt tgctttgcca cggaacggtc tgcgttgtcg ggaagatgcg tgatctgatc   6660
cttcaactca gcaaaagttc gatttattca caaagccgc cgtcccgtca agtcagcgta   6720
atgctctgcc agtgttacaa ccaattaacc aattctgatt agaaaactc atcgagcatc   6780 aaatgaaact gcaatttatt catatcagga ttatcaatac catattttg aaaaagccgt   6840 ttctgtaatg aaggagaaaa ctcaccgagg cagttccata ggatggcaag atcctggtat   6900
cggtctgcga ttccgactcg tccaacatca atacaaccta ttaatttccc ctcgtcaaaa   6960
ataaggttat caagtgagaa atcaccatga gtgacgactg aatccggtga gaatggcaaa   7020
agcttatgca tttctttcca gacttgttca acaggccagc cattacgctc gtcatcaaaa   7080
tcactcgcat caaccaaacc gttattcatt cgtgattgcg cctgagcgag acgaaatacg   7140
cgatcgctgt taaaaggaca attacaaaca ggaatcgaat gcaaccggcg caggaacact   7200
gccagcgcat caacaatatt ttcacctgaa tcaggatatt cttctaatac ctggaatgct   7260
gttttcccgg ggatcgcagt ggtgagtaac catgcatcat caggagtacg gataaaatgc   7320
ttgatggtcg gaagaggcat aaattccgtc agccagttta gtctgaccat ctcatctgta   7380
acatcattgg caacgctacc tttgccatgt ttcagaaaca actctggcgc atcgggcttc   7440
ccatacaatc gatagattgt cgcacctgat tgcccgacat tatcgcgagc ccatttatac   7500
```

```
ccatataaat cagcatccat gttggaattt aatcgcggcc tcgagcaaga cgtttcccgt    7560
tgaatatggc tcataacacc ccttgtatta ctgtttatgt aagcagacag ttttattgtt    7620
catgatgata tattttttatc ttgtgcaatg taacatcaga gattttgaga cacaacgtgg   7680
ctttcccccc cccccccatta ttgaagcatt tatcagggtt attgtctcat gagcggatac   7740
atatttgaat gtatttagaa aaataaacaa ataggggttc cgcgcacatt tccccgaaaa    7800
gtgccacctg acgtctaaga aaccattatt atcatgacat taacctataa aaataggcgt   7860
atcacgaggc cctttcgtc                                                 7879

<210> SEQ ID NO 25
<211> LENGTH: 39761
<212> TYPE: DNA
<213> ORGANISM: Artificial Sequence
<220> FEATURE:
<223> OTHER INFORMATION: Nucleotide sequence of expression vector the
      pChAd155 ?E1, ?E4_Ad5 orf6 hCMV-CHIKV
<220> FEATURE:
<221> NAME/KEY: misc_feature
<222> LOCATION: (15997)..(15997)
<223> OTHER INFORMATION: n is a, c, g, or t

<400> SEQUENCE: 25
catcatcaat aatatacctt attttggatt gaagccaata tgataatgag atgggcggcg     60
cggggcgggg cgcggggcgg gaggcgggtt tgggggcggg ccggcgggcg gggcggtgtg   120
gcggaagtgg actttgtaag tgtggcggat gtgacttgct agtgccgggc gcggtaaaag   180
tgacgttttc cgtgcgcgac aacgcccccg ggaagtgaca ttttttcccgc ggttttttacc   240 ggatgttgta gtgaatttgg gcgtaaccaa gtaagatttg gccatttttcg cgggaaaact   300 gaaacgggga agtgaaatct gattaatttt gcgttagtca taccgcgtaa tatttgtcta   360
gggccgaggg actttggccg attacgtgga ggactcgccc aggtgttttt tgaggtgaat   420
ttccgcgttc cgggtcaaag tctgcgtttt attattatag gatatcccat tgcatacgtt   480
gtatccatat cataatatgt acatttatat tggctcatgt ccaacattac cgccatgttg   540
acattgatta ttgactagtt attaatagta atcaattacg gggtcattag ttcatagccc   600
atatatggag ttccgcgtta cataacttac ggtaaatggc ccgcctggct gaccgcccaa   660 cgaccccgc ccattgacgt caataatgac gtatgttccc atagtaacgc caatagggac   720
tttccattga cgtcaatggg tggagtattt acggtaaact gcccacttgg cagtacatca   780
agtgtatcat atgccaagta cgccccctat tgacgtcaat gacggtaaat ggcccgcctg   840
gcattatgcc cagtacatga ccttatggga ctttcctact tggcagtaca tctacgtatt   900
agtcatcgct attaccatgg tgatgcggtt ttggcagtac atcaatgggc gtggatagcg   960
gtttgactca cggggatttc caagtctcca ccccattgac gtcaatggga gtttgttttg   1020
gcaccaaaat caacgggact ttccaaaatg tcgtaacaac tccgccccat tgacgcaaat   1080
gggcggtagg cgtgtacggt gggaggtcta taagcagagc tctccccta tcagtgatag   1140 agatctccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg agatcttccg   1320
tttatctagg taccagatat cgccaccatg gaattcatcc ccacccagac attctacaac   1380
aggaggtacc aacctagacc ctgggccccc aggcctacaa tccaggtcat caggcctagg   1440
cccagacctc aaagacaggc tggccagctc gcccaactga ttagcgctgt caataaactc   1500
```

```
acaatgaggg ccgtccccca gcagaagccc aggaggaata ggaaaaataa gaagcagagg    1560
cagaaaaagc aagcccccca gaacgacccc aagcagaaga agcaacccccc ccaaaagaag    1620 cctgctcaaa aaagaagaa gcccggcagg agggaaagaa tgtgtatgaa gatcgagaac    1680
gactgcatct ttgaggtgaa acacgaggga aaagtgatgg gatacgcctg cctcgtgggc    1740
gacaaagtga tgaaacctgc ccacgtcaag ggcacaattg acaatgccga cctggctaag    1800
ctggctttca aaaggagctc caaatatgac ctggagtgtg cccagatccc cgtgcacatg    1860
aagtccgacg cctccaagtt cacccacgaa aaacccgagg gatactacaa ctggcatcat    1920
ggagccgtcc agtacagcgg cggaaggttc acaattccta caggcgccgg aaagcccgga    1980
gactccggaa ggcccatctt cgacaacaaa ggaagagtgg tggccatcgt gctcggcgga    2040
gccaacgaag gcgctaggac cgccctgtcc gtggtgacct ggaacaaaga catcgtgacc    2100
aaaatcaccc ctgagggagc cgaagagtgg agcctcgccc tgcccgtgct gtgtctgctg    2160
gccaatacaa ccttttccttg cagccagcct ccttgcacac cctgctgcta cgagaaggaa    2220
cctgaaagca ccctgagaat gctcgaggac aacgtgatga ggcctggcta ttaccagctg    2280
ctgaaggcct ccctgacctg cagccctcac aggcaaagga ggagcacaaa ggacaacttc    2340
aacgtgtata aagctacaag gccctacctc gctcactgtc ctgattgtgg cgagggacac    2400
tcctgccact cccctattgc cctggagagg atcagaaacg aggctaccga cggaaccctg    2460
aagatccagg tgtccctgca gattggaatc aagaccgatg acagccacga ttggacaaag    2520
ctgaggtata tggacagcca cacccccgct gatgctgaaa gggccggcct gctggtgaga    2580
acctccgccc cttgcaccat caccggaacc atgggccact tcattctcgc caggtgtccc    2640
aaaggcgaga ccctgaccgt gggctttacc gacagcgaa aaatcagcca cacatgcacc    2700
caccctttcc atcacgagcc ccccgtgatc ggcagggaaa ggtttcactc caggccccag    2760
cacggcaaag aactcccctg cagcacctac gtgcaatcca ccgccgccac agccgaggaa    2820
attgaggtgc atatgcctcc tgatacccccc gacagaacac tcatgacaca gcaaagcggc    2880
aacgtcaaga ttaccgtgaa cggccagacc gtgagataca agtgcaactg tggaggaagc    2940 aatgagggc tgaccacaac agacaaggtg attaataact gtaaaattga ccaatgccac    3000
gccgctgtca ccaatcacaa gaattggcag tacaatagcc ctctggtgcc tagaaatgct    3060
gagctgggcg acaggaaagg caagattcac attccttttcc ccctggccaa cgtgacatgc    3120
agggtcccca agccaggaa ccccaccgtc acctacggca aaaatcaggt gaccatgctg    3180
ctctaccccg atcaccctac cctcctcagc tacaggaata tgggccagga acccaactac    3240
cacgaggagt gggtgaccca aagaaggag gtgacactga cagtccccac agaaggactg    3300
gaggtcacct ggggcaacaa tgagccctac aaatactggc ctcagatgtc caccaacgga    3360
accgctcacg gccatcccca tgagatcatc ctgtactact acgagctgta ccccacaatg    3420
acagtggtca tcgtcagcgt cgcctcctttt gtgctgctct ccatggtcgg cacagccgtg    3480
ggcatgtgtg tgtgtgccag aaggaggtgc atcaccccct atgaactgac ccctggcgct    3540
acagtgcctt ttctcctcag cctgctgtgt tgcgtcagaa ccaccaaagc cgccacctat    3600
tatgaggctg ccgcttacct gtggaatgag cagcagcctc tgttctggct ccaggctctg    3660
atccctctcg ctgccctcat cgtgctgtgt aactgcctca gctgctgcc ctgctgttgc    3720 aagaccttag cttttttag tgtgatgagc attggcgctc atacagtgtc cgcctatgag    3780
cacgtgaccc tgatccctaa cacagtgggc gtgccctata agaccctggt gaataggccc    3840
ggatatagcc ccatggtgct cgaaatggag ctgcagagcg tcaccctcga acccacctg    3900
```

```
agcctggact acatcacatg cgaatataaa accgtgatcc cctcccccta cgtgaagtgc   3960
tgcggcaccg ctgagtgtaa ggacaagagc ctgcccgact atagctgcaa ggtgtttacc   4020
ggcgtgtatc cctttatgtg gggcggcgct tactgcttct gtgacgctga aaatacccag   4080
ctgagcgagg ctcacgtgga gaagagcgaa agctgcaaga ccgagttcgc cagcgcttat   4140
agagctcaca ccgccagcgc tagcgccaaa ctgagagtgc tctaccaggg caacaatatc   4200
accgtcgctg cctacgctaa tggcgaccac gccgtgaccg tgaaggacgc caaattcgtc   4260
gtcggaccca tgtcctccgc ttggaccccc tttgacaaca agatcgtggt gtacaaggga   4320
gacgtgtaca acatggacta ccctcctttc ggcgctggca ggcctggaca gtttggagac   4380
attcagtcca ggaccccga atccaaggac gtgtatgcca cacccaact ggtgctccag   4440 agacccgccg ctggcacagt gcacgtgcct tacagccaag cccccagcgg atttaaatac   4500
tggctgaagg agagaggcgc cagcctgcaa cataccgctc cttttggatg ccagattgcc   4560
accaaccctg tgagggccgt caactgcgcc gtcggcaaca ttcccatcag catcgacatt   4620
cccgacgccg cctttaccag ggtggtggac gcccccagcg tcacagacat gtcctgcgag   4680
gtgcccgctt gcacccactc ctccgacttc ggaggagtgg ccatcatcaa ataccaccgcc   4740 agcaagaagg gcaagtgtgc cgtgcactcc atgaccaacg ccgtcaccat cagggaggcc   4800
gacgtggagg tcgaaggcaa ctcccaactg cagatctcct tcagccaccgc tctggctagc   4860 gccgagttca gggtgcaggt gtgcagcaca caggtgcatt gtgccgccgc ttgccatccc   4920
cctaaagacc acatcgtgaa ttaccccgcc tcccatacca ccctgggagt ccaggacatc   4980
agcaccacag ccatgtcctg ggtgcagaaa atcaccggag gcgtgggcct gatcgtggct   5040
gtggctgccc tgattctgat cgtcgtgctc tgcgtcagct ttagcaggca ctgatgatga   5100
gcggccgcga tctgctgtgc cttctagttg ccagccatct gttgtttgcc cctcccccgt   5160
gccttccttg accctggaag gtgccactcc cactgtcctt tcctaataaa atgaggaaat   5220
tgcatcgcat tgtctgagta ggtgtcattc tattctgggg gtgggtgg ggcaggacag   5280 caaggggag gattgggaag acaatagcag gcatgctggg gatgcggtgg gctctatggc   5340
cgatcagcga tcgctgaggt gggtgagtgg gcgtggcctg gggtggtcat gaaaatatat   5400
aagttggggg tcttagggtc tctttattg tgttgcagag accgccggag ccatgagcgg   5460
gagcagcagc agcagcagta gcagcagcgc cttggatggc agcatcgtga gcccttattt   5520
gacgacgcgg atgccccact gggccggggt gcgtcagaat gtgatgggct ccagcatcga   5580
cggccgaccc gtcctgcccg caaattccgc cacgctgacc tatgcgaccg tcgcggggac   5640
gccgttggac gccaccgccg ccgccgccgc caccgcagcc gcctcggccg tgcgcagcct   5700
ggccacggac tttgcattcc tgggaccact ggcgacaggg gctacttctc gggccgctgc   5760
tgccgccgtt cgcgatgaca agctgaccgc cctgctggcg cagttggatg cgcttactcg   5820
ggaactgggt gacctttctc agcaggtcat ggccctgcgc cagcaggtct cctccctgca   5880
agctggcggg aatgcttctc ccacaaatgc cgtttaagat aaataaaacc agactctgtt   5940
tggattaaag aaaagtagca agtgcattgc tctctttatt tcataatttt ccgcgcgcga   6000
taggccctag accagcgttc tcggtcgttg agggtgcggt gtatcttctc caggacgtgg   6060
tagaggtggc tctggacgtt gagatacatg ggcatgagcc cgtcccgggg gtggaggtag   6120
caccactgca gagcttcatg ctccggggtg gtgtttgtaga tgatccagtc gtagcaggag   6180
cgctgggcat ggtgcctaaa aatgtccttc agcagcaggc cgatggccag ggggaggccc   6240
```

```
ttggtgtaag tgtttacaaa acggttaagt tgggaagggt gcattcgggg agagatgatg    6300
tgcatcttgg actgtatttt tagattggcg atgtttccgc ccagatccct tctgggattc    6360
atgttgtgca ggaccaccag tacagtgtat ccggtgcact tggggaattt gtcatgcagc    6420
ttagagggaa aagcgtggaa gaacttggag acgcctttgt ggcctcccag attttccatg    6480
cattcgtcca tgatgatggc aatgggcccg cgggaggcag cttgggcaaa gatatttctg    6540
gggtcgctga cgtcgtagtt gtgttccagg gtgaggtcgt cataggccat ttttacaaag    6600
cgcgggcgga gggtgcccga ctgggggatg atggtcccct ctggccctgg ggcgtagttg    6660
ccctcgcaga tctgcatttc ccaggcctta atctcggagg ggggaatcat atccacctgc    6720
ggggcgatga agaaaacggt tccggagcc ggggagatta actgggatga gagcaggttt     6780
ctaagcagct gtgattttcc acaaccggtg ggcccataaa taacacctat aaccggttgc    6840
agctggtagt ttagagagct gcagctgccg tcgtcccgga ggagggggc cacctcgttg     6900 agcatgtccc tgacgcgcat gttctccccg accagatccg ccagaaggcg ctcgccgccc    6960
agggacagca gctcttgcaa ggaagcaaag tttttcagcg gcttgaggcc gtccgccgtg    7020
ggcatgtttt tcagggtctg gctcagcagc tccaggcggt cccagagctc ggtgacgtgc    7080
tctacggcat ctctatccag catatctcct cgtttcgcgg gttggggcga ctttcgctgt    7140
agggcaccaa gcggtggtcg tccagcgggg ccagagtcat gtccttccat gggcgcaggg    7200
tcctcgtcag ggtggtctgg gtcacggtga aggggtgcgc tccgggctga gcgcttgcca    7260
aggtgcgctt gaggctggtt ctgctggtgc tgaagcgctg ccggtcttcg ccctgcgcgt    7320
cggccaggta gcatttgacc atggtgtcat agtccagccc ctccgcggcg tgtcccttgg    7380
cgcgcagctt gcccttggag gtggcgccgc acgaggggca gagcaggctc ttgagcgcgt    7440
agagcttggg ggcgaggaag accgattcgg gggagtaggc gtccgcgccg cagacccccgc   7500 acacggtctc gcactccacc agccaggtga gctcggggcg cgccgggtca aaaaccaggt    7560
ttcccccatg ctttttgatg cgtttcttac ctcgggtctc catgaggtgg tgtccccgct    7620
cggtgacgaa gaggctgtcc gtgtctccgt agaccgactt gaggggtctt ttctccaggg    7680
gggtccctcg gtcttcctcg tagaggaact cggaccactc tgagacgaag gcccgcgtcc    7740
aggccaggac gaaggaggct atgtgggagg ggtagcggtc gttgtccact aggggtcca    7800 ccttctccaa ggtgtgaaga cacatgtcgc cttcctcggc gtccaggaag gtgattggct    7860
tgtaggtgta ggccacgtga ccggggttc ctgacggggg ggtataaaag ggggtggggg     7920
cgcgctcgtc gtcactctct tccgcatcgc tgtctgcgag gccagctgc tggggtgagt     7980 attccctctc gaaggcgggc atgacctccg cgctgaggtt gtcagtttcc aaaaacgagg    8040
aggatttgat gttcacctgt cccgaggtga tacctttgag ggtacccgcg tccatctggt    8100
cagaaaacac gatcttttta ttgtccagct tggtggcgaa cgacccgtag agggcgttgg    8160
agagcagctt ggcgatggag cgcagggtct ggttcttgtc cctgtcggcg cgctccttgg    8220
ccgcgatgtt gagctgcacg tactcgcgcg cgacgcagcg ccactcgggg aagacggtgg    8280
tgcgctcgtc gggcaccagg cgcacgcgcc agccgcggtt gtgcagggtg accaggtcca    8340
cgctggtggc gacctcgccg cgcaggcgct cgttggtcca gcagagacgg ccgcccttgc    8400
gcgagcagaa gggggcagg gggtcgagct gggtctcgtc cggggggtcc gcgtccacgg     8460
tgaaaacccc ggggcgcagg cgcgcgtcga agtagtctat cttgcaacct tgcatgtcca    8520
gcgcctgctg ccagtcgcgg gcggcgagcg cgcgctcgta ggggttgagc ggcgggcccc    8580
agggcatggg gtgggtgagt gcggaggcgt acatgccgca gatgtcatag acgtagaggg    8640
```

```
gctcccgcag gaccccgatg taggtggggt agcagcggcc gccgcggatg ctggcgcgca    8700
cgtagtcata cagctcgtgc gagggggcga ggaggtcggg gcccaggttg gtgcgggcgg    8760
ggcgctccgc gcggaagacg atctgcctga agatggcatg cgagttggaa gagatggtgg    8820
ggcgctggaa gacgttgaag ctggcgtcct gcaggccgac ggcgtcgcgc acgaaggagg    8880
cgtaggagtc gcgcagcttg tgtaccagct cggcggtgac ctgcacgtcg agcgcgcagt    8940
agtcgagggt ctcgcggatg atgtcatatt tagcctgccc cttcttttc cacagctcgc     9000
ggttgaggac aaactcttcg cggtctttcc agtactcttg gatcgggaaa ccgtccggtt    9060
ccgaacggta agagcctagc atgtagaact ggttgacggc ctggtaggcg cagcagccct    9120
tctccacggg gagggcgtag gcctgcgcgg ccttgcggag cgaggtgtgg gtcagggcga    9180
aggtgtccct gaccatgact ttgaggtact ggtgcttgaa gtcggagtcg tcgcagccgc    9240
cccgctccca gagcgagaag tcggtgcgct tcttggagcg ggggttgggc agagcgaagg    9300
tgacatcgtt gaagaggatt ttgcccgcgc ggggcatgaa gttgcgggtg atgcggaagg    9360
gccccggcac ttcagagcgg ttgttgatga cctgggcggc gagcacgatc tcgtcgaagc    9420
cgttgatgtt gtggcccacg atgtagagtt ccaggaagcg gggccggccc tttacggtgg    9480
gcagcttctt tagctcttcg taggtgagct cctcgggcga ggcgaggccg tgctcggcca    9540
gggcccagtc cgcgaggtgc gggttgtctc tgaggaagga cttccagagg tcgcgggcca    9600
ggagggtctg caggcggtct ctgaaggtcc tgaactggcg gcccacggcc attttttcgg    9660
gggtgatgca gtagaaggtg aggggtctt gctgccagcg gtcccagtcg agctgcaggg     9720
cgaggtcgcg cgcggcggtg accaggcgct cgtcgccccc gaatttcatg accagcatga    9780
agggcacgag ctgcttccg aaggcccca tccaagtgta ggtctctaca tcgtaggtga       9840
caaagaggcg ctccgtgcga ggatgcgagc cgatcgggaa gaactggatc tcccgccacc    9900
agttggagga gtggctgttg atgtggtgga agtagaagtc ccgtcgccgg gccgaacact    9960
cgtgctggct tttgtaaaag cgagcgcagt actggcagcg ctgcacgggc tgtacctcat    10020
gcacgagatg cacctttcgc ccgcgcacga ggaagccgag gggaaatctg agcccccgc     10080
ctggctcgcg gcatggctgg ttctcttcta ctttggatgc gtgtccgtct ccgtctggct    10140
cctcgagggg tgttacggtg gagcggacca ccacgccgcg cgagccgcag gtccagatat    10200
cggcgcgcgc cggtcggagt ttgatgacga catcgcgcag ctgggagctg tccatggtct    10260
ggagctcccg cggcggcggc aggtcagccg ggagttcttg caggttcacc tcgcagagtc    10320
gggccagggc gcggggcagg tctaggtggt acctgatctc taggggcgtg ttggtggcgg    10380
cgtcgatggc ttgcaggagc ccgcagcccc gggggcgac gacggtgccc cgcggggtgg      10440
tggtggtggt ggcggtgcag ctcagaagcg gtgccgcggg cggcccccg gaggtagggg      10500
gggctccggt cccgcgggca ggggcggcag cggcacgtcg gcgtggagcg cgggcaggag    10560
ttggtgctgt gcccggaggt tgctggcgaa ggcgacgacg cggcggttga tctcctggat    10620
ctggcgcctc tgcgtgaaga cgacgggccc ggtgagcttg aacctgaaag agagttcgac    10680
agaatcaatc tcggtgtcat tgaccgcggc ctggcgcagg atctcctgca cgtctcccga    10740
gttgtcttgg taggcgatct cggccatgaa ctgctcgatc tcttcctcct ggaggtctcc    10800
gcgtccggcg cgttccacgg tggccgccag gtcgttggag atgcgcccca tgagctgcga    10860
gaaggcgttg agtccgccct cgttccagac tcggctgtag accacgcccc cctggtcatc    10920
gcgggcgcgc atgaccacct gcgcgaggtt gagctccacg tgccgcgcga agacggcgta    10980
```

```
gttgcgcaga cgctggaaga ggtagttgag ggtggtggcg gtgtgctcgg ccacgaagaa   11040
gttcatgacc cagcggcgca acgtggattc gttgatgtcc cccaaggcct ccagccgttc   11100
catggcctcg tagaagtcca cggcgaagtt gaaaaactgg gagttgcgcg ccgacacggt   11160
caactcctcc tccagaagac ggatgagctc ggcgacggtg tcgcgcacct cgcgctcgaa   11220
ggctatgggg atctcttcct ccgctagcat caccacctcc tcctcttcct cctcttctgg   11280
cacttccatg atggcttcct cctcttcggg ggtggcggc ggcggcggtg ggggagggg    11340 cgctctgcgc cggcggcggc gcaccgggag gcggtccacg aagcgcgcga tcatctcccc   11400
gcggcggcgg cgcatggtct cggtgacggc gcggccgttc tcccgggggc gcagttggaa   11460
gacgccgccg gacatctggt gctggggcgg gtggccgtga ggcagcgaga cggcgctgac   11520
gatgcatctc aacaattgct gcgtaggtac gccgccgagg gacctgaggg agtccatatc   11580
caccggatcc gaaaaccttt cgaggaaggc gtctaaccag tcgcagtcgc aaggtaggct   11640
gagcaccgtg gcgggcggcg gggggtgggg ggagtgtctg gcggaggtgc tgctgatgat   11700
gtaattgaag taggcggact tgacacgcg gatggtcgac aggagcacca tgtccttggg   11760
tccggcctgc tggatgcgga ggcggtcggc tatgccccag gcttcgttct ggcatcggcg   11820
caggtccttg tagtagtctt gcatgagcct ttccaccggc acctcttctc cttcctcttc   11880
tgcttcttcc atgtctgctt cggccctggg gcggcgccgc gccccctgc ccccatgcg    11940 cgtgaccccg aaccccctga gcggttggag cagggccagg tcggcgacga cgcgctcggc   12000
caggatggcc tgctgcacct gcgtgagggt ggtttggaag tcatccaagt ccacgaagcg   12060
gtggtaggcg cccgtgttga tggtgtaggt gcagttggcc atgacggacc agttgacggt   12120
ctggtggccc ggttgcgaca tctcggtgta cctgagtcgc gagtaggcgc gggagtcgaa   12180
gacgtagtcg ttgcaagtcc gcaccaggta ctggtagccc accaggaagt gcggcggcgg   12240
ctggcggtag aggggccagc gcagggtggc gggggctccg ggggccaggt cttccagcat   12300
gaggcggtgg taggcgtaga tgtacctgga catccaggtg ataccgcgg cggtggtgga    12360 ggcgcgcggg aagtcgcgca cccggttcca gatgttgcgc aggggcagaa agtgctccat   12420
ggtaggcgtg ctctgtccag tcagacgcgc gcagtcgttg atactctaga ccagggaaaa   12480
cgaaagccgg tcagcgggca ctcttccgtg gtctggtgaa tagatcgcaa gggtatcatg   12540
gcggagggcc tcggttcgag ccccgggtcc gggccgacg gtccgccatg atccacgcgg    12600
ttaccgcccg cgtgtcgaac ccaggtgtgc gacgtcagac aacggtggag tgttcctttt   12660 ggcgttttc tggccgggcg ccggcgccg gtaagagact aagccgcgaa agcgaaagca     12720
gtaagtggct cgctccccgt agccggaggg atccttgcta agggttgcgt tgcggcgaac   12780
cccggttcga atcccgtact cgggccgcc ggacccgcgg ctaaggtgtt ggattggcct    12840
ccccctcgta taaagacccc gcttgcggat tgactccgga cacggggacg agccccttt    12900 attttttgctt tccccagatg catccggtgc tgcggcagat gcgcccccg ccccagcagc    12960 agcaacaaca ccagcaagag cggcagcaac agcagcggga gtcatgcagg gcccctcac   13020 ccaccctcgg cgggccggcc acctcggcgt ccgcggccgt gtctggcgcc tgcggcggcg   13080
gcggggggcc ggctgacgac cccgaggagc ccccgcggcg cagggccaga cactacctgg   13140
acctggagga gggcgagggc ctggcgcggc tgggggcgcc gtctcccgag cgccacccgc   13200
gggtgcagct gaagcgcgac tcgcgcgagg cgtacgtgcc tcggcagaac ctgttcaggg   13260
accgcgcggg cgaggagccc gaggagatgc gggacaggag gttcagcgca gggcgggagc   13320
tgcggcaggg gctgaaccgc gagcggctgc tgcgcgagga ggactttgag cccgacgcgc   13380
```

```
ggacggggat cagccccgcg cgcgcgcacg tggcggccgc cgacctggtg acggcgtacg   13440
agcagacggt gaaccaggag atcaacttcc aaaagagttt caacaaccac gtgcgcacgc   13500
tggtggcgcg cgaggaggtg accatcgggc tgatgcacct gtgggacttt gtaagcgcgc   13560
tggtgcagaa ccccaacagc aagcctctga cggcgcagct gttcctgata gtgcagcaca   13620
gcagggacaa cgaggcgttt agggacgcgc tgctgaacat caccgagccc gagggtcggt   13680
ggctgctgga cctgattaac atcctgcaga gcatagtggt gcaggagcgc agcctgagcc   13740
tggccgacaa ggtggcggcc atcaactact cgatgctgag cctgggcaag ttttacgcgc   13800
gcaagatcta ccagacgccg tacgtgccca tagacaagga ggtgaagatc gacggttttt   13860
acatgcgcat ggcgctgaag gtgctcaccc tgagcgacga cctgggcgtg taccgcaacg   13920
agcgcatcca caaggccgtg agcgtgagcc ggcggcgcga gctgagcgac cgcgagctga   13980
tgcacagcct gcagcgggcg ctggcgggcg ccggcagcgg cgacagggag gcggagtcct   14040
acttcgatgc gggggcggac ctgcgctggg cgcccagccg gcgggccctg gaggccgcgg   14100
gggtccgcga ggactatgac gaggacggcg aggaggatga ggagtacgag ctagaggagg   14160
gcgagtacct ggactaaacc gcgggtggtg tttccggtag atgcaagacc cgaacgtggt   14220
ggacccggcg ctgcgggcgg ctctgcagag ccagccgtcc ggccttaact cctcagacga   14280
ctggcgacag gtcatggacc gcatcatgtc gctgacggcg cgtaaccggg acgcgttccg   14340
gcagcagccg caggccaaca ggctctccgc catcctggag gcggtggtgc ctgcgcgctc   14400
gaaccccacg cacgagaagg tgctggccat agtgaacgcg ctggccgaga cagggccat    14460 ccgcccggac gaggccgggc tggtgtacga cgcgctgctg cagcgcgtgg cccgctacaa   14520
cagcggcaac gtgcagacca acctggaccg gctggtgggg gacgtgcgcg aggcggtggc   14580
gcagcgcgag cgcgcggatc ggcagggcaa cctgggctcc atggtggcgc tgaatgcctt   14640
cctgagcacg cagccggcca acgtgccgcg ggggcaggaa gactacacca actttgtgag   14700
cgcgctgcgg ctgatggtga ccgagacccc ccagagcgag gtgtaccagt cgggcccgga   14760
ctacttcttc cagaccagca gacagggcct gcagacggtg aacctgagcc aggctttcaa   14820
gaacctgcgg gggctgtggg gcgtgaaggc gcccaccggc gaccgggcga cggtgtccag   14880
cctgctgacg cccaactcgc gcctgctgct gctgctgatc gcgccgttca cggacagcgg   14940
cagcgtgtcc cgggacacct acctggggca cctgctgacc ctgtaccgcg aggccatcgg   15000
gcaggcgcag gtggacgagc acaccttcca ggagatcacc agcgtgagcc gcgcgctggg   15060
gcaggaggac acgagcagcc tggaggcgac tctgaactac ctgctgacca accggcggca   15120
gaagattccc tcgctgcaca gcctgacctc cgaggaggag cgcatcttgc gctacgtgca   15180
gcagagcgtg agcctgaacc tgatgcgcga cggggtgacg cccagcgtgg cgctggacat   15240
gaccgcgcgc aacatggaac cgggcatgta cgccgcgcac cggccttaca tcaaccgcct   15300
gatggactac ctgcatcgcg cggcggccgt gaaccccgag tactttacca acgccatcct   15360
gaacccgcac tggctcccgc cgcccgggtt ctacagcggg ggcttcgagg tcccggagac   15420
caacgatggc ttcctgtggg acgacatgga cgacagcgtg ttctccccgc ggccgcaggc   15480
gctggcggaa gcgtccctgc tgcgtcccaa gaaggaggag gaggaggagg cgagtcgccg   15540
ccgcggcagc agcggcgtgg cttctctgtc cgagctgggg gcggcagccg ccgcgcgccc   15600
cgggtccctg gcggcagcc ctttccgag cctggtgggg tctctgcaca gcgagcgcac   15660 caccgccct cggctgctgg gcgaggacga gtacctgaat aactccctgc tgcagccggt   15720
```

```
gcgggagaaa aacctgcctc ccgccttccc caacaacggg atagagagcc tggtggacaa   15780
gatgagcaga tggaagacct atgcgcagga gcacagggac gcgcctgcgc tccggccgcc   15840
cacgcggcgc cagcgccacg accggcagcg ggggctggtg tgggatgacg aggactccgc   15900
ggacgatagc agcgtgctgg acctgggagg gagcggcaac ccgttcgcgc acctgcgccc   15960
ccgcctgggg aggatgtttt aaaaaaaaaa aaaaaangca agaagcatga tgcaaaaatt   16020
aaataaaact caccaaggcc atggcgaccg agcgttggtt tcttgtgttc ccttcagtat   16080
gcggcgcgcg gcgatgtacc aggagggacc tcctccctct tacgagagcg tggtgggcgc   16140
ggcggcggcg gcgccctctt ctcccttttgc gtcgcagctg ctggagccgc cgtacgtgcc   16200
tccgcgctac ctgcggccta cgggggggag aaacagcatc cgttactcgg agctggcgcc   16260
cctgttcgac accacccggg tgtacctggt ggacaacaag tcggcggacg tggcctccct   16320
gaactaccag aacgaccaca gcaattttttt gaccacggtc atccagaaca atgactacag   16380
cccgagcgag gccagcaccc agaccatcaa tctggatgac cggtcgcact ggggcggcga   16440
cctgaaaacc atcctgcaca ccaacatgcc caacgtgaac gagttcatgt tcaccaataa   16500
gttcaaggcg cgggtgatgg tgtcgcgctc gcacaccaag gaagaccggg tggagctgaa   16560
gtacgagtgg gtggagttcg agctgccaga gggcaactac tccgagacca tgaccattga   16620
cctgatgaac aacgcgatcg tggagcacta tctgaaagtg ggcaggcaga acggggtcct   16680
ggagagcgac atcggggtca agttcgacac caggaacttc cgcctggggc tggacccccgt   16740 gaccgggctg gttatgcccg gggtgtacac caacgaggcc ttccatcccg acatcatcct   16800 gctgccggc tgcggggtgg acttcactta cagccgcctg agcaacctcc tgggcatccg   16860
caagcggcag cccttccagg agggcttcag gatcacctac gaggacctgg aggggggcaa   16920
catccccgcg ctcctcgatg tggaggccta ccaggatagc ttgaaggaaa atgaggcggg   16980
acaggaggat accgcccccg ccgcctccgc cgccgccgag cagggcgagg atgctgctga   17040
caccgcggcc gcgacggggg cagaggccga ccccgctatg gtggtggagg ctcccgagca   17100
ggaggaggac atgaatgaca gtgcggtgcg cggagacacc ttcgtcaccc gggggagga   17160 aaagcaagcg gaggccgagg ccgcggccga ggaaaagcaa ctggcggcag cagcggcggc   17220
ggcggcgttg gccgcggcgg aggctgagtc tgagggggacc aagcccgcca aggagcccgt   17280
gattaagccc ctgaccgaag atagcaagaa gcgcagttac aacctgctca aggacagcac   17340
caacaccgcg taccgcagct ggtacctggc ctacaactac ggcgaccgt cgacggggt   17400 gcgctcctgg accctgctgt gcacgccgga cgtgacctgc ggctcggagc aggtgtactg   17460
gtcgctgccc gacatgatgc aagacccgt gaccttccgc tccacgcggc aggtcagcaa   17520
cttcccggtg gtgggcgccg agctgctgcc cgtgcactcc aagagcttct acaacgacca   17580
ggccgtctac tcccagctca tccgccagtt cacctctctg acccacgtgt tcaatcgctt   17640
tcctgagaac cagattctgg cgcgcccgcc cgccccacc atcaccaccg tcagtgaaaa   17700
cgttcctgct ctcacagatc acgggacgct accgctgcgc aacagcatcg gaggagtcca   17760
gcgagtgacc gttactgacg ccagacgccg cacctgcccc tacgtttaca aggccttggg   17820
catagtctcg ccgcgcgtcc tttccagccg cacttttttga gcaacaccac catcatgtcc   17880
atcctgatct cacccagcaa taactccggc tggggactgc tgcgcgcgcc cagcaagatg   17940
ttcggagggg cgaggaagcg ttccgagcag caccccgtgc gcgtgcgcgg gcacttccgc   18000
gcccctgggg gagcgcacaa acgcggccgc gcggggcgca ccaccgtgga cgacgccatc   18060
gactcggtgg tggagcaggc gcgcaactac aggcccgcgg tctctaccgt ggacgcgcc    18120
```

```
atccagaccg tggtgcgggg cgcgcggcgg tacgccaagc tgaagagccg ccggaagcgc    18180
gtggcccgcc gccgccacca tggcccccg tacccgaaga cgcgcggccg ccgccgccgc    18240
cgccgccatc agtgacatgg ccagcaggcg ccggggcaac gtgtactggg tgcgcgactc    18300
ggtgaccggc acgcgcgtgc ccgtgcgctt ccgcccccg cggacttgag atgatgtgaa    18360
aaaacaacac tgagtctcct gctgttgtgt gtatcccagc ggcggcggcg cgcgcagcgt    18420
catgtccaag cgcaaaatca agaagagat gctccaggtc gtcgcgccgg agatctatgg    18480
gcccccgaag aaggaagagc aggattcgaa gccccgcaag ataaagcggg tcaaaaagaa    18540
aaagaaagat gatgacgatg ccgatgggga ggtggagttc ctgcgcgcca cggcgcccag    18600
gcgcccggtg cagtggaagg gccggcgcgt aaagcgcgtc ctgcgccccg gcaccgcggt    18660
ggtcttcacg cccggcgagc gctccacccg gactttcaag cgcgtctatg acgaggtgta    18720
cggcgacgaa gacctgctgg agcaggccaa cgagcgcttc ggagagtttg cttacgggaa    18780
gcgtcagcgg gcgctgggga aggaggacct gctggcgctg ccgctggacc agggcaaccc    18840
caccccagt ctgaagcccg tgaccctgca gcaggtgctg ccgagcagcg caccctccga    18900
ggcgaagcgg ggtctgaagc gcgagggcgg cgacctggcg cccaccgtgc agctcatggt    18960
gcccaagcgg cagaggctgg aggatgtgct ggagaaaatg aaagtagacc ccggtctgca    19020
gccggacatc agggtccgcc ccatcaagca ggtggcgccg ggcctcggcg tgcagaccgt    19080
ggacgtggtc atccccaccg gcaactcccc cgccgccgcc accactaccg ctgcctccac    19140
ggacatggag acacagaccg atcccgccgc agccgcagcc gcagccgccg ccgcgacctc    19200
ctcggcggag gtgcagacgg accctggct gccgccggcg atgtcagctc cccgcgcgcg    19260
tcgcgggcgc aggaagtacg gcgccgccaa cgcgctcctg cccgagtacg ccttgcatcc    19320
ttccatcgcg cccaccccg gctaccgagg ctatacctac cgcccgcgaa gagccaaggg    19380
ttccacccgc cgtccccgcc gacgcgccgc cgccaccacc cgccgccgcc gccgcagacg    19440
ccagcccgca ctggctccag tctccgtgag gaaagtggcg cgcgacggac acaccctggt    19500
gctgccagg gcgcgctacc accccagcat cgtttaaaag cctgttgtgg ttcttgcaga    19560
tatgcccctc acttgccgcc tccgtttccc ggtgccggga taccgaggag gaagatcgcg    19620
ccgcaggagg ggtctggccg gccgcggcct gagcggaggc agccgccgcg cgcaccggcg    19680
gcgacgcgcc accagccgac gcatgcgcgg cggggtgctg cccctgttaa tcccctgat    19740
cgccgcggcg atcggcgccg tgcccgggat cgcctccgtg gccttgcaag cgtcccagag    19800
gcattgacag acttgcaaac ttgcaaatat ggaaaaaaaa accccaataa aaaagtctag    19860
actctcacgc tcgcttggtc ctgtgactat tttgtagaat ggaagacatc aactttgcgt    19920
cgctggcccc cgtcacggc tcgcgcccgt tcctgggaca ctggaacgat atcggcacca    19980
gcaacatgag cggtggcgcc ttcagttggg gctctctgtg gagcggcatt aaaagtatcg    20040
ggtctgccgt taaaaattac ggctcccggg cctggaacag cagcacgggc cagatgttga    20100
gagacaagtt gaaagagcag aacttccagc agaaggtggt ggagggcctg gcctccggca    20160
tcaacggggt ggtggacctg gccaaccagg ccgtgcagaa taagatcaac agcagactgg    20220
accccccggcc gccggtggag gaggtgccgc cggcgctgga cggtgtcc cccgatgggc    20280
gtggcgagaa gcgcccgcgg cccgataggg aagagaccac tctggtcacg cagaccgatg    20340
agccgccccc gtatgaggag gccctgaagc aaggtctgcc caccacgcgg cccatcgcgc    20400
ccatggccac cggggtggtg ggccgccaca ccccgccac gctggacttg cctccgcccg    20460
```

```
ccgatgtgcc gcagcagcag aaggcggcac agccgggccc gcccgcgacc gcctcccgtt    20520
cctccgccgg tcctctgcgc cgcgcggcca gcggccccg cggggggtc gcgaggcacg       20580
gcaactggca gagcacgctg aacagcatcg tgggtctggg ggtgcggtcc gtgaagcgcc    20640
gccgatgcta ctgaatagct tagctaacgt gttgtatgtg tgtatgcgcc ctatgtcgcc    20700
gccagaggag ctgctgagtc gccgccgttc gcgcgcccac caccaccgcc actccgcccc    20760
tcaagatggc gacccatcg atgatgccgc agtggtcgta catgcacatc tcgggccagg      20820
acgcctcgga gtacctgagc cccgggctgg tgcagttcgc ccgcgccacc gagagctact    20880
tcagcctgag taacaagttt aggaacccca cggtggcgcc cacgcacgat gtgaccaccg    20940
accggtctca gcgcctgacg ctgcggttca ttcccgtgga ccgcgaggac accgcgtact    21000
cgtacaaggc gcggttcacc ctggccgtgg gcgacaaccg cgtgctggac atggcctcca    21060
cctactttga catccgcggg gtgctggacc ggggtcccac tttcaagccc tactctggca    21120
ccgcctacaa ctccctggcc cccaagggcg ctcccaactc ctgcgagtgg gagcaagagg    21180
aaactcaggc agttgaagaa gcagcagaag aggaagaaga agatgctgac ggtcaagctg    21240
aggaagagca agcagctacc aaaaagactc atgtatatgc tcaggctccc ctttctggcg    21300
aaaaaattag taaagatggt ctgcaaatag gaacggacgc tacagctaca gaacaaaaac    21360
ctatttatgc agaccctaca ttccagcccg aaccccaaat cggggagtcc cagtggaatg    21420
aggcagatgc tacagtcgcc ggcggtagag tgctaaagaa atctactccc atgaaaccat    21480
gctatggttc ctatgcaaga cccacaaatg ctaatggagg tcagggtgta ctaacggcaa    21540
atgcccaggg acagctagaa tctcaggttg aaatgcaatt cttttcaact tctgaaaacg    21600
cccgtaacga ggctaacaac attcagccca aattggtgct gtatagtgag gatgtgcaca    21660
tggagacccc ggatacgcac ctttcttaca agcccgcaaa aagcgatgac aattcaaaaa    21720
tcatgctggg tcagcagtcc atgcccaaca gacctaatta catcggcttc agagacaact    21780
ttatcggcct catgtattac aatagcactg gcaacatggg agtgcttgca ggtcaggcct    21840
ctcagttgaa tgcagtggtg gacttgcaag acagaaacac agaactgtcc taccagctct    21900
tgcttgattc catgggtgac agaaccagat acttttccat gtggaatcag gcagtggaca    21960
gttatgaccc agatgttaga attattgaaa atcatggaac tgaagacgag ctccccaact    22020
attgtttccc tctgggtggc ataggggtaa ctgacactta ccaggctgtt aaaaccaaca    22080
atggcaataa cggggggccag gtgacttgga caaaagatga aacttttgca gatcgcaatg    22140
aaataggggt gggaaacaat ttcgctatgg agatcaacct cagtgccaac ctgtggagaa    22200
acttcctgta ctccaacgtg gcgctgtacc taccagacaa gcttaagtac aaccccctcca    22260
atgtggacat ctctgacaac cccaacacct acgattacat gaacaagcga gtggtggccc    22320
cggggctggt ggactgctac atcaacctgg gcgcgcgctg gtcgctggac tacatggaca    22380
acgtcaaccc cttcaaccac caccgcaatg cgggcctgcg ctaccgctcc atgctcctgg    22440
gcaacgggcg ctacgtgccc ttccacatcc aggtgcccca gaagttcttt gccatcaaga    22500
acctcctcct cctgccgggc tcctacacct acgagtggaa cttcaggaag gatgtcaaca    22560
tggtcctcca gagctctctg ggtaacgatc tcagggtgga cggggccagc atcaagttcg    22620
agagcatctg cctctacgcc accttcttcc ccatggccca aacacggcc tccacgctcg    22680
aggccatgct caggaacgac accaacgacc agtccttcaa tgactacctc tccgccgcca    22740
acatgctcta ccccatcccc gccaacgcca ccaacgtccc catctccatc ccctcgcgca    22800
actgggcggc cttccgcggc tgggccttca cccgcctcaa gaccaaggag accccctccc    22860
```

```
tgggctcggg attcgacccc tactacacct actcgggctc cattccctac ctggacggca  22920
ccttctacct caaccacact ttcaagaagg tctcggtcac cttcgactcc tcggtcagct  22980
ggccgggcaa cgaccgtctg ctcaccccca acgagttcga gatcaagcgc tcggtcgacg  23040
gggagggcta caacgtggcc cagtgcaaca tgaccaagga ctggttcctg gtccagatgc  23100
tggccaacta caacatcggc taccagggct tctacatccc agagagctac aaggacagga  23160
tgtactcctt cttcaggaac ttccagccca tgagccggca ggtggtggac cagaccaagt  23220
acaaggacta ccaggaggtg ggcatcatcc accagcacaa caactcgggc ttcgtgggct  23280
acctcgcccc caccatgcgc gagggacagg cctaccccgc caacttcccc tatccgctca  23340
taggcaagac cgcggtcgac agcatcaccc agaaaaagtt cctctgcgac cgcaccctct  23400
ggcgcatccc cttctccagc aacttcatgt ccatgggtgc gctctcggac ctgggccaga  23460
acttgctcta cgccaactcc gcccacgccc tcgacatgac cttcgaggtc gaccccatgg  23520
acgagcccac ccttctctat gttctgttcg aagtctttga cgtggtccgg gtccaccagc  23580
cgcaccgcgg cgtcatcgag accgtgtacc tgcgtacgcc cttctcggcc ggcaacgcca  23640
ccacctaaag aagcaagccg cagtcatcgc cgcctgcatg ccgtcgggtt ccaccgagca  23700
agagctcagg gccatcgtca gagacctggg atgcgggccc tattttttgg gccacttcga  23760
caagcgcttc cctggctttg tctccccaca caagctggcc tgcgccatcg tcaacacggc  23820
cggccgcgag accggggggcg tgcactggct ggccttcgcc tggaacccgc gctccaaaac  23880
atgcttcctc tttgacccct tcggcttttc ggaccagcgg ctcaagcaaa tctacgagtt  23940
cgagtacgag ggcttgctgc gtcgcagcgc catcgcctcc tcgcccgacc gctgcgtcac  24000
cctcgaaaag tccacccaga ccgtgcaggg gcccgactcg gccgcctgcg gtctcttctg  24060
ctgcatgttt ctgcacgcct ttgtgcactg gcctcagagt cccatggacc gcaacccac   24120 catgaacttg ctgacggggg tgcccaactc catgctccag agcccccagg tcgagcccac  24180
cctgcgccgc aaccaggagc agctctacag cttcctggag cgccactcgc cttacttccg  24240
ccgccacagc gcacagatca ggagggccac ctccttctgc cacttgcaag agatgcaaga  24300
agggtaataa cgatgtacac actttttttc tcaataaatg gcatcttttt atttatacaa  24360
gctctctggg gtattcattt cccaccacca cccgccgttg tcgccatctg gctctatta   24420 gaaatcgaaa gggttctgcc gggagtcgcc gtgcgcacg ggcagggaca cgttgcgata  24480
ctggtagcgg gtgccccact tgaactcggg caccaccagg cgaggcagct cggggaagtt  24540
ttcgctccac aggctgcggg tcagcaccag cgcgttcatc aggtcgggcg ccgagatctt  24600
gaagtcgcag ttggggccgc cgccctgcgc gcgcgagttg cggtacaccg ggttgcagca  24660
ctggaacacc aacagcgccg ggtgcttcac gctggccagc acgctgcggt cggagatcag  24720
ctcggcgtcc aggtcctccg cgttgctcag cgcgaacggg gtcatcttgg gcacttgccg  24780
ccccaggaag ggcgcgtgcc ccggtttcga gttcagtcg cagcgcagcg ggatcagcag   24840
gtgcccgtgc ccggactcgg cgttggggta cagcgcgcgc atgaaggcct gcatctggcg  24900
gaaggccatc tgggccttgg cgccctccga gaagaacatg ccgcaggact tgcccgagaa  24960
ctggtttgcg gggcagctgg cgtcgtgcag gcagcagcgc gcgtcggtgt tggcgatctg  25020
caccacgttg cgcccccacc ggttcttcac gatcttggcc ttggacgatt gctccttcag  25080
cgcgcgctgc ccgttctcgc tggtcacatc catctcgatc acatgttcct tgttcaccat  25140
gctgctgccg tgcagacact tcagctcgcc ctccgtctcg gtgcagcggt gctgccacag  25200
```

```
cgcgcagccc gtgggctcga aagacttgta ggtcacctcc gcgaaggact gcaggtaccc   25260
ctgcaaaaag cggcccatca tggtcacgaa ggtcttgttg ctgctgaagg tcagctgcag   25320
cccgcggtgc tcctcgttca gccaggtctt gcacacggcc gccagcgcct ccacctggtc   25380
gggcagcatt ttgaagttca ccttcagctc attctccacg tggtacttgt ccatcagcgt   25440
gcgcgccgcc tccatgccct tctcccaggc cgacaccagc ggcaggctca cggggttctt   25500
caccatcacc gtggccgccg cctccgccgc gctttcgctt ccgccccgc tgttctcttc    25560
ctcttcctcc tcttcctcgc cgccgcccac tcgcagcccc cgcaccacgg ggtcgtcttc   25620
ctgcaggcgc tgcaccttgc gcttgccgtt gcgcccctgc ttgatgcgca cgggcgggtt   25680
gctgaagccc accatcacca cgcgcggcctc ttcttgctcg tcctcgctgt ccagaatgac  25740
ctccggggag gggggttgg tcatcctcag taccgaggca cgcttctttt tcttcctggg    25800
ggcgttcgcc agctccgcgg ctgcggccgc tgccgaggtc gaaggccgag ggctgggcgt   25860
gcgcggcacc agcgcgtcct gcgagccgtc ctcgtcctcc tcggactcga dacggaggcg   25920
ggcccgcttc ttcgggggcg cgcggggcgg cggaggcggc ggcggcgacg gagacgggga   25980
cgagacatcg tccagggtgg gtggacggcg ggccgcgccg cgtccgcgct cgggggtggt   26040
ctcgcgctgg tcctcttccc gactggccat ctcccactgc tccttctcct ataggcagaa   26100
agagatcatg gagtctctca tgcgagtcga aaggaggag acagcctaa ccgcccctc      26160
tgagccctcc accaccgccg ccaccaccgc caatgccgcc gcggacgacg cgcccaccga   26220
gaccaccgcc agtaccaccc tccccagcga cgcaccccg ctcgagaatg aagtgctgat    26280
cgagcaggac ccgggttttg tgagcggaga ggaggatgag gtggatgaga aggagaagga   26340
ggaggtcgcc gcctcagtgc caaaagagga taaaaagcaa gaccaggacg acgcagataa   26400
ggatgagaca gcagtcgggc gggggaacgg aagccatgat gctgatgacg gctacctaga  26460
cgtgggagac gacgtgctgc ttaagcacct gcaccgccag tgcgtcatcg tctgcgacgc   26520
gctgcaggag cgctgcgaag tgcccctgga cgtggcggag gtcagccgcg cctacgagcg   26580
gcacctcttc gcgccgcacg tgcccccaa gcgccgggag aacggcacct gcgagcccaa    26640
cccgcgtctc aacttctacc cggtcttcgc ggtacccgag gtgctggcca cctaccacat   26700
cttttttccaa aactgcaaga tccccctctc ctgccgcgcc aaccgcaccc gcgccgacaa   26760
aaccctgacc ctgcggcagg gcgcccacat acctgatatc gcctctctgg aggaagtgcc   26820
caagatcttc gagggtctcg gtcgcgacga gaaacgggcg gcgaacgctc tgcacggaga   26880
cagcgaaaac gagagtcact cggggggtgct ggtggagctc gagggcgaca acgcgcgcct   26940
ggccgtactc aagcgcagca tagaggtcac ccactttgcc tacccggcgc tcaacctgcc   27000
ccccaaggtc atgagtgtgg tcatgggcga gctcatcatg cgccgcgccc agccctggc    27060
cgcggatgca aacttgcaag agtcctccga ggaaggcctg cccgcggtca gcgacgagca   27120
gctggcgcgc tggctggaga cccgcgaccc cgcgcagctg gaggagcggc gcaagctcat   27180
gatggccgcg gtgctggtca ccgtggagct cgagtgtctg cagcgcttct tcgcggaccc   27240
cgagatgcag cgcaagctcg aggagaccct gcactacacc ttccgccagg gctacgtgcg   27300
ccaggcctgc aagatctcca acgtggagct ctgcaacctg gtctcctacc tgggcatcct   27360
gcacgagaac cgcctcgggc agaacgtcct gcactccacc ctcaaggggg aggcgcgccg   27420
cgactacatc cgcgactgcg cctacctctt cctctgctac acctggcaga cggccatggg   27480
ggtctggcag cagtgcctgg aggagcgcaa cctcaaggga ctggaaaagc tcctcaagcg   27540
caccctcagg gacctctgga cgggcttcaa cgagcgctcg gtggccgccg cgctggcgga   27600
```

```
catcatctttccccgagcgcctgctcaagaccctgcagcagggcctgcccgacttcaccag     27660
ccagagcatgctgcagaactctcaggactttcatcctggagcgctcgggcatcctgccggc    27720
cacttgctgcgcgctgcccagcgacttcgtgcccatcaagtacagggagtgcccgccgcc    27780
gctctggggccactgctacctcttccagctggccaactacctcgcctaccactcggacct    27840
catggaagacgtgagcggcgagggcctgctcgagtgccactgccgctgcaacctctgcac    27900
gccccaccgctctctagtctgcaacccgcagctgctcagcgagagtcagattatcggtac    27960
cttcgagctgcagggtccctcgcctgacgagaagtccgcggctccagggctgaaactcac    28020
tccggggctgtggacttccgcctacctacgcaaatttgtacctgaggactaccacgccca    28080
cgagatcaggttctacgaagaccaatcccgcccgcccaaggcggagctcaccgcctgcgt    28140
catcacccagggcacatcctgggccaattgcaagccatcaacaaagcccgccgagagtt    28200
cttgctgaaaaagggtcggggggtgtacctggaccccagtccggcgaggagctaaaccc    28260
gctaccccgccgccgccccagcagcgggaccttgcttccaggatggcacccagaaaga    28320
agcagcagccgccgccgccccgcagccatacatgcttctggaggaagaggaggaggact    28380
gggacagtcaggcagaggaggtttcggacgaggagcaggaggagatgatggaagactggg    28440
aggaggacagcagcctagacgaggaagcttcagaggccgaagaggtggcagacgcaacac    28500
catcgccctcggtcgcagcccctcgccgggcccctgaaatcctccgaacccagcaccag    28560
gcgctataacctccgctcctccggcgccggcgccacccgcccgcagacccaaccgtagat    28620
gggacaccacaggaacgggtcggtaagtccaagtgcccgccgccgccaccgcagcagc    28680
agcagcagcagcgccagggctaccgctcgtggcgcgggcaaagaacgccatagtcgcct    28740
gcttgcaagactgcgggggcaacatctcttcgcccgccgcttcctgctattccaccacg    28800
gggtcgcctttcccccgcaatgtcctgcattactaccgtcatctctacagcccctactgca    28860
gcggcgacccagaggcggcagcggcagccacagcggcgaccaccacctaggaagatatcc    28920
tccgcgggcaagacagcggcagcagcggccaggagacccggcagcagcggcgggagcg    28980
gtgggcgcactgcgcctctcgcccaacgaaccctctcgacccgggagctcagacacagg    29040
atcttccccactttgtatgccatcttccaacagagcagggccaggagcaggagctgaaa    29100
ataaaaaacagatctctgcgctccctcaccgcagctgtctgtatcacaaaagcgaagat    29160
cagcttcggcgcacgctggaggacgcgaggcactcttcagcaaatactgcgcgctcact    29220
cttaaagactagctccgcgcccttctcgaatttaggcgggagaaaactacgtcatcgccg    29280
gccgccgccagcccgcccagccgagatgagcaaagagatccccacgccatacatgtgga    29340
gctaccagccgcagatgggactcgcggcgggagcggcccaggactactccaccccgcatga    29400
actacatgagcgcgggacccacatgatctcacaggtcaacgggatccgccccagcgaa    29460
accaaatactgctggaacagcgggccatcaccgccacgcccgccataatctcaaccccc    29520
gaaattggcccgccgccctcgtgtaccaggaaaaccccctcgccaccaccgtactacttc    29580
cgcgtgacgcccaggccgaagtccagatgactaactcagggcgcagctcgcgggcggct    29640
ttcgtcacgggggcgcggccgctccgaccagtataagacacctgatgatcagaggccgag    29700
gtatccagctcaacgacgagtcggtgagctcttcgctcggtctccgtccgacgaaactt    29760
tccagctcgcggatccggccgctcttcgttcacgccccgccaggcgtactgactctgc    29820
agacctcgtcctcggagcccccgctccgcgcgcatcggaaaccctccagttcgtggaggagt    29880
tcgtgccctcggtctacttcaaccccttctcgggacctccccggacgctaccccgaccagt    29940
```

```
tcattccgaa ctttgacgcg gtgaaggact cggcggacgg ctacgactga atgtcaggtg   30000
tcgaggcaga gcagcttcgc ctgagacacc tcgagcactg ccgccgccac aagtgcttcg   30060
cccgcggttc tggtgagttc tgctactttc agctacccga ggagcatacc gaggggccgg   30120
cgcacgcgt ccgcctgacc acccagggcg aggttacctg ttccctcatc cgggagttta    30180
ccctccgtcc cctgctagtg gagcgggagc ggggtccctg tgtcctaact atcgcctgca   30240
actgccctaa ccctggatta catcaagatc tttgctgtca tctctgtgct gagtttaata   30300
aacgctgaga tcagaatcta ctggggctcc tgtcgccatc ctgtgaacgc caccgtcttc   30360
acccaccccg accaggccca ggcgaacctc acctgcggtc tgcatcggag gccaagaag    30420
tacctcacct ggtacttcaa cggcaccccc tttgtggttt acaacagctt cgacggggac   30480
ggagtctccc tgaaagacca gctctccggt ctcagctact ccatccacaa gaacaccacc   30540
ctccaactct tccctcccta cctgccggga acctacgagt gcgtcaccgg ccgctgcacc   30600
cacctcaccc gcctgatcgt aaaccagagc tttccgggaa cagataactc cctcttcccc   30660
agaacaggag gtgagctcag gaaactcccc ggggaccagg gcggagacgt accttcgacc   30720
cttgtggggt taggattttt tattaccggg ttgctggctc ttttaatcaa agtttccttg   30780
agatttgttc tttccttcta cgtgtatgaa cacctcaacc tccaataact ctacccttc    30840
ttcggaatca ggtgacttct ctgaaatcgg gcttggtgtg ctgcttactc tgttgatttt   30900
tttccttatc atactcagcc ttctgtgcct caggctcgcc gcctgctgcg cacacatcta   30960
tatctactgc tggttgctca agtgcagggg tcgccaccca agatgaacag gtacatggtc   31020
ctatcgatct taggcctgct ggccctggcg gcctgcagcg ccgccaaaaa agagattacc   31080
tttgaggagc ccgcttgcaa tgtaactttc aagcccgagg gtgaccaatg caccaccctc   31140
gtcaaatgcg ttaccaatca tgagaggctg cgcatcgact acaaaaacaa aactggccag   31200
tttgcggtct atagtgtgtt tacgcccgga gacccctcta actactctgt caccgtcttc   31260
cagggcggac agtctaagat attcaattac actttccctt tttatgagtt atgcgatgcg   31320
gtcatgtaca tgtcaaaaca gtacaacctg tggcctccct ctccccaggc gtgtgtggaa   31380
aatactgggt cttactgctg tatggctttc gcaatcacta cgctcgctct aatctgcacg   31440
gtgctataca taaaattcag gcagaggcga atctttatcg atgaaaagaa aatgccttga   31500
tcgctaacac cggctttcta tctgcagaat gaatgcaatc acctccctac taatcaccac   31560
caccctcctt gcgattgccc atgggttgac acgaatcgaa gtgccagtgg ggtccaatgt   31620
caccatggtg ggccccgccg gcaattccac cctcatgtgg gaaaaatttg tccgcaatca   31680
atgggttcat ttctgctcta accgaatcag tatcaagccc agagccatct gcgatgggca   31740
aaatctaact ctgatcaatg tgcaaatgat ggatgctggg tactattacg ggcagcgggg   31800
agaaatcatt aattactggc gaccccacaa ggactacatg ctgcatgtag tcgaggcact   31860
tcccactacc acccccacta ccacctctcc caccaccacc accactacta ctactactac   31920
tactactact actactacca ctaccgctgc ccgccatacc cgcaaaagca ccatgattag   31980
cacaaagccc cctcgtgctc actcccacgc cggcgggccc atcggtgcga cctcagaaac   32040
caccgagctt tgcttctgcc aatgcactaa cgccagcgct catgaactgt tcgacctgga   32100
gaatgaggat gtccagcaga gctccgcttg cctgacccag gaggctgtgg agcccgttgc   32160
cctgaagcag atcggtgatt caataattga ctcttcttct tttgccactc ccgaataccc   32220
tcccgattct actttccaca tcacgggtac caaagaccct aacctctctt tctacctgat   32280
gctgctgctc tgtatctctg tggtctcttc cgcgctgatg ttactgggga tgttctgctg   32340
```

```
cctgatctgc cgcagaaaga gaaaagctcg ctctcagggc caaccactga tgcccttccc   32400
ctaccccccg gattttgcag ataacaagat atgagctcgc tgctgacact aaccgcttta   32460
ctagcctgcg ctctaaccct tgtcgcttgc gactcgagat tccacaatgt cacagctgtg   32520
gcaggagaaa atgttacttt caactccacg gccgataccc agtggtcgtg gagtggctca   32580
ggtagctact taactatctg caatagctcc acttcccccg gcatatcccc aaccaagtac   32640
caatgcaatg ccagcctgtt caccctcatc aacgcttcca ccctggacaa tggactctat   32700
gtaggctatg tacccttggg tgggcaagga aagacccacg cttacaacct ggaagttcgc   32760
cagcccagaa ccactaccca agcttctccc accaccacca ccaccaccac catcaccagc   32820
agcagcagca gcagcagcca cagcagcagc agcagattat tgactttggt tttggccagc   32880
tcatctgccg ctacccaggc catctacagc tctgtgcccg aaaccactca gatccaccgc   32940
ccagaaacga ccaccgccac caccctacac acctccagcg atcagatgcc gaccaacatc   33000 accccccttgg ctcttcaaat gggacttaca agccccactc caaaaccagt ggatgcggcc   33060
gaggtctccg ccctcgtcaa tgactgggcg gggctgggaa tgtggtggtt cgccataggc   33120 atgatgcgc tctgcctgct tctgctctgg ctcatctgct gcctccaccg caggcgagcg   33180 agaccccca tctatagacc catcattgtc ctgaacccg ataatgatgg gatccataga   33240 ttggatggc tgaaaaacct acttttttct tttacagtat gataaattga acatgcctc   33300 gcattttctt gtacatgttc cttctcccac cttttctggg gtgttctacg ctggccgctg   33360
tgtctcacct ggaggtagac tgcctctcac ccttcactgt ctacctgctt tacggattgg   33420
tcaccctcac tctcatctgc agcctaatca cagtaatcat cgccttcatc cagtgcattg   33480
attacatctg tgtgcgcctc gcatacttca gacaccaccc gcagtaccga gacaggaaca   33540
ttgcccaact tctaagactg ctctaatcat gcataagact gtgatctgcc ttctgatcct   33600
ctgcatcctg cccaccctca cctcctgcca gtacaccaca aaatctccgc gcaaaagaca   33660
tgcctcctgc cgcttcaccc aactgtggaa tataccaaa tgctacaacg aaaagagcga   33720
gctctccgaa gcttggctgt atggggtcat ctgtgtctta gttttctgca gcactgtctt   33780
tgccctcata atctaccct actttgattt gggatggaac gcgatcgatg ccatgaatta   33840 ccccacctttt cccgcacccg agataattcc actgcgacaa gttgtacccg ttgtcgttaa   33900
tcaacgcccc ccatccccta cgcccactga aatcagctac tttaacctaa caggcggaga   33960
tgactgacgc cctagatcta gaaatggacg gcatcagtac cgagcagcgt ctcctagaga   34020
ggcgcaggca ggcggctgag caagagcgcc tcaatcagga gctccgagat tcgttaacc   34080 tgcaccagtg caaaagaggc atcttttgtc tggtaaagca ggccaaagtc acctacgaga   34140
agaccggcaa cagccaccgc ctcagttaca aattgcccac ccagcgccag aagctggtgc   34200
tcatggtggg tgagaatccc atcaccgtca cccagcactc ggtagagacc gaggggtgtc   34260
tgcactcccc ctgtcggggt ccagaagacc tctgcaccct ggtaaagacc ctgtgcggtc   34320
tcagagattt agtcccccttt aactaatcaa acactggaat caataaaaag aatcacttac   34380
ttaaaatcag acagcaggtc tctgtccagt ttattcagca gcacctcctt cccctcctcc   34440
caactctggt actccaaacg ccttctggcg gcaaacttcc tccacaccct gaagggaatg   34500
tcagattctt gctcctgtcc ctccgcaccc actatcttca tgttgttgca gatgaagcgc   34560
accaaaacgt ctgacgagag cttcaacccc gtgtacccct atgacacgga aagcggccct   34620
ccctccgtcc cttttcctcac ccctcccttc gtgtctcccg atggattcca agaaagtccc   34680
```

```
cccgggtcc    tgtctctgaa    cctggccgag    ccctggtca     cttcccacgg    catgctcgcc    34740
ctgaaaatgg   gaagtggcct    ctccctggac    gacgctggca    acctcacctc    tcaagatatc    34800
accaccgcta   gccctcccct    caaaaaaacc    aagaccaacc    tcagcctaga    aacctcatcc    34860
cccctaactg   tgagcacctc    aggcgccctc    accgtagcag    ccgccgctcc    cctggcggtg    34920
gccggcacct   ccctcaccat    gcaatcagag    gccccctga     cagtacagga    tgcaaaactc    34980
accctggcca   ccaaaggccc    cctgaccgtg    tctgaaggca    aactggcctt    gcaaacatcg    35040
gccccgctga   cggccgctga    cagcagcacc    ctcacagtca    gtgccacacc    acccttagc     35100
acaagcaatg   gcagcttggg    tattgacatg    caagccccca    tttacaccac    caatggaaaa    35160
ctaggactta   actttggcgc    tcccctgcat    gtggtagaca    gcctaaatgc    actgactgta    35220
gttactggcc   aaggtcttac    gataaacgga    acagccctac    aaactagagt    ctcaggtgcc    35280
ctcaactatg   acacatcagg    aaacctagaa    ttgagagctg    caggggggtat   gcgagttgat    35340
gcaaatggtc   aacttatcct    tgatgtagct    tacccatttg    atgcacaaaa    caatctcagc    35400
cttaggcttg   gacagggacc    cctgtttgtt    aactctgccc    acaacttgga    tgttaactac    35460
aacagaggcc   tctacctgtt    cacatctgga    aataccaaaa    agctagaagt    taatatcaaa    35520
acagccaagg   gtctcattta    tgatgacact    gctatagcaa    tcaatgcggg    tgatgggcta    35580
cagtttgact   caggctcaga    tacaaatcca    ttaaaaacta    aacttggatt    aggactggat    35640
tatgactcca   gcagagccat    aattgctaaa    ctgggaactg    gcctaagctt    tgacaacaca    35700
ggtgccatca   cagtaggcaa    caaaaatgat    gacaagctta    ccttgtggac    cacaccagac    35760
ccatccccta   actgtagaat    ctattcagag    aaagatgcta    aattcacact    tgttttgact    35820
aaatgcggca   gtcaggtgtt    ggccagcgtt    tctgttttat    ctgtaaaagg    tagccttgcg    35880
cccatcagtg   gcacagtaac    tagtgctcag    attgtcctca    gatttgatga    aaatggagtt    35940
ctactaagca   attcttccct    tgaccctcaa    tactggaact    acagaaaagg    tgaccttaca    36000
gagggcactg   catataccaa    cgcagtggga    tttatgccca    acctcacagc    atacccaaaa    36060
acacagagcc   aaactgctaa    aagcaacatt    gtaagtcagg    tttacttgaa    tggggacaaa    36120
tccaaaccca   tgaccctcac    cattaccctc    aatggaacta    atgaaacagg    agatgccaca    36180
gtaagcactt   actccatgtc    attctcatgg    aactggaatg    gaagtaatta    cattaatgaa    36240
acgttccaaa   ccaactcctt    caccttctcc    tacatcgccc    aagaataaaa    agcatgacgc    36300
tgttgatttg   attcaatgtg    tttctgtttt    attttcaagc    acaacaaaat    cattcaagtc    36360
attcttccat   cttagcttaa    tagacacagt    agcttaatag    acccagtagt    gcaaagcccc    36420
attctagctt   ataactagtg    gagaagtact    cgcctacatg    ggggtagagt    cataatcgtg    36480
catcaggata   gggcggtggt    gctgcagcag    gcgcgcaata    aactgctgcc    gccgccgctc    36540
cgtcctgcag   gaatacaaca    tggcagtggt    ctcctcagcg    atgattcgca    ccgcccgcag    36600
cataaggcgc   cttgtcctcc    gggcacagca    gcgcaccctg    atctcactta    aatcagcaca    36660
gtaactgcag   cacagcacca    caatattgtt    caaaatccca    cagtgcaagg    cgctgtatcc    36720
aaagctcatg   gcggggacca    cagaacccac    gtggccatca    taccacaagc    gcaggtagat    36780
taagtggcga   cccctcataa    acacgctgga    cataaacatt    acctcttttg    gcatgttgta    36840
attcaccacc   tcccggtacc    atataaacct    ctgattaaac    atggcgccat    ccaccaccat    36900
cctaaaccag   ctggccaaaa    cctgcccgcc    ggctatacac    tgcagggaac    cgggactgga    36960
acaatgacag   tggagagccc    aggactcgta    accatggatc    atcatgctcg    tcatgatatc    37020
aatgttggca   caacacaggc    acacgtgcat    acacttcctc    aggattacaa    gctcctcccg    37080
```

```
cgttagaacc atatcccagg gaacaaccca ttcctgaatc agcgtaaatc ccacactgca   37140
gggaagacct cgcacgtaac tcacgttgtg cattgtcaaa gtgttacatt cgggcagcag   37200
cggatgatcc tccagtatgg tagcgcgggt ttctgtctca aaaggaggta gacgatccct   37260
actgtacgga gtgcgccgag acaaccgaga tcgtgttggt cgtagtgtca tgccaaatgg   37320
aacgccggac gtagtcatat ttcctgaagt cttagatctc tcaacgcagc accagcacca   37380
acacttcgca gtgtaaaagg ccaagtgccg agagagtata tataggaata aaaagtgacg   37440
taaacgggca aagtccaaaa aacgcccaga aaaccgcac gcgaacctac gccccgaaac    37500
gaaagccaaa aaacactaga cactcccttc cggcgtcaac ttccgctttc ccacgctacg   37560
tcacttgccc cagtcaaaca aactacatat cccgaacttc caagtcgcca cgcccaaaac   37620
accgcctaca cctccccgcc cgccggcccg ccccaaaacc cgcctcccgc cccgcgcccc   37680
gccccgcgcc gcccatctca ttatcatatt ggcttcaatc caaaataagg tatattattg   37740
atgatggttt aaacggatcc aattcttgaa gacgaaaggg cctcgtgata cgcctatttt   37800
tataggttaa tgtcatgata ataatggttt cttagacgtc aggtggcact tttcggggaa   37860
atgtgcgcgg aacccctatt tgtttatttt tctaaataca ttcaaatatg tatccgctca   37920
tgagacaata accctgataa atgcttcaat aatattgaaa aaggaagagt atgagtattc   37980
aacatttccg tgtcgccctt attcctttt ttgcggcatt ttgccttcct gtttttgctc    38040
acccagaaac gctggtgaaa gtaaaagatg ctgaagatca gttgggtgca cgagtgggtt   38100
acatcgaact ggatctcaac agcggtaaga tccttgagag ttttcgcccc gaagaacgtt   38160
ttccaatgat gagcactttt aaagttctgc tatgtggcgc ggtattatcc cgtgttgacg   38220
ccgggcaaga gcaactcggt cgccgcatac actattctca gaatgacttg gttgagtact   38280
caccagtcac agaaaagcat cttacggatg gcatgacagt aagagaatta tgcagtgctg   38340
ccataaccat gagtgataac actgcggcca acttacttct gacaacgatc ggaggaccga   38400
aggagctaac cgcttttttg cacaacatgg gggatcatgt aactcgcctt gatcgttggg   38460
aaccggagct gaatgaagcc ataccaaacg acgagcgtga caccacgatg cctgtagcaa   38520
tggcaacaac gttgcgcaaa ctattaactg gcgaactact tactctagct tcccggcaac   38580
aattaataga ctggatggag gcggataaag ttgcaggacc acttctgcgc tcggcccttc   38640
cggctggctg gtttattgct gataaatctg gagccggtga gcgtgggtct cgcggtatca   38700
ttgcagcact ggggccagat ggtaagccct cccgtatcgt agttatctac acgacgggga   38760
gtcaggcaac tatggatgaa cgaaatagac agatcgctga gataggtgcc tcactgatta   38820
agcattggta actgtcagac caagtttact catatatact ttagattgat ttaaaaggat   38880
ctaggtgaag atcctttttg ataatctcat gaccaaaatc ccttaacgtg agttttcgtt   38940
ccactgagcg tcagaccccg tagaaaagat caaaggatct tcttgagatc ctttttttct   39000
gcgcgtaatc tgctgcttgc aaacaaaaaa accaccgcta ccagcggtgg tttgtttgcc   39060
ggatcaagag ctaccaactc tttttccgaa ggtaactggc ttcagcagag cgcagatacc   39120
aaatactgtc cttctagtgt agccgtagtt aggccaccac ttcaagaact ctgtagcacc   39180
gcctacatac ctcgctctgc taatcctgtt accagtggct gctgccagtg gcgataagtc   39240
gtgtcttacc gggttggact caagacgata gttaccggat aaggcgcagc ggtcgggctg   39300
aacggggggt tcgtgcacac agcccagctt ggagcgaacg acctacaccg aactgagata   39360
cctacagcgt gagctatgag aaagcgccac gcttcccgaa gggagaaagg cggacaggta   39420
```

-continued

```
tccggtaagc ggcagggtcg gaacaggaga gcgcacgagg gagcttccag ggggaaacgc    39480
ctggtatctt tatagtcctg tcgggtttcg ccacctctga cttgagcgtc gatttttgtg    39540
atgctcgtca gggggcgga gcctatggaa aaacgccagc aacgcggcct ttttacggtt    39600 cctggcctt tgctggcctt gaagctgtcc ctgatggtcg tcatctacct gcctggacag    39660
catggcctgc aacgcgggca tcccgatgcc gccggaagcg agaagaatca taatggggaa    39720
ggccatccag cctcgcgtcg cagatccgaa ttcgtttaaa c                       39761
```